US007504214B2

(12) United States Patent
Erlander et al.

(10) Patent No.: US 7,504,214 B2
(45) Date of Patent: Mar. 17, 2009

(54) PREDICTING OUTCOME WITH TAMOXIFEN IN BREAST CANCER

(75) Inventors: Mark G. Erlander, Encinitas, CA (US); Xiao-Jun Ma, San Diego, CA (US); Dennis C. Sgroi, Winchester, MA (US)

(73) Assignee: bioTheranostics, Inc., San Diego, CA (US)

( * ) Notice: Subject to any disclaimer, the term of this patent is extended or adjusted under 35 U.S.C. 154(b) by 438 days.

(21) Appl. No.: 10/727,100

(22) Filed: Dec. 2, 2003

(65) Prior Publication Data

US 2005/0239079 A1 Oct. 27, 2005

Related U.S. Application Data

(60) Provisional application No. 60/504,087, filed on Sep. 19, 2003.

(51) Int. Cl.
*C12Q 1/68* (2006.01)
*C07H 21/04* (2006.01)

(52) U.S. Cl. ........................................ 435/6; 536/24.33

(58) Field of Classification Search ...................... None
See application file for complete search history.

(56) References Cited

U.S. PATENT DOCUMENTS

2003/0219760 A1 11/2003 Gordon et al.

FOREIGN PATENT DOCUMENTS

WO WO02/103320 A2 12/2002

OTHER PUBLICATIONS

Wu, T.D. Analysing Gene Expression Data from DNA Microarrays to Identify Candidate Genes, Journal of Pathology 195:53-65, 2001.*

Chen, G. et al. Discordant Protein and mRNA Expression in Lung Adenocarcinomas, Molecular & Cellular Proteomics 1(4):304-313, 2002.*

Lucentini, J. Gene Association Studies Typically Wrong, The Scientist 18(24):20, 2004.*

Daidone, M.G., et al. "Biomarkers and outcome after tamoxifen treatment in node-positive breast cancers from elderly women", *British Journal of Cancer* (2000) 82(2):270-277.

Van Der Flier, Silvia, et al. "Bcar 1/p130Cas Protein and Primary Breast Cancer: Prognosis and Response to Tamoxifen Treatment", *Journal of the National Cancer Institute*, (2000) vol. 92(2):120-127.

Luo, L-Y, et al. "Higher expression of human kallikrein 10 in breast cancer tissue predicts tamoxifen resistance", *British Journal of Cancer* (2002) 86:1790-1796.

Ellis, Matthew J., et al. "Neoadjuvant comparisons of aromatase inhibitors and tamoxifen: pretreatment determinants of response and on-treatment effect", *Journal of Steroid Biochemistry & Molecular Biology* (2003) 86:301-307.

Hilsenbeck, Susan G., et al. "Statistical Analysis of Array Expression Data as Applied to the Problem of Tamoxifen Resistance", *Journal of the National Cancer Institute* (1999) 91(5):453-459.

Van't Veer, Laura, et al. "Gene expression profiling predicts clinical outcome of breast cancer", *Nature* (2002) 415:530-536.

Ma, Xiao-Jun, et al. "A two-gene expression ratio predicts clinical outcome in breast cancer patients treated with tamoxifen", *Cancer Cell* (2004) 5:607-615.

Becker, Michael, et al. "Distinct gene expression patterns in a tamoxifen-sensitive human mammary carcinoma xenograft and its tamoxifen-resistent subline MaCa 3366/TAM", *Molecular Cancer Therapeutics* (2005) 4(1):151-168.

Ramaswamy, Sridhar, et al., "A molecular signature of metastasis in primary solid tumors", *nature genetics* (2003) 33:49-54.

Bardou, V.J., et al. "Progesterone receptor status significantly improves outcome prediction over estrogen receptor status alone for adjuvant endocine therapy in two breast cancer databases", *J. Clin Oncol* (2003) 21:1973-9.

Huang, E. et al. "Gene expression predictors of breast cancer outcomes", *Lancet* (2003) 361:1590-6.

Sørlie, T., et al. "Gene expression patterns of breast carcinomas distinguish tumor subclasses with clinical implications", *Proc Natl Acad Sci USA* (2001) 98:10869-74.

Sørlie, T, et al. "Repeated observation of breast tumor subtypes in independent gene expression data sets", *Proc Natl Acad Sci USA* (2003) 100:8418-23.

Sotiriou, C., et al. "Breast cancer classification and prognosis based on gene expression profiles from a population-based study", *Proc Natl Acad Sci USA* (2003) 100:10393-8.

van de Vijver, M.J., et al. "A gene-expression signature as a predictor of survival in breast cancer", *N. Engl. J Med* (2002) 347:1999-2009.

Fernandez M. D., et al. "Quantitative oestrogen and progesterone receptor values in primary breast cancer and predictability of response to endocrine therapy", *Clin Oncol* (1983) 9:245-50.

Fernö, M., et al. "Results of two or five years of adjuvant tamoxifen correlated to steroid receptor and S-phase levels", *Breast Cancer Res Treat* (2000) 59:69-76.

Nardelli, G.B., et al. "Estrogen and progesterone receptors status in the prediction of response of breast cancer to endocrine therapy (preliminary report)", *Eur J Gynaecol Oncol* (1986) 7:151-8.

Osborne, C.K., et al. "The value of estrogen and progesterone receptors in the treatment of breast cancer", *Cancer* (1980) 46:2884-8.

Howell, Sacha J., et al. "The use of selective estrogen receptor modulators and selective estrogen receptor down-regulators in breast cancer", *Best Practice & Research Clinical Endocrinology & Metabolism* (2004) 18(1):47-66.

(Continued)

*Primary Examiner*—Celine X Qian
(74) *Attorney, Agent, or Firm*—Patentique PLLC

(57) ABSTRACT

Methods and compositions are provided for the identification of expression signatures in ER+ breast cancer cases, where the signatures correlate with responsiveness, or lack thereof, to tamoxifen treatment. The signature profiles are identified based upon sampling of reference breast tissue samples from independent cases of breast cancer and provide a reliable set of molecular criteria for predicting the efficacy of treating a subject with ER+ breast cancer with tamoxifen. Additional methods and compositions are provided for predicting tamoxifen responsiveness in cases of ER+ breast cancer by use of three biomarkers. Two biomarkers display increased expression correlated with tamoxifen response while the third biomarker displays decreased expression correlated with tamoxifen response.

43 Claims, 8 Drawing Sheets

OTHER PUBLICATIONS

Fabian, Carol J., et al. "Short-Term Breast Cancer Prediction by Random Periareolar Fine-Needle Aspiration Cytology and the Gail Risk Model", *Journal of the National Cancer Institute* (2000) 92(15):1217-1227.

Tan-Chiu, Elizabeth, et al. "Effects of Tamoxifen on Benign Breast Disease in Women at High Risk for Breast Cancer", *Journal of the National Cancer Institute* (2003) 95(4):302-307.

Hall, Julie M., et al. "The Multifaceted Mechanisms of Estradiol and Estrogen Receptor Signaling", *The Journal of Biological Chemistry* (2001) 276(40):36869-36872.

Levenson, Anait S., et al. "Gene Expression Profiles with Activation of the Estrogen Receptor α-Selective Estrogen Receptor Modulator Complex in Breast Cancer Cells Expressing Wild-Type Estrogen Receptor", *Cancer Research* (2002) 62:4419-4426.

Jordan, V. Craig, et al. "Introducing a new section to *Breast Cancer Research*: Endocrinology and hormone therapy", *Breast Cancer Research* (2003) 5:281-283.

Dauvois, Sophie, et al. "Antiestrogen ICI 164,384 reduces cellular estrogen receptor content by increasing its turnover", *Proc. Natl. Acad. Sci*. (1992) 89:4037-4041.

Willson, T.M., et al. "Dissection of the Molecular Mechanism of Action of GW5638, a Novel Estrogen Receptor Ligand, Provides Insights into the Role of Estrogen Receptor in Bone", *Endocrinology* (1997) 138(9):3901-3911.

Wijayaratne, Ashini L., et al. "Comparative Analyses of Mechanistic Differences Among Antiestrogens", *Endocrinology* (1999) 140(12):5828-5840.

Dutertre, Martin, et al "Molecular Mechanisms of Selective Estrogen Receptor Modulator (SERM) Action", *The Journal of Pharmacology and Experimental Therapeutics* (2000) 295(2):431-437.

* cited by examiner

FIG. 7 (con't.)
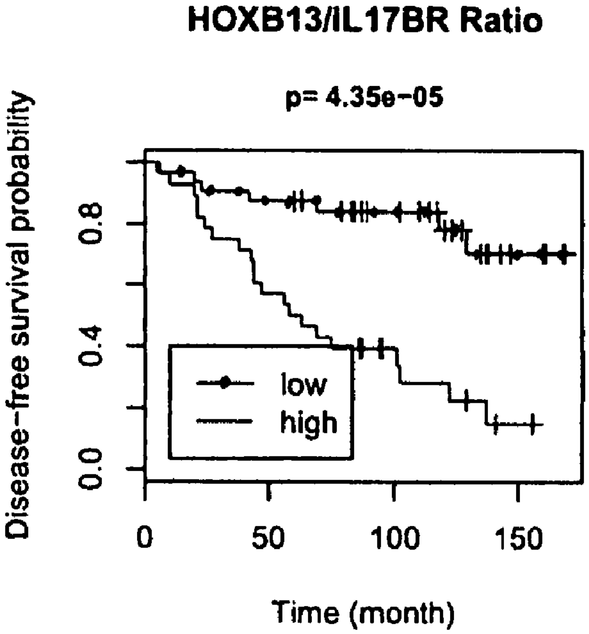

SEQUENCE LISTING

<160> NUMBER OF SEQ ID NOS: 400

<210> SEQ ID NO 1
<211> LENGTH: 2077
<212> TYPE: DNA
<213> ORGANISM: Homo sapiens

<400> SEQUENCE: 1
agcgcagcgt gcgggtggcc tggatcccgc gcagtggccc ggcgatgtcg ctcgtgctgc 60
taagcctggc cgcgctgtgc aggagcgccg taccccgaga gccgaccgtt caatgtggct 120
ctgaaactgg gccatctcca gagtggatgc tacaacatga tctaatcccc ggagacttga 180
gggacctccg agtagaacct gttacaacta gtgttgcaac aggggactat tcaattttga 240
tgaatgtaag ctgggtactc cgggcagatg ccagcatccg cttgttgaag gccaccaaga 300
tttgtgtgac gggcaaaagc aacttccagt cctacagctg tgtgaggtgc aattacacag 360
aggccttcca gactcagacc agaccctctg gtggtaaatg gacattttcc tacatcggct 420
tccctgtaga gctgaacaca gtctatttca ttggggccca taatattcct aatgcaaata 480
tgaatgaaga tggcccttcc atgtctgtga atttcacctc accaggctgc ctagaccaca 540
taatgaaata taaaaaaaag tgtgtcaagg ccggaagcct gtgggatccg aacatcactg 600
cttgtaagaa gaatgaggag acagtagaag tgaacttcac aaccactccc ctgggaaaca 660
gatacatggc tcttatccaa cacagcacta tcatcgggtt ttctcaggtg tttgagccac 720
accagaagaa acaaacgcga gcttcagtgg tgattccagt gactggggat agtgaaggtg 780
ctacggtgca gctgactcca tattttccta cttgtggcag cgactgcatc cgacataaag 840
gaacagttgt gctctgccca caaacaggcg tccctttccc tctggataac aacaaaagca 900
agccgggagg ctggctgcct ctcctcctgc tgtctctgct ggtggccaca tgggtgctgg 960
tggcagggat ctatctaatg tggaggcacg aaaggatcaa gaagacttcc ttttctacca 1020
ccacactact gccccccatt aaggttcttg tggtttaccc atctgaaata tgtttccatc 1080
acacaatttg ttacttcact gaatttcttc aaaaccattg cagaagtgag gtcatccttg 1140
aaaagtggca gaaaaagaaa atagcagaga tgggtccagt gcagtggctt gccactcaaa 1200
agaaggcagc agacaaagtc gtcttccttc tttccaatga cgtcaacagt gtgtgcgatg 1260
gtacctgtgg caagagcgag ggcagtccca gtgagaactc tcaagacctc ttcccccttg 1320
cctttaacct tttctgcagt gatctaagaa gccagattca tctgcacaaa tacgtggtgg 1380
tctactttag agagattgat acaaaagacg attacaatgc tctcagtgtc tgccccaagt 1440
accacctcat gaaggatgcc actgctttct gtgcagaact tctccatgtc aagcagcagg 1500
tgtcagcagg aaaaagatca caagcctgcc acgatggctg ctgctccttg tagcccaccc 1560
atgagaagca agagacctta aaggcttcct atcccaccaa ttacagggaa aaaacgtgtg 1620
atgatcctga agcttactat gcagcctaca aacagcctta gtaattaaaa cattttatac 1680
caataaaatt ttcaaatatt gctaactaat gtagcattaa ctaacgattg gaaactacat 1740
ttacaacttc aaagctgttt tatacataga aatcaattac agttttaatt gaaaactata 1800
accattttga taatgcaaca ataaagcatc ttcagccaaa catctagtct tccatagacc 1860
atgcattgca gtgtacccag aactgtttag ctaatattct atgtttaatt aatgaatact 1920
aactctaaga acccctcact gattcactca atagcatctt aagtgaaaaa ccttctatta 1980
catgcaaaaa atcattgttt ttaagataac aaaagtaggg aataaacaag ctgaacccac 2040

-continued ttttaaaaaa aaaaaaaaaa aaaaaaaaaa aaaaaaa 2077

<210> SEQ ID NO 2
<211> LENGTH: 3105
<212> TYPE: DNA
<213> ORGANISM: Homo sapiens

<400> SEQUENCE: 2
agcgcagcgt gcgggtggcc tggatcccgc gcagtggccc ggcgatgtcg ctcgtgctgc 60
taagcctggc cgcgctgtgc aggagcgccg taccccgaga gccgaccgtt caatgtggct 120
ctgaaactgg gccatctcca gagtggatgc tacaacatga tctaatcccc ggagacttga 180
gggacctccg agtagaacct gttacaacta gtgttgcaac aggggactat tcaattttga 240
tgaatgtaag ctgggtactc cgggcagatg ccagcatccg cttgttgaag gccaccaaga 300
tttgtgtgac gggcaaaagc aacttccagt cctacagctg tgtgaggtgc aattacacag 360
aggccttcca gactcagacc agaccctctg gtggtaaatg gacattttcc tacatcggct 420
tccctgtaga gctgaacaca gtctatttca ttggggccca taatattcct aatgcaaata 480
tgaatgaaga tggcccttcc atgtctgtga atttcacctc accaggctgc ctagaccaca 540
taatgaaata taaaaaaaag tgtgtcaagg ccggaagcct gtgggatccg aacatcactg 600
cttgtaagaa gaatgaggag acagtagaag tgaacttcac aaccactccc ctgggaaaca 660
gatacatggc tcttatccaa cacagcacta tcatcgggtt ttctcaggtg tttgagccac 720
accagaagaa acaaacgcga gcttcagtgg tgattccagt gactggggat agtgaaggtg 780
ctacggtgca ggtaaagttc agtgagctgc tctggggagg gaagggacat agaagactgt 840
tccatcattc attgctttta aggatgagtt ctctcttgtc aaatgcactt ctgccagcag 900
acaccagtta agtggcgttc atgggggctc tttcgctgca gcctccaccg tgctgaggtc 960
aggaggccga cgtggcagtt gtggtccctt ttgcttgtat taatggctgc tgaccttcca 1020
aagcactttt tattttcatt ttctgtcaca gacactcagg gatagcagta ccattttact 1080
tccgcaagcc tttaactgca agatgaagct gcaaagggtt tgaaatggga aggtttgagt 1140
tccaggcagc gtatgaactc tggagagggg ctgccagtcc tctctgggcc gcagcggacc 1200
cagctggaac acaggaagtt ggagcagtag gtgctccttc acctctcagt atgtctcttt 1260
caactctagt ttttgaggtg gggacacagg aggtccagtg ggacacagcc actccccaaa 1320
gagtaaggag cttccatgct tcattccctg gcataaaaag tgctcaaaca caccagaggg 1380
ggcaggcacc agccagggta tgatggctac taccctttc tggagaacca tagacttccc 1440
ttactacagg gacttgcatg tcctaaagca ctggctgaag gaagccaaga ggatcactgc 1500
tgctcctttt ttctagagga aatgtttgtc tacgtggtaa gatatgacct agccctttta 1560
ggtaagcgaa ctggtatgtt agtaacgtgt acaaagttta ggttcagacc ccgggagtct 1620
tgggcacgtg ggtctcgggt cactggtttt gactttaggg ctttgttaca gatgtgtgac 1680
caaggggaaa atgtgcatga caacactaga ggtatgggcg aagccagaaa gaagggaagt 1740
tttggctgaa gtaggagtct tggtgagatt ttgctctgat gcatggtgtg aactttctga 1800
gcctcttgtt tttcctcagc tgactccata ttttcctact tgtggcagcg actgcatccg 1860
acataaagga acagttgtgc tctgcccaca aacaggcgtc cctttccctc tggataacaa 1920
caaaagcaag ccgggaggct ggctgcctct cctcctgctg tctctgctgg tggccacatg 1980
ggtgctggtg gcagggatct atctaatgtg gaggcacgaa aggatcaaga agacttcctt 2040

-continued

```
ttctaccacc acactactgc cccccattaa ggttcttgtg gtttacccat ctgaaatatg   2100

tttccatcac acaatttgtt acttcactga atttcttcaa aaccattgca gaagtgaggt   2160

catccttgaa aagtggcaga aaaagaaaat agcagagatg ggtccagtgc agtggcttgc   2220

cactcaaaag aaggcagcag acaaagtcgt cttccttctt tccaatgacg tcaacagtgt   2280

gtgcgatggt acctgtggca agagcgaggg cagtcccagt gagaactctc aagacctctt   2340

ccccccttgcc tttaaccttt tctgcagtga tctaagaagc cagattcatc tgcacaaata   2400

cgtggtggtc tactttagag agattgatac aaaagacgat tacaatgctc tcagtgtctg   2460

ccccaagtac cacctcatga aggatgccac tgctttctgt gcagaacttc tccatgtcaa   2520

gcagcaggtg tcagcaggaa aaagatcaca agcctgccac gatggctgct gctccttgta   2580

gcccacccat gagaagcaag agaccttaaa ggcttcctat cccaccaatt acagggaaaa   2640

aacgtgtgat gatcctgaag cttactatgc agcctacaaa cagccttagt aattaaaaca   2700

ttttatacca ataaaatttt caaatattgc taactaatgt agcattaact aacgattgga   2760

aactacattt acaacttcaa agctgtttta tacatagaaa tcaattacag ttttaattga   2820

aaactataac cattttgata atgcaacaat aaagcatctt cagccaaaca tctagtcttc   2880

catagaccat gcattgcagt gtacccagaa ctgtttagct aatattctat gtttaattaa   2940

tgaatactaa ctctaagaac ccctcactga ttcactcaat agcatcttaa gtgaaaaacc   3000

ttctattaca tgcaaaaaat cattgttttt aagataacaa aagtagggaa taaacaagct   3060

gaacccactt ttaaaaaaaa aaaaaaaaaa aaaaaaaaaa aaaaa                   3105
```

<210> SEQ ID NO 3
<211> LENGTH: 2856
<212> TYPE: DNA
<213> ORGANISM: Homo sapiens
<220> FEATURE:
<221> NAME/KEY: misc_feature
<222> LOCATION: (1325)..(1325)
<223> OTHER INFORMATION: a or g or c or t/u

<400> SEQUENCE: 3

```
cggcgatgtc gctcgtgctg ataagcctgg ccgcgctgtg caggagcgcc gtaccccgag     60

agccgaccgt tcaatgtggc tctgaaactg ggccatctcc agagtggatg ctacaacatg    120

atctaatccc cggagacttg agggacctcc gagtagaacc tgttacaact agtgttgcaa    180

caggggacta ttcaattttg atgaatgtaa gctgggtact ccgggcagat gccagcatcc    240

gcttgttgaa ggccaccaag atttgtgtga cgggcaaaag caacttccag tcctacagct    300

gtgtgaggtg caattacaca gaggccttcc agactcagac cagaccctct ggtggtaaat    360

ggacattttc ctatatcggc ttccctgtag agctgaacac agtctatttc attggggccc    420

ataatattcc taatgcaaat atgaatgaag atggcccttc catgtctgtg aatttcacct    480

caccaggctg cctagaccac ataatgaaat ataaaaaaaa gtgtgtcaag gccggaagcc    540

tgtgggatcc gaacatcact gcttgtaaga agaatgagga gacagtagaa gtgaacttca    600

caaccactcc cctgggaaac agatacatgg ctcttatcca acacagcact atcatcgggt    660

tttctcaggt gtttgagcca caccagaaga aacaaacgcg agcttcagtg gtgattccag    720

tgactgggga tagtgaaggt gctacggtgc aggtaaagtt cagtgagctg ctctggggag    780

ggaagggaca tagaagactg ttccatcatt cattgctttt aaggatgagt tctctcttgt    840

caaatgcact tctgccagca gacaccagtt aagtggcgtt catgggggtt ctttcgctgc    900

agcctccacc gtgctgaggt caggaggccg acgtggcagt tgtggtccct tttgcttgta    960
```

-continued ttaatggctg ctgaccttcc aaagcacttt ttattttcat tttctgtcac agacactcag 1020
ggatagcagt accattttac ttccgcaagc ctttaactgc aagatgaagc tgcaaagggt 1080
ttgaaatggg aaggtttgag ttccaggcag cgtatgaact ctggagaggg gctgccagtc 1140
ctctctgggc cgcagcggac ccagctggaa cacaggaagt tggagcagta ggtgctcctt 1200
cacctctcag tatgtctctt tcaactctag tttttgaagt ggggacacag gaagtccagt 1260
ggggacacag ccactcccca aagaataagg aacttccatg cttcattccc tggcataaaa 1320
agtgntcaaa cacaccagag ggggcaggca ccagccaggg tatgatgggt actacccttt 1380
tctggagaac catagacttc ccttactaca gggacttgca tgtcctaaag cactggctga 1440
aggaagccaa gaggatcact gctgctcctt ttttgtagag gaaatgtttg tgtacgtggt 1500
aagatatgac ctagcccttt taggtaagcg aactggtatg ttagtaacgt gtacaaagtt 1560
taggttcaga ccccgggagt cttgggcatg tgggtctcgg gtcactggtt ttgactttag 1620
ggctttgtta cagatgtgtg accaagggga aaatgtgcat gacaacacta gaggtagggg 1680
cgaagccaga aagaagggaa gttttggctg aagtaggagt cttggtgaga ttttgctgtg 1740
atgcatggtg tgaactttct gagcctcttg tttttcctca gctgactcca tattttccta 1800
cttgtggcag cgactgcatc cgacataaag gaacagttgt gctctgccca caaacaggcg 1860
tccctttccc tctggataac aacaaaagca agccgggagg ctggctgcct ctcctcctgc 1920
tgtctctgct ggtggccaca tgggtgctgg tggcagggat ctatctaatg tggaggcacg 1980
aaaggatcaa gaagacttcc ttttctacca ccacactact gccccccatt aaggttcttg 2040
tggtttaccc atctgaaata tgtttccatc acacaatttg ttacttcact gaatttcttc 2100
aaaaccattg cagaagtgag gtcatccttg aaaagtggca gaaaaagaaa atagcagaga 2160
tgggtccagt gcagtggctt gccactcaaa agaaggcagc agacaaagtc gtcttccttc 2220
tttccaatga cgtcaacagt gtgtgcgatg gtacctgtgg caagagcgag ggcagtccca 2280
gtgagaactc tcaagacctc ttccccttg cctttaacct tttctgcagt gatctaagaa 2340
gccagattca tctgcacaaa tacgtggtgg tctactttag agagattgat acaaaagacg 2400
attacaatgc tctcagtgtc tgccccaagt accacttcat gaaggatgcc actgctttct 2460
gtgcagaact tctccatgtc aagcagcagg tgtcagcagg aaaaagatca caagcctgcc 2520
acgatggctg ctgctccttg tagcccaccc atgagaagca agagacctta aaggcttcct 2580
atcccaccaa ttacagggaa aaaacgtgtg atgatcctga agcttactat gcagcctaca 2640
aacagcctta gtaattaaaa cattttatac caataaaatt ttcaaatatt actaactaat 2700
gtagcattaa ctaacgattg gaaactacat ttacaacttc aaagctgttt tatacataga 2760
aatcaattac agctttaatt gaaaactgta accattttga taatgcaaca ataaagcatc 2820
ttccaaaaaa aaaaaaaaaa aaaaaaaaaa aaaaaa 2856

<210> SEQ ID NO 4
<211> LENGTH: 7193
<212> TYPE: DNA
<213> ORGANISM: Homo sapiens

<400> SEQUENCE: 4
agaataaggg cagggaccgc ggctcctatc tcttggtgat ccccttcccc attccgcccc 60
cgcctcaacg cccagcacag tgccctgcac acagtagtcg ctcaataaat gttcgtggat 120
gatgatgatg atgatgatga aaaaaatgca gcatcaacgg cagcagcaag cggaccacgc 180

-continued

```
gaacgaggca aactatgcaa gaggcaccag acttcctctt tctggtgaag gaccaacttc    240
tcagccgaat agctccaagc aaactgtcct gtcttggcaa gctgcaatcg atgctgctag    300
acaggccaag gctgcccaaa ctatgagcac ctctgcaccc ccacctgtag gatctctctc    360
ccaaagaaaa cgtcagcaat acgccaagag caaaaaacag ggtaactcgt ccaacagccg    420
acctgcccgc gccctttct  gtttatcact caataacccc atccgaagag cctgcattag    480
tatagtggaa tggaaaccat ttgacatatt tatattattg gctatttttg ccaattgtgt    540
ggccttagct atttacatcc cattccctga agatgattct aattcaacaa atcataactt    600
ggaaaaagta gaatatgcct tcctgattat ttttacagtc gagacatttt tgaagattat    660
agcgtatgga ttattgctac atcctaatgc ttatgttagg aatggatgga atttactgga    720
ttttgttata gtaatagtag gattgtttag tgtaattttg gaacaattaa ccaaagaaac    780
agaaggcggg aaccactcaa gcggcaaatc tggaggcttt gatgtcaaag ccctccgtgc    840
ctttcgagtg ttgcgaccac ttcgactagt gtcaggggtg cccagtttac aagttgtcct    900
gaactccatt ataaaagcca tggttcccct ccttcacata gccctttttgg tattatttgt    960
aatcataatc tatgctatta taggattgga actttttatt ggaaaaatgc acaaaacatg   1020
tttttttgct gactcagata tcgtagctga agaggaccca gctccatgtg cgttctcagg   1080
gaatggacgc cagtgtactg ccaatggcac ggaatgtagg agtggctggg ttggcccgaa   1140
cggaggcatc accaactttg ataactttgc ctttgccatg cttactgtgt ttcagtgcat   1200
caccatggag ggctggacag acgtgctcta ctgggtaaat gatgcgatag gatgggaatg   1260
gccatgggtg tattttgtta gtctgatcat ccttggctca tttttcgtcc ttaacctggt   1320
tcttggtgtc cttagtggag aattctcaaa ggaaagagag aaggcaaaag cacggggaga   1380
tttccagaag ctccgggaga agcagcagct ggaggaggat ctaaagggct acttggattg   1440
gatcacccaa gctgaggaca tcgatccgga gaatgaggaa gaaggaggag aggaaggcaa   1500
acgaaatact agcatgccca ccagcgagac tgagtctgtg aacacagaga acgtcagcgg   1560
tgaaggcgag aaccgaggct gctgtggaag tctctggtgc tggtggagac ggagaggcgc   1620
ggccaaggcg gggccctctg ggtgtcggcg gtggggtcaa gccatctcaa aatccaaact   1680
cagccgacgc tggcgtcgct ggaaccgatt caatcgcaga agatgtaggg ccgccgtgaa   1740
gtctgtcacg ttttactggc tggttatcgt cctggtgttt ctgaacacct taaccatttc   1800
ctctgagcac tacaatcagc cagattggtt gacacagatt caagatattg ccaacaaagt   1860
cctcttggct ctgttcacct gcgagatgct ggtaaaaatg tacagcttgg gcctccaagc   1920
atatttcgtc tctcttttca accggtttga ttgcttcgtg gtgtgtggtg gaatcactga   1980
gacgatcctg gtggaactgg aaatcatgtc tcccctgggg atctctgtgt ttcggtgtgt   2040
gcgcctctta agaatcttca aagtgaccag gcactggact tccctgagca acttagtggc   2100
atccttatta aactccatga agtccatcgc ttcgctgttg cttctgcttt ttctcttcat   2160
tatcatcttt tccttgcttg ggatgcagct gtttggcggc aagtttaatt ttgatgaaac   2220
gcaaaccaag cggagcacct ttgacaattt ccctcaagca cttctcacag tgttccagat   2280
cctgacaggc gaagactgga atgctgtgat gtacgatggc atcatggctt acgggggccc   2340
atcctcttca ggaatgatcg tctgcatcta cttcatcatc ctcttcattt gtggtaacta   2400
tattctactg aatgtcttct tggccatcgc tgtagacaat ttggctgatg ctgaaagtct   2460
gaacactgct cagaaagaag aagcggaaga aaaggagagg aaaaagattg ccagaaaaga   2520
gagcctagaa aataaaaaga acaacaaacc agaagtcaac cagatagcca acagtgacaa   2580
```

-continued

```
caaggttaca attgatgact atagagaaga ggatgaagac aaggacccct atccgccttg   2640
cgatgtgcca gtaggggaag aggaagagga agaggaggag gatgaacctg aggttcctgc   2700
cggaccccgt cctcgaagga tctcggagtt gaacatgaag gaaaaaattg cccccatccc   2760
tgaagggagc gctttcttca ttcttagcaa gaccaacccg atccgcgtag gctgccacaa   2820
gctcatcaac caccacatct tcaccaacct catccttgtc ttcatcatgc tgagcagcgc   2880
tgccctggcc gcagaggacc ccatccgcag ccactccttc cggaacacga tactgggtta   2940
ctttgactat gccttcacag ccatctttac tgttgagatc ctgttgaaga tgacaacttt   3000
tggagctttc ctccacaaag gggccttctg caggaactac ttcaatttgc tggatatgct   3060
ggtggttggg gtgtctctgg tgtcatttgg gattcaatcc agtgccatct ccgttgtgaa   3120
gattctgagg gtcttaaggg tcctgcgtcc cctcagggcc atcaacagag caaaaggact   3180
taagcacgtg gtccagtgcg tcttcgtggc catccggacc atcggcaaca tcatgatcgt   3240
cactaccctc ctgcagttca tgtttgcctg tatcggggtc cagttgttca aggggaagtt   3300
ctatcgctgt acggatgaag ccaaaagtaa ccctgaagaa tgcaggggac ttttcatcct   3360
ctacaaggat ggggatgttg acagtcctgt ggtccgtgaa cggatctggc aaaacagtga   3420
tttcaacttc gacaacgtcc tctctgctat gatggcgctc ttcacagtct ccacgtttga   3480
gggctggcct gcgttgctgt ataaagccat cgactcgaat ggagagaaca tcggcccaat   3540
ctacaaccac cgcgtggaga tctccatctt cttcatcatc tacatcatca ttgtagcttt   3600
cttcatgatg aacatctttg tgggctttgt catcgttaca tttcaggaac aaggagaaaa   3660
agagtataag aactgtgagc tggacaaaaa tcagcgtcag tgtgttgaat acgccttgaa   3720
agcacgtccc ttgcggagat acatccccaa aaacccctac cagtacaagt tctggtacgt   3780
ggtgaactct tcgcctttcg aatacatgat gtttgtcctc atcatgctca acacactctg   3840
cttggccatg cagcactacg agcagtccaa gatgttcaat gatgccatgg acattctgaa   3900
catggtcttc accggggtgt tcaccgtcga gatggttttg aaagtcatcg catttaagcc   3960
taaggggtat tttagtgacg cctggaacac gtttgactcc ctcatcgtaa tcggcagcat   4020
tatagacgtg gccctcagcg aagcggaccc aactgaaagt gaaaatgtcc ctgtcccaac   4080
tgctacacct gggaactctg aagagagcaa tagaatctcc atcacctttt tccgtctttt   4140
ccgagtgatg cgattggtga agcttctcag caggggggaa ggcatccgga cattgctgtg   4200
gacttttatt aagtcctttc aggcgctccc gtatgtggcc ctcctcatag ccatgctgtt   4260
cttcatctat gcggtcattg gcatgcagat gtttgggaaa gttgccatga gagataacaa   4320
ccagatcaat aggaacaata acttccagac gtttccccag gcggtgctgc tgctcttcag   4380
gtgtgcaaca ggtgaggcct ggcaggagat catgctggcc tgtctcccag ggaagctctg   4440
tgaccctgag tcagattaca accccgggga ggagtataca tgtgggagca actttgccat   4500
tgtctatttc atcagttttt acatgctctg tgcatttctg atcatcaatc tgtttgtggc   4560
tgtcatcatg gataatttcg actatctgac ccgggactgg tctattttgg ggcctcacca   4620
tttagatgaa ttcaaaagaa tatggtcaga atatgaccct gaggcaaagg gaaggataaa   4680
acaccttgat gtggtcactc tgcttcgacg catccagcct cccctggggt ttgggaagtt   4740
atgtccacac agggtagcgt gcaagagatt agttgccatg aacatgcctc tcaacagtga   4800
cgggacagtc atgtttaatg caaccctgtt tgctttggtt cgaacggctc ttaagatcaa   4860
gaccgaaggg aacctggagc aagctaatga agaacttcgg gctgtgataa agaaaatttg   4920
```

-continued

```
gaagaaaacc agcatgaaat tacttgacca agttgtccct ccagctggtg atgatgaggt   4980

aaccgtgggg aagttctatg ccactttcct gatacaggac tactttagga aattcaagaa   5040

acggaaagaa caaggactgg tgggaaagta ccctgcgaag aacaccacaa ttgccctaca   5100

ggcgggatta aggacactgc atgacattgg gccagaaatc cggcgtgcta tatcgtgtga   5160

tttgcaagat gacgagcctg aggaaacaaa acgagaagaa gaagatgatg tgttcaaaag   5220

aaatggtgcc ctgcttggaa accatgtcaa tcatgttaat agtgatagga gagattccct   5280

tcagcagacc aataccaccc accgtcccct gcatgtccaa aggccttcaa ttccacctgc   5340

aagtgatact gagaaaccgc tgtttcctcc agcaggaaat tcggtgtgtc ataaccatca   5400

taaccataat tccataggaa agcaagttcc cacctcaaca aatgccaatc tcaataatgc   5460

caatatgtcc aaagctgccc atggaaagcg gcccagcatt gggaaccttg agcatgtgtc   5520

tgaaaatggg catcattctt cccacaagca tgaccgggag cctcagagaa ggtccagtgt   5580

gaaaagaacc cgctattatg aaacttacat taggtccgac tcaggagatg aacagctccc   5640

aactatttgc cgggaagacc cagagataca tggctatttc agggaccccc actgcttggg   5700

ggagcaggag tatttcagta gtgaggaatg ctacgaggat gacagctcgc ccacctggag   5760

caggcaaaac tatggctact acagcagata cccaggcaga aacatcgact ctgagaggcc   5820

ccgaggctac catcatcccc aaggattctt ggaggacgat gactcgcccg tttgctatga   5880

ttcacggaga tctccaagga gacgcctact acctcccacc ccagcatccc accggagatc   5940

ctccttcaac tttgagtgcc tgcgccggca gagcagccag gaagaggtcc cgtcgtctcc   6000

catcttcccc catcgcacgg ccctgcctct gcatctaatg cagcaacaga tcatggcagt   6060

tgccggccta gattcaagta aagcccagaa gtactcaccg agtcactcga cccggtcgtg   6120

ggccacccct ccagcaaccc ctccctaccg ggactggaca ccgtgctaca ccccccctgat   6180

ccaagtggag cagtcagagg ccctggacca ggtgaacggc agcctgccgt ccctgcaccg   6240

cagctcctgg tacacagacg agcccgacat ctcctaccgg actttcacac cagccagcct   6300

gactgtcccc agcagcttcc ggaacaaaaa cagcgacaag cagaggagtg cggacagctt   6360

ggtggaggca gtcctgatat ccgaaggctt gggacgctat gcaagggacc caaaatttgt   6420

gtcagcaaca aaacacgaaa tcgctgatgc ctgtgacctc accatcgacg agatggagag   6480

tgcagccagc accctgctta atgggaacgt gcgtccccga gccaacgggg atgtgggccc   6540

cctctcacac cggcaggact atgagctaca ggactttggt cctggctaca gcgacgaaga   6600

gccagaccct gggagggatg aggaggacct ggcggatgaa atgatatgca tcaccacctt   6660

gtagccccca gcgaggggca gactggctct ggcctcaggt ggggcgcagg agagccaggg   6720

gaaaagtgcc tcatagttag gaaagtttag gcactagttg ggagtaatat tcaattaatt   6780

agacttttgt ataagagatg tcatgcctca agaaagccat aaacctggta ggaacaggtc   6840

ccaagcggtt gagcctggca gagtaccatg cgctcggccc cagctgcagg aaacagcagg   6900

ccccgccctc tcacagagga tgggtgagga ggccagacct gccctgcccc attgtccaga   6960

tgggcactgc tgtggagtct gcttctccca tgtaccaggg caccaggccc acccaactga   7020

aggcatggcg gcggggtgca ggggaaagtt aaaggtgatg acgatcatca cacctcgtgt   7080

cgttacctca gccatcggtc tagcatatca gtcactgggc ccaacatatc cattttttaaa   7140

ccctttcccc caaatacact gcgtcctggt tcctgtttag ctgttctgaa ata          7193
```

<210> SEQ ID NO 5
<211> LENGTH: 675

-continued

<212> TYPE: DNA
<213> ORGANISM: Homo sapiens

<400> SEQUENCE: 5
tttttttttt tttttttttt tcttacaaag aaaaatttaa tattcgatga gaggttgaac 60
caggcttaaa gcagacatac taggaaatgg tgcagcctgt aagaatgcca gtttgtaagt 120
actgactttg gaaaagatca tcgcctctat cagacactta gggtcctggt ctggcaattt 180
tggcctgatg tgatgccaca agacccaaca gagagagaca cagagtccag gataatgttg 240
acagtggtgt agccctttag gagaaatggc gctccctgcg gctggtatta ggttaccatt 300
ggcaccgaag gaaccaggag gataagaata tccataattt cagagctgcc ctggcacagt 360
acctgccccg tcggaggctc tcactggcaa atgacagctc tgtgcaagga gcactcccaa 420
gtataaaaat tattacacag ttttattctg aagaacattt tgcattttaa taaaaaagga 480
tttatgtcag gaaagagtca tttacaaacc ttgaagtgtt tttgcctgga tcagagtaag 540
aatgtcttaa gaagaggttt gtaaggtctt cataacaaag tggtgtttgt tatttacaaa 600
aaaaaaaaaa aaaaaaatta acaggttgtc tgtatactat taaaaatttt ggaccaaaaa 660
aaaaaaaaaa aaaaa 675

<210> SEQ ID NO 6
<211> LENGTH: 1270
<212> TYPE: DNA
<213> ORGANISM: Homo sapiens

<400> SEQUENCE: 6
cgaatgcagg cgacttgcga gctgggagcg atttaaaacg ctttggattc ccccggcctg 60
ggtggggaga gcgagctggg tgccccctag attccccgcc cccgcacctc atgagccgac 120
cctcggctcc atggagcccg gcaattatgc caccttggat ggagccaagg atatcgaagg 180
cttgctggga gcgggagggg ggcggaatct ggtcgcccac tcccctctga ccagccaccc 240
agcggcgcct acgctgatgc ctgctgtcaa ctatgccccc ttggatctgc caggctcggc 300
ggagccgcca aagcaatgcc acccatgccc tggggtgccc caggggacgt ccccagctcc 360
cgtgccttat ggttactttg gaggcgggta ctactcctgc cgagtgtccc ggagctcgct 420
gaaaccctgt gcccaggcag ccaccctggc cgcgtacccc gcggagactc ccacggccgg 480
ggaagagtac cccagtcgcc ccactgagtt tgccttctat ccgggatatc cgggaaccta 540
ccacgctatg gccagttacc tggacgtgtc tgtggtgcag actctgggtg ctcctggaga 600
accgcgacat gactccctgt tgcctgtgga cagttaccag tcttgggctc tcgctggtgg 660
ctggaacagc cagatgtgtt gccagggaga acagaaccca ccaggtccct tttggaaggc 720
agcatttgca gactccagcg ggcagcaccc tcctgacgcc tgcgcctttc gtcgcggccg 780
caagaaacgc attccgtaca gcaaggggca gttgcgggag ctggagcggg agtatgcggc 840
taacaagttc atcaccaagg acaagaggcg caagatctcg gcagccacca gcctctcgga 900
gcgccagatt accatctggt ttcagaaccg ccgggtcaaa gagaagaagg ttctcgccaa 960
ggtgaagaac agcgctaccc cttaagagat ctccttgcct gggtgggagg agcgaaagtg 1020
ggggtgtcct ggggagacca gaaacctgcc aagcccaggc tggggccaag gactctgctg 1080
agaggcccct agagacaaca cccttcccag gccactggct gctggactgt tcctcaggag 1140
cggcctgggt acccagtatg tgcagggaga cggaacccca tgtgacaggc ccactccacc 1200
agggttccca aagaacctgg cccagtcata atcattcatc ctcacagtgg caataatcac 1260

-continued gataaccagt 1270

<210> SEQ ID NO 7
<211> LENGTH: 1356
<212> TYPE: DNA
<213> ORGANISM: Homo sapiens

<400> SEQUENCE: 7
ggattccccc ggcctgggtg gggagagcga gctgggtgcc ccctagattc cccgcccccg 60
cacctcatga gccgaccctc ggctccatgg agcccggcaa ttatgccacc ttggatggag 120
ccaaggatat cgaaggcttg ctgggagcgg gaggggggcg gaatctggtc gcccactccc 180
ctctgaccag ccacccagcg gcgcctacgc tgatgcctgc tgtcaactat gccccccttgg 240 atctgccagg ctcggcggag ccgccaaagc aatgccaccc atgccctggg gtgccccagg 300
ggacgtcccc agctcccgtg ccttatggtt actttggagg cgggtactac tcctgccgag 360
tgtcccggag ctcgctgaaa ccctgtgccc aggcagccac cctggccgcg taccccgcgg 420
agactcccac ggccggggaa gagtacccca gccgccccac tgagtttgcc ttctatccgg 480
gatatccggg aacctaccag cctatggcca gttacctgga cgtgtctgtg gtgcagactc 540
tgggtgctcc tggagaaccg cgacatgact ccctgttgcc tgtggacagt taccagtctt 600
gggctctcgc tggtggctgg aacagccaga tgtgttgcca gggagaacag aacccaccag 660
gtcccttttg gaaggcagca tttgcagact ccagcgggca gcaccctcct gacgcctgcg 720
cctttcgtcg cggccgcaag aaacgcattc cgtacagcaa ggggcagttg cgggagctgg 780
agcgggagta tgcggctaac aagttcatca ccaaggacaa gaggcgcaag atctcggcag 840
ccaccagcct ctcggagcgc cagattacca tctggtttca gaaccgccgg gtcaaagaga 900
agaaggttct cgccaaggtg aagaacagcg ctacccctta agagatctcc ttgcctgggt 960
gggaggagcg aaagtggggg tgtcctgggg agaccaggaa cctgccaagc ccaggctggg 1020
gccaaggact ctgctgagag gcccctagag acaacaccct tcccaggcca ctggctgctg 1080
gactgttcct caggagcggc ctgggtaccc agtatgtgca gggagacgga accccatgtg 1140
acagcccact ccaccagggt tcccaaagaa cctggcccag tcataatcat tcatcctgac 1200
agtggcaata atcacgataa ccagtactag ctgccatgat cgttagcctc atattttcta 1260
tctagagctc tgtagagcac tttagaaacc gctttcatga attgagctaa ttatgaataa 1320
atttggaaaa aaaaaaaaaa aaaaaaaaaa aaaaaa 1356

<210> SEQ ID NO 8
<211> LENGTH: 60
<212> TYPE: DNA
<213> ORGANISM: Homo sapiens

<400> SEQUENCE: 8
caattacagg gaaaaaacgt gtgatgatcc tgaagcttac tatgcagcct acaaacagcc 60

<210> SEQ ID NO 9
<211> LENGTH: 60
<212> TYPE: DNA
<213> ORGANISM: Homo sapiens

<400> SEQUENCE: 9
gctctcactg gcaaatgaca gctctgtgca aggagcactc ccaagtataa aaattattac 60

<210> SEQ ID NO 10
<211> LENGTH: 60

-continued

<212> TYPE: DNA
<213> ORGANISM: Homo sapiens

<400> SEQUENCE: 10
gatcgttagc ctcatatttt ctatctagag ctctgtagag cactttagaa accgctttca 60

<210> SEQ ID NO 11
<211> LENGTH: 60
<212> TYPE: DNA
<213> ORGANISM: Homo sapiens

<400> SEQUENCE: 11
tgcctaattt cactctcaga gtgaggcagg taactggggc tccactgggt cactctgaga 60

<210> SEQ ID NO 12
<211> LENGTH: 60
<212> TYPE: DNA
<213> ORGANISM: Homo sapiens

<400> SEQUENCE: 12
ttggaagcag agtccctcta aaggtaactc ttgtggtcac tcaatattgt attggcattt 60

<210> SEQ ID NO 13
<211> LENGTH: 60
<212> TYPE: DNA
<213> ORGANISM: Homo sapiens

<400> SEQUENCE: 13
acgttagact tttgctggca ttcaagtcat ggctagtctg tgtatttaat aaatgtgtgt 60

<210> SEQ ID NO 14
<211> LENGTH: 60
<212> TYPE: DNA
<213> ORGANISM: Homo sapiens

<400> SEQUENCE: 14
ctggtcagcc actctgactt ttctaccaca ttaaattctc cattacatct cactattggt 60

<210> SEQ ID NO 15
<211> LENGTH: 60
<212> TYPE: DNA
<213> ORGANISM: Homo sapiens

<400> SEQUENCE: 15
tacaacttct gaatgctgca cattcttcca aaatgatcct tagcacaatc tattgtatga 60

<210> SEQ ID NO 16
<211> LENGTH: 60
<212> TYPE: DNA
<213> ORGANISM: Homo sapiens

<400> SEQUENCE: 16
gggatggcct ttaggccaca gtagtgtctg tgttaagttc actaaatgtg tatttaatga 60

<210> SEQ ID NO 17
<211> LENGTH: 60
<212> TYPE: DNA
<213> ORGANISM: Homo sapiens

<400> SEQUENCE: 17
ctcaaagtgc taaagctatg gttgactgct ctggtgtttt tatattcatt cgtgctttag 60

<210> SEQ ID NO 18

-continued

<211> LENGTH: 60
<212> TYPE: DNA
<213> ORGANISM: Homo sapiens

<400> SEQUENCE: 18
ctatggggat ggtccactgt cactgtttct ctgctgttgc aaatacatgg ataacacatt 60

<210> SEQ ID NO 19
<211> LENGTH: 60
<212> TYPE: DNA
<213> ORGANISM: Homo sapiens

<400> SEQUENCE: 19
actggaaaag cagatggtct gactgtgcta tggcctcatc atcaagactt tcaatcctat 60

<210> SEQ ID NO 20
<211> LENGTH: 60
<212> TYPE: DNA
<213> ORGANISM: Homo sapiens

<400> SEQUENCE: 20
acgccaagct cttcagtgaa gacacgatgt tattaaaagc ctgttttagg gactgcaaaa 60

<210> SEQ ID NO 21
<211> LENGTH: 60
<212> TYPE: DNA
<213> ORGANISM: Homo sapiens

<400> SEQUENCE: 21
tttttgtaaa atctttaacc ttccctttgt tcttcatgta cacgctgaac tgcaattctt 60

<210> SEQ ID NO 22
<211> LENGTH: 60
<212> TYPE: DNA
<213> ORGANISM: Homo sapiens

<400> SEQUENCE: 22
aacctggggc atttagggca gaggacaaaa ggatgtcagc aattgcttgg gctgcttggc 60

<210> SEQ ID NO 23
<211> LENGTH: 60
<212> TYPE: DNA
<213> ORGANISM: Homo sapiens

<400> SEQUENCE: 23
ctggaacctc tggactcccc atgctctaac tcccacactc tgctatcaga aacttaaact 60

<210> SEQ ID NO 24
<211> LENGTH: 60
<212> TYPE: DNA
<213> ORGANISM: Homo sapiens

<400> SEQUENCE: 24
aaccccagaa ccatctaaga catgggattc agtgatcatg tggttctcct tttaacttac 60

<210> SEQ ID NO 25
<211> LENGTH: 60
<212> TYPE: DNA
<213> ORGANISM: Homo sapiens

<400> SEQUENCE: 25
ggccatgtgc catggtattt gggtcctggg agggtgggtg aaataaaggc atactgtctt 60

-continued

<210> SEQ ID NO 26
<211> LENGTH: 60
<212> TYPE: DNA
<213> ORGANISM: Homo sapiens

<400> SEQUENCE: 26
gtgtaggcag tcatggcacc aaagccacca gactgacaaa tgtgtatcag atgcttttgt 60

<210> SEQ ID NO 27
<211> LENGTH: 60
<212> TYPE: DNA
<213> ORGANISM: Homo sapiens

<400> SEQUENCE: 27
gaaaacctct tcaaaagaca aaaagctggc actgcattct ctctctgtag caggacagaa 60

<210> SEQ ID NO 28
<211> LENGTH: 60
<212> TYPE: DNA
<213> ORGANISM: Homo sapiens

<400> SEQUENCE: 28
cacatcttta gggtcagtga acaatggggc acatttggca ctagcttgag cccaactctg 60

<210> SEQ ID NO 29
<211> LENGTH: 60
<212> TYPE: DNA
<213> ORGANISM: Homo sapiens

<400> SEQUENCE: 29
gccttaattt cctcatctga aaactggaag gcctgacttg acttgttgag cttaagatcc 60

<210> SEQ ID NO 30
<211> LENGTH: 60
<212> TYPE: DNA
<213> ORGANISM: Homo sapiens

<400> SEQUENCE: 30
cttcagggga ggatcaagct ttgaaccaaa gccaatcact ggcttgattt gtgtttttta 60

<210> SEQ ID NO 31
<211> LENGTH: 60
<212> TYPE: DNA
<213> ORGANISM: Homo sapiens

<400> SEQUENCE: 31
acaagttttc actgaatgag catggcagtg ccactcaaga aaatgaatct ccaaagtatc 60

<210> SEQ ID NO 32
<211> LENGTH: 561
<212> TYPE: DNA
<213> ORGANISM: Homo sapiens
<220> FEATURE:
<221> NAME/KEY: misc_feature
<222> LOCATION: (475)..(475)
<223> OTHER INFORMATION: a or g or c or t/u

<400> SEQUENCE: 32
ccggcgatgt cgctcgtgct gctaagcctg gccgcgctgt gcaggagcgc cgtaccccga 60
gagccgaccg ttcaatgtgg ctctgaaact gggccatctc cagagtggat gctacaacat 120
gatctaatcc cgggagactt gagggacctc cgagtagaac ctgttacaac tagtgttgca 180
acaggggact attcaatttt gatgaatgta agctgggtac tccgggcaga tgccagcatc 240

-continued

```
cgcttgttga aggccaccaa gatttgtgtg acgggcaaaa gcaacttcca gtcctacagc    300

tgtgtgaggt gcaattacac agaggccttc cagactcaga ccagaccctc tggtggtaaa    360

tggacatttt cctacatcgg cttccctgta gagctgaaca cagtctattt cattggggcc    420

cataatattc ctaatgcaaa tatgaatgaa gatggccctt ccatgtctgt gaatntcacc    480

tcaccaggct gcctagacca cataatgaaa tataaaaaaa agtgtgtcaa ggccggaagc    540

ctgtgggatc cgaacatcac t                                              561
```

<210> SEQ ID NO 33
<211> LENGTH: 467
<212> TYPE: DNA
<213> ORGANISM: Homo sapiens

<400> SEQUENCE: 33

```
ttttttttt ttttttttta aaagtgggtt cagcttgttt attccctact tttgttatct     60

taaaaacaat gattttttgc atgtaataga aggtttttca cttaagatgc tattgagtga    120

atcagtgagg ggttcttaga gttagtattc attaattaaa catagaatat tagctaaaca    180

gttctgggta cactgcaatg catggtctat ggaagactag atgtttggct gaagatgctt    240

tattgttgca ttatcaaaat ggttatagtt ttcaattaaa actgtaattg atttctatgt    300

ataaaacagc tttgaagttg taaatgtagt ttccaatcgt tagttaatgc tacattagtt    360

agcaatattt gaaaatttta ttggtataaa atgttttaat tactaaggct gtttgtaggc    420

tgcatagtaa gcttcaggat catcacacgt tttttccctg taattgg                  467
```

<210> SEQ ID NO 34
<211> LENGTH: 2042
<212> TYPE: DNA
<213> ORGANISM: Homo sapiens

<400> SEQUENCE: 34

```
ggcccggcga tgtcgctcgt gctgctaagc ctggccgcgc tgtgcaggag cgccgtaccc     60

cgagagccga ccgttcaatg tggctctgaa actgggccat ctccagagtg gatgctacaa    120

catgatctaa tcccgggaga cttgagggac ctccgagtag aacctgttac aactagtgtt    180

gcaacagggg actattcaat tttgatgaat gtaagctggg tactccgggc agatgccagc    240

atccgcttgt tgaaggccac caagatttgt gtgacgggca aaagcaactt ccagtcctac    300

agctgtgtga ggtgcaatta cacagaggcc ttccagactc agaccagacc ctctggtggt    360

aaatggacat tttcctacat cggcttccct gtagagctga acacagtcta tttcattggg    420

gcccataata ttcctaatgc aaatatgaat gaagatggcc cttccatgtc tgtgaatttc    480

acctcaccag gctgcctaga ccacataatg aaatataaaa aaaagtgtgt caaggccgga    540

agcctgtggg atccgaacat cactgcttgt aagaagaatg aggagacagt agaagtgaac    600

ttcacaacca ctcccctggg aaacagatac atggctctta tccaacacag cactatcatc    660

gggttttctc aggtgtttga gccacaccag aagaaacaaa cgcgagcttc agtggtgatt    720

ccagtgactg gggatagtga aggtgctacg gtgcagctga ctccatattt tcctacttgt    780

ggcagcgact gcatccgaca taaaggaaca gttgtgctct gcccacaaac aggcgtccct    840

ttccctctgg ataacaacaa aagcaagccg ggaggctggc tgcctctcct cctgctgtct    900

ctgctggtgg ccacatgggt gctggtggca gggatctatc taatgtggag gcacgaaagg    960

atcaagaaga cttccttttc taccaccaca ctactgcccc ccattaaggt tcttgtggtt   1020

tacccatctg aaatatgttt ccatcacaca atttgttact tcactgaatt tcttcaaaac   1080
```

-continued cattgcagaa gtgaggtcat ccttgaaaag tggcagaaaa agaaaatagc agagatgggt 1140
ccagtgcagt ggcttgccac tcaaaagaag gcagcagaca aagtcgtctt ccttctttcc 1200
aatgacgtca acagtgtgtg cgatggtacc tgtggcaaga gcgagggcag tcccagtgag 1260
aactctcaag acctcttccc ccttgccttt aacctttttct gcagtgatct aagaagccag 1320
attcatctgc acaaatacgt ggtggtctac tttagagaga ttgatacaaa agacgattac 1380
aatgctctca gtgtctgccc caagtaccac ctcatgaagg atgccactgc tttctgtgca 1440
gaacttctcc atgtcaagca gcaggtgtca gcaggaaaaa gatcacaagc ctgccacgat 1500
ggctgctgct ccttgtagcc cacccatgag aagcaagaga ccttaaaggc ttcctatccc 1560
accaattaca gggaaaaaac gtgtgatgat cctgaagctt actatgcagc ctacaaacag 1620
ccttagtaat taaaacattt tataccaata aaattttcaa atattgctaa ctaatgtagc 1680
attaactaac gattggaaac tacatttaca acttcaaagc tgttttatac atagaaatca 1740
attacagttt taattgaaaa ctataaccat tttgataatg caacaataaa gcatcttcag 1800
ccaaacatct agtcttccat agaccatgca ttgcagtgta cccagaactg tttagctaat 1860
attctatgtt taattaatga atactaactc taagaacccc tcactgattc actcaatagc 1920
atcttaagtg aaaaaccttc tattacatgc aaaaaatcat tgtttttaag ataacaaaag 1980
tagggaataa acaagctgaa cccactttta aaaaaaaaaa aaaaaaaaaa aaaaaaaaaa 2040
aa 2042

<210> SEQ ID NO 35
<211> LENGTH: 842
<212> TYPE: DNA
<213> ORGANISM: Homo sapiens

<400> SEQUENCE: 35
agcggagctg cgggtggcct ggatcccgcg cagtggcccg gcgatgtcgc tcgtgctgct 60
aagcctggcc acgctgtgca ggagcgccgt accccgagag ccgaccgttc aatgtggctc 120
tgaaactgtg gacattttcc tatatcggct tccctgtaga gctgaaaaca gtctatttca 180
ttggggccca taatattcct aatgcaaata tgaatgaaga tggcccttcc atgtctgtga 240
atttcacctc accaggctgc ctagaccaca taatgaaata taaaaaaagt gtgtcaaggc 300
cggaagcctg tgggatccga acatcactgc ttgtaagaag aatgaggaga cagtagaagt 360
gaacttcaca accactcccc tgggaaacag atacatggct catccaacac agcactatca 420
tcgggttttc tcaggtgttt gagccacacc agaagaaaca aacgcgagct tcagtggtga 480
ttccagtgac tggggatagt gaaggtgcta cggtgcagct gactccatat tttcctactt 540
gtggcagcga ctgcatccga cataaaggaa cagttgtgct ctgcccacaa acaggcgtcc 600
ctttcccctc tggataacaa caaaagcaag ccgggaggct ggctgcctct cctcctgctg 660
tctctgctgg ttggccacat tgggtgctgg tggcagggat ctatctaatg tggaggcacg 720
aaaggatcca gaagacttcc ttttctacca caaactactg cccccattaa ggtcctgtgg 780
ttacccatct tgaaatatgt tcctcacaca atttgttact tcactgaatt cttcaaaacc 840
tg 842

<210> SEQ ID NO 36
<211> LENGTH: 788
<212> TYPE: DNA
<213> ORGANISM: Homo sapiens
<220> FEATURE:

-continued

<221> NAME/KEY: misc_feature
<222> LOCATION: (675)..(675)
<223> OTHER INFORMATION: a or g or c or t/u

<400> SEQUENCE: 36
agcggagcgt gcgggtggcc tggatcccgc gcagtggccc ggcgatgtcg ctcgtgctgc 60
taagcctggc cacgctgtgc aggagcgccg taccccgaga gccgaccgtt caatgtggct 120
ctgaaactgt ggacattttc ctatatcggc ttccctgtag agctgaaaac agtctatttc 180
attggggccc ataatattcc taatgcaaat atgaatgaag atggcccttc catgtctgtg 240
aatttcacct caccaggctg cctagaccac ataatgaaat ataaaaaaaa gtgtgtcaag 300
gccggaagcc tgtgggatcc gaacatcact gcttgtaaga agaatgagga gacagtagaa 360
gtgaacttca caaccactcc cctgggaaac agatacatgg ctcatccaac acagcactat 420
catcgggttt tctcaggtgt ttgagccaca ccagaagaaa caaacgcgag cttcagtggt 480
gattccagtg actggggata gtgaaggtgc tacggtgcag ctgactccat attttcctac 540
ttgtggcagc gactgcatcc gacataaagg aacagttgtg ctctgcccac aaacaggcgt 600
ccctttccct ctggataaca acaaaagcaa gccgggaggc tggctgcctc tcctcctgct 660
gtctctgctg gtggncacat tgggtgctgg tggcagggat ctatctaatg tggaggcacg 720
aaaggatcag aagacttcct tttctaccac cacatactgc cccccattaa ggttcttgtg 780
gtttaccc 788

<210> SEQ ID NO 37
<211> LENGTH: 946
<212> TYPE: DNA
<213> ORGANISM: Homo sapiens

<400> SEQUENCE: 37
ggcgatgtcg ctcgtgctgc taagcctggc cgcgctgtgc aggagcgccg taccccgaga 60
gccgaccgtt caatgtggct ctgaaactgg gccatctcca gagtggatgc tacaacatga 120
tctaatcccg ggagacttga gggacctccg agtagaacct gttacaacta gtgttgcaac 180
aggggactat tcaattttga tgaatgtaag ctgggtactc cgggcagatg ccagcatccg 240
cttgttgaag gccaccaaga tttgtgtgac gggcaaaagc aacttccagt cctacagctg 300
tgtgaggtgc aattacacag aggccttcca gactcagacc agaccctctg gtggtaaatg 360
gacattttcc tatatcggct tccctgtaga gctgaacaca gtctatttca ttggggccca 420
taatattcct aatgcaaata tgaatgaaga tggcccttcc atgtctgtga atttcacctc 480
accaggaagc ctgtgggatc cgaacatcac tgcttgtaag aaagaatgag gagacagtag 540
aagtgaactt cacaaccact cccctgggaa acagatacat ggctcttatc caacacagca 600
ctatcatcgg gtttctcagg tgtttgagcc acaccagaag aaacaaacgc gagcttcagt 660
ggtgattcca gtgactgggg atagtgaagg tgctacggtg cagctgactc catattttcc 720
tacttgtggc agcgactgca atccgacata aaggaacagt tgtgctctgc ccacaaacag 780
gcgtcccttt ccctcttgga tagcaacaga agcaagccgg gaggctggtg cctcttcttc 840
tggtgtctct gctggtggca cattgagtgc tggtggcagg atccatctaa tgtggaggcc 900
ccaaaggacc aggaaagact tcctttatta gcaccaagta ttgccc 946

<210> SEQ ID NO 38
<211> LENGTH: 488
<212> TYPE: DNA
<213> ORGANISM: Homo sapiens -continued

<400> SEQUENCE: 38
tggctgaaga tgctttattg ttgcattatc aaaatggtta tagttttcaa ttaaaactgt 60
aattgatttc tatgtataaa acagctttga agttgtaaat gtagtttcca atcgttagtt 120
aatgctacat tagttagcaa tatttgaaaa ttttattggt ataaaatgtt ttaattacta 180
aggctgtttg taggctgcat agtaagcttc aggatcatca cacgtttttt ccctgtaatt 240
ggtgggatag gaagccttta aggtctcttg cttctcatgg gtgggctaca aggagcagca 300
gccatcgtgg caggcttgtg atctttttcc tgctgacacc tgctacttga catggagaag 360
ttctgcacag aaagcagtgg catccttcat gaggtggtac ttggggcaga cactgagagc 420
attgtaatcg tcttttgtat caatctctct aaagtagacc accacgtatt tgtgcagatg 480
aatctggc 488

<210> SEQ ID NO 39
<211> LENGTH: 509
<212> TYPE: DNA
<213> ORGANISM: Homo sapiens

<400> SEQUENCE: 39
tttgtttggc tgaagatgct ttattgttgc attatcaaaa tggttatagt tttcaattaa 60
aactgtaatt gatttctatg tataaaacag ctttgaagtt gtaaatgtag tttccaatcg 120
ttagttaatg ctacattagt tagcaatatt tgaaaatttt attggtataa aatgttttaa 180
ttactaaggc tgtttgtagg ctgcatagta agcttcagga tcatcacacg ttttttccct 240
gtaattggtg ggataggaag cctttaaggt ctcttgcttt tcatgggtgg gctacaagga 300
gcagcagcca tcgtggcagg cttgtgatct ttttcctgct gacacctgct gcttgacatg 360
gagaagttct gcacagaaag cagtggcatc cttcatgagg tggtacttgg ggcagacact 420
gagagcattg taatcgtctt ttgtatcaat ctctctaaag tagaccacca cgtatttgtg 480
cagatgaatc tggcttctta gatcactgc 509

<210> SEQ ID NO 40
<211> LENGTH: 502
<212> TYPE: DNA
<213> ORGANISM: Homo sapiens

<400> SEQUENCE: 40
tggcatgaga tgctatattg ttgcattatc aaaatgggtt tagtcttcaa ttaacactgt 60
aattgatttc tatgtataaa acagctttga agttgtaaat gtggtttcca atcgtcagtt 120
aatgctacat tagttagcaa tatttgaaaa ttttattggt ataaaatgtt ttaattacta 180
aggctgtttg taggctgcat agtaagcttc aggatcatca cacgtttttt ccctgtaatt 240
ggtgggatag gaagccttta aggtctcttg cttctcatgg gtgggctaca aggagcagca 300
gccatcgtgg caggcttgtg atctttttcc tgctgacacc tgctgcttga catggagaag 360
ttctgcacag aaagcagtgg catccttcat gaggtggtac ttggggcaga cactgagagc 420
attgtaatcg tcttttgtat caatctctct aaagtagacc accacgtatt tgtgcagatg 480
aatctggctt cttagatcac tg 502

<210> SEQ ID NO 41
<211> LENGTH: 460
<212> TYPE: DNA
<213> ORGANISM: Homo sapiens -continued

<400> SEQUENCE: 41

```
gtttggctga agatgcttta ttgttgcatt atcaaaatgg ttatagtttt caattaaaac     60

tgtaattgat ttctatgtat aaaacacgct ttgaagttgt aaatgtagtt tccaatcgtt    120

agttaatgct acattagtta gcaatatttg aaaattttat tggtataaaa tgttttaatt    180

actaaggctg tttgtaggct gcatagtaag cttcaggatc atcacacgtt ttttccctgt    240

aattggtggg ataggaagcc tttaaggtct cttgcttctc atgggtgggc tacaaggagc    300

agcagccatc gtggcaggct tgtgatcttt ttcctgctga cacctgctgc ttgacatgga    360

gaagttctgc acagaaagca gtggcatcct tcatgaggtg gtacttgggg cagacactga    420

gagcattgta atcgtctttt gtatcaatct ctctaaagta                         460
```

<210> SEQ ID NO 42
<211> LENGTH: 510
<212> TYPE: DNA
<213> ORGANISM: Homo sapiens

<400> SEQUENCE: 42

```
tggctgaaga tgctttattg ttgcattatc aaaatggtta tagttttcaa ttaaaactgt     60

aattgatttc tatgtataaa acagcgttga agttgtaaat gtagtttcca atcgttagtt    120

aatgctacat tagttagcaa tatttgaaaa ttttattggt ataaaatgtt ttaattacta    180

aggctgtttg taggctgcat agtaagcttc aggatcatca cacgtttttt ccctgtaatt    240

ggtgggatag gaagccttta aggtctcttg cttctcatgg gtgggctaca aggagcagca    300

gccatcgtgg caggcttgtg atctttttcc tgctgacacc tgctgcttga catggagaag    360

ttctgcacag aaagcagtgg catccttcat gaggtggtac ttggggcaga cactgagagc    420

attgtaatcg tcttttgtat caatctctct aaagtagacc accacgtatt tgtgcagatg    480

aatctggctt cttagatcac tgcagaaaag                                     510
```

<210> SEQ ID NO 43
<211> LENGTH: 465
<212> TYPE: DNA
<213> ORGANISM: Homo sapiens

<400> SEQUENCE: 43

```
tttttttttt acaacttcaa agctgtttta tacatagaaa tcaattacag ttttaattga     60

aaactataac cattttgata atgcaacaat aaagcatctt cagccaaaca tctagtcttc    120

catagaccat gcattgcagt gtacccagaa ctgtttagct aatattctat gtttaattaa    180

tgaatactaa ctctaagaac ccctcactga ttcactcaat agcatcttaa gtgaaaaacc    240

ttctattaca tgcaaaaaat cattgttttt aagataacaa aagtagggaa taaacaagct    300

gaacccactt ttactggacc aaatgatcta ttatatgtgt accacttgta tgatttggta    360

tttgcataag accttccctc tacaaactag attcatatct tgattcttgt acaggtgcct    420

tttaacatga acaacaaaat acccacaaac ttgtctactt ttgcc                    465
```

<210> SEQ ID NO 44
<211> LENGTH: 506
<212> TYPE: DNA
<213> ORGANISM: Homo sapiens

<400> SEQUENCE: 44

```
tagtaattaa aacattttat accaataaaa ttttcaaata ttgctaacta atgtagcatt     60

aactaacgat tggaaactac atttacaact tcaaagctgt tttatacata gaaatcaatt    120
```

-continued

```
acagttttaa ttgaaaacta taaccatttt gataatgcaa caataaagca tcttcagcca    180

aacatctagt cttccataga ccatgcattg cagtgtaccc agaactgttt agctaatatt    240

ctatgtttaa ttaatgaata ctaactctaa gaacccctca ctgattcact caatagcatc    300

ttaagtgaaa aaccttctat tacatgcaaa aaatcattgt ttttaagata acaaaagtag    360

ggaataaaca agctgaaccc acttttactg gaccaaatga tctattatat gtgtaaccac    420

ttgtatgatt tggtatttgc ataagacctt ccctctacaa actagattca tatcttgatt    480

cttgtacagg tgccttttaa catgaa                                          506
```

<210> SEQ ID NO 45
<211> LENGTH: 427
<212> TYPE: DNA
<213> ORGANISM: Homo sapiens

<400> SEQUENCE: 45

```
tttttttttt ttttttagca atatttgaaa attttattgg tataaaatgt tttaattact     60

aaggctgttt gtaggctgca tagtaagctt caggatcatc acacgttttt tccctgtaat    120

tggtgggata ggaagccttt aaggtctctt gcttctcatg ggtgggctac aaggagcagc    180

agccatcgtg gcaggcttgt gatctttttc ctgctgacac ctgctacttg acatggagaa    240

gttctgcaca gaaagcagtg gcatccttca tgaggtggta cttggggcag acactgagag    300

cattgtaatc gtcttttgta tcaatctctc taaagtagac caccacgtat ttgtgcagat    360

gaatctggct tcttagatca ctgcagaaaa ggttaaaggc aagggggaag aggtcttgag    420

agttctc                                                               427
```

<210> SEQ ID NO 46
<211> LENGTH: 467
<212> TYPE: DNA
<213> ORGANISM: Homo sapiens
<220> FEATURE:
<221> NAME/KEY: misc_feature
<222> LOCATION: (434)..(434)
<223> OTHER INFORMATION: a or g or c or t/u

<400> SEQUENCE: 46

```
ttaaagtggg ttcagcttgt ttattcccta cttttgttat cttaaaaaca atgatttttt     60

gcatgtaata gaaggttttt cacttaagat gctattgagt gaatcagtga ggggttctta    120

gagttagtat tcattaatta aacatagaat attagctaaa cagttctggg tacactgcaa    180

tgcatggtct atggaagact agatgtttgg ctgaagatgc tttattgttg cattatcaaa    240

atggttacag ttttcaatta aagctgtaat tgatttctat gtataaaaca gctttgaagt    300

tgtaaatgta gtttccaatc gttagttaat gctacattag ttagcaatat ttgaaaattt    360

tattggtata aaatgtttta attactaagg ctgtttgtag gctgcatagt aagcttcagg    420

atcatcacac gttntttccc tgtaattggt gggataggaa gccttta                   467
```

<210> SEQ ID NO 47
<211> LENGTH: 420
<212> TYPE: DNA
<213> ORGANISM: Homo sapiens

<400> SEQUENCE: 47

```
agttagcaat atttgaaaat tttattggta taaaatgttt taattactaa ggctgtttgt     60

aggctgcata gtaagcttca ggatcatcac acgttttttc cctgtaattg gtgggatagg    120
```

-continued aagcctttaa ggtctcttgc ttctcatggg tgggctacaa ggagcagcag ccatcgtggc 180
aggcttgtga tctttttcct gctgacacct gctacttgac atggagaagt tctgcacaga 240
aagcagtggc atccttcatg aggtggtact tggggcagac actgagagca ttgtaatcgt 300
cttttgtatc aatctctcta aagtagacca ccacgtattt gtgcagatga atctggcttc 360
ttagatcact gcagaaaagg ttaaaggcaa gggggaagag gtcttgagag ttctcactgg 420

<210> SEQ ID NO 48
<211> LENGTH: 434
<212> TYPE: DNA
<213> ORGANISM: Homo sapiens

<400> SEQUENCE: 48
ttggctgaag atgctttatt gttgcattat caaaatggtt atagttttca attaaaactg 60
taattgattt ctatgtataa aacagctttg aagttgtaaa tgtagtttcc aatcgttagt 120
taatgctaca ttagttagca atatttgaaa attttattgg tataaaatgt tttaattact 180
aaggctgttt gtaggcttgc atagaagctt caggatcatc acacgttttt tccctgtaat 240
tggtgggata ggaagccttt aaggtctctt gcttctcatg ggtgggctac aaggagcagc 300
agccatcgtg gcaggcttgt gatctttttc ctgctgacac ctgctgcttg acatggagaa 360
gttctgcaca gaaagcagtg gcatccttca tgaggtggta cttggggcag acactgagag 420
cattgtaatc gtct 434

<210> SEQ ID NO 49
<211> LENGTH: 416
<212> TYPE: DNA
<213> ORGANISM: Homo sapiens

<400> SEQUENCE: 49 ttttttttt agcaatattt gaaaatttta ttggtataaa atgttttaat tactaaggct 60
gtttgtaggc tgcatagtaa gcttcaggat catcacacgt tttttccctg taattggtgg 120
gataggaagc ctttaaggtc tcttgcttct catgggtggg ctacaaggag cagcagccat 180
cgtggcaggc ttgtgatctt tttcctgctg acacctgcta cttgacatgg agaagttctg 240
cacagaaagc agtggcatcc ttcatgaggt ggtacttggg gcagacactg agagcattgt 300
aatcgtcttt tgtatcaatc tctctaaagt agaccaccac gtatttgtgc agatgaatct 360
ggcttcttag atcactgcag aaaaggttaa aggcaagggg gaagaggtct tgagag 416

<210> SEQ ID NO 50
<211> LENGTH: 414
<212> TYPE: DNA
<213> ORGANISM: Homo sapiens

<400> SEQUENCE: 50
tttggctgaa gatgctttat tgttgcatta tcaaaatggt tacagttttc aattaaagct 60
gtaattgatt tctatgtata aaacagcttt gaagttgtaa atgtagtttc caatcgttag 120
ttaatgctac attagttagc aatatttgaa aattttattg gtataaaatg ttttaattac 180
taaggctgtt tgtaggctgc atagtaagct tcaggatcat cacacgtttt ttccctgtaa 240
ttggtgggat aggaagcctt taaggtctct tgcttctcat gggtgggcta caaggagcag 300
cagccatcgt ggcaggcttg tgatcttttt cctgctgaca cctgctgctt gacatggaga 360
agttctgcac agaaagcagt ggcatccttc atgaggtggt acttggggca gaca 414

-continued

<210> SEQ ID NO 51
<211> LENGTH: 409
<212> TYPE: DNA
<213> ORGANISM: Homo sapiens

<400> SEQUENCE: 51
ttctctggct gaagatgctt tattgttgca ttatcaaaat ggttacagtt ttcaattaaa 60
gctgtaattg atttctatgt ataaaacagc tttgaagttg taaatgtagt ttccaatcgt 120
tagttaatgc tacattagtt agcaatattt gaaaatttta ttggtataaa atgttttaat 180
tactaaggct gtttgtaggc tgcatagtaa gcttcaggat catcacacgt tttttccctg 240
taattggtgg gataggaagc ctttaaggtc tcttgcttct catgggtggg ctacaaggag 300
cagcagccat cgtggcaggc ttgtgatctt tttcctgctg acacctgctg cttgacatgg 360
agaagttctg cacagaaagc agtggcatcc ttcatgaggt ggtacttgg 409

<210> SEQ ID NO 52
<211> LENGTH: 414
<212> TYPE: DNA
<213> ORGANISM: Homo sapiens

<400> SEQUENCE: 52
tttttttttt ttttttacaa ccttgaaagc tgttttatac atagaaatca attacagttt 60
taattgaaaa ctataaccat tttgataatg caacaataaa gcatcttcag ccaaacatct 120
agtcttccat agaccatgca ttgcagtgta cccagaactg tttagctaat attctatgtt 180
taattaatga atactaactc taagaacccc tcactgattc actcaatagc atcttaagtg 240
aaaaaccttc tattacatgc aaaaaatcat tgtttttaag ataacaaaag tagggaataa 300
acaagctgaa cccactttta ctggaccaaa tgatctatta tatgtgtaac cacttgtatg 360
atttggattt gcataagacc ttccctctac aaactagatt catatcttga ttct 414

<210> SEQ ID NO 53
<211> LENGTH: 414
<212> TYPE: DNA
<213> ORGANISM: Homo sapiens

<400> SEQUENCE: 53
tttttttttt ttttttacaa ctgcaaagct gttttataca tagaaatcaa ttacagtttt 60
aattgaaaac tataaccatt ttgataatgc aacaataaag catcttcagc caaacatcta 120
gtcttccata gaccatgcat tgcagtgtac ccagaactgt ttagctaata ttctatgttt 180
aattaatgaa tactaactct aagaacccct cactgattca ctcaatagca tcttaagtga 240
aaaaccttct attacatgca aaaaatcatt gtttttaaga taacaaaagt agggaataaa 300
caagctgaac ccacttttac tggaccaaat gatctattat atgtgtaacc acttgtatga 360
tttggtattt gcataagacc ttccctctac aaactagatt catatcttga ttct 414

<210> SEQ ID NO 54
<211> LENGTH: 484
<212> TYPE: DNA
<213> ORGANISM: Homo sapiens

<400> SEQUENCE: 54
ttttttagtt agcaatattt gaaaatttta ttggtataaa atgttttaat tactaaggct 60
gtttgtaggc tgcatagtaa gcttcaggat catcacacgt tttttccctg taattggtgg 120
gataggaagc ctttaaggtc tcttgcttct catgggtggg ctacaaggag cagcagccat 180

-continued

```
cgtggcaggc ttgtgatctt tttcctgctg acacctgcta cttgacatgg agaagttctg    240

cacagaaagc agtggcatcc ttcatgaggt ggtacttggg gcagacactg agagcattgt    300

aatcgtcttt tgtatcaatc tctctaaagt agaccaccac gtatttgtgc agatgaatct    360

ggcttcttag atcactgcag aaaaggttaa aggcaagggg gaagaggtct tgagagttct    420

cactgggact gccctcgctc ttgccacagg taccatcgca cacactgttg acgtcattgg    480

aaag                                                                  484
```

<210> SEQ ID NO 55
<211> LENGTH: 398
<212> TYPE: DNA
<213> ORGANISM: Homo sapiens

<400> SEQUENCE: 55

```
ggctgaagat gctttattgt tgcattatca aaatggttat agttttcaat taaaactgta     60

attgatttct atgtataaaa cagctttgaa gttgtaaatg tagtttccaa tcgttagtta    120

atgctacatt agttagcaat atttgaaaat tttattggta taaaatgttt taattactaa    180

ggctgtttgt aggctgcata gtaagcttca ggatcatcac acgtttttc cctgtaattg    240

gtgggatagg aagcctttaa ggtctcttgc ttctcatggg tgggctacaa ggagcagcag    300

ccatcgtggc aggcttgtga tctttttcct gctgacacct gctgcttgac atggagaagt    360

tctgcacaga aagcagtggc atccttcatg aggtggta                            398
```

<210> SEQ ID NO 56
<211> LENGTH: 401
<212> TYPE: DNA
<213> ORGANISM: Homo sapiens

<400> SEQUENCE: 56

```
ttggctgaag atgctttatt gttgcattat caaaatggtt acagttttca attaaagctg     60

taattgattt ctatgtataa aacagctttg aagttgtaaa tgtagtttcc aatcgttagt    120

taatgctaca ttagttagca atatttgaaa attttattgg tataaaatgt tttaattact    180

aaggctgttt gtaggctgca tagtaagctt caggatcatc acacgttttt tccctgtaat    240

tggtgggata ggaagccttt aaggtctctt gcttctcatg ggtgggctac aaggagcagc    300

agccatcgtg gcaggcttgt gatctttttc ctgctgacac ctgctgcttg acatggagaa    360

gttctgcaca gaaagcagtg gcatccttca tgaggtggta c                        401
```

<210> SEQ ID NO 57
<211> LENGTH: 392
<212> TYPE: DNA
<213> ORGANISM: Homo sapiens
<220> FEATURE:
<221> NAME/KEY: misc_feature
<222> LOCATION: (228)..(228)
<223> OTHER INFORMATION: a or g or c or t/u

<400> SEQUENCE: 57

```
ttggctgaag atgctttatt gttgcattat caaaatggtt atagttttca attaaaactg     60

taattgattt ctatgtataa aacagctttg aagttgtaaa tgtagtttcc aatcgttagt    120

taatgctaca ttagttagca atatttgaaa attttattgg tataaaatgt tttaattact    180

aaggctgttt gtaggctgca tagtaagctt caggatcatc acacgttntt tccctgtaat    240

tggtgggata ggaagccttt aaggtctctt gcttctcatg ggtgggctac aaggagcagc    300

agccatcgtg gcaggcttgt gatctttttc ctgctgacac ctgctgcttg acatggagaa    360
```

-continued

```
gttctgcaca gaaagcagtg gcatccttca tg                                392

<210> SEQ ID NO 58
<211> LENGTH: 386
<212> TYPE: DNA
<213> ORGANISM: Homo sapiens

<400> SEQUENCE: 58

gtttggctga agatgcttta ttgttgcatt atcaaaatgg ttatagtttt caattaaaac   60

tgtaattgat ttctatgtat aaaacagctt tgaagttgta aatgtagttt ccaatcgtta  120

gttaatgcta cattagttag caatatttga aaattttatt ggtataaaat gttttaatta  180

ctaaggctgt ttgtaggctg catagtaagc ttcaggatca tcacacgttt tttccctgta  240

attggtggga taggaagcct ttaaggtctc ttgcttctca tgggtgggct acaaggagca  300

gcagccatcg tggcagcttg gtgatctttt tcctgctgac acctgctgct tgacatgaag  360

aagttctgca cagaaagcag tggcat                                       386

<210> SEQ ID NO 59
<211> LENGTH: 386
<212> TYPE: DNA
<213> ORGANISM: Homo sapiens

<400> SEQUENCE: 59

gtttggctga agatgcttta ttgttgcatt atcaaaatgg ttatagtttt caattaaaac   60

tgtaattgat ttctatgtat aaaacagctt tgaagttgta aatgtagttt ccaatcgtta  120

gttaatgcta cattagttag caatatttga aaattttatt ggtataaaat gttttaatta  180

ctaaggctgt ttgtaggctg catagtaagc ttcaggatca tcacacgttt tttccctgta  240

attggtggga taggaagcct ttaaggtctc ttgcttctca tgggtgggct acaaggagca  300

gcagccatcg tggcaggctt ggatcttttt cctgctgaca cctgctgctt gacattggaa  360

agttctgcac agaaagcagt ggcatc                                       386

<210> SEQ ID NO 60
<211> LENGTH: 386
<212> TYPE: DNA
<213> ORGANISM: Homo sapiens

<400> SEQUENCE: 60

ttttggctga tgatgcttta ttgttgcatt atcaaaatgg ttacagtttt caattaaagc   60

tgtaattgat ttctatgtat aaaacagctt tgaagttgta aatgtagttt ccaatcgtta  120

gttaatgcta cattagttag caatatttga aaattttatt ggtataaaat gttttaatta  180

ctaaggctgt ttgtaggctg catagtaagc ttcaggatca tcacacgttt tttccctgta  240

attggtggga taggaagcct ttaaggtctc ttgcttctca tgggtgggct acaaggagca  300

gcagccatcg tggcaggctt gtgatctttt tcctgctgac acctgctgct tgacatggag  360

aagttctgca cagaaagcag tggcat                                       386

<210> SEQ ID NO 61
<211> LENGTH: 373
<212> TYPE: DNA
<213> ORGANISM: Homo sapiens

<400> SEQUENCE: 61

ggctgaagat gctttattgt tgcattatca aaatggttac agttttcaat taaagctgta   60
```

-continued

```
attgatttct atgtataaaa cagctttgaa gttgtaaatg tagtttccaa tcgttagtta    120

atgctacatt agttagcaat atttgaaaat tttattggta taaaatgttt taattactaa    180

ggctgtttgt aggctgcata gtaagcttca ggatcatcac acgttttttc cctgtaattg    240

gtgggatagg aagcctttaa ggtctcttgc ttctcatggg tgggctacaa ggagcagcag    300

ccatcgtggc aggcttgtga tctttttcct gctgacacct gctgcttgac atggagaagt    360

tctgcacaga aag                                                       373
```

<210> SEQ ID NO 62
<211> LENGTH: 403
<212> TYPE: DNA
<213> ORGANISM: Homo sapiens

<400> SEQUENCE: 62

```
gattggctgt tttatgcttt attgttgcat tatcaaaatg gttatagttt tcaattaaaa     60

ctgtaattga tttctatgta taaaacagct ttgaagttgt aaatgtagtt tccaatcgtt    120

agttaatgct acattagtta gcaatatttg aaaattttat tggtataaaa tgttttaatt    180

actaaggctg tttgtaggct gcatagtaag cttcaggatc atcacacgtt ttttccctgt    240

tattggtggg ataggaagcc tttaaggtct cttgcttctc atgggtgggc tacaaggagc    300

agcagccatc gtggcaggct tgtgatcttt ttcctgctga cacctgctgc ttgacatgga    360

gaagttctgc acaaaaagca gtggcatcct tcatgaggtg gta                      403
```

<210> SEQ ID NO 63
<211> LENGTH: 457
<212> TYPE: DNA
<213> ORGANISM: Homo sapiens

<400> SEQUENCE: 63

```
gcaatatttt aaaattttat tggtataaaa tgttttaatt actaaggctg tttgtaggct     60

gcatagtaag cttcaggatc atcacacgtt ttttccctgt aattggtggc ataggaagcc    120

tttaaggtct cttgcttctc atggtgtggg ctacaaggag cagcagccat cgtggcaggc    180

ttgtgatctt tttcctgctg acacctgctg cttgacatgg agaagttctg cacagaaagc    240

agtggcatcc ttcatgaggt ggtacttggg gcagacactg agagcattgt aatcgtcttt    300

tgtatcaatc tctctaaagt agaccaccac gtatttgtgc agatgaatct ggcttcttag    360

atcactgcag aaaaggttaa aggcaagggg gaagaggtct tgagagttct cactgggact    420

gccctcgctc ttgccacagg taccatcgca cacactg                              457
```

<210> SEQ ID NO 64
<211> LENGTH: 365
<212> TYPE: DNA
<213> ORGANISM: Homo sapiens

<400> SEQUENCE: 64

```
ttttttttt acaacttcaa agctgtttta tacatagaaa tcaattacag ttttaattga     60

aaactataac cattttgata atgcaacaat aaagcatctt cagccaaaca tctagtcttc    120

catagaccat gcattgcagt gtacccagaa ctgtttagct aatattctat gtttaattaa    180

tgaatactaa ctctaagaac ccctcactga ttcactcaat agcatcttaa gtgaaaaacc    240

ttctattaca tgcaaaaaat cattgttttt aagataacaa aagtagggaa taaacaagct    300

gaacccactt ttactggacc aaatgatcta ttatatgtgt aaccacttgt atgatttggt    360

atttg                                                                365
```

-continued

<210> SEQ ID NO 65
<211> LENGTH: 356
<212> TYPE: DNA
<213> ORGANISM: Homo sapiens
<220> FEATURE:
<221> NAME/KEY: misc_feature
<222> LOCATION: (277)..(277)
<223> OTHER INFORMATION: a or g or c or t/u
<220> FEATURE:
<221> NAME/KEY: misc_feature
<222> LOCATION: (322)..(322)
<223> OTHER INFORMATION: a or g or c or t/u

<400> SEQUENCE: 65
gtttcgctga agatgcttta ttgttgcatt atcaaaatgg ttatagtttt caattaaaac 60
tgtaattgat ttctatgtat aaaacagctt tgaagttgta aatgtagttt ccaatcgtta 120
gttaatgcta cattagttag caatatttga aaattttatt ggtataaaat gttttaatta 180
ctaaggctgt ttgtaggctg catagtaagc ttaaggccca tcacacgttt tttccctgta 240
attggtggga taggaagcct ttaaggtctc ttgcttntca tgggtgggct acaaggagca 300
gcagccatcg tggcaggctt gngatctttt tcctgctggc ccctgctgct tgacat 356

<210> SEQ ID NO 66
<211> LENGTH: 413
<212> TYPE: DNA
<213> ORGANISM: Homo sapiens
<220> FEATURE:
<221> NAME/KEY: misc_feature
<222> LOCATION: (1)..(1)
<223> OTHER INFORMATION: a or g or c or t/u
<220> FEATURE:
<221> NAME/KEY: misc_feature
<222> LOCATION: (264)..(264)
<223> OTHER INFORMATION: a or g or c or t/u

<400> SEQUENCE: 66
naaagcactg gctgaaggaa gccaagagga tcactgctgc tcctttttc tagaggaaat 60 gtttgtctac gtggtaagat atgacctagc ccttttaggt aagcgaactg gtatgttagt 120
aacgtgtaca aagtttaggt tcagaccccg ggagtcttgg gcacgtgggt ctcgggtcac 180
tggttttgac tttagggctt tgttacagat gtgtgaccaa ggggaaaatg tgcatgacaa 240
cactagaggt atgggcgaca cganaacgaa cgggaagttt tggctgaagt aggagtcttg 300
gtgagatttt gctctgatgc atggtgtgaa ctttctgagc ctcttgtttt tcctcaagct 360
gactccatat tttcctactt gtggcagcga ctgcatccga cataaaggaa cag 413

<210> SEQ ID NO 67
<211> LENGTH: 394
<212> TYPE: DNA
<213> ORGANISM: Homo sapiens

<400> SEQUENCE: 67
tagcaatatt tgaaaatttt attggtataa aatgttttaa ttactaaggc tgtttgtagg 60
ctgcatagta agcttcagga tcatcacacg ttttttccct gtaattggtg ggataggaag 120
cctttaaggt ctcttgcttc tcatgggtgg gctacaagga gcagcagcca tcgtggcagg 180
cttgtgatct tttcctgct gacacctgct gcttgacatg gagaagttct gcacagaaag 240
cagtggcatc cttcatgagg tggtacttgg ggcagacact gagagcattg taatcgtctt 300
ttgtatcaat ctctctaaag tagaccacca cgtatttgtg cagatgaatc tggcttctta 360

| | |
|---|---:|
| gatcactgca gaaaaggtta aaggcaaggg ggga | 394 |

<210> SEQ ID NO 68
<211> LENGTH: 437
<212> TYPE: DNA
<213> ORGANISM: Homo sapiens

<400> SEQUENCE: 68

| | |
|---|---:|
| agcaatattt gaaaatttta ttggtataaa atgttttaat tactaaggct gtttgtaggc | 60 |
| tgcatagtaa gcttcaggat catcacacgt ttttteectg taattggtgg cataggaagc | 120 |
| ctttaaggtc tcttgcttct catgggtggg ctacaaggag cagcagccat cgtggcaggc | 180 |
| ttgtgatctt tttcctgctg acacctgctg cttgacatgg agaagttctg cacagaaagc | 240 |
| agtggcatcc ttcatgaggt ggtacttggg gcagacactg agagcattgt aatcgtcttt | 300 |
| tgtatcaatc tctctaaagt agaccaccac gtatttgtgc agatgaatct ggcttcttag | 360 |
| atcactgcag aaaaggttaa aggcaagggg gaagaggtct tgagagttct cactgggact | 420 |
| gccctcgctc ttgccac | 437 |

<210> SEQ ID NO 69
<211> LENGTH: 321
<212> TYPE: DNA
<213> ORGANISM: Homo sapiens

<400> SEQUENCE: 69

| | |
|---|---:|
| tttttttttt tagcaatatt tgaaaatttt attggtataa aatgttttaa ttactaaggc | 60 |
| tgtttgtagg ctgcatagta agcttcagga tcatcacacg ttttttccct gtaattggtg | 120 |
| ggataggaag cctttaaggt ctcttgcttc tcatgggtgg gctacaagga gcagcagcca | 180 |
| tcgtggcagg cttgtgatct ttttcctgct gacacctgct gcttgacatg gagaagttct | 240 |
| gcacaaaaag cagtggcatc cttcatgagg tggtacttgg ggcagacact gagagcattg | 300 |
| taatcgtctt ttgtatcaat c | 321 |

<210> SEQ ID NO 70
<211> LENGTH: 321
<212> TYPE: DNA
<213> ORGANISM: Homo sapiens

<400> SEQUENCE: 70

| | |
|---|---:|
| tttttttttt tagcaatatt tgaaaatttt attggtataa aatgttttaa ttactaaggc | 60 |
| tgtttgtagg ctgcatagta agcttcagga tcatcacacg ttttttccct gtaattggtg | 120 |
| ggataggaag cctttaaggt ctcttgcttc tcatgggtgg gctacaagga gcagcagcca | 180 |
| tcgtggcagg cttgtgatct ttttcctgct gacacctgct gcttgacatg gagaagttct | 240 |
| gcacaaaaag cagtggcatc cttcatgagg tggtacttgg ggcagacact gagagcattg | 300 |
| taatcgtctt ttgtatcaat c | 321 |

<210> SEQ ID NO 71
<211> LENGTH: 314
<212> TYPE: DNA
<213> ORGANISM: Homo sapiens

<400> SEQUENCE: 71

| | |
|---|---:|
| ttttatacat agaaatcaat tacagcttta attgaaaact ataaccattt tgataatgca | 60 |
| acaataaagc atcttcagcc aaacatctag tcttccatag accatgcatt gcagtgtacc | 120 |
| cagaactgtt tagctaatat tctatgttta attaatgaat actaactcta agaacccctc | 180 |

-continued

```
actgattcac tcaatagcat cttaagtgaa aaaccttcta ttacatgcaa aaaatcattg    240

tttttaagat aacaaaagta gggaataaac aagctgaacc cacttttact ggaccaaatg    300

atctattata tgtg                                                      314


<210> SEQ ID NO 72
<211> LENGTH: 286
<212> TYPE: DNA
<213> ORGANISM: Homo sapiens

<400> SEQUENCE: 72

ggctgaagat gctttattgt tgcattatca aaatggttat agttttcaat taaaactgta     60

attgatttct atgtataaaa cagctttgaa gttgtaaatg tagtttccaa tcgttagtta    120

atgctacatt agttagcaat atttgaaaat tttattggta taaaatgttt taattactaa    180

ggctgtttgt aggctgcata gtaagcttca ggatcatcac acgtttttc ccctgtatgg    240

gtgggatagg aagcctttaa ggtctcttgc ttctcatggg tgggct                   286


<210> SEQ ID NO 73
<211> LENGTH: 333
<212> TYPE: DNA
<213> ORGANISM: Homo sapiens
<220> FEATURE:
<221> NAME/KEY: misc_feature
<222> LOCATION: (2)..(2)
<223> OTHER INFORMATION: a or g or c or t/u
<220> FEATURE:
<221> NAME/KEY: misc_feature
<222> LOCATION: (8)..(8)
<223> OTHER INFORMATION: a or g or c or t/u
<220> FEATURE:
<221> NAME/KEY: misc_feature
<222> LOCATION: (24)..(25)
<223> OTHER INFORMATION: a or g or c or t/u
<220> FEATURE:
<221> NAME/KEY: misc_feature
<222> LOCATION: (27)..(28)
<223> OTHER INFORMATION: a or g or c or t/u
<220> FEATURE:
<221> NAME/KEY: misc_feature
<222> LOCATION: (30)..(31)
<223> OTHER INFORMATION: a or g or c or t/u
<220> FEATURE:
<221> NAME/KEY: misc_feature
<222> LOCATION: (39)..(39)
<223> OTHER INFORMATION: a or g or c or t/u
<220> FEATURE:
<221> NAME/KEY: misc_feature
<222> LOCATION: (48)..(48)
<223> OTHER INFORMATION: a or g or c or t/u
<220> FEATURE:
<221> NAME/KEY: misc_feature
<222> LOCATION: (51)..(51)
<223> OTHER INFORMATION: a or g or c or t/u
<220> FEATURE:
<221> NAME/KEY: misc_feature
<222> LOCATION: (67)..(67)
<223> OTHER INFORMATION: a or g or c or t/u
<220> FEATURE:
<221> NAME/KEY: misc_feature
<222> LOCATION: (75)..(75)
<223> OTHER INFORMATION: a or g or c or t/u
<220> FEATURE:
<221> NAME/KEY: misc_feature
<222> LOCATION: (80)..(80)
<223> OTHER INFORMATION: a or g or c or t/u
<220> FEATURE:
<221> NAME/KEY: misc_feature
<222> LOCATION: (85)..(87)
<223> OTHER INFORMATION: a or g or c or t/u
<220> FEATURE:
```

-continued

<221> NAME/KEY: misc_feature
<222> LOCATION: (95)..(95)
<223> OTHER INFORMATION: a or g or c or t/u
<220> FEATURE:
<221> NAME/KEY: misc_feature
<222> LOCATION: (98)..(98)
<223> OTHER INFORMATION: a or g or c or t/u
<220> FEATURE:
<221> NAME/KEY: misc_feature
<222> LOCATION: (106)..(106)
<223> OTHER INFORMATION: a or g or c or t/u
<220> FEATURE:
<221> NAME/KEY: misc_feature
<222> LOCATION: (109)..(109)
<223> OTHER INFORMATION: a or g or c or t/u
<220> FEATURE:
<221> NAME/KEY: misc_feature
<222> LOCATION: (123)..(123)
<223> OTHER INFORMATION: a or g or c or t/u
<220> FEATURE:
<221> NAME/KEY: misc_feature
<222> LOCATION: (128)..(128)
<223> OTHER INFORMATION: a or g or c or t/u
<220> FEATURE:
<221> NAME/KEY: misc_feature
<222> LOCATION: (144)..(146)
<223> OTHER INFORMATION: a or g or c or t/u
<220> FEATURE:
<221> NAME/KEY: misc_feature
<222> LOCATION: (180)..(180)
<223> OTHER INFORMATION: a or g or c or t/u
<220> FEATURE:
<221> NAME/KEY: misc_feature
<222> LOCATION: (191)..(191)
<223> OTHER INFORMATION: a or g or c or t/u
<220> FEATURE:
<221> NAME/KEY: misc_feature
<222> LOCATION: (217)..(217)
<223> OTHER INFORMATION: a or g or c or t/u
<220> FEATURE:
<221> NAME/KEY: misc_feature
<222> LOCATION: (234)..(234)
<223> OTHER INFORMATION: a or g or c or t/u
<220> FEATURE:
<221> NAME/KEY: misc_feature
<222> LOCATION: (307)..(307)
<223> OTHER INFORMATION: a or g or c or t/u
<220> FEATURE:
<221> NAME/KEY: misc_feature
<222> LOCATION: (327)..(327)
<223> OTHER INFORMATION: a or g or c or t/u

<400> SEQUENCE: 73
tnaggaanga gaagaagcga gatnnanntn nagaaatang tggtggcnta ntttagagag 60
attgatncaa aagcngattn caatnnnctc agtgnctncc caagtnccnc ctcatgaagg 120
atncactnct ttctgtgcag actnnncatg tcaagcagca ggtgtcagca ggaaaaagan 180
cacaagctcc ncgatggctg ctgctccttg tagcccncca tgagaagcaa gagncttaaa 240
ggcttcctat cccaccaatt acagggaaaa acgtgtgatg acctgagctt actatgcagc 300
ctacaancag ccttagtaat taaaccnttt att 333

<210> SEQ ID NO 74
<211> LENGTH: 522
<212> TYPE: DNA
<213> ORGANISM: Homo sapiens
<220> FEATURE:
<221> NAME/KEY: misc_feature
<222> LOCATION: (1)..(1)
<223> OTHER INFORMATION: a or g or c or t/u
<220> FEATURE:
<221> NAME/KEY: misc_feature
<222> LOCATION: (3)..(4)
<223> OTHER INFORMATION: a or g or c or t/u -continued
<220> FEATURE:
<221> NAME/KEY: misc_feature
<222> LOCATION: (161)..(161)
<223> OTHER INFORMATION: a or g or c or t/u
<220> FEATURE:
<221> NAME/KEY: misc_feature
<222> LOCATION: (231)..(231)
<223> OTHER INFORMATION: a or g or c or t/u
<220> FEATURE:
<221> NAME/KEY: misc_feature
<222> LOCATION: (299)..(299)
<223> OTHER INFORMATION: a or g or c or t/u
<220> FEATURE:
<221> NAME/KEY: misc_feature
<222> LOCATION: (339)..(339)
<223> OTHER INFORMATION: a or g or c or t/u
<220> FEATURE:
<221> NAME/KEY: misc_feature
<222> LOCATION: (445)..(445)
<223> OTHER INFORMATION: a or g or c or t/u
<220> FEATURE:
<221> NAME/KEY: misc_feature
<222> LOCATION: (467)..(467)
<223> OTHER INFORMATION: a or g or c or t/u
<220> FEATURE:
<221> NAME/KEY: misc_feature
<222> LOCATION: (490)..(490)
<223> OTHER INFORMATION: a or g or c or t/u
<220> FEATURE:
<221> NAME/KEY: misc_feature
<222> LOCATION: (516)..(516)
<223> OTHER INFORMATION: a or g or c or t/u

<400> SEQUENCE: 74
nannatgaag atgctttatt gttgcattat caaaatggtt acagttttca attaaagctg 60
taattgattt ctatgtataa aacagctttg aagttgtaaa tgtagtttcc aatcgttagt 120
taatgctaca ttagttagca atatttgaaa attttattgg nataaaatgt tttaattact 180
aaggctgttt gtaggctgca tagtaagctt caggatcatc acacgttttt nccctgtaat 240
tgggtgggga tagggaagcc ctttaagggt ctcttgcttc tcatggggtg gggcctacna 300
agggagcagc cagcccatcg tggccagggc cttgtggganc cttttccct gcctggacac 360 cctgcctgcc ttggaccatg gggaggaagg ttctggcacc aggaaagcca ggtggcccat 420
cccttccatg agggtggggt acttnggggg gccaggacca ctgaggngcc attggtaatc 480
cgtccttttn gtatccaatc ccctcctaag gtaggncccc cc 522

<210> SEQ ID NO 75
<211> LENGTH: 277
<212> TYPE: DNA
<213> ORGANISM: Homo sapiens
<220> FEATURE:
<221> NAME/KEY: misc_feature
<222> LOCATION: (240)..(240)
<223> OTHER INFORMATION: a or g or c or t/u

<400> SEQUENCE: 75
ttttgtgggt tcagcttgtt tattccctac ttttgttatc ttaaaaacaa tgattttttg 60
catgtaatag aaggtttttc acttaagatg ctattgagtg aatcagtgag gggttcttag 120
agttagtatt cattaattaa acatagaata ttagctaaac agttctgggt acactgcaat 180
gcatggtcta tggaagacta gatgtttggc tgaagatgct tttattgttg cattatcaan 240
atggtttata gttttcaatt aaaactgtaa ttgattt 277

<210> SEQ ID NO 76
<211> LENGTH: 265
<212> TYPE: DNA

-continued

<213> ORGANISM: Homo sapiens
<220> FEATURE:
<221> NAME/KEY: misc_feature
<222> LOCATION: (211)..(211)
<223> OTHER INFORMATION: a or g or c or t/u
<220> FEATURE:
<221> NAME/KEY: misc_feature
<222> LOCATION: (220)..(220)
<223> OTHER INFORMATION: a or g or c or t/u
<220> FEATURE:
<221> NAME/KEY: misc_feature
<222> LOCATION: (250)..(250)
<223> OTHER INFORMATION: a or g or c or t/u

<400> SEQUENCE: 76
ggctgaagat gctttattgt tgcattatca aaatggttat agttttcaat taaaactgta 60
attgatttct atgtataaaa cagctttgaa gttgtaaatg tagtttccaa tcgttagtta 120
atgctacatt agttagcaat atttgaaaat tttattggta taaaatgttt taattactaa 180
ggctgtttgt aggctgcata gtaagcttaa ngatcatacn cacgtttttc cctgaatttg 240
gtgggataan gaagccttta aaggt 265

<210> SEQ ID NO 77
<211> LENGTH: 350
<212> TYPE: DNA
<213> ORGANISM: Homo sapiens
<220> FEATURE:
<221> NAME/KEY: misc_feature
<222> LOCATION: (17)..(17)
<223> OTHER INFORMATION: a or g or c or t/u
<220> FEATURE:
<221> NAME/KEY: misc_feature
<222> LOCATION: (72)..(72)
<223> OTHER INFORMATION: a or g or c or t/u
<220> FEATURE:
<221> NAME/KEY: misc_feature
<222> LOCATION: (326)..(326)
<223> OTHER INFORMATION: a or g or c or t/u
<220> FEATURE:
<221> NAME/KEY: misc_feature
<222> LOCATION: (341)..(341)
<223> OTHER INFORMATION: a or g or c or t/u

<400> SEQUENCE: 77
ttgaaaattt tattggnata aaatgtttta attactaagg ctgtttgtag gctgcatagt 60
aagcttcagg ancatcacac gtttttttccc tgtaattggt ggcataggaa gcctttaagg 120
tctcttgctt ctcatgggtg ggctacaagg agcagcagcc atcgtggcag gcttgtgatc 180
tttttcctgc tgacacctgc tgcttgacat ggagaagttc tgcacagaaa gcagtggcat 240
ccttcatgag gtggtacttg gggcagacac tgagagcatt gtaatcgtct tttgtatcaa 300
tctctctaaa gtagaccacc accgtntttg tgcagatgga ntctggcttc 350

<210> SEQ ID NO 78
<211> LENGTH: 452
<212> TYPE: DNA
<213> ORGANISM: Homo sapiens
<220> FEATURE:
<221> NAME/KEY: misc_feature
<222> LOCATION: (227)..(227)
<223> OTHER INFORMATION: a or g or c or t/u
<220> FEATURE:
<221> NAME/KEY: misc_feature
<222> LOCATION: (230)..(230)
<223> OTHER INFORMATION: a or g or c or t/u
<220> FEATURE:
<221> NAME/KEY: misc_feature
<222> LOCATION: (234)..(234)
<223> OTHER INFORMATION: a or g or c or t/u -continued
<220> FEATURE:
<221> NAME/KEY: misc_feature
<222> LOCATION: (429)..(429)
<223> OTHER INFORMATION: a or g or c or t/u

<400> SEQUENCE: 78
aggcactatc atcgggtttt ctcaggtgtt tgagccacac cagaagaaac aaacgcgagc 60
ttcagtggtg attccagtga ctggggatag tgaaggtgct acggtgcagc tgactccata 120
ttttcctact tgtggcagcg actgcatccg acataaagga acagttgtgc tctgcccaca 180
aacaggcgtc cctttccctc tggataacaa caaaagcaag ccgggangg n ctgncctctc 240 ctcctgctgt ctctgctggt ggccacatgg gtgctggtgg cagggatcta tctaatgtgg 300
aggcacgaaa ggatcaagaa gacttccttt tctaaccacc acattactgc cccccattta 360
aggttcttgt ggttttaccc atctggaaat atgttttccc ttcacacatt tgtttatttc 420
attgatttnt ttcaaaacct tggcaggagt tt 452

<210> SEQ ID NO 79
<211> LENGTH: 465
<212> TYPE: DNA
<213> ORGANISM: Homo sapiens
<220> FEATURE:
<221> NAME/KEY: misc_feature
<222> LOCATION: (22)..(22)
<223> OTHER INFORMATION: a or g or c or t/u
<220> FEATURE:
<221> NAME/KEY: misc_feature
<222> LOCATION: (403)..(403)
<223> OTHER INFORMATION: a or g or c or t/u
<220> FEATURE:
<221> NAME/KEY: misc_feature
<222> LOCATION: (415)..(415)
<223> OTHER INFORMATION: a or g or c or t/u
<220> FEATURE:
<221> NAME/KEY: misc_feature
<222> LOCATION: (437)..(437)
<223> OTHER INFORMATION: a or g or c or t/u
<220> FEATURE:
<221> NAME/KEY: misc_feature
<222> LOCATION: (449)..(449)
<223> OTHER INFORMATION: a or g or c or t/u

<400> SEQUENCE: 79
gggtccagtg cagtggcttg cntgcagaaa gaaggcagca gacaaagtcg tcttccttct 60
ttccaatgac gtcaacagtg tgtgcgatgg tacctgtggc aagagcgagg gcagtcccag 120
tgagaactct caagacctct tccccccttgc ctttaacctt ttctgcagtg atctaagaag 180
ccagattcat ctgcacaaat acgtggtggt ctactttaga gagattgata caaaagacga 240
ttacaatgct ctcagtgtct gccccaagta ccacctcatg aaggatgcca ctgctttctg 300
tgcagaactt ctccatgtca agcagcaggt gtcagcagga aaaagattca caagcctgcc 360
acgatggctg cttgcttcct ttgtagccca cccatgagga agncaagaga ccttnaaagg 420
gttccttttc ccatcanttt acaggggana aaacgtgtga tgatc 465

<210> SEQ ID NO 80
<211> LENGTH: 440
<212> TYPE: DNA
<213> ORGANISM: Homo sapiens
<220> FEATURE:
<221> NAME/KEY: misc_feature
<222> LOCATION: (13)..(13)
<223> OTHER INFORMATION: a or g or c or t/u
<220> FEATURE:
<221> NAME/KEY: misc_feature
<222> LOCATION: (16)..(16)

-continued

<223> OTHER INFORMATION: a or g or c or t/u
<220> FEATURE:
<221> NAME/KEY: misc_feature
<222> LOCATION: (18)..(19)
<223> OTHER INFORMATION: a or g or c or t/u
<220> FEATURE:
<221> NAME/KEY: misc_feature
<222> LOCATION: (77)..(77)
<223> OTHER INFORMATION: a or g or c or t/u
<220> FEATURE:
<221> NAME/KEY: misc_feature
<222> LOCATION: (175)..(175)
<223> OTHER INFORMATION: a or g or c or t/u
<220> FEATURE:
<221> NAME/KEY: misc_feature
<222> LOCATION: (277)..(277)
<223> OTHER INFORMATION: a or g or c or t/u
<220> FEATURE:
<221> NAME/KEY: misc_feature
<222> LOCATION: (330)..(330)
<223> OTHER INFORMATION: a or g or c or t/u
<220> FEATURE:
<221> NAME/KEY: misc_feature
<222> LOCATION: (336)..(336)
<223> OTHER INFORMATION: a or g or c or t/u
<220> FEATURE:
<221> NAME/KEY: misc_feature
<222> LOCATION: (420)..(420)
<223> OTHER INFORMATION: a or g or c or t/u

<400> SEQUENCE: 80
ttttgtttgg ctnatntnnt tcttattgtt gcattatcaa aatggttata gttttcaatt 60
aaaactgtaa ttgattncta tgtataaaac agctttgaag ttgtaaatgt agtttccaat 120
cgttagttaa tgctacatta gttagcaata tttgaaaatt ttattggtat aaaangtttt 180
aattactaag gctgtttgta ggctgcatag taagcttcag gatcatcaca cgtttttccc 240
ctgtaattgg tgggatagga agcctttaag gtctctngct tctcatgggt gggctacaag 300
gagcagcagc catcgtggca ggcttgtgan cttttncctg ctgacacctg ctgcttgaca 360
tgggagaagt tctgcacaga aaggcagtgg gcatccttca tgaggtgggt acttgggggn 420
cagacactga ggagcattgt 440

<210> SEQ ID NO 81
<211> LENGTH: 641
<212> TYPE: DNA
<213> ORGANISM: Homo sapiens

<400> SEQUENCE: 81
actcaaaaga aggcagcaga caaagtcgtc ttccttcttt ccaatgacgt caacagtgtg 60
tgcgatggta cctgtggcaa gagcgagggc agtcccagtg agaactctca agacctcttc 120
ccccttgcct ttaacctttt ctgcagtgat ctaagaagcc agattcatct gcacaaatac 180
gtggtggtct actttagaga gattgataca aaagacgatt acagtgctct cagtgtctgc 240
cccaagtacc acctcatgaa ggatgccact gctttctgtg cagaacttct ccatgtcaag 300
cagcaggtgt cagcaggaaa aagatcacaa gcctgccacg atggccgctg ctccttgtag 360
cccacccatg agaagcaaga gaccttaaag gcttcctatc ccaccaatta cagggaaaaa 420
acgtgtgatg atcctgaagc ttactatgca gcctacaaac agccttagta attaaaacat 480
tttataccaa taaaattttc aaatatgcta actaatgtag cattaactaa cgattggaaa 540
ctacatttac aacttcaaag ctgttttata catagaaatc aattacagct ttaattgaaa 600
actgtaacca ttttgataat gcaacaataa agcatcttca g 641

-continued

<210> SEQ ID NO 82
<211> LENGTH: 468
<212> TYPE: DNA
<213> ORGANISM: Homo sapiens

<400> SEQUENCE: 82
gtccagtgca gtggcttgcc actcaaaaga aggcagcaga caaagtcgtc ttccttcttt 60
ccaatgacgt caacagtgtg tgcgatggta cctgtggcaa gagcgagggc agtcccagtg 120
agaactctca agacctcttc ccccttgcct ttaacctttt ctgcagtgat ctaagaagcc 180
agattcatct gcacaaatac gtggtggtct actttagaga gattgataca aaagacgatt 240
acagtgctct cagtgtctgc cccaagtacc acctcatgaa ggatgccact gctttctgtg 300
cagaacttct ccatgtcaag cagcaggtgt cagcaggaaa aagatcacaa gcctgccacg 360
atggccgctg ctccttgtag cccacccatg agaagcaaga gaccttaaag gcttcctatc 420
ccaccaatta caggggaaaa aacgtgtgat gatcctgaag cttactat 468

<210> SEQ ID NO 83
<211> LENGTH: 507
<212> TYPE: DNA
<213> ORGANISM: Homo sapiens
<220> FEATURE:
<221> NAME/KEY: misc_feature
<222> LOCATION: (215)..(215)
<223> OTHER INFORMATION: a or g or c or t/u
<220> FEATURE:
<221> NAME/KEY: misc_feature
<222> LOCATION: (427)..(427)
<223> OTHER INFORMATION: a or g or c or t/u
<220> FEATURE:
<221> NAME/KEY: misc_feature
<222> LOCATION: (438)..(438)
<223> OTHER INFORMATION: a or g or c or t/u
<220> FEATURE:
<221> NAME/KEY: misc_feature
<222> LOCATION: (445)..(445)
<223> OTHER INFORMATION: a or g or c or t/u
<220> FEATURE:
<221> NAME/KEY: misc_feature
<222> LOCATION: (454)..(454)
<223> OTHER INFORMATION: a or g or c or t/u
<220> FEATURE:
<221> NAME/KEY: misc_feature
<222> LOCATION: (459)..(459)
<223> OTHER INFORMATION: a or g or c or t/u
<220> FEATURE:
<221> NAME/KEY: misc_feature
<222> LOCATION: (471)..(471)
<223> OTHER INFORMATION: a or g or c or t/u
<220> FEATURE:
<221> NAME/KEY: misc_feature
<222> LOCATION: (477)..(477)
<223> OTHER INFORMATION: a or g or c or t/u
<220> FEATURE:
<221> NAME/KEY: misc_feature
<222> LOCATION: (486)..(486)
<223> OTHER INFORMATION: a or g or c or t/u
<220> FEATURE:
<221> NAME/KEY: misc_feature
<222> LOCATION: (499)..(499)
<223> OTHER INFORMATION: a or g or c or t/u
<220> FEATURE:
<221> NAME/KEY: misc_feature
<222> LOCATION: (507)..(507)
<223> OTHER INFORMATION: a or g or c or t/u

<400> SEQUENCE: 83
tattgttgca ttatcaaaat ggttatagtt ttcaattaaa actgtaattg atttctatgt 60
ataaaacagc tttgaagttg taaatgtagt ttccaatcgt tagttaatgc tacattagtt 120

-continued

```
agcaatattt gaaaatttta ttggtataaa atgttttaat tactaaggct gtttgtaggc    180

tgcatagtaa gcttcaggat catcacacgt ttttnccctg taattgggtg gggataggga    240

agcctttaag gtctcttgct tctcatgggg tggggctaca agggaggcag gcagccatcg    300

tgggcagggc ttgtgatctt tttccctgct gacacctgct gcttgacatg gggggaaggt    360

tctggcacag aaagcagtgg gcatccttca tgagggtggt acttgggggg cagacactga    420

ggaggcnttg taaatcgnct ttttngtatc caanctctnc taaagtaggg nccaccncgt    480

tttttnttgc aggtggatnc ggggctn                                        507
```

```
<210> SEQ ID NO 84
<211> LENGTH: 440
<212> TYPE: DNA
<213> ORGANISM: Homo sapiens
<220> FEATURE:
<221> NAME/KEY: misc_feature
<222> LOCATION: (22)..(22)
<223> OTHER INFORMATION: a or g or c or t/u
<220> FEATURE:
<221> NAME/KEY: misc_feature
<222> LOCATION: (24)..(24)
<223> OTHER INFORMATION: a or g or c or t/u
<220> FEATURE:
<221> NAME/KEY: misc_feature
<222> LOCATION: (364)..(364)
<223> OTHER INFORMATION: a or g or c or t/u
<220> FEATURE:
<221> NAME/KEY: misc_feature
<222> LOCATION: (382)..(382)
<223> OTHER INFORMATION: a or g or c or t/u
<220> FEATURE:
<221> NAME/KEY: misc_feature
<222> LOCATION: (414)..(414)
<223> OTHER INFORMATION: a or g or c or t/u
<220> FEATURE:
<221> NAME/KEY: misc_feature
<222> LOCATION: (424)..(424)
<223> OTHER INFORMATION: a or g or c or t/u
<220> FEATURE:
<221> NAME/KEY: misc_feature
<222> LOCATION: (430)..(430)
<223> OTHER INFORMATION: a or g or c or t/u

<400> SEQUENCE: 84

gggtccagtg cagtggcttg cntncaaaag aaggcagcag acaaagtcgt cttccttctt     60

tccaatgacg tcaacagtgt gtgcgatggt acctgtggca agagcgaggg cagtcccagt    120

gagaactctc aagacctctt ccccccttgcc tttaaccttt tctgcagtga tctaagaagc    180

cagattcatc tgcacaaata cgtggtggtc tactttagag agattgatac aaaagacgat    240

tacaatgctc tcagtgtctg ccccaagtac cacctcatga aggatgccac tgctttctgt    300

gcagaacttc tccatgtcaa gcagcaggtg tcagcaggaa aaagatcaca agcctgccac    360

gatngctgct gctccttgta gnccacccat gagaagcaag tgacctttaa aggntttcct    420

attnccaccn atttacaggg                                                440
```

```
<210> SEQ ID NO 85
<211> LENGTH: 630
<212> TYPE: DNA
<213> ORGANISM: Homo sapiens

<400> SEQUENCE: 85

gactagatgt ttggctgaag atgctttatt gttgcattat caaaatggtt atagttttca     60

attaaaactg taattgattt ctatgtataa aacagctttg aagttgtaaa tgtagtttcc    120

aatcgttagt taatgctaca ttagttagca atatttgaaa attttattgg tataaaatgt    180
```

-continued

```
tttaattact aaggctgttt gtaggctgca tagtaagctt caggatcatc acacgttttt    240

tccctgtaat tggtgggata ggaagccttt aaggtctctt gcttctcatg ggtgggctac    300

aaggagcagc agccatcgtg gcaggcttgt gatctttttc ctgctgacac ctgctgcttg    360

acatggagaa gttctgcaca gaaagcagtg gcatccttca tgaggtggta cttggggcag    420

acactgagag cattgtaatc gtcttttgta tcaatctctc taaagtagac caccacgtat    480

ttgtgcagat gaatctggct tcttagatca ctgcagaaaa ggttaaaggc aaggggggaag    540

aggtcttgag agttctcact gggactgccc tcgctcttgc cacaggtacc atcgcacaca    600

ctgttgacgt cattggaaaa gaaggaagac                                      630
```

<210> SEQ ID NO 86
<211> LENGTH: 788
<212> TYPE: DNA
<213> ORGANISM: Homo sapiens

<400> SEQUENCE: 86

```
gagttctcac tgggactgcc ctcgctcttg ccacaggtac catcgcacac actgttgacg     60

tcattggaaa gaaggaagac gaccttgtct gctaccttct tttgagtggc aagccactgc    120

actggaccca tctctgctat tttctttttc tgccactttt caaggatgac ctcacttctg    180

caatggtttt gaagaaattc agtgaagtaa caaattgtgt gatggaaaca tatttcagat    240

gggtaaacca caagaacctt aatgggggggc agtagtgtgg tggtagaaaa ggaagtcttc    300

ttgatccttt ctgtgagagg agaaaagcat ttgttatctg tgaatagcaa acagcaggct    360

ttcactctgt aaaccatccc tgacaaatga tcccttgcta gagaatgtca gctgagcacc    420

aagggccttg ttagtgacag caaggaaaaa catcctgatg ttccttttga acacatcacc    480

tgaaacacac tgatgcttaa accttaactt tttttttttg ggggacatag tctcactctg    540

tcgcccaggc tggagtgcgt gggagaggac ctcggaaaga ctggcaagca tccgcataca    600

agggagtaac agcacaatac tccgtgaact tcggagccct ccaaaggaat actcaagggc    660

gggtaaagga tggcaagggt cgacggagag cccacgagga gagcggaagg tagagaggag    720

acaagcataa gacgcgagag gaactccaag gcggggccaa agagagaaac cacggtcacc    780

aacagaag                                                              788
```

<210> SEQ ID NO 87
<211> LENGTH: 307
<212> TYPE: DNA
<213> ORGANISM: Homo sapiens
<220> FEATURE:
<221> NAME/KEY: misc_feature
<222> LOCATION: (34)..(34)
<223> OTHER INFORMATION: a or g or c or t/u
<220> FEATURE:
<221> NAME/KEY: misc_feature
<222> LOCATION: (263)..(263)
<223> OTHER INFORMATION: a or g or c or t/u
<220> FEATURE:
<221> NAME/KEY: misc_feature
<222> LOCATION: (270)..(270)
<223> OTHER INFORMATION: a or g or c or t/u
<220> FEATURE:
<221> NAME/KEY: misc_feature
<222> LOCATION: (279)..(279)
<223> OTHER INFORMATION: a or g or c or t/u
<220> FEATURE:
<221> NAME/KEY: misc_feature
<222> LOCATION: (306)..(306)
<223> OTHER INFORMATION: a or g or c or t/u -continued

<400> SEQUENCE: 87

```
agaagccaga ttcatctgca caaatacgtg gtgntctact ttagagagat tgatacaaaa     60
gacgattaca atgctctcag tgtctgcccc aagtaccacc tcatgaagga tgccactgct    120
ttctgtgcag aacttctcca tgtcaagcag caggtgtcag caggaaaaag atcacaagcc    180
tgccacgatg gctgctgctc cttgtagccc acccatgaga agcaagagac cttaaaggct    240
tcctatccca ccaattacag ggnaaaaacn gtagtgatna tccctgacag cttactatgc    300
cagccnt                                                              307
```

<210> SEQ ID NO 88
<211> LENGTH: 335
<212> TYPE: DNA
<213> ORGANISM: Homo sapiens
<220> FEATURE:
<221> NAME/KEY: misc_feature
<222> LOCATION: (67)..(67)
<223> OTHER INFORMATION: a or g or c or t/u
<220> FEATURE:
<221> NAME/KEY: misc_feature
<222> LOCATION: (315)..(315)
<223> OTHER INFORMATION: a or g or c or t/u
<220> FEATURE:
<221> NAME/KEY: misc_feature
<222> LOCATION: (333)..(333)
<223> OTHER INFORMATION: a or g or c or t/u

<400> SEQUENCE: 88

```
ttggctgaag atgctttatt gttgcattat caaaatcggt tacagttttc aattaaagct     60
gtaattngat ttctatgtat aaaacagctt tgaagttgta aatgtagttt ccaatcgtta    120
gttaatgcta cattagttag caatatttga aaattttatt ggtataaaat gttttaatta    180
ctaaggctgt ttgtaggctg catagtaagc ttcaggatca tcacacgttt tttccctgta    240
attgggtggg ataggaagcc tttaaggtct cttgcttctc attgggtggg ctacaaggag    300
cagcagccat ccgtnggcaa ggctttgtgg atnct                              335
```

<210> SEQ ID NO 89
<211> LENGTH: 639
<212> TYPE: DNA
<213> ORGANISM: Homo sapiens

<400> SEQUENCE: 89

```
ggaagagaaa gatcgtccag aggttccatc gcacacactg tatgacgtca ttggaaatga     60
aggaagacga ctttgtctgc tggcttcttg tgagtggcaa gccactgcag tggacccatc    120
tctgctattt tctttattct gccacttttc aaggatgacc tcacttctgc aatggttttg    180
aagaaagttc agtgaagtaa caaattgtgt gatggaaaca tatttcagat gggtaaacca    240
caagaacctt aatgggggc agtagtgtgg tggtagaaaa ggaagtcttc ttgatccttt     300
ctgtgagagg agaaaagcat tagttatctg tgaacagcaa acagcaggca tttcacatct    360
gtaaaccatc cctgacaaat gatcccttgc tagagaatgt cagctgagca ccaaggggcc    420
ttgttagtga cagcaaggac aaaacatcct gatgttcctt ttgaacacat cagctgaaac    480
acactgatgc tctaaaccgt taactattta ttaatggggg aacataggtc tcaactcatg    540
tacgaccagg ctggagtgca gtggggttga acatcgacag acatagcaaa ccaccgatca    600
ctagggaaac aacgcacaga actccagact taaaacacc                          639
```

<210> SEQ ID NO 90
<211> LENGTH: 477

-continued

<212> TYPE: DNA
<213> ORGANISM: Homo sapiens
<220> FEATURE:
<221> NAME/KEY: misc_feature
<222> LOCATION: (365)..(365)
<223> OTHER INFORMATION: a or g or c or t/u

<400> SEQUENCE: 90
attcggcacc tggggggcag acactgagag cattgtaatc gtcttttgta tcaatctctc 60
taaagtagac caccacgtat ttgtgcagat gaatctggct tcttagatca ctgcagaaaa 120
ggttaaaggc aagggggaag aggtcttgag agttctcact gggactgccc tcgctcttgc 180
cacaggtacc atcgcacaca ctgttgacgt cattggaaag aaggaagacg actttgtctg 240
ctgccttctt ttgagtggca agccactgca ctggacccat ctctgctatt ttctttttct 300
gccacttttc aaggatgacc tcacttctgc aatggttttg aagaaattca gtgaagtaac 360
aaatntgtgt gatggaaaca tatttcagat gggtaaacca caagaacctt aatgggggc 420 agtagtgtgg tggtagaaaa ggaagtcttc ttgatccttt ctgtgagagg agaaagc 477

<210> SEQ ID NO 91
<211> LENGTH: 432
<212> TYPE: DNA
<213> ORGANISM: Homo sapiens

<400> SEQUENCE: 91
ttttgatggt ccacttccat ttaatgaatt agtaaatatc ttttctcatg attttaatta 60 cattttttc tctagcttac tttattataa tacagcacat aatacaccta acatgcaaaa 120
tatgtgttaa ttggctgttt atgttattgg taagacttcc agtcaacagt aggctattag 180
aagttaagtt gtgggaaaat caaaggttat aggagatttt caactgcatg cagggccggt 240
gccctcccca ctgtgttgtt caagggtcag ctgtactctc taagggcttt gctaacttca 300
aaacatggag tatttgaata cagaaaccag agcatttaca tactcagctc aaggcagagc 360
tattaaaaaa actcctcttc tccatatgta ggaaaggaaa tacaaatgca tcctttgagt 420
catttgtgat gt 432

<210> SEQ ID NO 92
<211> LENGTH: 316
<212> TYPE: DNA
<213> ORGANISM: Homo sapiens
<220> FEATURE:
<221> NAME/KEY: misc_feature
<222> LOCATION: (68)..(68)
<223> OTHER INFORMATION: a or g or c or t/u
<220> FEATURE:
<221> NAME/KEY: misc_feature
<222> LOCATION: (70)..(70)
<223> OTHER INFORMATION: a or g or c or t/u
<220> FEATURE:
<221> NAME/KEY: misc_feature
<222> LOCATION: (74)..(74)
<223> OTHER INFORMATION: a or g or c or t/u
<220> FEATURE:
<221> NAME/KEY: misc_feature
<222> LOCATION: (120)..(120)
<223> OTHER INFORMATION: a or g or c or t/u
<220> FEATURE:
<221> NAME/KEY: misc_feature
<222> LOCATION: (140)..(140)
<223> OTHER INFORMATION: a or g or c or t/u
<220> FEATURE:
<221> NAME/KEY: misc_feature
<222> LOCATION: (211)..(211)
<223> OTHER INFORMATION: a or g or c or t/u
<220> FEATURE:

-continued

<221> NAME/KEY: misc_feature
<222> LOCATION: (289)..(289)
<223> OTHER INFORMATION: a or g or c or t/u

<400> SEQUENCE: 92
aacagttgtg ctctgcccac aaacaggcgt ccctttccct ctggataaca acaaaagcaa 60
gccgggangn ctgncgctct cctcctgctg tctctgctgg tggccacatg ggtgctggtn 120
gcagggatct atctaatgtn gaggcacgaa agggatcaag aggacttcct tttctaccac 180
cacactactg ccccccatta aggttcttgt nggtttaccc atctggaaat atgtttccat 240
cacacaattt gttacttcac tggaatttct tcaaaaccat tggcaggang tgagggtcat 300
ccttggaaaa gtgggc 316

<210> SEQ ID NO 93
<211> LENGTH: 401
<212> TYPE: DNA
<213> ORGANISM: Homo sapiens
<220> FEATURE:
<221> NAME/KEY: misc_feature
<222> LOCATION: (274)..(274)
<223> OTHER INFORMATION: a or g or c or t/u

<400> SEQUENCE: 93
cctcacttct gcaatggttt tgaagaaatt cagtgaagta acaaattgtg tgatggaaac 60
atatttcaga tgggtaaacc acaagaacct taatgggggg cagtagtgtg gtggtagaaa 120
aggaagtctt cttgatcctt tcgtgcctcc acattagata gatccctgcc accagcaccc 180
atgtggccac cagcagagac agcaggagga gaggcagcca gcctcccggc tttgcttttg 240
ttgttatcca gaggggaaag gggacgcctg tttntggggc agagcacaac tgtttccctc 300
gtgcccgaat tctttgggcc ttcgaggggc caaatttccc tattaggtga ggtcgtattt 360
taaatttcgg taattcatgg tcataggctt gtttttcccc g 401

<210> SEQ ID NO 94
<211> LENGTH: 516
<212> TYPE: DNA
<213> ORGANISM: Homo sapiens
<220> FEATURE:
<221> NAME/KEY: misc_feature
<222> LOCATION: (400)..(400)
<223> OTHER INFORMATION: a or g or c or t/u
<220> FEATURE:
<221> NAME/KEY: misc_feature
<222> LOCATION: (462)..(462)
<223> OTHER INFORMATION: a or g or c or t/u
<220> FEATURE:
<221> NAME/KEY: misc_feature
<222> LOCATION: (483)..(483)
<223> OTHER INFORMATION: a or g or c or t/u
<220> FEATURE:
<221> NAME/KEY: misc_feature
<222> LOCATION: (509)..(509)
<223> OTHER INFORMATION: a or g or c or t/u

<400> SEQUENCE: 94
gtttcaacac aattttggat cagctgcctg tttgcaaaaa cataatatat ttctgttaaa 60
cagttcttca cctaacagca tattgctctt ataactggta gagctgtttc aaaggaagtt 120
ggtttctggt ccaagttttg acctaaacca tgtccatctt ctattaccag cacttacaag 180
cactgtgaaa actgatcatg acaaataagt aaaatttgct acattaaaca tattgcctca 240
gccattacta agcgtccact tgtaaagctg gacacagttt ttactttatg cttcattttg 300
attttttatc cgtaagacat aaattagaag gcatgaggtg gccctttaag gataatctgc 360

-continued aaatatacac attttaaata gtcatccatc tggaaatcgn tccaccattc caggggaagg 420
attccaggta ttggtgctgt ggtggaaata aagcattccc cngggaaaaa aaccatttta 480
tgnctaaata attaccacca ttaacctcnt ggggtt 516

<210> SEQ ID NO 95
<211> LENGTH: 187
<212> TYPE: DNA
<213> ORGANISM: Homo sapiens

<400> SEQUENCE: 95
gaatactaac tctaagaacc cctcactgat tcactcaata gcatcttaag tgaaaaacct 60
tctattacat gcaaaaaatc attgttttta agataacaaa agtagggaat aaacaagctg 120
aacccacttt tactggacca aatgatctat tatatgtgta accacttgta tgatttggga 180
tttgcat 187

<210> SEQ ID NO 96
<211> LENGTH: 156
<212> TYPE: DNA
<213> ORGANISM: Homo sapiens

<400> SEQUENCE: 96
ttttttacaa cttcaaagct gttttataca tagaaatcaa ttacagtttt aattgaaaac 60
tataaccatt ttgataatgc aacaataaag catcttcagc caaacatcta gtcttccata 120
gaccatgcat tgcagtgtac ccagaactgt ttagct 156

<210> SEQ ID NO 97
<211> LENGTH: 491
<212> TYPE: DNA
<213> ORGANISM: Homo sapiens
<220> FEATURE:
<221> NAME/KEY: misc_feature
<222> LOCATION: (478)..(478)
<223> OTHER INFORMATION: a or g or c or t/u
<220> FEATURE:
<221> NAME/KEY: misc_feature
<222> LOCATION: (491)..(491)
<223> OTHER INFORMATION: a or g or c or t/u

<400> SEQUENCE: 97
ctgagtgtga tggtgtaagc ctgtggtccc agctactagg gaggctgaga tgggattaca 60
ggtgtgagcc acggcgcctg gcctaaaagc atctttttct ttaacgcaga ggttatgttg 120
tattattagc ataaatgttt ttttctggga atgcttattt cacacagcac aatactgaat 180
cttctctgga atgtggatcg atttcagatg gatgactatt aaaatgtgta tatttgcaga 240
ttatccttaa agggccacct catgccttct aatttatgtc ttacggataa aaaatcaaaa 300
tgaagcataa agtaaaaact gtgtccagct ttacaagtgg acgcttagta atggctgagg 360
caatatgttt aatgtagcca aattttactt atttgtccat gatccagttt ttcacagtgc 420
ttgttaagtg ctggtaatta ggaaggtggg acatgggtta ggtcaaaact tgggaccnga 480
aaccaacttg n 491

<210> SEQ ID NO 98
<211> LENGTH: 270
<212> TYPE: DNA
<213> ORGANISM: Homo sapiens

<400> SEQUENCE: 98

-continued

```
ttttttttt acaacttcaa agctgtttta tacatagaaa tcaattacag ttttaattga     60

aaactataac cattttgata atgcaacaat aaagcatctt cagccaaaca tctagtcttc    120

catagaccat gcattgcatt gtacccagaa ctgtttagct aatattctat gtttaattaa    180

tgaatactaa ctctaagaac ccctcactga ttcactcaat agcatcttaa gtgaaaaacc    240

ttctattaca tgcaaaaaat cattggtttt                                     270


<210> SEQ ID NO 99
<211> LENGTH: 478
<212> TYPE: DNA
<213> ORGANISM: Homo sapiens

<400> SEQUENCE: 99

ttttctgagt aagaacaggc tttatttgta aaaccactcg tgactcttta caaagcagga     60

tacacagaag ggaaaaaaat acacagtgca aaatggatgt tctgagtgcc acaaggatct    120

gctgaaaaaa gccaaagatg taagatggct gggtatatat gagaatgaat atttcactat    180

attctgattc aattaccagt ctcagtggcc caggatgagc ttttggtgtg gtcacatggc    240

caacatttgg ataacaaatg aggaataatg gtaccgcctc actagtgcct gagaacagca    300

tgttctggaa aatgtctctg gagttagaga tgtgttagct ttttcattac agatggagaa    360

atacaatgtt tacacaacag tccaggggtg gggtcaaaag ttggaaggtg tcattagacg    420

cagccaaata aagtgaagac aacccaggtg actggcagcc ctgacttgtg cgtgggcg      478


<210> SEQ ID NO 100
<211> LENGTH: 263
<212> TYPE: DNA
<213> ORGANISM: Homo sapiens

<400> SEQUENCE: 100

tttctgagta agaacaggct ttatttgtaa aaccactcgt gactctttac aaagcaggat     60

acacagaagg gaaaaaaata cacagtgcaa aatggatgtt ctgagtgcca caaggatctg    120

ctgaaaaaag ccaaagatgt aagatggctg ggtatatatg agaatgaata tttcactata    180

ttctgattca attaccagtc tcagtggccc aggatgagct ttggtggtgg tcacatggcc    240

aacatttgga taacaaatga gga                                            263


<210> SEQ ID NO 101
<211> LENGTH: 388
<212> TYPE: DNA
<213> ORGANISM: Homo sapiens

<400> SEQUENCE: 101

gagatggagg tctcgctttg tgacgtagcc tggtcttgag cgatcctttt gccttggcct     60

tgccaaagtg ctgggattgg aggcatgagc cactgcaccc acccctgttt tttttttaag    120

taaaccatta taataactca tttataaaaa ggttacttca agagggcttt caacttaaga    180

attattttca ttttgaacat gaaaagttaa atagtaacta agaaactgag aactctgaca    240

gtgacctcta ataggtaact ttaggcaaaa gtagacaagt ttgtgggtat tttgttgttc    300

atgttaaaag gcacctgtac aagaatcaag atatgaatct agtttgtaga gggaaggtct    360

tatgcaaata ccaaatcata caagtggt                                       388


<210> SEQ ID NO 102
<211> LENGTH: 450
<212> TYPE: DNA
<213> ORGANISM: Homo sapiens
```

-continued

<400> SEQUENCE: 102
agagatgttg gtctcgcttt gtgacgtagc ctgggcttga gcgatccttt tgccttggcc 60
ttgccaaagt gctgggattg gaggcatgag ccactgcacc cacccctgtt ttttttttaa 120
gtaaaccatt ataataactc atttataaaa aggttacttc aagagggctt tcaacttaag 180
aattattttc attttgaaca tgaaaagtta aatagtaact aagaaactga gaactctgac 240
agtgacctct aataggtaac tttaggcaaa agtagacaag tttgtgggta ttttgttgtt 300
catgttaaaa ggcacctgta caagaatcaa gatatgaatc tagtttgtag agggaaggtc 360
ttatgcaaat accaaatcat acaagtggtt acacatataa tagatcattt ggtccagtaa 420
aagtgggttc agcttgttta ttccctactt 450

<210> SEQ ID NO 103
<211> LENGTH: 162
<212> TYPE: DNA
<213> ORGANISM: Homo sapiens

<400> SEQUENCE: 103
gagatggagg tctcgctttg tgacgtagcc tggtcttgag cgatcctttt gccttggctt 60
gcaaagtgct gggattggag gcatgagcac tgcacccacc cctgtttttt tttttaagta 120
aaccattata ataactcatt tataaaaagg ttacttcaag ag 162

<210> SEQ ID NO 104
<211> LENGTH: 392
<212> TYPE: DNA
<213> ORGANISM: Homo sapiens
<220> FEATURE:
<221> NAME/KEY: misc_feature
<222> LOCATION: (117)..(117)
<223> OTHER INFORMATION: a or g or c or t/u
<220> FEATURE:
<221> NAME/KEY: misc_feature
<222> LOCATION: (345)..(345)
<223> OTHER INFORMATION: a or g or c or t/u
<220> FEATURE:
<221> NAME/KEY: misc_feature
<222> LOCATION: (378)..(378)
<223> OTHER INFORMATION: a or g or c or t/u
<220> FEATURE:
<221> NAME/KEY: misc_feature
<222> LOCATION: (388)..(388)
<223> OTHER INFORMATION: a or g or c or t/u

<400> SEQUENCE: 104
ttcactcaat agcatcttaa gtgaaaaacc ttctattaca tgcaaaaaat cattgttttt 60
aagataacaa aagtagggaa taaacaagct gaacccactt ttactggacc aaatgancta 120
ttatatgtat aaccacttgt atgatttggt atttgcataa gaccttccct ctacaaacta 180
gattcatatc ttgattcttg tacaggtgcc tttttaatat tctgtgatga aatcgttcac 240
agtcagagta catgtctgct gcatatggga aatagggact gttgttctga gggacaaggc 300
actcaattca gccgtaaagg ctgacccggg ctactttttt tccangggaa tacaattttt 360
ttaccttgga ataaaatngg gcccgacngg ac 392

<210> SEQ ID NO 105
<211> LENGTH: 428
<212> TYPE: DNA
<213> ORGANISM: Homo sapiens

<400> SEQUENCE: 105

-continued

```
ttttttttt tgagtaagaa caggctttat ttgtaaaacc actcgtgact ctttacaaag     60

caggatacac agaagggaaa aaaatacaca gtgcaaaatg gatgttctga gtgccacaag    120

gatctgctga aaaaaagcca aagatgtaag atggctgggt atatatgaga atgaatattt    180

cactatattc tgattcaatt accagtctca gtggcccagg atgagctttt ggtgtggtca    240

catggccaac atttggataa caaatgagga ataatggtac cgcctcacta gtgcctgaga    300

acagcatgtt ctggaaaatg tctctggagt tagagatgtg ttagcttttt cattacagat    360

ggagaaatac aatgtttaca caacagtcca ggggtggggt caaaagttgg aaggtgtcat    420

tagacgca                                                              428
```

<210> SEQ ID NO 106
<211> LENGTH: 430
<212> TYPE: DNA
<213> ORGANISM: Homo sapiens

<400> SEQUENCE: 106

```
aaatttttaa cttttaatag ttaaaatagt taactattgg tatggtagga aatgataaag     60

tagactagta tctgtataca ttttctgcat ttatgacata cctttttctt catttttttc    120

aatattttaa ttgaaaagtt catccgagtt tcatctaagt tttttcaaag tgatacaaat    180

ctccaaaaaa ttttccaata tatgtattga aaaaatccag gtgtaagtgg ctctgcgcag    240

tccaaacctg tgttgttcaa gggtcaactg tgtatgaatc caagcgaaag cttttcttaa    300

cacctcataa gaactatttt ttaaaaaaca ggaactagca tagagtaacc atcacaggta    360

aagtgtaatt tgttatcagc catcttttgc ccatttcagt actggtagaa ggctcaatgg    420

taaaaataaa                                                            430
```

<210> SEQ ID NO 107
<211> LENGTH: 368
<212> TYPE: DNA
<213> ORGANISM: Homo sapiens

<400> SEQUENCE: 107

```
ttttttttt ttttttttt ttttctgact gtcccgtttt tatttttacc attgagcctt     60

ctaccagtac tgaaatgggc aaaagatggc tgataacaaa ttacacttta cctgtgatgg    120

ttactctatg ctagttcctg ttttttaaaa aatagttctt atgaggtgtt aagaaaagct    180

ttcgcttgga ttcatacaca gttgaccctt gaacaacaca ggtttggact gcgcagacca    240

cttacacctg gatttttca atacatatat tggaaaattt tttggggatt tgtatcactt     300

tgaaaaaact tagatgaaac tcggatggac ttttccatta aaatattgga aaaaatgaag    360

aaaaaggt                                                              368
```

<210> SEQ ID NO 108
<211> LENGTH: 435
<212> TYPE: DNA
<213> ORGANISM: Homo sapiens

<400> SEQUENCE: 108

```
ttttttttt ttttttttt ttttctgact ggcccgtttt tatttttacc attgagcctt     60

ctaccagtac tgaaatgggc aaaagatggc tgataacaaa ttacacttta cctgggatgg    120

ttactctatg ctagttcctg ttttttaaaa aatagttctt atgaggggtt aaaaaaagct    180

ttcgcttgga ttcatacaca gttgaccctt gaacaacaca ggtttggact gcgcagagcc    240

acttacacct ggatttttc aatacatata ttggaaaatt ttttggagat ttgtatcact     300
```

-continued ttgaaaaaac ttagatgaaa ctcggatgaa cttttcaatt aaaatattga aaaaaatgaa 360
gaaaaaggta tgtcataaat gcagaaaatg tatacagata ctagtctact ttatcatttc 420
ctaccatacc aatag 435

<210> SEQ ID NO 109
<211> LENGTH: 880
<212> TYPE: DNA
<213> ORGANISM: Homo sapiens
<220> FEATURE:
<221> NAME/KEY: misc_feature
<222> LOCATION: (788)..(788)
<223> OTHER INFORMATION: a or g or c or t/u

<400> SEQUENCE: 109
taaaggaaca gttgtgctct gcccacaaac aggcgtccct ttccctctgg ataacagtaa 60
gtgcccagta acttcaacca gatgatcaaa gtggctcaca cacagtcact gccccccact 120
cagtatgtgg aagggttgtg tgtatgtggg cagtgcaagg ggtcgctgcc tgtgtacact 180
gaactggggt gcagagaaag ccaacagtgc tgtcccagag aacctagaat ctgagtaaga 240
acaggcttta tttgtaaaac cactcgtgac tctttacaaa gcaggataca cagaagggaa 300
aaaaatacac agtgcaaaat ggatgttctg agtgccacaa ggatctgctg aaaaaagcca 360
aagatgtaag atggctgggt atatatgaga atgaatattt cactatattc tgattcaatt 420
accagtctca gtggcccagg atgagctttt ggtgtggtca catggccaac atttggataa 480
caaatgagga ataatggtac cgcctcacta gtgcctgaga acagcatgtt ctggaaaatg 540
tctctggagt tagagatgtg ttagcttttt cattacagat ggagaaatac aatgtttaca 600
caacagtcca ggggtggggg tcaaaagttg gaaggtgtca ttagacgcag ccaaataaag 660
tgaagaccac ccaggtgact ggcagccctg acttgtgcgt gggcgaaacc ttacagattc 720
ctggggcact ctgtgcctga acttacctgg atggtctttg tgaggcgggt gggcacttat 780
cctccatnaa tggtcagtct aacaagaccg gcctgtaaaa atggcatcta ataggggcta 840
tggaatggaa aacagttggt acccagaaat aactttaatt 880

<210> SEQ ID NO 110
<211> LENGTH: 437
<212> TYPE: DNA
<213> ORGANISM: Homo sapiens
<220> FEATURE:
<221> NAME/KEY: misc_feature
<222> LOCATION: (34)..(34)
<223> OTHER INFORMATION: a or g or c or t/u
<220> FEATURE:
<221> NAME/KEY: misc_feature
<222> LOCATION: (192)..(192)
<223> OTHER INFORMATION: a or g or c or t/u

<400> SEQUENCE: 110
gacagtctgg gagcccagag ctctgggagg agtngggaaa atgctgcttc ctgctgcttg 60
cttctaggca cctgcttccg ccatctcact taccatggct agagatgggg gtgagactgg 120
ggaaggacaa aagcagggaa cagataaggg atggaaatca gaagggaata tagaaagaac 180
tctggatatg cnagaaatgc cggtacctga gcattttgta tcaatgggag taccctctgt 240
aactgctcag taggttacaa atgaagagtc caccagtatt agaaacaatt taaacttgcc 300
agtaccaact gggatgtgtg ccttcaattt gaaaattgta tgttttattt tttaaatttg 360
gttaacagca ttaatttata gagtatttga tgtcatttat ggttcccgag gtgtttccaa 420

-continued

```
cacaatttt gggatca                                                437

<210> SEQ ID NO 111
<211> LENGTH: 1107
<212> TYPE: DNA
<213> ORGANISM: Homo sapiens
<220> FEATURE:
<221> NAME/KEY: misc_feature
<222> LOCATION: (893)..(893)
<223> OTHER INFORMATION: a or g or c or t/u

<400> SEQUENCE: 111

cttttaatag ttaaaatagt taactattgg tatggtagga aatgataaag tagactagta      60

tctgtataca ttttctgcat ttatgacata cctttttctt catttttttc aatattttaa     120

ttgaaaagtt catccgagtt tcatctaagt tttttcaaag tgatacaaat ctccaaaaaa     180

ttttccaata tatgtattga aaaaatccag gtgtaagtgg ctctgcgcag tccaaacctg     240

tgttgttcaa gggtcaactg tgtatgaatc caagcgaaag cttttcttaa cacctcataa     300

gaactatttt ttaaaaaaca ggaactagca tagagtaacc atcacaggta aagtgtaatt     360

tgttatcagc catcttttgc ccatttcagt actggtagaa ggctcaatgg taaaaataaa     420

aacgggacag tcagaagatc tggaagtcct gaccctgctt tcacctggca tgtgtaatcc     480

agtcatgctc gtatcagtct ctgtaggagc acttgaaggt attacataaa tgctatctaa     540

ctctgggaaa cgccaacatg tgattgcctc cagaggaatc ttctttaaaa aaaaattcaa     600

aatgttattt ccttactagg atgtctttaa agaattataa cccttaccgt gcctccacat     660

tagatagatc cctgccacca gcacccatgt ggccaccagc agagacagca ggaggagagg     720

cagccagcct cccggcttgc ttttgtctgg aaaaaaacaa agcttattca cctttggaaa     780

aaaatccaca cttatctctt aatttaaaaa ctaagacttg gtatacttta tagagggtta     840

tttatttttt attatttttt agttttgaga cagagtctcg ctttgttgcc tangctggag     900

tgcagtggcg caatctcggt tcactgcagc ctccgttctc cggggttcaa ggcatgctgg     960

ctcagcctcc tgtatagctg ggattaaag gcatgtgttc acgcggccca gcccctttttg   1020

taaaagattt agatcccttt taaaaccatc agtcaggagg ctcctttaaa aagtctggcc    1080

atctaatctt ttttccccca aaagggg                                        1107

<210> SEQ ID NO 112
<211> LENGTH: 290
<212> TYPE: DNA
<213> ORGANISM: Homo sapiens

<400> SEQUENCE: 112

tttttttttt tctttttttct gagtaagaac aggctttatt tgtaaaacca ctcgtgactc     60

tttacaaagc aggatacaca gaagggaaaa aaatacacag tgcaaaatgg atgttctgag    120

tgccacaagg atctgctgaa aaaagccaaa gatgtaagat ggctgggtat atatgagaat    180

gaatatttca ctatattctg attcaattac cagtctcagt ggcccaggat gagcttttgg    240

tgtggtcaca tggccaacat ttggataaca aatgaggaat aatctcgtgc               290

<210> SEQ ID NO 113
<211> LENGTH: 812
<212> TYPE: DNA
<213> ORGANISM: Homo sapiens

<400> SEQUENCE: 113

aatttataga gtattgatgt catttatgtt tctgaggtgt ttcaacacaa ttttggatca     60
```

-continued

```
gctgcctgtt tgcaaaaaca taatatattt ctgttaaaca gttcttcacc taacagcata    120

ttgctcttat aactggtaga gctgtttcaa aggaagttgg tttctggtcc aagttttgac    180

ctaaaccatg tccatcttct attaccagca cttacaagca ctgtgaaaac tgatcatgac    240

aaataagtaa aatttgctac attaaacata ttgcctcagc cattactaag cgtccacttg    300

taaagctgga cacagttttt actttatgct tcattttgat tttttatccg taagacataa    360

attagaaggc atgaggtggc cctttaagga taatctgcaa atatacacat tttaatagtc    420

atccatctga aatcgatcca cattccagag aagattcagt attgtgctgt gtgaaataag    480

cattcccaga aaaaaaacat ttatgctaat aatacaacat aacctctgca ttaaagaaaa    540

agatgctttt aggccaggcg ccgtggctca cgcctgtaat ccctgcactt tgagaggctg    600

aggtgggtgg atcatgaggt caggagatca agaccatcct ggctaacagg gtgaaacccc    660

gtctctactg ggatataac aaagttagct gggtgtggtg gtgggtgctt gtggtcccag    720

ctactcagga ggctgaggca ggagaatggc gtgaacccgg aaggcagagg ttgtagtgac    780

gcgaggttca cgccactgca ttccagtctg gg                                  812


<210> SEQ ID NO 114
<211> LENGTH: 679
<212> TYPE: DNA
<213> ORGANISM: Homo sapiens
<220> FEATURE:
<221> NAME/KEY: misc_feature
<222> LOCATION: (8)..(8)
<223> OTHER INFORMATION: a or g or c or t/u

<400> SEQUENCE: 114

caggaagnta agaacagtcc taaaatctct ttggcttctt tgtcctgata tgcaccggca     60

ttttcacagt aggaactagg gtttctgtcc agttttttg gttctttaag gaattaatgt    120

tattctgggt acaactgctt acatacatag cacatataga tgacattttt acaggccgtc    180

ttgttagact gacatacatg gaggatagtg ccacccgcct cacaagaaca tcaggtaagc    240

tcaggcacag agtgcccagg aatctgtaag gcttcgccca cgcacaagtc agggctgcca    300

gtcacctggg ttgtcttcac tttatttggc tgcgtctaat gacaccttcc aacttttgac    360

cccacccctg gactgttgtg taaacattgt atttctccat ctgtaatgaa aaagctaaca    420

catctctaac tccagagaca ttttccagaa catgctgttc tcaggcacta gtgaggcggt    480

accattattc ctcatttgtt atccaaatgt tggccatgtg accacaccaa aagctcatcc    540

tgggccactg agactggtaa ttgaatcaga atatagtgaa atattcattc tcatatatac    600

ccagccatct tacatctttg gctttttca gcagatcctt gtggcactca gaacatccat    660

tttgcactgt gtattttt                                                  679


<210> SEQ ID NO 115
<211> LENGTH: 449
<212> TYPE: DNA
<213> ORGANISM: Homo sapiens

<400> SEQUENCE: 115

aaatttttaa cttttaatag ttaaaatagt taactattgg tatggtagga aatgataaag     60

tagactagta tctgtataca ttttctgcat ttatgacata cctttttctt catttttttc    120

aatattttaa ttgaaaagtt catccgagtt tcatctaagt tttttcaaag tgatacaaat    180

ctccaaaaaa ttttccaata tatgtattga aaaaatccag gtgtaagtgg ctctgcgcag    240
```

-continued

```
tccaaacctg tgttgttcaa gggtcaactg tgtatgaatc caagcgaaag cttttcttaa    300

cacctcataa gaactatttt ttaaaaaaca ggaactagca tagagtaacc atcacaggta    360

aagtgtaatt tgttatcagc catcttttgc ccatttcagt actggtagaa ggctcaatgg    420

taaaaataaa aacgggacag tcagaaaaa                                      449
```

<210> SEQ ID NO 116
<211> LENGTH: 396
<212> TYPE: DNA
<213> ORGANISM: Homo sapiens

<400> SEQUENCE: 116

```
tctgagtaag aacaggcttt atttgtaaaa ccactcgtga ctctttacaa agcaggatac     60

acagaaggga aaaaaataca cagtgcaaaa tggatgttct gagtgccaca aggatctgct    120

gaaaaaagcc aaagatgtaa gatggctggg tatatatgag aatgaatatt tcactatatt    180

ctgattcaat taccagtctc agtggcccag gatgagcttt tggtgtggtc acatggccaa    240

catttggata acaaatgagg aataatggta ccgcctcact agtgcctgag aacagcatgt    300

tctggaaaat gtctctggag ttagagatgt gttagctttt tcattacaga tggagaaata    360

caatgtttac acaacagtcc aggggtgggg tcaaag                              396
```

<210> SEQ ID NO 117
<211> LENGTH: 232
<212> TYPE: DNA
<213> ORGANISM: Homo sapiens

<400> SEQUENCE: 117

```
ctgactgtcc cgtttttatt tttaccattg agccttctac cagtactgaa atgggcaaaa     60

gatggctgat aacaaattac actttacctg tgatggttac tctatgctag ttcctgtttt    120

ttaaaaaata gttcttatga ggtgttaaga aaagctttcg cttggattca tacacagttg    180

acccttgaac aacacaggtt tggactgcgc agagccaccc tcgtgccgaa tt            232
```

<210> SEQ ID NO 118
<211> LENGTH: 185
<212> TYPE: DNA
<213> ORGANISM: Homo sapiens

<400> SEQUENCE: 118

```
ctgactgtcc cgtttttatt tttaccattg agccttctac cagtactgaa atgggcaaaa     60

gatggctgat aacaaattac actttacctg tgatggttac tctatgctag ttcctgtttt    120

ttaaaaaata gttcttatga ggtgttaaga aaagctttcg cttggattca tacacagttg    180

accct                                                                185
```

<210> SEQ ID NO 119
<211> LENGTH: 726
<212> TYPE: DNA
<213> ORGANISM: Homo sapiens

<400> SEQUENCE: 119

```
ggaaatgata aagtagacta gtatctgtat acattttctg catttatgac ataccttttt     60

cttcattttt ttcaatattt taattgaaaa gttcatccga gtttcatcta agttttttca    120

aagtgataca aatctccaaa aaattttcca atatatgtat tgaaaaaatc caggtgtaag    180

tggctctgcg cagtccaaac ctgtgttgtt caagggtcaa ctgtgtatga atccaagcga    240

aagcttttct taacacctca taagaactat tttttaaaaa acaggaacta gcatagagta    300
```

-continued

```
accatcacag gtaaagtgta atttgttatc agccatcttt gcccatttca gtactggtag    360

aaggctcaat ggtaaaaata aaaacgggac agtcagaaga tctggaagtc ctgaccctgc    420

tttcacctgg catgtgtaat ccagtcatgc tcgtatcagt ctctgtagga gcacttgaag    480

gtattacata aatgctatct aactctggga aacgccaaca tgtgattgcc tccagaggaa    540

tcttctttaa aaaaaaattc aaaatgttat ttccttacta ggatgtcttt aaagaattat    600

aacccttacc gtgcctccac attagataga tccctgcaac agacccatgt ggcaccagca    660

gagacagcag gaggagaggc agcagctccc ggttgtttgt ctggaaaaac aaaggttatc    720

actttg                                                               726


<210> SEQ ID NO 120
<211> LENGTH: 185
<212> TYPE: DNA
<213> ORGANISM: Homo sapiens

<400> SEQUENCE: 120

ctgactgtcc cgtttttatt tttaccattg agccttctac cagtactgaa atgggcaaaa     60

gatggctgat aacaaattac actttacctg tgatggttac tctatgctag ttcctgtttt    120

ttaaaaaata gttcttatga ggtgttaaga aaagctttcg cttggattca tacacagttg    180

accct                                                                185


<210> SEQ ID NO 121
<211> LENGTH: 291
<212> TYPE: DNA
<213> ORGANISM: Homo sapiens

<400> SEQUENCE: 121

gcacgagatt attcctcatt tgttatccaa atgttggcca tgtgaccaca ccaaaagctc     60

atcctgggcc actgagactg gtaattgaat cagaatatag tgaaatattc attctcatat    120

atacccagcc atcttacatc tttggctttt ttcagcagat ccttgtggca ctcagaacat    180

ccattttgca ctgtgtattt ttttcccttc tgtgtatcct gctttgtaaa gagtcacgag    240

tggttttaca aataaagcct gttcttactc agaaaaaaaa aaaaaaaaaa a             291


<210> SEQ ID NO 122
<211> LENGTH: 795
<212> TYPE: DNA
<213> ORGANISM: Homo sapiens
<220> FEATURE:
<221> NAME/KEY: misc_feature
<222> LOCATION: (1)..(2)
<223> OTHER INFORMATION: a or g or c or t/u
<220> FEATURE:
<221> NAME/KEY: misc_feature
<222> LOCATION: (770)..(770)
<223> OTHER INFORMATION: a or g or c or t/u

<400> SEQUENCE: 122

nnttgaacag gcgtgacggt ccggattccc gggatgttgt gctctgccca caaacaggcg     60

tccctttccc tctggataac aacaaaagca agccgggagg ctggctgcct ctcctcctgc    120

tgtctctgct ggtggccaca tgggtgctgg tggcagggat ctatctaatg tggaggcacg    180

aaaggatcaa gaagacttcc ttttctacca ccacactact gccccccatt aaggttcttg    240

tggtttaccc atctgaaata tgtttccatc acacaatttg ttacttcact gaatttcttc    300

aaaaccattg cagaagtgag gtcatccttg aaaagtggca gaaaaagaaa atagcagaga    360
```

-continued

```
tgggtccagt gcagtggctt gccactcaaa agaaggcagc agacaaagtc gtcttccttc    420

tttccaatga cgtcaacagt gtgtgcgatg gtacctgtgg caagagcgag ggcagtccca    480

gtgagaactc tcaagacctc ttcccccttg cctttaacct tttctgcagt gatctaagaa    540

gccagattca tctgcacaaa tacgtggtgg tctactttag agagattgat acaaaagacg    600

attacaatgc tctcagtgtc tgccccaagt accacctcat gaaggatgcc actgctttct    660

gtgcagaact tctccatgtc aagcagcagg tgtcagcagg aaaaagatca caagcctgcc    720

acgatggctg ctgctccttg tagcccaccc atgagaagca agagaccttn aaggcttcct    780

atcccaccat tacag                                                     795
```

```
<210> SEQ ID NO 123
<211> LENGTH: 387
<212> TYPE: DNA
<213> ORGANISM: Homo sapiens

<400> SEQUENCE: 123

ttttttttt tttctgagta agaacaggct ttatttgtaa aaccactcgt gactctttac      60

aaagcaggat acacagaagg gaaaaaaata cacagggcaa aatggatgtt ctgagtgcca    120

caaggatctg ctgaaaaaag ccaaagatgt aagatggctg ggtatatatg agaatgaata    180

tttcactata ttctgattca attaccagtc tcagtggccc aggatgagct tttggtgtgg    240

tcacatggcc aacatttgga taacaaatga ggaataatgg taccgcctca ctagtgcctg    300

agaacagcat gttctggaaa atgtctctgg agttagagat gtgttagctt tttcattaca    360

gatggagaaa tacaatgttt acacaac                                        387
```

```
<210> SEQ ID NO 124
<211> LENGTH: 561
<212> TYPE: DNA
<213> ORGANISM: Homo sapiens

<400> SEQUENCE: 124

catgatgttc agtatgatca gttaacctta acctctgagc atcctgaagc aaaatctaaa     60

taatgcagct attaccactg gtggtccagg ctctggtgaa gccctctgag cccaggagga    120

agagaaagca ttgtccagag gtaggaacac agtctgggag cccagagctc tgggaggagt    180

gggaaaatgc tgcttcctgc tgcttgcttc taggcacctg cttccgccat ctcacttacc    240

atggctagag atgggggtga gactggggaa ggacaaaagc agggaacaga taagggatgg    300

aaatcagaag ggaatataga aagaactctg gatgtggaga aatgccggta cctgagcatt    360

ttgtatcaat gggagtaccc tctgtaactg ctcagtaggt tacaaatgaa gagtccacca    420

gtattagaaa caatttaaac ttgccagtac caactgggat gtgtgccttc aatttgaaaa    480

ttgtatgttt tattttttaa atttgttaac agcattaatt tatagagtat tgatgtcatt    540

tatgtttctg aggtgtttca a                                              561
```

```
<210> SEQ ID NO 125
<211> LENGTH: 476
<212> TYPE: DNA
<213> ORGANISM: Homo sapiens

<400> SEQUENCE: 125

tctgagtaag aacaggcttt atttgtaaaa ccactcgtga ctctttacaa agcaggatac     60

acagaaggga aaaaaataca cagtgcaaaa tggatgttct gagtgccaca aggatctgct    120

gaaaaaagcc aaagatgtaa gatggctggg tatatatgag aatgaatatt tcactatatt    180
```

-continued

```
ctgattcaat taccagtctc agtggcccag gatgagcttt tggtgtggtc acatggccaa    240

catttggata acaaatgagg aataatggta ccgcctcact agtgcctgag aacagcatgt    300

tctggaaaat gtctctggag ttagagatgt gttagctttt tcattacaga tggagaaata    360

caatgtttac acaacagtcc aggggtgggg tcaaaagttg gaaggtgtca ttagacgcag    420

ccaaataaag tgaagacaac ccaggtgact ggcagccctg acttgtgcgt gggcga        476


<210> SEQ ID NO 126
<211> LENGTH: 186
<212> TYPE: DNA
<213> ORGANISM: Homo sapiens

<400> SEQUENCE: 126

ctgactgtcc cgtttttatt tttaccattg agccttctac cagtactgaa atgggcaaaa     60

gatggctgat aacaaattac actttacctg tgatggttac tctatgctag tatcctgttt    120

tttaaaaaat agttcttatg aggtgttaag aaaagctttc gcttggattc atacacagtt    180

gaccct                                                               186


<210> SEQ ID NO 127
<211> LENGTH: 456
<212> TYPE: DNA
<213> ORGANISM: Homo sapiens
<220> FEATURE:
<221> NAME/KEY: misc_feature
<222> LOCATION: (255)..(255)
<223> OTHER INFORMATION: a or g or c or t/u
<220> FEATURE:
<221> NAME/KEY: misc_feature
<222> LOCATION: (260)..(260)
<223> OTHER INFORMATION: a or g or c or t/u
<220> FEATURE:
<221> NAME/KEY: misc_feature
<222> LOCATION: (307)..(307)
<223> OTHER INFORMATION: a or g or c or t/u
<220> FEATURE:
<221> NAME/KEY: misc_feature
<222> LOCATION: (350)..(350)
<223> OTHER INFORMATION: a or g or c or t/u
<220> FEATURE:
<221> NAME/KEY: misc_feature
<222> LOCATION: (406)..(406)
<223> OTHER INFORMATION: a or g or c or t/u
<220> FEATURE:
<221> NAME/KEY: misc_feature
<222> LOCATION: (431)..(431)
<223> OTHER INFORMATION: a or g or c or t/u
<220> FEATURE:
<221> NAME/KEY: misc_feature
<222> LOCATION: (446)..(446)
<223> OTHER INFORMATION: a or g or c or t/u

<400> SEQUENCE: 127

aggaagttaa gaacagtcct aaaatctctt tggcttcttt gtcctgatat gcaccggcat     60

tttcacagta ggaactaggg tttctgtcca gtttttttgg ttctttaagg aattaatgtt    120

attctgggta caactgctta catacatagc acatatagat gacattttta caggccgtct    180

tgttagactg acatacatgg aggatagtgc cacccgcctc acaagaacat caggtaagct    240

caggcacaga gtccnagggn atctgtaagg gcttcgccca cgcacaagtc agggctgcca    300

gtcaccnggg ttgtcttcac tttatttggg ctgcgtctaa tgacaccttn ccaacttttt    360

gaccccaccc tggggcttgt tgtgtaaacc attgttattt ctcccntctg taatggaaaa    420

aggttaacac ntttttaact tccggngaca tttttc                              456
```

-continued

<210> SEQ ID NO 128
<211> LENGTH: 1816
<212> TYPE: DNA
<213> ORGANISM: Homo sapiens

<400> SEQUENCE: 128
gcacgagcga tgtcgctcgt gctgctaagc ctggccgcgc tgtgcaggag cgccgtaccc 60
cgagagccga ccgttcaatg tggctctgaa actgggccat ctccagagtg gatgctacaa 120
catgatctaa tccccggaga cttgagggac ctccgagtag aacctgttac aactagtgtt 180
gcaacagggg actattcaat tttgatgaat gtaagctggg tactccgggc agatgccagc 240
atccgcttgt tgaaggccac caagatttgt gtgacgggca aaagcaactt ccagtcctac 300
agctgtgtga ggtgcaatta cacagaggcc ttccagactc agaccagacc ctctggtggt 360
aaatggacat tttcctacat cggcttccct gtagagctga acacagtcta tttcattggg 420
gcccataata ttcctaatgc aaatatgaat gaagatggcc cttccatgtc tgtgaatttc 480
acctcaccag gctgcctaga ccacataatg aaatataaaa aaaagtgtgt caaggccgga 540
agcctgtggg atccgaacat cactgcttgt aagaagaatg aggagacagt agaagtgaac 600
ttcacaacca ctcccctggg aaacagatac atggctctta tccaacacag cactatcatc 660
gggttttctc aggtgtttga gccacaccag aagaaacaaa cgcgagcttc agtggtgatt 720
ccagtgactg gggatagtga aggtgctacg gtgcagctga ctccatattt tcctacttgt 780
ggcagcgact gcatccgaca taaaggaaca gttgtgctct gcccacaaac aggcgtccct 840
ttccctctgg ataacaacaa aagcaagccg ggaggctggc tgcctctcct cctgctgtct 900
ctgctggtgg ccacatgggt gctggtggca gggatctatc taatgtggag gcacgaaagg 960
atcaagaaga cttccttttc taccaccaca ctactgcccc ccattaaggt tcttgtggtt 1020
tacccatctg aaatatgttt ccatcacaca atttgttact tcactgaatt tcttcaaaac 1080
cattgcagaa gtgaggtcat ccttgaaaag tggcagaaaa agaaaatagc agagatgggt 1140
ccagtgcagt ggcttgccac tcaaaagaag gcagcagaca aagtcgtctt ccttctttcc 1200
aatgacgtca acagtgtgtg cgatggtacc tgtggcaaga gcgagggcag tcccagtgag 1260
aactctcaag actcttcccc ttgcctttaa ccttttctgc agtgatctaa gaagccagat 1320
tcatctgcac aaatacgtgg tggtctactt tagagagatt gatacaaaag acgattacaa 1380
tgctctcagt gtctgcccca agtaccacct catgaaggat gccactgctt tctgtgcaga 1440
acttctccat gtcaagtagc aggtgtcagc aggaaaaaga tcacaagcct gccacgatgg 1500
ctgctgctcc ttgtagccca cccatgagaa gcaagagacc ttaaaggctt cctatcccac 1560
caattacagg gaaaaaacgt gtgatgatcc tgaagcttac tatgcagcct acaaacagcc 1620
ttagtaatta aaacatttta taccaataaa attttcaaat attgctaact aatgtagcat 1680
taactaacga ttggaaacta catttacaac ttcaaagctg ttttatacat agaaatcaat 1740
tacagtttta attgaaaact ataaccattt tgataatgca acaataaagc atcttcagcc 1800
aaaaaaaaaa aaaaaa 1816

<210> SEQ ID NO 129
<211> LENGTH: 1828
<212> TYPE: DNA
<213> ORGANISM: Homo sapiens

<400> SEQUENCE: 129
cggcgatgtc gctcgtgctg ataagcctgg ccgcgctgtg caggagcgcc gtaccccgag 60

-continued

```
agccgaccgt tcaatgtggc tctgaaactg ggccatctcc agagtggatg ctacaacatg    120

atctaatccc cggagacttg agggacctcc gagtagaacc tgttacaact agtgttgcaa    180

caggggacta ttcaattttg atgaatgtaa gctgggtact ccgggcagat gccagcatcc    240

gcttgttgaa ggccaccaag atttgtgtga cgggcaaaag caacttccag tcctacagct    300

gtgtgaggtg caattacaca gaggccttcc agactcagac cagaccctct ggtggtaaat    360

ggacattttc ctatatcggc ttccctgtag agctgaacac agtctatttc attggggccc    420

ataatattcc taatgcaaat atgaatgaag atggcccttc catgtctgtg aatttcacct    480

caccaggctg cctagaccac ataatgaaat ataaaaaaaa gtgtgtcaag gccggaagcc    540

tgtgggatcc gaacatcact gcttgtaaga agaatgagga gacagtagaa gtgaacttca    600

caaccactcc cctgggaaac agatacatgg ctcttatcca acacagcact atcatcgggt    660

tttctcaggt gtttgagcca caccagaaga aacaaacgcg agcttcagtg gtgattccag    720

tgactgggga tagtgaaggt gctacggtgc agctgactcc atattttcct acttgtggca    780

gcgactgcat ccgacataaa ggaacagttg tgctctgccc acaaacaggc gtccctttcc    840

ctctggataa caacaaaagc aagccgggag gctggctgcc tctcctcctg ctgtctctgc    900

tggtggccac atgggtgctg gtggcaggga tctatctaat gtggaggcac gaaaggatca    960

agaagacttc cttttctacc accacactac tgccccccat taaggttctt gtggtttacc   1020

catctgaaat atgtttccat cacacaattt gttacttcac tgaatttctt caaaaccatt   1080

gcagaagtga ggtcatcctt gaaaagtggc agaaaaagaa aatagcagag atgggtccag   1140

tgcagtggct tgccactcaa aagaaggcag cagacaaagt cgtcttcctt ctttccaatg   1200

acgtcaacag tgtgtgcgat ggtacctgtg gcaagagcga gggcagtccc agtgagaact   1260

ctcaagacct cttccccctt gcctttaacc ttttctgcag tgatctaaga agccagattc   1320

atctgcacaa atacgtggtg gtctacttta gagagattga tacaaaagac gattacaatg   1380

ctctcagtgt ctgccccaag taccacttca tgaaggatgc cactgctttc tgtgcagaac   1440

ttctccatgt caagcagcag gtgtcagcag gaaaaagatc acaagcctgc cacgatggct   1500

gctgctcctt gtagcccacc catgagaagc aagagacctt aaaggcttcc tatcccacca   1560

attacaggga aaaaacgtgt gatgatcctg aagcttacta tgcagcctac aaacagcctt   1620

agtaattaaa acattttata ccaataaaat tttcaaatat tactaactaa tgtagcatta   1680

actaacgatt ggaaactaca tttacaactt caaagctgtt ttatacatag aaatcaatta   1740

cagctttaat tgaaaactgt aaccattttg ataatgcaac aataaagcat cttccaaaaa   1800

aaaaaaaaaa aaaaaaaaaa aaaaaaaa                                      1828
```

<210> SEQ ID NO 130
<211> LENGTH: 2856
<212> TYPE: DNA
<213> ORGANISM: Homo sapiens
<220> FEATURE:
<221> NAME/KEY: misc_feature
<222> LOCATION: (1325)..(1325)
<223> OTHER INFORMATION: a or g or c or t/u

<400> SEQUENCE: 130

```
cggcgatgtc gctcgtgctg ataagcctgg ccgcgctgtg caggagcgcc gtaccccgag     60

agccgaccgt tcaatgtggc tctgaaactg ggccatctcc agagtggatg ctacaacatg    120

atctaatccc cggagacttg agggacctcc gagtagaacc tgttacaact agtgttgcaa    180
```

-continued

```
caggggacta ttcaattttg atgaatgtaa gctgggtact ccgggcagat gccagcatcc    240
gcttgttgaa ggccaccaag atttgtgtga cgggcaaaag caacttccag tcctacagct    300
gtgtgaggtg caattacaca gaggccttcc agactcagac cagaccctct ggtggtaaat    360
ggacattttc ctatatcggc ttccctgtag agctgaacac agtctatttc attggggccc    420
ataatattcc taatgcaaat atgaatgaag atggcccttc catgtctgtg aatttcacct    480
caccaggctg cctagaccac ataatgaaat ataaaaaaaa gtgtgtcaag gccggaagcc    540
tgtgggatcc gaacatcact gcttgtaaga agaatgagga gacagtagaa gtgaacttca    600
caaccactcc cctgggaaac agatacatgg ctcttatcca acacagcact atcatcgggt    660
tttctcaggt gtttgagcca caccagaaga aacaaacgcg agcttcagtg gtgattccag    720
tgactgggga tagtgaaggt gctacggtgc aggtaaagtt cagtgagctg ctctggggag    780
ggaagggaca tagaagactg ttccatcatt cattgctttt aaggatgagt tctctcttgt    840
caaatgcact tctgccagca gacaccagtt aagtggcgtt catgggggtt ctttcgctgc    900
agcctccacc gtgctgaggt caggaggccg acgtggcagt tgtggtccct tttgcttgta    960
ttaatggctg ctgaccttcc aaagcacttt ttattttcat tttctgtcac agacactcag   1020
ggatagcagt accattttac ttccgcaagc ctttaactgc aagatgaagc tgcaaagggt   1080
ttgaaatggg aaggtttgag ttccaggcag cgtatgaact ctggagaggg gctgccagtc   1140
ctctctgggc cgcagcggac ccagctggaa cacaggaagt tggagcagta ggtgctcctt   1200
cacctctcag tatgtctctt tcaactctag tttttgaagt ggggacacag gaagtccagt   1260
ggggacacag ccactcccca aagaataagg aacttccatg cttcattccc tggcataaaa   1320
agtgntcaaa cacaccagag ggggcaggca ccagccaggg tatgatgggt actacccttt   1380
tctggagaac catagacttc ccttactaca gggacttgca tgtcctaaag cactggctga   1440
aggaagccaa gaggatcact gctgctcctt ttttgtagag gaaatgtttg tgtacgtggt   1500
aagatatgac ctagcccttt taggtaagcg aactggtatg ttagtaacgt gtacaaagtt   1560
taggttcaga ccccgggagt cttgggcatg tgggtctcgg gtcactggtt ttgactttag   1620
ggctttgtta cagatgtgtg accaagggga aaatgtgcat gacaacacta gaggtagggg   1680
cgaagccaga aagaagggaa gttttggctg aagtaggagt cttggtgaga ttttgctgtg   1740
atgcatggtg tgaactttct gagcctcttg tttttcctca gctgactcca tattttccta   1800
cttgtggcag cgactgcatc cgacataaag gaacagttgt gctctgccca caaacaggcg   1860
tccctttccc tctggataac aacaaaagca agccgggagg ctggctgcct ctcctcctgc   1920
tgtctctgct ggtggccaca tgggtgctgg tggcagggat ctatctaatg tggaggcacg   1980
aaaggatcaa gaagacttcc ttttctacca ccacactact gccccccatt aaggttcttg   2040
tggtttaccc atctgaaata tgtttccatc acacaatttg ttacttcact gaatttcttc   2100
aaaaccattg cagaagtgag gtcatccttg aaaagtggca gaaaaagaaa atagcagaga   2160
tgggtccagt gcagtggctt gccactcaaa agaaggcagc agacaaagtc gtcttccttc   2220
tttccaatga cgtcaacagt gtgtgcgatg gtacctgtgg caagagcgag ggcagtccca   2280
gtgagaactc tcaagacctc ttcccccttg cctttaacct tttctgcagt gatctaagaa   2340
gccagattca tctgcacaaa tacgtggtgg tctactttag agagattgat acaaaagacg   2400
attacaatgc tctcagtgtc tgccccaagt accacttcat gaaggatgcc actgctttct   2460
gtgcagaact tctccatgtc aagcagcagg tgtcagcagg aaaaagatca caagcctgcc   2520
acgatggctg ctgctccttg tagcccaccc atgagaagca agagacctta aaggcttcct   2580
```

-continued

```
atcccaccaa ttacagggaa aaaacgtgtg atgatcctga agcttactat gcagcctaca   2640

aacagcctta gtaattaaaa cattttatac caataaaatt ttcaaatatt actaactaat   2700

gtagcattaa ctaacgattg gaaactacat ttacaacttc aaagctgttt tatacataga   2760

aatcaattac agctttaatt gaaaactgta accattttga taatgcaaca ataaagcatc   2820

ttccaaaaaa aaaaaaaaaa aaaaaaaaaa aaaaaa                             2856
```

<210> SEQ ID NO 131
<211> LENGTH: 1583
<212> TYPE: DNA
<213> ORGANISM: Homo sapiens

<400> SEQUENCE: 131

```
atgtcgctcg tgctgctaag cctggccgcg ctgtgcagga gcgccgtacc ccgagagccg     60

accgttcaat gtggctctga aactgggcca tctccagagt ggatgctaca acatgatcta    120

atcccgggag acttgaggga cctccgagta gaacctgtta caactagtgt tgcaacaggg    180

gactattcaa ttttgatgaa tgtaagctgg gtactccggg cagatgccag catccgcttg    240

ttgaaggcca ccaagatttg tgtgacgggc aaaagcaact tccagtccta cagctgtgtg    300

aggtgcaatt acacagaggc cttccagact cagaccagac cctctggtgg taaatggaca    360

ttttcctata tcggcttccc tgtagagctg aacacagtct atttcattgg ggcccataat    420

attcctaatg caaatatgaa tgaagatggc ccttccatgt ctgtgaattt cacctcacca    480

ggctgcctag accacataat gaaatataaa aaaaagtgtg tcaaggccgg aagcctgtgg    540

gatccgaaca tcactgcttg taagaagaat gaggagacag tagaagtgaa cttcacaacc    600

actcccctgg gaaacagata catggctctt atccaacaca gcactatcat cgggttttct    660

caggtgtttg agccacacca gaagaaacaa acgcgagctt cagtggtgat tccagtgact    720

ggggatagtg aaggtgctac ggtgcagctg actccatatt ttcctacttg tggcagcgac    780

tgcatccgac ataaaggaac agttgtgctc tgcccacaaa caggcgtccc tttccctctg    840

gataacaaca aaagcaagcc gggaggctgg ctgcctctcc tcctgctgtc tctgctggtg    900

gccacatggg tgctggtggc agggatctat ctaatgtgga ggcacgaaag gatcaagaag    960

acttcctttt ctaccaccac actactgccc cccattaagg ttcttgtggt ttacccatct   1020

gaaatatgtt tccatcacac aatttgttac ttcactgaat ttcttcaaaa ccattgcaga   1080

agtgaggtca tccttgaaaa gtggcagaaa aagaaaatag cagagatggg tccagtgcag   1140

tggcttgcca ctcaaaagaa ggcagcagac aaagtcgtct tccttctttc caatgacgtc   1200

aacagtgtgt gcgatggtac ctgtggcaag agcgagggca gtcccagtga gaactctcaa   1260

gacctcttcc cccttgcctt taaccttttc tgcagtgatc taagaagcca gattcatctg   1320

cacaaatacg tggtggtcta ctttagagag attgatacaa aagacgatta caatgctctc   1380

agtgtctgcc ccaagtacca cctcatgaag gatgccactg ctttctgtgc agaacttctc   1440

catgtcaagc agcaggtgtc agcaggaaaa agatcacaag cctgccacga tggctgctgc   1500

tccttgtagc ccacccatga gaagcaagag accttaaagg gttccttttc ccatcattta   1560

caggggaaaa acgtgtgatg atc                                           1583
```

<210> SEQ ID NO 132
<211> LENGTH: 2584
<212> TYPE: DNA
<213> ORGANISM: Homo sapiens -continued

<400> SEQUENCE: 132

```
catattagag tctacagata tgcctttctt acagcaatcc tgcacccaca taaaagctac     60
attttcaata caagattaaa aggtattctg caaaatgtgc aaggttttca tgtctgctgg    120
tgtagctgta gtgatggctt catgaatttt tttctttttt gactatggtc cttacgctgg    180
attcatttat cttgaaatgg tgaacaatca cagctgcaga ccctcaattt atggtacata    240
tcaagcaatt tggctttttt tcttgtaatg aaaaaaaaaa gttttttttg cttttttttca    300
tgacactgct tcttgggagc actgccagca ttactagtgg cacttcgtat gggtcctaag    360
gtgttattga aggtttacga tattgcacta aacacgaaaa ataccagaga accactggag    420
atacttttta ctgtgatatg taatttactg gagacaggaa ctgctcgttt ggagatggtt    480
agcatcacag ggtgttttaa gtcgatactt gcaacccttg agctcaccac agtagcaaca    540
ggaggtggct aggaaattat tcacagcagg acagtacgca ctgcaattaa ttgtatgcag    600
ttatgattta ataccacatc tttatgctca cgtttctctc aactgtgaat ggtgccatgt    660
acagttggta tgtgtgtgtt taagttttga taaattttta acttttaata gttaaaatag    720
ttaactattg gtatggtagg aaatgataaa gtagactagt atctgtatac attttctgca    780
tttatgacat accttttctt tcattttttt caatatttta attgaaaagt tcatccgagt    840
ttcatctaag ttttttcaaa gtgatacaaa tctccaaaaa attttccaat atatgtattg    900
aaaaaatcca ggtgtaagtg gctctgcgca gtccaaacct gtgttgttca agggtcaact    960
gtgtatgaat ccaagcgaaa gcttttctta acacctcata agaactattt tttaaaaaac   1020
aggaactagc atagagtaac catcacaggt aaagtgtaat ttgttatcag ccatcttttg   1080
cccatttcag tactggtaga aggctcaatg gtaaaaataa aaacgggaca gtcagaagat   1140
ctggaagtcc tgaccctgct ttcacctggc atgtgtaatc cagtcatgct cgtatcagtc   1200
tctgtaggag cacttgaagg tattacataa atgctatcta actctgggaa acgccaacat   1260
gtgattgcct ccagaggaat cttctttaaa aaaaaattca aaatgttatt tccttactag   1320
gatgtcttta aagaattata acccttaccg tgcctccaca ttagatagat ccctgccacc   1380
agcacccatg tggccaccag cagagacagc aggaggagag gcagccagcc tcccggcttg   1440
cttttgtctg gaaaaaacaa agcttattca cctttggaaa acaaatccac acttatctct   1500
taatttaaaa actaagactt ggtatacttt atagaggttt atttattttt tattattttt   1560
tagttttgag acagagtctc gctttgttgc ctaggctgga gtgcagtggc gcaatctcgg   1620
ttcactgcag cctccgtctc ccgggttcaa gcaatgctgc ctcagcctcc tgagtagctg   1680
ggattacagg catgtgtcac cgcgcccagc cactttgtag agatttagat ccctttaaaa   1740
ccatcagtca gaagctcttt agatagtctg ccaatcatat ctttttccct agagtgtgca   1800
ggtcttgcat tagattctca aaagggatat gggacccagg aagttaagaa cagtcctaaa   1860
atctctttgg cttctttgtc ctgatatgca ccggcatttt cacagtagga actagggttt   1920
ctgtccagtt tttttggttc tttaaggaat taatgttatt ctgggtacaa ctgcttacat   1980
acatagcaca tatagatgac atttttacag gccgtcttgt tagactgaca tacatggagg   2040
atagtgccac ccgcctcaca agaacatcag gtaagctcag gcacagagtg cccaggaatc   2100
tgtaaggctt cgcccacgca caagtcaggg ctgccagtca cctgggttgt cttcacttta   2160
tttggctgcg tctaatgaca ccttccaact tttgacccca cccctggact gttgtgtaaa   2220
cattgtattt ctccatctgt aatgaaaaag ctaacacatc tctaactcca gagacatttt   2280
ccagaacatg ctgttctcag gcactagtga ggcggtacca ttattcctca tttgttatcc   2340
```

-continued

```
aaatgttggc catgtgacca caccaaaagc tcatcctggg ccactgagac tagtaattga   2400
atcagaatat agtgaaatat tcattctcat atatacccag ccatcttaca tctttggctt   2460
ttttcagcag atccttgtgg cactcagaac atccattttg cactgtgtat ttttttccct   2520
tctgtgtatc ctgctttgta aagagtcacg agtggtttta caaataaagc ctgttcttac   2580
tcag                                                                2584
```

<210> SEQ ID NO 133
<211> LENGTH: 665
<212> TYPE: DNA
<213> ORGANISM: Homo sapiens

<400> SEQUENCE: 133

```
tttttttttt ttttttctga gtaagaacag gctttatttg taaaaccact cgtgactctt     60
tacaaagcag gatacacaga agggaaaaaa atacacagtg caaaatggat gttctgagtg    120
ccacaaggat ctgctgaaaa aagccaaaga tgtaagatgg ctgggtatat atgagaatga    180
atatttcact atattctgat tcaattacca gtctcagtgg cccaggatga gcttttggtg    240
tggtcacatg gccaacattt ggataacaaa tgaggaataa tggtaccgcc tcactagtgc    300
ctgagaacag catgttctgg aaaatgtctc tggagttaga gatgtgttag ctttttcatt    360
acagatggag aaatacaatg tttacacaac agtccagggg tggggtcaaa agttggaagg    420
tgtcattaga cgcagccaaa taaagtgaag acaacccagg tgactggcag ccctgacttg    480
tgcgtgggcg aagccttaca gattcctggg cactctgtgc ctgagcttac ctgatgttct    540
tgtgaggcgg gtggcactat cctccatgta tgtcagtcta acaagacggc ctgtaaaaat    600
gtcatctata tgtgctatgt atgtaagcag ttgtacccag aataacatta atcctcgtgc    660
cgaat                                                                665
```

<210> SEQ ID NO 134
<211> LENGTH: 664
<212> TYPE: DNA
<213> ORGANISM: Homo sapiens
<220> FEATURE:
<221> NAME/KEY: misc_feature
<222> LOCATION: (613)..(613)
<223> OTHER INFORMATION: a or g or c or t/u

<400> SEQUENCE: 134

```
tttttttttt tttttgttgg gctgaagatg ctttattatt gcattatcaa aatggttata     60
gttttcaatt aaaactgtaa ttgatttcta tgtataaaac agctttgaag ttgtaaatgt    120
agtttccaat cgttagttaa tgctacatta gttagcaata tttgaaaatt ttattggtat    180
aaaatgtttt aattactaag gctgtttgta ggctgcatag taagcttcag gatcatcaca    240
cgtttttttcc ctgtaattgg tgggatagga agcctttaag gtctcttgct tctcatgggt    300
gggctacaag gagcagcagc catcgtggca ggcttgtgat ctttttcctg ctgacacctg    360
ctgcttgaca tggagaagtt ctgcacagaa agcagtggca tccttcatga ggtggtactt    420
ggggcagaca ctgagagcat tgtaatcgtc ttttgtatca atctctctaa agtagaccac    480
cacgtatttg tgcagatgaa tctggcttct tagatcactg cagaaaaggt taaaggcaag    540
ggggaagagg tcttgagagt tctcactggg actgccctcg ctcttgccac aggtaccatc    600
gcacacactg ttnacgtcat tggaaagaag gaagacgact ttgtctgctg ccttcttttg    660
agtg                                                                664
```

-continued

<210> SEQ ID NO 135
<211> LENGTH: 739
<212> TYPE: DNA
<213> ORGANISM: Homo sapiens

<400> SEQUENCE: 135
tggtttttgt ttttttttca ttttctgttg gattacagaa aaagaatggg acccattcag 60
gtctcgattt ccaaaggtaa agatggaagg ctgggcagac tggcttttgt tacctgacat 120
gccgtagggt gagcttagag gaagaaagaa aacaattttt atttggccaa aacagaacaa 180
atgctgaaaa ggaaatcttg tttttttcct aaagccaaat agaaatgatt tgggtataat 240
ttaagagtcc ttgtgttgta cagatatggt gactgatgta gttattaata ctaccaactt 300
agtcatcaag cctcaatttt cctttacctg aaggattaag tgaaagcttt tggagttcat 360
gatgttcagt atgatcagtt aaccttaacc tctgagcatc ctgaagcaaa atctaaataa 420
tgcagctatt accactggtg gtccaggctc tggtgaagcc ctctgagccc aggaggaaga 480
gaaagcattg tccagaggta ggaacacagt ctgggagccc agagctctgg gaggagtggg 540
aaaatgctgc ttcctgctgc ttgcttctag gcacctgctt ccgccatctc acttaccatg 600
gctagagatg gggtgagac tggggaagga cacaagcagg gaacagataa gggatggaaa 660
tcagaaggga atatagaaag aactctggat gtggagacat gccggtacct gagcattttg 720
tatcaatggg agtacctct 739

<210> SEQ ID NO 136
<211> LENGTH: 657
<212> TYPE: DNA
<213> ORGANISM: Homo sapiens

<400> SEQUENCE: 136
tttttttttt ttttttttgg ctgaagatgc tttattgttg cattatcaaa atggttacag 60
ttttcaatta aagctgtaat tgatttctat gtataaaaca gctttgaagt tgtaaatgta 120
gtttccaatc gttagttaat gctacattag ttagcaatat ttgaaaattt tattggtata 180
aaatgtttta attactaagg ctgtttgtag gctgcatagt aagcttcagg atcatcacac 240 gttttttcc ctgtaattgg tgggatagga agcctttaag gtctcttgct tctcatgggt 300
gggctacaag gagcagcagc catcgtggca ggcttgtgat ctttttcctg ctgacacctg 360
ctgcttgaca tggagaagtt ctgcacagaa agcagtggca tccttcatga ggtggtactt 420
ggggcagaca ctgagagcat tgtaatcgtc ttttgtatca atctctctaa agtagaccac 480
cacgtatttg tgcagatgaa tctggcttct tagatcactg cagaaaaggt taaaggcaag 540
ggggaagagg tcttgagagt tctcactggg acttgcctcg ctcttgccac aggtaccatc 600
gcacacactg ttgacgtcat tggaaagaaa gaagacgact ttgtctgctg ccttctt 657

<210> SEQ ID NO 137
<211> LENGTH: 102
<212> TYPE: DNA
<213> ORGANISM: Homo sapiens

<400> SEQUENCE: 137
gctgaagatg ctttattgtt gcattatcaa aatggttaca gttttcaatt aaagctgtaa 60
ttgatttcta tgtataaaac agctttgaag ttgtaaatgt ag 102

<210> SEQ ID NO 138
<211> LENGTH: 187

-continued

<212> TYPE: DNA
<213> ORGANISM: Homo sapiens

<400> SEQUENCE: 138
cacgcgtccg attttatacc aataaaattt tcaaatattg ctaactaatg tagcattaac 60
taacgattgg aaactacatt tacaacttca aagctgtttt atacatagaa atcaattaca 120
gctttaattg aaaactgtaa ccattttgat aatgcaacaa taaagcatct tcagccaaaa 180
aaaaaaa 187

<210> SEQ ID NO 139
<211> LENGTH: 361
<212> TYPE: DNA
<213> ORGANISM: Homo sapiens

<400> SEQUENCE: 139
agaaaaagaa aatagcagag atgggtccag tgcagtggct tgcataaaaa agaaggcagc 60
agacaaagtc gtcttccttc tttccaatga cgtcaacagt gtgtgcgatg gtacctgtgg 120
caagagcgag ggcagtccca gtgagaactc tcaagacctc ttcccccctt gcctttaacc 180
ttttctgcag tgatctaaga agccagattc atctgcacaa atacgtggtg gtctacttta 240
gagagattga tacaaaagac gattacaatg ctctcagtgt ctgccccaag taccacctca 300
tgaaggatgc cactgctttc tgtgcagaac ttctccatgt caagcagcag gtttcagcag 360
g 361

<210> SEQ ID NO 140
<211> LENGTH: 783
<212> TYPE: DNA
<213> ORGANISM: Homo sapiens
<220> FEATURE:
<221> NAME/KEY: misc_feature
<222> LOCATION: (707)..(707)
<223> OTHER INFORMATION: a or g or c or t/u

<400> SEQUENCE: 140
tttttttttt ttttgtttgg ctgaagatgc tttattgttg cattatcaaa atggttacag 60
ttttcaatta aagctgtaat tgatttctat gtataaaaca gctttgaagt tgtaaatgta 120
gtttccaatc gttagttaat gctacattag ttagcaatat ttgaaaattt tattggtata 180
aaatgtttta attactaagg ctgtttgtag gctgcatagt aagcttcagg atcatcacac 240
gttttttccc tgtaattggt gggataggaa gcctttaagg tctcttgctt ctcatgggtg 300
ggctacaagg agcagcagcc atcgtggcag gcttgtgatc tttttcctgc tgacacctgc 360
tgcttgacat ggagaagttc tgcacagaaa gcagtggcat ccttcatgag gtggtacttg 420
gggcagacac tgagagcatt gtaatcgtct tttgtatcaa tctctctaaa gtagaccacc 480
acgtatttgt gcagatgaat ctggcttctt agatcactgc agaaaaggtt aaaggcaagg 540
gggaagaggt cttgagagtt ctcactggga ctgccctcgc tcttgccaca ggtaccatcg 600
cacacactgt tgacgtcatt ggaaagaagg aagacgactt tgtctgctgc cttcttttga 660
gtggcaagcc actgcactgg acccatctct gctattttct ttttctngca cttttcaagg 720
atgactcact tctgcaatgg tttttgagaa ttcagtgaag tacaaatgtg tgatggaaca 780
tat 783

<210> SEQ ID NO 141
<211> LENGTH: 399
<212> TYPE: DNA

-continued

<213> ORGANISM: Homo sapiens

<400> SEQUENCE: 141
cgctcgtgct gctaagcctg gccgcgctgt gcaggagcgc cgtaccccga gagccgaccg 60
ttcaatgtgg ctctgaaact gggccatctc cagagtggat gctacaacat gatctaatcc 120
ccggagactt gagggacctc cgagtagaac ctgttacaac tagtgttgca acaggggact 180
attcaatttt gatgaatgta agctgggtac tccgggcaga tgccacacca gaagaaacaa 240
acgcgagctt cagtggtgat tccagtgact ggggatagtg aaggtgctac ggtgcagctg 300
actccatatt ttcctacttg tggcagcgac tgcatccgac ataaaggaac agttgtgctc 360
tgcccacaaa caggcgtccc tttccctctg gataacaac 399

<210> SEQ ID NO 142
<211> LENGTH: 518
<212> TYPE: DNA
<213> ORGANISM: Homo sapiens
<220> FEATURE:
<221> NAME/KEY: misc_feature
<222> LOCATION: (503)..(503)
<223> OTHER INFORMATION: a or g or c or t/u

<400> SEQUENCE: 142
gctgagtgtg atggtgtaag cctgtggtcc cagctactag ggaggctgag atgggattac 60
aggtgtgagc cacggcgcct ggcctaaaag catctttttc tttaacgcag aggttatgtt 120
gtattattag cataaatgtt tttttctggg aatgcttatt tcacacagca caatactgaa 180
tcttctctgg aatgtggatc gatttcagat ggatgactat taaaatgtgt atatttgcag 240
attatcctta aagggccacc tcatgccttc taatttatgt cttacggata aaaaatcaaa 300
atgaagcata aagtaaaaac tgtgtccagc tttacaagtg gacgcttagt aatggctgag 360
gcaatatgtt taatgtagca aattttactt atttgtcatg atcagttttc acagtgcttg 420
taagtgctgg taatagaaga tggacatggt ttaggtcaaa acttggacca gaaaccaact 480
tcctttgaaa cagctctacc agntataaga gcaatatg 518

<210> SEQ ID NO 143
<211> LENGTH: 490
<212> TYPE: DNA
<213> ORGANISM: Homo sapiens

<400> SEQUENCE: 143
ctgttgacgt cattggaaag aaggaagacg actttgtctg ctgccttctt ttgagtggca 60
agccactgca ctggacccat ctctgctatt ttctttttct gccacttttc aaggatgacc 120
tcacttctgc aatggttttg aagaaattca gtgaagtaac aaattgtgtg atggaaacat 180
atttcagatg ggtaaaccac aagaacctta atgggggca gtagtgtggt ggtagaaaag 240
gaagtcttct tgatcctttc tgtgagagga gaaaagcatt tgttatctgt gaacagcaaa 300
cagcaggctt tcactctgta aaccatccct gacaaatgat cccttgctag agaatgtcag 360
ctgagcacca agggccttgt tagtgacagc aaggaaaaac atcctgatgt tcctttgaa 420 cacatcacct gaaacacact gatgcttaaa ccttaacttt ttttttttg gagacacagt 480 ctcactctgt 490

<210> SEQ ID NO 144
<211> LENGTH: 421
<212> TYPE: DNA
<213> ORGANISM: Homo sapiens -continued

<400> SEQUENCE: 144 ttttttttt tttttttct gagtaagaac aggctttatt tgtaaaacca ctcgtgactc 60
tttacaaagc aggatacaca gaagggaaaa aaatacacag tgcaaaatgg atgttctgag 120
tgccacaagg atctgctgaa aaaagccaaa gatgtaagat ggctgggtat atatgagaat 180
gaatatttca ctatattctg attcaattac cagtctcagt ggcccaggat gagcttttgg 240
tgtggtcaca tggccaacat ttggataaca aatgaggaat aatggtaccg cctcactagt 300
gcctgagaac agcatgttct ggaaaatgtc tctggagtta gagatgtgtt agctttttca 360
ttacagatgg agaaatacaa tgtttacaca acagtccagg ggtggggtca aaagttggaa 420
g 421

<210> SEQ ID NO 145
<211> LENGTH: 547
<212> TYPE: DNA
<213> ORGANISM: Homo sapiens

<400> SEQUENCE: 145 ttttttttt tttttttgg ctgaagatgc tttattgttg cattatcaaa atggttatag 60
ttttcaatta aaactgtaat tgatttctat gtataaaaca gctttgaagt tgtaaatgta 120
gtttccaatc gttagttaat gctacattag ttagcaatat ttgaaaattt tattggtata 180
aaatgtttta attactaagg ctgtttgtag gctgcatagt aagcttcagg atcatcacac 240 gtttttccc tgtaattggt gggataggaa gcctttaagg tctcttgctt ctcatgggtg 300
ggctacaagg agcagcagcc atcgtggcag gcttgtgatc tttttcctgc tgacacctgc 360
tgcttgacat ggagaagttc tgcacagaaa gcagtggcat ccttcatgag gtggtacgtg 420
gggcagacac tgagagcatt gtaatcgtct tttgtatcaa tctctctaaa gtagaccacc 480
acgtatttgt gcagatgaat ctggcttctt agatcactgc agaaaaggtt aaaggcaagg 540
gggaaga 547

<210> SEQ ID NO 146
<211> LENGTH: 644
<212> TYPE: DNA
<213> ORGANISM: Homo sapiens

<400> SEQUENCE: 146 ttttttttt tttttttga aagggtcagg acttccagat cttctgactg tcccgttttt 60
atttttacca ttgagccttc taccagtact gaaatgggca aaagatggct gataacaaat 120
tacactttac ctgtgatggt tactctatgc tagttcctgt tttttaaaaa atagttctta 180
tgaggtgtta agaaaagctt tcgcttggat tcatacacag ttgacccttg aacaacacag 240
gtttggactg cgcagagcca cttacacctg gatttttca atacatatat tggaaaattt 300
tttggagatt tgtatcactt tgaaaaaact tagatgaaac tcggatgaac ttttcaatta 360
aaatattgaa aaaaatgaag aaaaaggtat gtcataaatg cagaaaatgt atacagatac 420
tagtctactt tatcatttcc taccatacca atagttaact attttaacta ttaaaagtta 480
aaaatttatc aaaacttaaa cacacacata ccaactgtac atggcaccat tcacagttga 540
gagaaacgtg agcataaaga tgtggtatta aatcataact gcatacaatt aattgcagtg 600
cgtactgtcc tgctgtgaat atttcctagc cctcgtgccg aatc 644

<210> SEQ ID NO 147

-continued

<211> LENGTH: 470
<212> TYPE: DNA
<213> ORGANISM: Homo sapiens

<400> SEQUENCE: 147
gtgggtgacc gtggcttgcc actcaaaaga aggcagcaga caaagtcgtc ttccttcttt 60
ccaatgacgt caacagtgtg tgcgatggta cctgtggcaa gagcgagggc agtcccagtg 120
agaactctca agacctcttc cccttgcct ttaacctttt ctgcagtgat ctaagaagcc 180
agattcatct gcacaaatac gtggtggtct actttagaga gattgataca aaagacgatt 240
acaatgctct cagtgtctgc cccaagtacc acctcatgaa ggatgccact gctttctgtg 300
cataacttct ccatgtcaag cagcaggtgt cagcaggaaa aagatcacaa gcctgccacg 360
atggctgctg ctccttgtag cccacccatg agaagcaaga gaccttaaag gcttcctatc 420
ccaccaatta cagggaaaaa aacgtgtgat gatcctgaag ccacggtcaa 470

<210> SEQ ID NO 148
<211> LENGTH: 499
<212> TYPE: DNA
<213> ORGANISM: Homo sapiens

<400> SEQUENCE: 148
tagaggatcc cggtcgacgg tggttcagtg atcatcacac tttttccctg taataggtgg 60
gataggaagc ctttaaggtc tcttgcttct catgggtggg ctacaaggag cagcagccat 120
cgtggcaggc ttgtgatctt tttcctgctg acacctgctg cttgacatgg agaagttatg 180
cacagaaagc agtggcatcc ttcatgaggt ggtacttggg gcagacactg agagcattgt 240
aatcgtcttt tgtatcaatc tctctaaagt agaccaccac gtatttgtgc agatgaatct 300
ggcttcttag atcactgcag aaaaggttaa aggcaagggg gaagaggtct tgagagttct 360
cactgggact gccctcgctc ttgccacagg taccatcgca cacactgttg acgtcattgg 420
aaagaaggaa gacgactttg tctgctgcct tcttttgagt ggcaagccac ggtcaaccca 480
caagccacgg tcaacccac 499

<210> SEQ ID NO 149
<211> LENGTH: 615
<212> TYPE: DNA
<213> ORGANISM: Homo sapiens

<400> SEQUENCE: 149
tctacgtggt aagatatgac ctagcccttt taggtaagcg aactggtatg ttagtaacgt 60
gtacaaagtt taggttcaga ccccgggagt cttgggcatg tgggtctcgg gtcactggtt 120
ttgactttag ggctttgtta cagatgtgtg accaagggga aaatgtgcat gacaacacta 180
gaggtagggg cgaagccaga aagaagggaa gttttggctg aagtaggagt cttgcgactg 240
catccgacat aaaggaacag ttgtgctctg cccacaaaca ggcgtccctt tccctctgga 300
taacaacaaa agcaagccgg gaggctggct gcctctcctc ctgctgtctc tgctggtggc 360
cacatgggtg ctggtggcag ggatctatct aatgtggagg cacgaaagga tcaagaagac 420
ttccttttct accaccacac tactgccccc cattaaggtt cttgtggttt acccatctga 480
aatatgtttc catcacacaa tttgttactt cactgaattt cttcaaaacc attgcagaag 540
tgaggtcatc cttgaaagtg gcagagtagc agagatgggt ccagtgcagt ggcttgccac 600
tcgtgcgatg gtctt 615

-continued

<210> SEQ ID NO 150
<211> LENGTH: 636
<212> TYPE: DNA
<213> ORGANISM: Homo sapiens
<220> FEATURE:
<221> NAME/KEY: misc_feature
<222> LOCATION: (50)..(50)
<223> OTHER INFORMATION: a or g or c or t/u
<220> FEATURE:
<221> NAME/KEY: misc_feature
<222> LOCATION: (203)..(203)
<223> OTHER INFORMATION: a or g or c or t/u
<220> FEATURE:
<221> NAME/KEY: misc_feature
<222> LOCATION: (323)..(323)
<223> OTHER INFORMATION: a or g or c or t/u
<220> FEATURE:
<221> NAME/KEY: misc_feature
<222> LOCATION: (463)..(463)
<223> OTHER INFORMATION: a or g or c or t/u
<220> FEATURE:
<221> NAME/KEY: misc_feature
<222> LOCATION: (467)..(467)
<223> OTHER INFORMATION: a or g or c or t/u
<220> FEATURE:
<221> NAME/KEY: misc_feature
<222> LOCATION: (502)..(502)
<223> OTHER INFORMATION: a or g or c or t/u
<220> FEATURE:
<221> NAME/KEY: misc_feature
<222> LOCATION: (507)..(507)
<223> OTHER INFORMATION: a or g or c or t/u
<220> FEATURE:
<221> NAME/KEY: misc_feature
<222> LOCATION: (595)..(595)
<223> OTHER INFORMATION: a or g or c or t/u
<220> FEATURE:
<221> NAME/KEY: misc_feature
<222> LOCATION: (600)..(600)
<223> OTHER INFORMATION: a or g or c or t/u

<400> SEQUENCE: 150
ggcacgagca ctggctgaag gaagccaaga ggatcactgc tgctcctttn ttctagagga 60
aatgtttgtc tacgtggtaa gatatgacct agccctttta ggtaagcgaa ctggtatgtt 120
agtaacgtgt acaaagttta ggttcagacc ccgggagtct tgggcatgtg ggtctcgggt 180
cactggtttt gactttaggg ctntgttaca gatgtgtgac caaggggaaa atgtgcatga 240
caacactaga gctgactcca tattttccta cttgtggcag cgactgcatc cgacataaag 300
gaacagttgt gctctgccca canacaggcg tccctttccc tctggataac aacataagca 360
agccgggagg ctggctgcct ctcctcctgc tgtctctgct ggtggcacat gggtgctggt 420
ggagggatct atctaatgtg gaggcacgga tcaagaagac ttncttntct accaccacac 480
tactggcccc aataagggtc tngtggntac cccatctgaa tatgttcata cacaatttgt 540
actcactgaa ttctcaaaac attgagagtg aggcatcctg aaagtgcgaa aaganatgcn 600
aatggtcagt gcatgctgca ctagcagcat ggactt 636

<210> SEQ ID NO 151
<211> LENGTH: 676
<212> TYPE: DNA
<213> ORGANISM: Homo sapiens

<400> SEQUENCE: 151
gatcccgcgc agtggcccgg cgatgtcgct cgtgctgcta agcctggccg cgctgtgcag 60
gagcgccgta ccccgagagc cgaccgttca atgtggctct gaaactgggc catctccaga 120
gtggatgcta caacatgatc taatccccgg agacttgagg gacctccgag tagaacctgt 180

-continued

```
tacaactagt gttgcaacag gggactattc aattttgatg aatgtaagct gggtactccg    240

ggcagatgcc agcatccgct tgttgaaggc caccaagatt tgtgtgacgg gcaaaagcaa    300

cttccagtcc tacagctgtg tgaggtgcaa ttacacagag gccttccaga ctcagaccag    360

accctctggt ggtaaatgga cattttccta catcggcttc cctgtagagc tgaacacagt    420

ctatttcatt ggggcccata atattcctaa tgcaaatatg aatgaagatg gcccttccat    480

gtctgtgaat ttcacctcac caggctgcct agaccacata atgaaatata aaaaaaagtg    540

tgtcaaggcc ggaagcctgt gggatccgaa catcactgct tgtaagaaga atgaggagac    600

agtagaagtg aacttcacaa ccactcccct gggaaacaga tacatggctc ttatccaaca    660

cagcactatc attcgg                                                    676
```

```
<210> SEQ ID NO 152
<211> LENGTH: 722
<212> TYPE: DNA
<213> ORGANISM: Homo sapiens

<400> SEQUENCE: 152

gtcttgcatt agattctcaa aagggatatg ggacccagga agttaagaac agtcctaaaa     60

tctctttggc ttctttgtcc tgatatgcac cggcattttc acagtaggaa ctagggtttc    120

tgtccagttt ttttggttct ttaaggaatt aatgttattc tgggtacaac tgcttacata    180

catagcacat atagatgaca tttttacagg ccgtcttgtt agactgacat acatggagga    240

tagtgccacc cgcctcacaa gaacatcagg taagctcagg cacagagtgc ccaggaatct    300

gtaaggcttc gcccacgcac aagtcagggc tgccagtcac ctgggttgtc ttcactttat    360

ttggctgcgt ctaatgacac cttccaactt ttgaccccac ccctggactg ttgtgtaaac    420

attgtatttc tccatctgta atgaaaaagc taacacatct ctaactccag agacattttc    480

cagaacatgc tgttctcagg cactagtgag gcggtaccat tattcctcat ttgttatcca    540

aatgttggcc atgtgaccac accaaaagct catcctgggc cactgagact ggtaattgaa    600

tcagaatata gtgaaatatt cattctcata tatacccagc catcttacat ctttggcttt    660

tttcagcaga tccttgtggc actcagaaca tccattttgc actgtgtatt tttttccctt    720

ct                                                                   722
```

```
<210> SEQ ID NO 153
<211> LENGTH: 335
<212> TYPE: DNA
<213> ORGANISM: Homo sapiens

<400> SEQUENCE: 153

tgtgtaactc tcaagacctc ttccccctg cctttaacct tttctgcagt gatctaagaa      60

gccagattca tctgcacaaa tacgtggtgg tctactttag agagattgat acaaaagacg    120

attacaatgc tctcagtgtc tgccccaagt accacctcat ggaggatgcc actgctttct    180

gtgcagaact tctccatgtc aagtagcagg tgtcagcagg aaaaagatca caagcctgcc    240

acgatggctg ctgctccttg tagcccaccc atgagaagca agagacctta aaggcttcct    300

atcccaccaa ttacagggaa aaaacgtgtg atgat                               335
```

```
<210> SEQ ID NO 154
<211> LENGTH: 680
<212> TYPE: DNA
<213> ORGANISM: Homo sapiens
<220> FEATURE:
<221> NAME/KEY: misc_feature
```

-continued

<222> LOCATION: (591)..(591)
<223> OTHER INFORMATION: a or g or c or t/u

<400> SEQUENCE: 154
ctgaaatatg tttccatcac acaatttgtt acttcactga atttcttcaa aaccattgca 60
gaagtgaggt catccttgaa aagtggcaga aaaagaaaat agcagagatg ggtccagtgc 120
agtggcttgc cactcaaaag aaggcagcag acaaagtcgt cttccttctt tccaatgacg 180
tcaacagtgt gtgcgatggt acctgtggca agagcgaggg cagtcccagt gagaactctc 240
aagacctctt ccccttgcc tttaaccttt tctgcagtga tctaagaagc cagattcatc 300
tgcacaaata cgtggtggtc tactttagag agattgatac aaaagacgat tacaatgctc 360
tcagtgtctg ccccaagtac cacctcatga aggatgccac tgctttctgt gcagaacttc 420
tccatgtcaa gtagcaggtg tcagcaggaa aaagatcaca agcctgccac gatggctgct 480
gctccttgta gcccacccat gagaagcaag agaccttaaa ggcttcctat cccaccaatt 540
acagggaaaa aaacgtgtga tgatccctga agcttactat gcagcctaca nacagcctta 600
gtaataaaac attttatcca ataaaatttc aaattttgct taactatgtg cataaactac 660
gattgaaaac tctttacact 680

<210> SEQ ID NO 155
<211> LENGTH: 491
<212> TYPE: DNA
<213> ORGANISM: Homo sapiens

<400> SEQUENCE: 155
cattgtggtt gcagctgcat agtaagcttc aggatcatca cacgtttttt ccctgtaatt 60
ggtgggatag gaagccttta aggtctcttg cttctcatgg gtgggctaca aggagcagca 120
gccatcgtgg caggcttgtg atcttttttcc tgctgacacc tgctgcttga catggagaag 180
ttctgcacag aaagcagtgg catccttcat gaggtggtac ttggggcaga cactgagagc 240
attgtaatcg tcttttgtat caatctccct aaagtagacc accacgtatt tgtgcagatg 300
aatctggctt cttagatcac tgcagaaaag gttaaaggca agggggaaga ggtcttgaga 360
gttctcactg ggactgccct cgctcttgcc acaggtacca tcgcacacac tgttgacgtc 420
attggaaaga aggaagacga ctttgtctgc tgccttcttt tgagtggcaa gccactgcac 480
tggacccatc t 491

<210> SEQ ID NO 156
<211> LENGTH: 533
<212> TYPE: DNA
<213> ORGANISM: Homo sapiens

<400> SEQUENCE: 156
gtgaataagc tttgtttttt ccagacaaaa gcaagccagg aggctggctg cctctcctcc 60
tgctgtctct gctggtggcc acatggttgc tggtggcagg gatctatcta atgtggaggc 120
acggtaaggg ttataattct ttaaagtcat cctagtaagg aaataacatt tggaattttt 180
ttttaaagaa gattcctctg gaggcaatca cctgttggcg tttcccagag ttagatagca 240
tttatgtaat accttcaagt gctcctacag agactgatac gagcatgact ggattacaca 300
tgccaggtga aagcagggcc aggacttcca gatcttctga ctgtcccgtt tttattttta 360
ccattgagcc ttctaccaga actgaaatgg gcaaaagatg gctgataaca aattacactt 420
tacctgtgat ggttactcta tgctagttcc tgtttttaaa aaaatagttc ttatgaggtg 480

-continued

```
tcaagaaaag ctttcgcttg gattcataca cagttgaccc ttgaacaaca cag          533


<210> SEQ ID NO 157
<211> LENGTH: 218
<212> TYPE: DNA
<213> ORGANISM: Homo sapiens
<220> FEATURE:
<221> NAME/KEY: misc_feature
<222> LOCATION: (119)..(120)
<223> OTHER INFORMATION: a or g or c or t/u
<220> FEATURE:
<221> NAME/KEY: misc_feature
<222> LOCATION: (199)..(199)
<223> OTHER INFORMATION: a or g or c or t/u

<400> SEQUENCE: 157

gatcctgaag cttactatgc agcctacaaa cagccttagt aattaaaaca ttttatacca     60

ataaaatttt caaatattgc taactaatgt agcattaact aacgattgga aactacatnn    120

acaacttcaa agctgtttta tacatagaaa tcaattacag ctttaattga aaactataac    180

cattttgata atgcaacant aaagcatctt cagccaaa                            218


<210> SEQ ID NO 158
<211> LENGTH: 703
<212> TYPE: DNA
<213> ORGANISM: Homo sapiens
<220> FEATURE:
<221> NAME/KEY: misc_feature
<222> LOCATION: (554)..(554)
<223> OTHER INFORMATION: a or g or c or t/u
<220> FEATURE:
<221> NAME/KEY: misc_feature
<222> LOCATION: (703)..(703)
<223> OTHER INFORMATION: a or g or c or t/u

<400> SEQUENCE: 158

gcaacttcca gtcctacagc tgtgtgaggt gcaattacac agaggccttc cagactcaga     60

ccagaccctc tggtggtaaa tggacatttt cctatatcgg cttccctgta gagctgaaca    120

cagtctattt cattggggcc cataatattc ctaatgcaaa tatgaatgaa gatggccctt    180

ccatgtctgt gaatttcacc tcaccaggct gcctagacca cataatgaaa tataaaaaaa    240

agtgtgtcaa ggccggaagc ctgtgggatc cgaacatcac tgcttgtaag aagaatgagg    300

agacagtaga agtgaacttc acaaccactc ccctgggaaa cagatacatg gctcttatcc    360

aacacagcac tatcatcggg ttttctcagg tgtttgagcc acaccagaag aaacaaacgc    420

gagcttcagt ggtgattcca gtgactgggg atagtgaagg tgctacggtg cagctgactc    480

catattttcc tacttgtggc agcgactgca tccgacataa aggaacagtt gtgctctgcc    540

cacaaacagg cgtncctttt cctctggata acaacaaaag caagccggga ggcttggctg    600

ctctccttct gctggccttt gctgtggcca cattggtgct ggtggcaggg atctatctaa    660

tgtggatgca cgtctcgtgg tttacccatc tgaaatatgt tcn                      703


<210> SEQ ID NO 159
<211> LENGTH: 893
<212> TYPE: DNA
<213> ORGANISM: Homo sapiens
<220> FEATURE:
<221> NAME/KEY: misc_feature
<222> LOCATION: (798)..(798)
<223> OTHER INFORMATION: a or g or c or t/u
<220> FEATURE:
<221> NAME/KEY: misc_feature
<222> LOCATION: (805)..(805)
<223> OTHER INFORMATION: a or g or c or t/u
```

-continued

<400> SEQUENCE: 159

```
attttcctc ttgtggcagc gactggcatc cgacataaag gaacagttgt gctctgccca     60
caaacaggcg tccctttccc tctggataac aacaaaagca agccgggagg ctggctgcct    120
ctcctcctgc tgtctctgct ggtggccaca tgggtgctgg tggcagggat ctatctaatg    180
tggaggcacg aaaggatcaa gaagacttcc ttttctacca ccacactact gccccccatt    240
aaggttcttg tggtttaccc atctgaaata tgtttccatc acacaatttg ttacttcact    300
gaatttcttc aaaaccattg cagaagtgag gtcatccttg aaaagtggca gaaaaagaaa    360
atagcagaga tgggtccagt gcagtggctt gccactcaaa agaaggcagc agacaaagtc    420
gtcttccttc tttccaatga cgtcaacagt gtgtgcgatg gtacctgtgg caagagcgag    480
ggcagtccca gtgagaactc tcaagacctc ttcccccttg cctttaacct tttctgcagt    540
gatctaagaa gccagattca tctgcacaaa tacgtggtgg tctactttag agagattgat    600
acaaaagacg attacaatgc tctcagtgtc tgccccaagt accacctcat gaaggatgcc    660
actgctttct gtgcagaact tctccatgtc aagcagcagg tgtcagcagg aaaaagatca    720
caagcctgcc acgatggctg ctgctccttg tagcccaccc atgagaagca agagacctta    780
aggcttctat cccaccanta caggnaaaaa cgtgtgatga tcctgaagct tactatgcag    840
cctacaacag gcttagtatt aaaacattta tacccataaa ttttcaaatt gct           893
```

<210> SEQ ID NO 160
<211> LENGTH: 959
<212> TYPE: DNA
<213> ORGANISM: Homo sapiens

<400> SEQUENCE: 160

```
taggtgacac tatagaacaa gtttgtacaa aaaagcaggc tggtaccggt ccggaattcc     60
cgggatagtg gmccggcgak gtcgctcgtg ctgctaagcc tggccgcgct gtgcaggagc    120
gccgtacccc gagagccgac cgttcaatgt ggctctgaaa ctgggccatc tccaragtgg    180
atgskacaac atgatctaat cccgggagac ttgagggacc tccgagtaga acctgttaca    240
actagtgttg caacagggga ctattcaatt ttgatgaatg taagctgggt actccgggsa    300
gatgccagca tccgcttgtt gaaggccacc aagatttgtg tgamgggcaa aagcaacwtc    360
cagtcctaca gcwgtgtgag gtagcaatta cacagagagc acatatccag actctagacc    420
agaccctctg gwggtaaatg gacattttcc tatatcggct tccctgtaga gctgaacaca    480
gtctatattc attggggccc awaatawwcc taatgcaaat atgaatgaag atggcccttc    540
catgtctgtg aatttcacct caccaggctg cctagaccac ataatgaaat awaaaaaaaa    600
gtgtgtcaag gccggaagcc tgtgggatcc gaacatcact gcttgtaaga agaatgarga    660
gacagtagaa gtgaacttca caaccactcc cctgggaaac agatamatkg ctcttatcca    720
acacarmact atcatcgggt tttctcaggt gtttgagcca caccagaaga aacaaacgcg    780
agcttcagtg gtgattccag tgactgggga tagtgaaggt gctacggtgc agctgactcc    840
atattttcct acttgtggca gcgwctgcat ccgacataaa ggaacagttg tgctctgccc    900
acaaacaggc gtccctttyc ctctggataa caacaaaagc aacygggags tggytgyct     959
```

<210> SEQ ID NO 161
<211> LENGTH: 1200
<212> TYPE: DNA
<213> ORGANISM: Homo sapiens
<220> FEATURE:

-continued

<221> NAME/KEY: misc_feature
<222> LOCATION: (15)..(15)
<223> OTHER INFORMATION: a or g or c or t/u
<220> FEATURE:
<221> NAME/KEY: misc_feature
<222> LOCATION: (35)..(35)
<223> OTHER INFORMATION: a or g or c or t/u
<220> FEATURE:
<221> NAME/KEY: misc_feature
<222> LOCATION: (43)..(43)
<223> OTHER INFORMATION: a or g or c or t/u
<220> FEATURE:
<221> NAME/KEY: misc_feature
<222> LOCATION: (45)..(45)
<223> OTHER INFORMATION: a or g or c or t/u
<220> FEATURE:
<221> NAME/KEY: misc_feature
<222> LOCATION: (48)..(48)
<223> OTHER INFORMATION: a or g or c or t/u

<400> SEQUENCE: 161
waatwakadd ratanhtgaa aactataacc atttntgata atngnaanaa taaagcatct 60
tcagccaaac atctagtctt ccatagacca tgcattgcag tgtacccaga wctgtttagc 120
taatattcta tgtttaatta atgaatacta actctaagaa cccctcactg attcactcaa 180
tagcatctta agtgaaaaac cttctattac atgcaaaaaa tcattgtttt taagataaca 240
aaagtaggga ataaacaagc tgaacccact tttactggac caaatgatct attatatgtg 300
taaccacttg tatgatttgg tatttgcata agaccttccc tctacaaact agattcatat 360
cttgattctt gtacaggtgc cttttaacat gaacaacaaa atacccacaa acttgtctac 420
ttttgcctaa agttacctat tagaggtcac tgtsagagtk ctcagtttct tagttactat 480
ttaastttts atgttcaaaa tgaaaataat tctkaagtkg aaagsgctct tgaagtaacc 540
tttttataaa tgagttatta taatggttta cttaaataaa avagaggggk ttttgcggtg 600
gctcatgcct ccaatcccag cactttggca aggccaaggc aaaavgatcg ctcaagacca 660
ggctacgtca caaagcgaga cctccatctc tacaaaagat ttaaaaaatt agctgagtgt 720
gatggtgtga gcctgtggtc ccagctacta gggaggctga gatgggagga tcacttgagc 780
cctggaggtc aagggtgcag taaacggtga ttgtgccact gcactccatc ctgggtgaga 840
gcagaccctg tctaaaacaa acaaacgaaa aaaccccccac agaatgacag aacataaaag 900
atgcacattt tgtcttccaa ctttttactc ttctaaaagc atcttttttta aattttttaa 960 attttttttt ttttgagaca gagtttcact ctgtcacaca ggctggagtg mgtggcgtga 1020
ctcggctcac tamaactctg cytccggggt yacscatctc ctgcwcagct cctgagaagc 1080
kggayamagg mccacacaaa ccagtaaytt tatwttttga aaaagggtty acctgtasma 1140
graggctgaa tccgacmaar tmaccmccac yycaaadgag gawaagkgkr smggscbggc 1200

<210> SEQ ID NO 162
<211> LENGTH: 899
<212> TYPE: DNA
<213> ORGANISM: Homo sapiens
<220> FEATURE:
<221> NAME/KEY: misc_feature
<222> LOCATION: (483)..(483)
<223> OTHER INFORMATION: a or g or c or t/u
<220> FEATURE:
<221> NAME/KEY: misc_feature
<222> LOCATION: (485)..(485)
<223> OTHER INFORMATION: a or g or c or t/u

<400> SEQUENCE: 162
ttatgggggg cagtagtgtg gtggtagaaa aggaagtctt cttgatcctt tcgtgcctcc 60

-continued

```
cattagatag atccctgcca ccagcaccca tgtggccacc agcagagaca gcaggaggag    120
aggcagccag cctcccggct tgcttttgtt gttatccaga gggaaaggga cgcctgtttg    180
tgggcagagc acaactgttc ctttatgtcg gatgcagtcg ctgccacaag taggaaaata    240
tggagtcagc tgcaccgtag caccttcact atccccagtc actggaatca ccactgaagc    300
tcgcgtttgt ttcttctggt gtggctcaaa cacctgagaa aacccgatga tagtgctgtg    360
ttggataaga gccatgtatc tgtttcccag gggagtggtt gtgaagttca cttctactgt    420
ctcctcattc ttcttacaag cagtgatgtt cggatcccac aggcttccgg ccttgacaca    480
ctntntttta tatttcatta tgtggtctag gcagcctggt gaggtgaaat tcacagacat    540
ggaagggcca tcttcattca tatttgcatt aggaatatta tgggccccaa tgaaatagac    600
tgtgttcagc tctacagggg aagccgatat aggaaaatgt ccatttacca ccagagggtc    660
tggtctgagt cttgaaggcc ttttgtgtta ttgcacctta cacagctgtt agactgggaa    720
gttgcttttg ccccgcacac aaatcttgtg ggccttcaac agcggatgct gccatttgcc    780
ccgaagtccc cagctcaatt cattaaaaat tgaataggcc ccttgtggca accctagttg    840
gtacagggtt ttacttgggg ggcccctcta agtttccccg ggatataaac aaagtgtgg     899
```

<210> SEQ ID NO 163
<211> LENGTH: 877
<212> TYPE: DNA
<213> ORGANISM: Homo sapiens

<400> SEQUENCE: 163

```
ttatgggggg cagtagtgtg gtggtagaaa aggaagtctt cttgatcctt tcgtgcctcc     60
acattagata gatccctgcc accagcaccc atgtggccac cagcagagac agcaggagga    120
gaggcagcca gcctcccggc ttgcttttgt tgttatccag agggaaaggg acgcctgttt    180
gtgggcagag cacaactgtt cctttatgtc ggatgcagtc gctgccacaa gtaggaaaat    240
atggagtcag ctgcaccgta gcaccttcac tatccccagt cactggaatc accactgaag    300
ctcgcgtttg tttcttctgg tgtggctcaa acacctgaga aaacccgatg atagtgctgt    360
gttggataag agccatgtat ctgtttccca ggggagtggt tgtgaagttc acttctactg    420
tctcctcatt cttcttacaa gcagtgatgt tcggatccca caggcttccg gccttgacac    480
actttttttt atatttcatt atgtggtcta ggcagcctgg tgaggtgaaa ttcacagaca    540
tggaagggcc atcttcattc atatttgcat taggaatatt atgggcccca atgaaataga    600
ctgtgttcag ctctacaggg aagccgatat aggaaaatgt ccatttacca ccagagggtc    660
tggtctgagt ctggaaggcc tctgtgtaat tgcacctcac acagctgtag gactgggagt    720
tgcttttgcc cgtacacaaa tcttgttggc cttcaacaag cggatgctgg catctggcgg    780
gggtacccag cttacattca tcaaaattga atagtcccct tgttgcaaca ctagtttgta    840
aacaggttct actccggggg tcccctcagt ctcccgg                             877
```

<210> SEQ ID NO 164
<211> LENGTH: 419
<212> TYPE: DNA
<213> ORGANISM: Homo sapiens

<400> SEQUENCE: 164

```
caaatatgaa tgaagatggc ccttccatgt ctgtgaattt cacctcacca ggctgcctag     60
accacataat gaaatataaa aaaaagtgtg tcaaggccgg aagcctgtgg gatccgaaca    120
```

-continued tcactgcttg taagaagaat gaggagacag tagaagtgaa cttcacaacc actcccctgg 180
gaaacagata catggctctt atccaacaca gcactatcat cgggttttct caggtgtttg 240
agccacacca gaagaaacaa acgcgagctt cagtggtgat tccagtgact ggggatagtg 300
aaggtgctac ggtgcaactg actccatatt ttcctacttg tggcagcgac tgcatccgac 360
ataaaggaac agttgtgctc tgcccacaaa caggcgtccc tttccctctg gataacaac 419

<210> SEQ ID NO 165
<211> LENGTH: 420
<212> TYPE: DNA
<213> ORGANISM: Homo sapiens

<400> SEQUENCE: 165
gcaaatatga atgaagatgg cccttccatg tctgtgaatt tcacctcacc aggctgccta 60
gaccacataa tgaaatataa aaaaaagtgt gtcaaggccg gaagcctgtg ggatccgaac 120
atcactgctt gtaagaagaa tgaggagaca gtagaagtga acttcacaac cactcccctg 180
ggaaacagat acatggctct tatccaacac agcactatca tcgggttttc tcaggtgttt 240
gagccacacc agaagaaaca aacgcgagct tcagtggtga ttccagtgac tggggatagt 300
gaaggtgcta cggtgcagct gactccatat tttcctactt gtggcagcga ctgcatccga 360
cataaaggaa cagttgtgct ctgcccacaa acaggcgtcc ctttccctct ggataacaac 420

<210> SEQ ID NO 166
<211> LENGTH: 676
<212> TYPE: DNA
<213> ORGANISM: Homo sapiens

<400> SEQUENCE: 166
gcaaatatga atgaagatgg cccttccatg tctgtgaatt tcacctcacc aggctgccta 60
gaccacataa tgaaatataa aaaaaagtgt gtcaaggccg gaagcctgtg ggatccgaac 120
atcactgctt gtaagaagaa tgaggagaca gtagaagtga acttcacaac cactcccctg 180
ggaaacagat acatggctct tatccaacac agcactatca tcgggttttc tcaggtgttt 240
gagccacacc agaagaaaca aacgcgagct tcagtggtga ttccagtgac tggggatagt 300
gaaggtgcta cggtgcagct gactccatat tttcctactt gtggcagcga ctgcatccga 360
cataaaggaa cagttgtgct ctgcccacaa acaggcgtcc ctttccctct ggataacaac 420
aaaagcaagc cgggaggctg gctgcctctc ctcctgctgt ctctgctggt ggccacatgg 480
gtgctggtgg cagggatcta tctaatgtgg aggcacgaaa ggatcaagaa gacttccttt 540
tttaccacca cactactgtc tcccattaaa gatcttgtgg tttatccatc tgaaatattg 600
ttccattaca catattggta cctaactgaa attctttaaa accattgcaa attgaggtca 660
ctcttgaaag ggcgtg 676

<210> SEQ ID NO 167
<211> LENGTH: 517
<212> TYPE: DNA
<213> ORGANISM: Homo sapiens

<400> SEQUENCE: 167
cggctcctac cttttgcccg atccccttcc ccattccgcc cccgccccaa cgcagtgcac 60
agtgccctgc acacagtagt cgctcaataa atgttcgtgg atgatgatga tgatgatgat 120
gaaaaaaatg cagcatcaac ggcagcagca agcggaccac gcgaacgagg caaactatgc 180
aagaggcacc agacttcctc tttctggtga aggaccaact tctcagctga atagctccaa 240

-continued gcaaactgtc ctgtcttggc aagctgcaat cgatgctgct agacaggcca aggctgccca 300
aactatgagc acctctgcac ccccacctgt aggatctctc tcccaaagaa aacgtcagca 360
atacgccaag agcaaaaaac agggtaactc gtccaacagc cgacctgccc gcgccctttt 420
ctgtttatca ctcaataacc ccatccgaag agcctgcatt agtatagtgg aatggaaaca 480
tttgacatat ttatattatt ggctattttt tgccaat 517

<210> SEQ ID NO 168
<211> LENGTH: 860
<212> TYPE: DNA
<213> ORGANISM: Homo sapiens

<400> SEQUENCE: 168
gaatatgacc ctgaggcaaa gggaaggata aacaccttga tgtggtcact ctgcttcgac 60
gcatccagcc tcccctgggg tttgggaagt tatgtccaca cagggtagcg tgcaagagat 120
tagttgccat gaacatgcct ctcaacagtg acgggacagt catgtttaat gcaaccctgt 180
ttgctttggt tcgaacggct cttaagatca agaccgaagg gaacctggag caagctaatg 240
aagaacttcg ggctgtgata aagaaaattt ggaagaaaac cagcatgaaa ttacttgacc 300
aagttgtccc tccagctggt gatgatgagg taaccgtggg gaagttctat gccactttcc 360
tgatacagga ctactttagg aaattcaaga aacggaaaga acaaggactg gtgggaaagt 420
accctgcgaa gaacaccaca attgccctac aggcgggatt aaggacactg catgacattg 480
ggccagaaat ccggcgtgct atatcgtgtg atttgcaaga tgacgagcct gaggaaacaa 540
aacgagaaga agaagatgat gtgttcaaaa gaaatggtgc cctgcttgga aaccatgtca 600
atcatgttaa tagtgatagg agagattccc ttcagcagac caatagcacc accgtcccct 660
gcattgtcca aaggccttca attccacctg caagtgatac tgagaaaccg ctgtttcctc 720
cagcaggaaa ttcggggtgt cataaccatc ataaccatta attccatagg aaagcaaggt 780
tcccacttca acaatgccag tctcgaatag tgccaatatg tccaaagctt gccatggtaa 840
gcgggccagc attgggaacc 860

<210> SEQ ID NO 169
<211> LENGTH: 495
<212> TYPE: DNA
<213> ORGANISM: Homo sapiens

<400> SEQUENCE: 169
gcacgagatt aattagactt ttgtataaga gatgtcatgc ctcaagaaag ccataaacct 60
ggtaggaaca ggtcccaagc ggttgagcct ggcagagtac catgcgctcg gccccagctg 120
caggaaacag caggccccgc cctctcacag aggatgggtg aggaggccag acctgccctg 180
ccccattgtc cagatgggca ctgctgtgga gtctgcttct cccatgtacc agggcaccag 240
gcccacccaa ctgaaggcat ggcggcgggg tgcaggggaa agttaaaggt gatgacgatc 300
atcacacctg tgtcgttacc tcagccatcg gtctagcata tcagtcactg ggcccaacat 360
atccattttt aaaccctttc ccacaaatac actgcgtcct ggttcctgtt tagctgttct 420
gaaatacggt gtgtaagtaa gtcagaaccc agctaccagt gattattgcg agggcaatgg 480
gacctcataa ataag 495

<210> SEQ ID NO 170
<211> LENGTH: 557
<212> TYPE: DNA

-continued

<213> ORGANISM: Homo sapiens

<400> SEQUENCE: 170
tttttttttt tttttttag tggggaacta caattattag gacccatgga tattgctgca 60
gttcaaatac aatacagtaa ttacaaaata tagaccatct ctttacaaat acaaattata 120
gtatattaca agtcatgtac agtaaatcta taattttaaa caaactagtg tatctaagtt 180
tacctggttg cgagtgcatt attattccag tttacagttg cccttagcgt gacagtcaga 240
aaccgaccat cggagtgata ttctcttatg taaactggcg tcacatcaca gaaaacctta 300
tttatgaggt cccattgccc tcgcaataat cactggtagc tgggttctga cttacttaca 360
caccgtattt cagaacagct aaacaggaac caggacgcag tgtatttgtg ggaaagggtt 420
taaaaatgga tatgttgggc ccagtgactg atatgctaga ccgatggctg aggtaacgac 480
acaggtgtga tgatcgtcat cacctttaac tttcccctgc accccgccgc catgccttcc 540
agttgggtgg gcctggt 557

<210> SEQ ID NO 171
<211> LENGTH: 416
<212> TYPE: DNA
<213> ORGANISM: Homo sapiens

<400> SEQUENCE: 171
ctctgagcac tacaatcagc cagattggtt gacacagatt caagatattg ccaacaaagt 60
cctcttggct ctgttcacct gcgagatgct ggtaaaaatg tacagcttgg gcctccaagc 120
atactcttgt tctctttaca accggtttga ttgcttcgtg gtgtgtggtg gaatcactga 180
gacgatcttg gtggaactgg aaatcatgtc tcccctgggg atctctgtgt ttcggtgtgt 240
gcgcctctta agaatcttca aagtgaccag gcactggact tccctgagca acttagtggc 300
atccttatta aactccatga agtccatcgc ttcgctgttg cttctgcttt ttctcttcat 360
tatcatcttt tccttgcttg ggatgcagct gtttggcggc aagtttaatt ttgatg 416

<210> SEQ ID NO 172
<211> LENGTH: 401
<212> TYPE: DNA
<213> ORGANISM: Homo sapiens
<220> FEATURE:
<221> NAME/KEY: misc_feature
<222> LOCATION: (365)..(365)
<223> OTHER INFORMATION: a or g or c or t/u

<400> SEQUENCE: 172
accagcagac ctgactgtcc ccagcagctt ccggaacaaa aacagcgaca agagaggagt 60
gcggacagtt ggtggaggca gtcctgatat ccgaagcttg ggacgctatg caagggaccc 120
aaaatttgtg tcagcaacaa aacacgaaat cgctgatgcc tgtgacctca ccatcgacga 180
gatggagagt gcagccagca ccctgcttaa tgggaacgtg cgtccccgag ccaacgggga 240
tgtgggcccc ctctcacacc ggcagactat gagctacagg actttggtcc tgggcttaca 300
gcgacgaaga gccagaccct ggggagggat tgagggagga cctgggcgga tgaattgatt 360
ttgcntcacc acctttgtta ggccccccagg cgaggggcaa g 401

<210> SEQ ID NO 173
<211> LENGTH: 186
<212> TYPE: DNA
<213> ORGANISM: Homo sapiens
<220> FEATURE:
<221> NAME/KEY: misc_feature -continued
<222> LOCATION: (11)..(11)
<223> OTHER INFORMATION: a or g or c or t/u
<220> FEATURE:
<221> NAME/KEY: misc_feature
<222> LOCATION: (172)..(172)
<223> OTHER INFORMATION: a or g or c or t/u

<400> SEQUENCE: 173 ttttttttt nttttttttt ttgtggaaag atgataggtt tatagtgact caaaatattt 60
tagaaaaatt tctgtagtgt caagttcttt caaacttaaa attttaaccc cagaggattt 120
tcgctgaata aatgagaatt ggctctattt cttctacttc tggatagccc gngtaaaaat 180
actaat 186

<210> SEQ ID NO 174
<211> LENGTH: 433
<212> TYPE: DNA
<213> ORGANISM: Homo sapiens
<220> FEATURE:
<221> NAME/KEY: misc_feature
<222> LOCATION: (45)..(45)
<223> OTHER INFORMATION: a or g or c or t/u
<220> FEATURE:
<221> NAME/KEY: misc_feature
<222> LOCATION: (296)..(296)
<223> OTHER INFORMATION: a or g or c or t/u
<220> FEATURE:
<221> NAME/KEY: misc_feature
<222> LOCATION: (303)..(303)
<223> OTHER INFORMATION: a or g or c or t/u
<220> FEATURE:
<221> NAME/KEY: misc_feature
<222> LOCATION: (345)..(345)
<223> OTHER INFORMATION: a or g or c or t/u
<220> FEATURE:
<221> NAME/KEY: misc_feature
<222> LOCATION: (366)..(366)
<223> OTHER INFORMATION: a or g or c or t/u
<220> FEATURE:
<221> NAME/KEY: misc_feature
<222> LOCATION: (386)..(386)
<223> OTHER INFORMATION: a or g or c or t/u
<220> FEATURE:
<221> NAME/KEY: misc_feature
<222> LOCATION: (391)..(391)
<223> OTHER INFORMATION: a or g or c or t/u
<220> FEATURE:
<221> NAME/KEY: misc_feature
<222> LOCATION: (420)..(420)
<223> OTHER INFORMATION: a or g or c or t/u
<220> FEATURE:
<221> NAME/KEY: misc_feature
<222> LOCATION: (428)..(428)
<223> OTHER INFORMATION: a or g or c or t/u

<400> SEQUENCE: 174
tttttttttt tttttttttt tgtggaaaga tgataggttt atagngactc aaaatatttt 60
agaaaaattt ctgtagtgtc aagttctttc aaacttaaaa ttttaacccc agaggatttt 120
cgctgaataa atgagaattg gctctatttc ttctacttct ggatagcccg agtaaaaata 180
ctaataattt ctagatttta gtggggaact acaattatta ggacccatgg atattgctgc 240
agttcaaata caatacagta attacaaaat atagaccatc tctttacaaa tacaanttat 300
agnatattac aagtcatgta cagtaaatct ataattttgg acaanctagt gtatctaagt 360
ttaccngggg tgcgagtgcc ttattnttcc ngtttacagt tgcccttagc gtgacagtcn 420
ggaaccgncc ttc 433

<210> SEQ ID NO 175

<211> LENGTH: 331
<212> TYPE: DNA
<213> ORGANISM: Homo sapiens
<220> FEATURE:
<221> NAME/KEY: misc_feature
<222> LOCATION: (61)..(61)
<223> OTHER INFORMATION: a or g or c or t/u

<400> SEQUENCE: 175
gcctgactgt ccccagcagc ttccggaaca aaaacagcga caagcagagg agtgcggaca 60
ntttggtgga ggcagtcctg atatccgaag cttgggacgc tatgcaaggg acccaaaatt 120
tgtgtcagca acaaaacacg aaatcgctga tgcctgtgac ctcaccatcg acgagatgga 180
gagtgcagcc agcaccctgc ttaatgggaa cgtgcgtccc cgagccaacg gggatgtggg 240
ccccctctca caccggcaga ctatgagcta caggactttg gtcctgggct acagcgacga 300
agagccagac cctgggaggg atgaggagga c 331

<210> SEQ ID NO 176
<211> LENGTH: 643
<212> TYPE: DNA
<213> ORGANISM: Homo sapiens

<400> SEQUENCE: 176
agcggtcgta ataatgtagt tccccactaa aatctagaaa ttattagtat ttttactcgg 60
gctatccaga agtagaagaa atagagcaaa ttctcattta ttcagcgaaa atcctctggg 120
gttaaaattt taagttgaaa gaacttgaca ctacagaaat tttctaaaa tatttgagtc 180 actataaacc tatcatcttt ccacaagata taccagatga ctattgcagt cttctcttgg 240
gcaagagttc catgatttga tactgtacct tggatccacc atgggtgcaa ctgtcttggt 300
ttgttgttga cttgaaccac cctctggtaa gtaagtgaat tacagagcag gtctagctgg 360
ctgctctgcc ccttgggtat ccatagttac ggttttctct gtggcccacc caggtgtttt 420
tgcatcgctg gtgcagaaat gcacaggtgg atgagatata gctgctcttg tcctctgggg 480
actggtggtg ctgcttaaga aataaggggt gctggggaca gaggagcaac gtggtgatct 540
ataggattgg agtgtcgggg tctgtacaaa tcgtattgtt gccttttaca aaactgtgta 600
ctgtatgttc tctttgaggg cttttgtatg caattgaatg agg 643

<210> SEQ ID NO 177
<211> LENGTH: 357
<212> TYPE: DNA
<213> ORGANISM: Homo sapiens

<400> SEQUENCE: 177
ttttcttgtg gaaagatgat aggtttatag tgactcaaaa tattttagaa aaatttctgt 60
agtgtcaagt tctttcaaac ttaaaatttt aaccccagag gattttcgct gaataaatga 120
gaattggctc tatttcttct acttctggat agcccgagta aaaatactaa taatttctag 180
attttagtgg ggaactacaa ttattaggac ccatggatat tgctgcagtt caaatacaat 240
acagtaatta caaaatatag accatctctt tacaaataca aattatagta tattacaagt 300
catgtacagt aaatctataa ttttaaacaa acctgtgtat ctaagtttac ctggttg 357

<210> SEQ ID NO 178
<211> LENGTH: 420
<212> TYPE: DNA
<213> ORGANISM: Homo sapiens

<400> SEQUENCE: 178

```
gacaaataaa gcaattataa atgtatctca ctttagaaca gacaaaaaaa gggcatgcta     60
tggaaattgt ttaaatctca agcaacaatg ctgattaatt tctggtcaat aatcgttcta    120
tagttctcct tcatgaagcc tggtgaggtt ccaggaaaca gcttgatttg ggaagcctca    180
gcagaaaaga aagcatctca gaggacacat aaaatgtctg gcaacccctc ttggcggccc    240
tcatccagca aagcttgtgt ggtcttggca actgtcctca ggactctgct ttcaagatga    300
aagaggtgta gcttacccgc tcaatacacc aagtacaaga tttagtacga aaaatgaccc    360
aaagatgacg agactgacaa gatacaccca gggcaattcc aatcccatag catcattcat    420
```

<210> SEQ ID NO 179
<211> LENGTH: 465
<212> TYPE: DNA
<213> ORGANISM: Homo sapiens

<400> SEQUENCE: 179

```
tttatattat tcaccacttt gttatgaaga ccttacaaac ctcttcttaa gacattctta     60
ctctgatcca ggcaaaaaca cttcaaggtt tgtaaatgac tctttcctga cataaatcct    120
tttttattaa aatgcaaaat gttcttcaga ataaaactgt gtaataattt ttatacttgg    180
gagtgctcct tgcacagagc tgtcatttgc cagtgagagc ctccgacagg gcaggtactg    240
tgccagggca gctctgaaat tatggatatt cttatcctcc tggttccttc ggtgccaatg    300
gtaacctaat accagccgca gggagcgcca tttctcctaa agggctacac cactgtcaac    360
attatcctgg actctgtgtc tctctctgtt gggtcttgtg gcatcacatc aggccaaaat    420
tgccagacca ggaccctaag tgtctgatag aggcgatgat ctttt                    465
```

<210> SEQ ID NO 180
<211> LENGTH: 330
<212> TYPE: DNA
<213> ORGANISM: Homo sapiens

<400> SEQUENCE: 180

```
tttttttttt tttttttttt tcttacaaag aaaaatttaa tattcgatga gaggttgaac     60
caggcttaaa gcaaacatac taggaaatgg ggcagcctgt aagaatgcca gtttgtaagt    120
actgactttg gaaaagatca tcgcctctat cagacactta gggtcctggt ctggcaattt    180
tggcctgatg tgatgccaca agacccaaca gagagagaca cagagtccag gataatgttg    240
acagggggta gccctttagg agaaatggcg ctccctgcgg ctggtattag gttaccattg    300
gcaccgaagg aaccaggagg ataagaatat                                     330
```

<210> SEQ ID NO 181
<211> LENGTH: 502
<212> TYPE: DNA
<213> ORGANISM: Homo sapiens

<400> SEQUENCE: 181

```
tgtaaataac aaacaccact ttgttatgaa gaccttacaa acctcttctt aagacattct     60
tactctgatc caggcaaaaa cacttcaagg tttgtaaatg actctttcct gacataaatc    120
ctttttttatt aaaatgcaaa atgttcttca gaataaaact gtgtaataat ttttatactt    180
gggagtgctc cttgcacaga gctgtcattt gccagtgaga gcctccgacg ggcaggtac    240
tgtgccaggg cagctctgaa attatggata ttcttatcct cctggttcct tcggtgccaa    300
tggtaaccta ataccagccg cagggagcgc catttctcct aaagggctac accactgtca    360
```

| | |
|---|---|
| acattatcct ggactctgtg tctctctctg ttgggtcttg tggcatcaca tcaggccaaa | 420 |
| attgccagac caggacccta agtgtctgat agaggcgatg atcttttcca aagtcagtac | 480 |
| ttacaaactg gcattcttac ag | 502 |

<210> SEQ ID NO 182
<211> LENGTH: 410
<212> TYPE: DNA
<213> ORGANISM: Homo sapiens

<400> SEQUENCE: 182

| | |
|---|---|
| ttttttttt tgtaaataac aaacaccact ttgttatgaa gaccttacaa acctcttctt | 60 |
| aagacattct tactctgatc caggcaaaaa cacttcaagg tttgtaaatg actctttcct | 120 |
| gacataaatc cttttttatt aaaatgcaaa atgttcttca gaataaaact gtgtaataat | 180 |
| ttttatactt gggagtgctc cttgcacaga gctgtcattt gccagtgaga gcctccgacg | 240 |
| gggcaggtac tgtgccaggg cagctctgaa attatggata ttcttatcct cctggttcct | 300 |
| tcggtgccaa tggtaaccta ataccagccg cagggagcgc catttctcct aaagggctac | 360 |
| accactgtca acattatcct ggactctgtg tctctctctg ttgggtcttg | 410 |

<210> SEQ ID NO 183
<211> LENGTH: 333
<212> TYPE: DNA
<213> ORGANISM: Homo sapiens

<400> SEQUENCE: 183

| | |
|---|---|
| gtaaataaca aacaccactt tgttatgaag accttacaaa cctcttctta agacattctt | 60 |
| actctgatcc aggcaaaaac acttcaaggt ttgtaaatga ctctttcctg acataaatcc | 120 |
| ttttttatta aaatgcaaaa tgttcttcag aataaaactg tgtaataatt tttatacttg | 180 |
| ggagtgctcc ttgcacagag ctgtcatttg ccagtgagag cctccgacgg gcaggtactg | 240 |
| tgccagggca gctctgaaat atggatattc ttacctcctg gttctttcgg tgcaaatggt | 300 |
| aacctaatac cagccgcagg gagcgccatt tct | 333 |

<210> SEQ ID NO 184
<211> LENGTH: 282
<212> TYPE: DNA
<213> ORGANISM: Homo sapiens
<220> FEATURE:
<221> NAME/KEY: misc_feature
<222> LOCATION: (231)..(231)
<223> OTHER INFORMATION: a or g or c or t/u

<400> SEQUENCE: 184

| | |
|---|---|
| gtaaataaca aacaccactt tgttatgaag accttacaaa cctcttctta agacattctt | 60 |
| actctgatcc aggcaaaaac acttcaaggt ttgtaaatga ctctttcctg acataaatcc | 120 |
| ttttttatta aaatgcaaaa tgttcttcag aataaaactg tgtaataatt tttatacttg | 180 |
| ggagtgctcc ttgcacagag ctgtcatttg ccagtgagag cctccgacgg ngcaggtact | 240 |
| gtgccagggc agctctgaat tatggatatt cttatcctcc tg | 282 |

<210> SEQ ID NO 185
<211> LENGTH: 400
<212> TYPE: DNA
<213> ORGANISM: Homo sapiens

<400> SEQUENCE: 185

| | |
|---|---|
| tttttcttac aaagaaaaat ttaatattcg atgagaggtt gaaccaggct taaagcagac | 60 |

-continued

```
atactaggaa atggtgcagc ctgtaagaat gccagtttgt aagtactgac tttggaaaag    120

atcatcgcct ctatcagaca cttagggtcc tggtctggca attttggcct gatgtgatgc    180

cacaagaccc aacagagaga gacacagagt ccaggataat gttgacagtg gtgtagccct    240

ttaggagaaa tggcgctccc tgcggctggt attaggttac cattggcacc gaaggaacca    300

ggaggataag aatatccata atttcagagc tgccctggca cagtacctgc cccgtcggag    360

gctctcactg gcaaatgaca gctctgtgca aggagcactc                         400
```

<210> SEQ ID NO 186
<211> LENGTH: 482
<212> TYPE: DNA
<213> ORGANISM: Homo sapiens

<400> SEQUENCE: 186

```
ttatcttgtg gaaagatgat aggtttatag tgactcaaaa tattttagaa aaatttctgt     60

agtgtcaagt tctttcaaac ttaaaatttt aaccccagag gattttcgct gaataaatga    120

gaattggctc tatttcttct acttctggat agcccgagta aaaatactaa taatttctag    180

attttagtgg ggaactacaa ttattaggac ccatggatat tgctgcagtt caaatacaat    240

acagtaatta caaaatatag accatctctt tacaaataca aattatagga tattacaagg    300

catgtacagt aaatctataa ttttaaacaa actagtgtat ctaagtttac ctggttgcga    360

gtgcattatt attccagttt acagttgccc ttagcgtgac agtcagaaac cgaccatcgg    420

agtgatattc tcttatgtaa actggcgtca catcacagaa aaccttattt atgaggtccc    480

at                                                                   482
```

<210> SEQ ID NO 187
<211> LENGTH: 459
<212> TYPE: DNA
<213> ORGANISM: Homo sapiens

<400> SEQUENCE: 187

```
gccctcacag cccaccacgc ctggccttcg cccaattctg aaacttcgta ggatagagct     60

ggaaagtgcc acatggtgaa gcgagatcca gctgtctggg tggatgtcgg agtccatagg    120

ctgagcagag atggttctta gtgaggttct cgctgccagt tgacggtgaa atcatagctg    180

ccatttacat tttgtgagat tatgaaaaac ataagactaa agaaactaaa tgtgttattc    240

ctgtggacac aaaaatgtgt gtttttcaga tggggagggg accaaaaagg aaaaacattt    300

catcttaaaa ctttcctaag acaaaggaaa acaaaaaacc atgctcctac aacttcaaat    360

ttttcttacc aaagaaaaat ttaatattcg atgagaggtt gaaccaggct taaagcagac    420

atactaggga atgggtgcag cctgtaagaa tgccagttt                           459
```

<210> SEQ ID NO 188
<211> LENGTH: 487
<212> TYPE: DNA
<213> ORGANISM: Homo sapiens

<400> SEQUENCE: 188

```
gtaaataaca aacaccactt tgttatgaag accttacaaa cctcttctta agacattctt     60

actctgatcc aggcaaaaac acttcaaggt ttgtaaatga ctctttcctg acataaatcc    120

ttttttatta aaatgcaaaa tgttcttcag aataaaactg tgtaataatt tttatacttg    180

ggagtgctcc ttgcacagag ctgtcatttg ccagtgagag cctccgacgg ggcaggtact    240
```

-continued gtgccagggc agctctgaaa ttatggatat tcttatcctc ctggttcctt cggtgccaat 300
ggtaacctaa taccagccgc aggagcgcca tttctcctaa agggctacac cactgtcaac 360
attatcctgg gactctgtgt ctctctctgt tgggtcttgt ggcatcacat caggccaaaa 420
ttggccagac caggacccca agtggtctga tagaaggcga tgatcttttc caaagtcagt 480
acttaca 487

<210> SEQ ID NO 189
<211> LENGTH: 445
<212> TYPE: DNA
<213> ORGANISM: Homo sapiens

<400> SEQUENCE: 189
gtttaaaatt atagatttac tgtacatgac ttgtaatata ctataatttg tatttgtaaa 60
gagatggtct atattttgta attactgtat tgtatttgaa ctgcagcaat atccatgggt 120
cctaataatt gtagttcccc actaaaatct agaaattatt agtattttta ctcgggctat 180
ccagaagtag aagaaataga gccaattctc atttattcag cgaaaatcct ctggggttaa 240
aattttaagt ttgaaagaac ttgacactac agaaattttt ctaaaatatt ttgagtcact 300
ataaacctat catctttcca caagatatac cagatgacta tttgcagtct tttctttggg 360
caagagttcc atgattttga tactgtacct ttggatccac catgggttgc aactgtcttt 420
ggttttgttt gtttgacttg aacca 445

<210> SEQ ID NO 190
<211> LENGTH: 313
<212> TYPE: DNA
<213> ORGANISM: Homo sapiens

<400> SEQUENCE: 190
ttcgctgaat aaatgagaat tggctctatt tcttctactt ctggatagcc cgagtaaaaa 60
tactaataat ttctagattt tagtggggaa ctacaattat taggacccat ggatattgct 120
gcagttcaaa tacaatacag taattacaaa atatagacca tctctttaca aatacaaatt 180
atagtatatt acaagtcatg tacagtaaat ctataatttt aaacaaacta gtgtatctaa 240
gtttacctgg ttgcgagtgc attattattc cagtttacag ttgcccttag cgtgacagtc 300
agaaaccgac cat 313

<210> SEQ ID NO 191
<211> LENGTH: 413
<212> TYPE: DNA
<213> ORGANISM: Homo sapiens

<400> SEQUENCE: 191
ttttatcttg tggaaagatg ataggtttat agtgactcaa aatattttag aaaaatttct 60
gtagtgtcaa gttctttcaa acttaaaatt ttaaccccag aggattttcg ctgaataaat 120
gagaattggc tctatttctt ctacttctgg atagcccgag taaaaatact aataatttct 180
agattttagt ggggaactac aattattagg acccatggat attgctgcag ttcaaataca 240
atacagtaat tacaaaatat agaccatctc tttacaaata caaattatag tatattacaa 300
gtcatgtaca gtaaatctat aattttaaac aaactagtgt atctaagttt acctggttgc 360
gagtgcatta ttattccagt ttacagttgc ccttagcgtg acagtcagaa acc 413

<210> SEQ ID NO 192
<211> LENGTH: 476

-continued

<212> TYPE: DNA
<213> ORGANISM: Homo sapiens

<400> SEQUENCE: 192
ttttatcttg tggaaagatg ataggtttat agtgactcaa aatattttag aaaaatttct 60
gtagtgtcaa gttctttcaa acttaaaatt ttaaccccag aggattttcg ctgaataaat 120
gagaattggc tctatttctt ctacttctgg atagcccgag taaaaatact aataatttct 180
agattttagt ggggaactac aattattagg acccatggat attgctgcag ttcaaataca 240
atacagtaat tacaaaatat agaccatctc tttacaaata caaattatag tatattacaa 300
gtcatgtaca gtaaatctat aattttaaac aaactagtgt atctaagttt acctggttgc 360
gagtgcatta ttattccagt ttacagttgc ccttagcgtg acagtcagaa accgaccatc 420
ggagtgatat tctcttatgt aaactggcgt cacatcacag aaaaccttat ttattt 476

<210> SEQ ID NO 193
<211> LENGTH: 406
<212> TYPE: DNA
<213> ORGANISM: Homo sapiens

<400> SEQUENCE: 193 ttttttttt agagccaatt ctcatttatt cagcgaaaat cctctggggt taaaatttta 60
agtttgaaag aacttgacac tacagaaatt tttctaaaat attttgagtc actataaacc 120
tatcatcttt ccacaagata taccagatga ctatttgcag tcttttcttt gggcaagagt 180
tccatgattt tgatactgta cctttggatc caccatgggt tgcaactgtc tttggttttg 240
tttgtttgac ttgaaccacc ctctggtaag taagtgaatt acagagcagg tccagctggc 300
tgctctgccc cttgggtatc catagttacg gttttctctg tggcccaccc agggtgtttt 360
ttgcatcgct ggtgcagaaa tgcacaggtg gatgagatat agctgc 406

<210> SEQ ID NO 194
<211> LENGTH: 473
<212> TYPE: DNA
<213> ORGANISM: Homo sapiens

<400> SEQUENCE: 194
tttttttttg taaataacaa acaccacttt gttatgaaga ccttacaaac ctcttcttaa 60
gacattctta ctctgatcca ggcaaaaaca cttcaaggtt tgtaaatgac tctttcctga 120
cataaatcct tttttattaa aatgcaaaat gttcttcaga ataaaactgt gtaataattt 180
ttatacttgg gagtgctcct tgcacagagc tgtcatttgc cagtgagagc ctccgacagg 240
gcaggtactg tgccagggca gctctgaaat tatggatatt cttatcctcc tggttccttc 300
ggtgccaatg gtaacctaat accagccgca gggagcgcca tttctcctaa agggctacac 360
cactgtcaac attatcctgg actctgtgtc tctctctgtt gagtcttgtg gcatcacatc 420
aggccaaaat tgccagacca ggaccctaag tgtctgatag aggcgatgat ctt 473

<210> SEQ ID NO 195
<211> LENGTH: 463
<212> TYPE: DNA
<213> ORGANISM: Homo sapiens

<400> SEQUENCE: 195
tttagagcca attctcattt attcagcgaa aatcctctgg ggttaaaatt ttaagtttga 60
aagaacttga cactacagaa atttttctaa aatattttga gtcactataa acctatcatc 120

-continued

```
tttccacaag atataccaga tgactatttg cagtcttttc tttgggcaag agttccatga    180

ttttgatact gtacctttgg atccaccatg ggttgcaact gtctttggtt ttgtttgttt    240

gacttgaacc accctctggt aagtaagtga attacagagc aggtccagct ggctgctctg    300

ccccttgggt atccatagtt acggttttct ctgtggccca cccagggtgt tttttgcatc    360

gctggtgcag aaatgcacag gtggatgaga tatagctgct cttgtcctct ggggactggt    420

ggtgctgctt aagaaataag gggtgctggg gacagaggag caa                      463


<210> SEQ ID NO 196
<211> LENGTH: 140
<212> TYPE: DNA
<213> ORGANISM: Homo sapiens

<400> SEQUENCE: 196

tttttttttt ttttgtaaat aacaaacacc actttgttat gaagacctta caaacctctt     60

cttaagacat tcttactctg atccaggcaa aaacacttca aggtttgtaa atgactcttt    120

cctgacataa atcctttttg                                                140


<210> SEQ ID NO 197
<211> LENGTH: 237
<212> TYPE: DNA
<213> ORGANISM: Homo sapiens
<220> FEATURE:
<221> NAME/KEY: misc_feature
<222> LOCATION: (208)..(208)
<223> OTHER INFORMATION: a or g or c or t/u
<220> FEATURE:
<221> NAME/KEY: misc_feature
<222> LOCATION: (221)..(221)
<223> OTHER INFORMATION: a or g or c or t/u
<220> FEATURE:
<221> NAME/KEY: misc_feature
<222> LOCATION: (229)..(229)
<223> OTHER INFORMATION: a or g or c or t/u

<400> SEQUENCE: 197

acaaagaaaa atttaatatt cgatgagagg ttgaaccagg cttaaagcag acatactagg     60

aaatggtgca gcctgtaaga atgccagttt gtaagtactg actttggaaa agatcatcgc    120

ctctatcaga cacttagggt cctggtctgg caattttggc ctgatgtgat gccacaagac    180

ccaacagaga gagacacaga gtccaggnta atattgacag naggtggang cccccct       237


<210> SEQ ID NO 198
<211> LENGTH: 292
<212> TYPE: DNA
<213> ORGANISM: Homo sapiens

<400> SEQUENCE: 198

tttttttttt tttttttttt ggtccaaaat ttttaatagt atacagacaa cctgttaatt     60

tttttttttt tttttttggg aaataacaaa caccactttg ttatgaagac cttacaaacc    120

tcttcttaag acattcttac tctgatccag gcaaaaacac ttcaaggttt ggaaatgact    180

ctttcctgac ataaatcctt ttttattaaa atgcaaaagg ttcttcagaa taaaactgtg    240

taataatttt tatacttggg agtgctcctt gcacagagct gtcatttgcc ag            292


<210> SEQ ID NO 199
<211> LENGTH: 434
<212> TYPE: DNA
<213> ORGANISM: Homo sapiens

<400> SEQUENCE: 199
```

-continued

```
tttttcttac aaagaaaaat ttaatattcg atgagaggtt gaaccaggct taaagcagac     60

atactaggaa atggtgcagc ctgtaagaat gccagtttgt aagtactgac tttggaaaag    120

atcatcgcct ctatcagaca cttagggtcc tggtctggca attttggcct gatgtgatgc    180

cacaagaccc aacagagaga gacacagagt ccaggataat gttgacagtg gtgtagccct    240

ttaggagaaa tggcgctccc tgcggctggt attaggttac cattggcacc gaagagacca    300

ggaggataag aatatccata atttcagagc tgccctggca cagtacctgc cccgtcggag    360

gctctcactg gcaaatgaca gctctgtgca aggagcactc ccaagtataa aaattattac    420

acagttttat tctg                                                      434


<210> SEQ ID NO 200
<211> LENGTH: 451
<212> TYPE: DNA
<213> ORGANISM: Homo sapiens

<400> SEQUENCE: 200

taaataacaa acaccacttt gttatgaaga ccttacaaac ctcttcttaa gacattctta     60

ctctgatcca ggcaaaaaca cttcaaggtt tgtaaatgac tctttcctga cataaatcct    120

tttttattaa aatgcaaaat gttcttcaga ataaaactgt gtaataattt ttatacttgg    180

gagtgctcct tgcacagagc tgtcatttgc cagtgagagc ctccgacggg gcaggtactg    240

tgccagggca gctctgaaat tatggatatt cttatcctcc tggttccttc ggtgccaatg    300

gtaacctaat accagccgca gggagcgcca tttctcctaa agggctacac cactgtcaac    360

attatcctgg actctgtgtc tctctctgtt gggtcttgtg gcatcacatc aggccaaaat    420

tgccagacca ggaccctaag tgtctgatag a                                   451


<210> SEQ ID NO 201
<211> LENGTH: 231
<212> TYPE: DNA
<213> ORGANISM: Homo sapiens

<400> SEQUENCE: 201

tttgtaaata acaaacacca ctttgttatg aagaccttac aaacctcttc ttaagacatt     60

cttactctga tccaggcaaa aacacttcaa ggtttgtaaa tgactctttc ctgacataaa    120

tccttttta ttaaaatgca aaatgttctt cagaataaaa ctgtgtaata atttttatac    180

ttgggagtgc tccttgcaca gagctgtcat ttgccagtga gagcctccga c             231


<210> SEQ ID NO 202
<211> LENGTH: 483
<212> TYPE: DNA
<213> ORGANISM: Homo sapiens

<400> SEQUENCE: 202

ttgtaaataa caaacaccac tttgttatga agaccttaca aacctcttct taagacattc     60

ttactctgat ccaggcaaaa acacttcaag gtttgtaaat gactctttcc tgacataaat    120

ccttttttat taaaatgcaa aatgttcttc agaataaaac tgtgtaataa tttttatact    180

tgggagtgct ccttgcacag agctgtcatt tgccagtgag agcctccgaa ggggcaggta    240

ctgtgccagg gcagctctga aattatggat attcttatcc tcctggttcc ttcggtgcca    300

atggtaacct aataccagcc gcaggagcgc catttctcct aaagggctac accactgtca    360

acattatcct ggactctgtg tctctctctg ttgggtcttg tggcatcaca tcaggccaaa    420
```

-continued attgccagac caggacccta agtgtctgat agaggcgatg atcttttcca aagtcagtac 480
tta 483

<210> SEQ ID NO 203
<211> LENGTH: 507
<212> TYPE: DNA
<213> ORGANISM: Homo sapiens

<400> SEQUENCE: 203
gctcgacttt tttttgggg gaacgttttc attaggttaa cagtgtttgg caagcattgg 60
aaacacggaa tctcacagac agatacaggc agaaagaatc acagttcaat ccaaaagcaa 120
cacactgaga ggacatcaga gtccaaacac atgcagagaa gctgtcaggg agcagctagg 180
agacacgcag agttgcctca cacgtggcag caggagaagg tgcaacacgg atccgactgc 240
ttacccacta aggacaccaa gaaccaggtt aaggacgaaa aatgagccaa ggatgatcag 300
actaacaaaa tacacccatg gccattccca tcctatcgca tcatttaccc agtagagcac 360
gtctgtccag ccctccatgg tgatgcactg aaacacagta agcatggcaa aggcaaagtt 420
atcaaagttg gtgatgcctc cgttcgggcc aacccagcca ctcctacatt ccgtgccatt 480
ggcagtacac tggcgtccat tccctgt 507

<210> SEQ ID NO 204
<211> LENGTH: 443
<212> TYPE: DNA
<213> ORGANISM: Homo sapiens

<400> SEQUENCE: 204
tttttttttt tttttttggt ccaaaatttt taatagtata cagacaacct gttaattttt 60
tttttttttt tttttgtaaa taacaaacac cactttgtta tgaagacctt acaaacctct 120
tcttaagaca ttcttactct gatccaggca aaaacacttc aaggtttgta aatgactctt 180
tcctgacata aatccttttt tattaaaatg caaaatgttc ttcagaataa aactgtgtaa 240
taatttttat acttgggagt gctccttgca cagagctgtc atttgccagt gagagcctcc 300
gacggggcag gtactgtgcc agggcagctc tgaaattatg gatattctta tcctcctggt 360
tccttcggtg ccaatggtaa cctaatacca gccgcaggga gcgccatttc tcctaaaggg 420
ctacaccact gtcaacatta tcc 443

<210> SEQ ID NO 205
<211> LENGTH: 305
<212> TYPE: DNA
<213> ORGANISM: Homo sapiens

<400> SEQUENCE: 205
tttttttttt ttttttttct tacaaagaaa aatttaatat tcgatgagag gttgaaccag 60
gcttaaagca gacatactag gaaatggtgc agcctgtaag aatgccagtt tgtaagtact 120
gactttggaa aagatcatcg cctctatcag acacttaggg tcctggtctg gcaattttgg 180
cctgatgtga tgccacaaga cccaacagag agagacacag agtccaggat aatgttgaca 240
gtggtgtagc cctttaggag aaatggcgct ccctgcggct ggtattaggt taccattggc 300
accga 305

<210> SEQ ID NO 206
<211> LENGTH: 376
<212> TYPE: DNA
<213> ORGANISM: Homo sapiens -continued

<400> SEQUENCE: 206
tgtaaataac aaacaccact tggttatgaa gaccttacaa acctcttctt aagacattct 60
tactctgatc caggcaaaaa cacttcaagg tttgtaaatg actctttcct gacataaatc 120 ctttttttatt aaaatgcaaa atgttcttca gaataaaact gtgtaataat ttttatactt 180
gggagtgctc cttgcacaga gctgtcattt gccagtgaga gcctccgacg gggcaggtac 240
tgtgccaggg cagctctgaa attatggata ttcttatcct cctggttcct tcggtgccaa 300
tggtaaccta ataccagccg cagggagcgc catttctcct aaagggctac accactgtca 360
acattatcct ggactc 376

<210> SEQ ID NO 207
<211> LENGTH: 544
<212> TYPE: DNA
<213> ORGANISM: Homo sapiens

<400> SEQUENCE: 207
attcctgtta attttgacaa gctcaacggc tgaaatctag gaatggttac taccaaaagc 60
ccacccaatc cagctcattt tgctatcgtt ttataacaat taatctgcat tatatttgga 120
tccagacaaa taaagcaatt ataaatgtat ctcactttac aacagacaaa aaaagggcat 180
gctatggaaa ttgtttaaat ctcaagcaac aatgctgatt aatttctggt caataatcgt 240
tctatagttc tccttcatga agcctggtga ggttccagga aacagcttga tttgggaagc 300
ctcagcagaa aagaaagcat ctcagaggac acataaaatg tctggcaacc cctcttggcg 360
gccctcatcc agcaaagctt gtgtggtctt ggcaactgtc ctcaggactc tgctttcaag 420
atgaaagagg tgtagcttac ccgctcaata caccaagtac aagatttagt acgaaaaatg 480
acccaaagat gacgagactg acacaataca cccagggcaa ttcaaatccc atagcatcat 540
tcat 544

<210> SEQ ID NO 208
<211> LENGTH: 308
<212> TYPE: DNA
<213> ORGANISM: Homo sapiens

<400> SEQUENCE: 208
ggtcgacgta tttgtaaaga gatggtctat atcttgtaat tactgtattg tatttgaact 60
gcagcaatat ccatgggtcc taataattgt agttccccac taaaatctag aaattattag 120
tatttttact cgggctatcc agaagtagaa gaaatagagc caattctcat ttattcagcg 180
aaaatcctct ggggttaaaa ttttaagttt gaaagaactt gacactacag aaatttttct 240
aaaatatttt gagtcactat aaacctatca tctttccaca agaaaaaaaa acaaaaaaaa 300
agtcgacg 308

<210> SEQ ID NO 209
<211> LENGTH: 939
<212> TYPE: DNA
<213> ORGANISM: Homo sapiens
<220> FEATURE:
<221> NAME/KEY: misc_feature
<222> LOCATION: (674)..(674)
<223> OTHER INFORMATION: a or g or c or t/u
<220> FEATURE:
<221> NAME/KEY: misc_feature
<222> LOCATION: (684)..(684)
<223> OTHER INFORMATION: a or g or c or t/u
<220> FEATURE:

-continued

<221> NAME/KEY: misc_feature
<222> LOCATION: (687)..(687)
<223> OTHER INFORMATION: a or g or c or t/u
<220> FEATURE:
<221> NAME/KEY: misc_feature
<222> LOCATION: (781)..(781)
<223> OTHER INFORMATION: a or g or c or t/u
<220> FEATURE:
<221> NAME/KEY: misc_feature
<222> LOCATION: (795)..(795)
<223> OTHER INFORMATION: a or g or c or t/u

<400> SEQUENCE: 209
caaagtactt ccccacattt agctggattt gtctttggtt tgaagaggct aatacgtgaa 60
agatttgttc acagttggat gtccccttttt ctgaaccatg aagtaatatt gtgaatggag 120
ttgaatgctg aggttagggt gccggaaaga ttcagggtcc ttcggtaccc tcacatggct 180
tggctttggt agaacaagaa actaagctct gatttggctt taaatgagag tgctaaattt 240
cctttttcta ataaagaacc tagctaaaca tttatatata cttttgaaca ctgaactttc 300
ttgttgcaga gttaacagct gttgggggta gctgacagct ggatcctggt gctgttggta 360
ccatggtacc tgaagtgcac aggctggtag ccacacctga cattaacaag tgagtggtaa 420
cctctctgcc gctggctcac agctactgtt tccatagaaa tggctgtcgg gatcagtgga 480
aacgaggtaa gtgaaagttt tcgctgatcc ttgtttccat caagctgacg tctgtttccc 540
tggcaacagc agtggacagc agccaggcgc tagcaacaga ttcagtagag ctctcacttg 600
tcagctgtgg ctatcatctg ttcctgacca agttcttttt ttttttttta ataatgtaca 660
gaaagacctc tganggacca ggangcnact ctggccacat gtgccctcct ggatgctcgt 720
tttgcaaatg gagagctgtg tgctgagttg acttctctgt ccgcagttcc ccctccactg 780
nggctctggg gttgntgatg tgcaggtaaa aaaaaggagg gttgttgaag gttattagtt 840
gttccaaggg gaagcctgtt gaaacctggt tgatccccaa tccctatggg gaagaaaaat 900
ctctttaagg ggcttttcat gcccagagac ccaaatttt 939

<210> SEQ ID NO 210
<211> LENGTH: 966
<212> TYPE: DNA
<213> ORGANISM: Homo sapiens

<400> SEQUENCE: 210
ggtggcgatt cggacgaggg caaagacttc ccccatttag ctggatttgt ctttggtttg 60
aagaggctaa tacgtgaaag atttgttcac agttggatgt ccccttttct gaaccatgaa 120
gtaatattgt gaatggagtt gaatgctgag gttagggtgc cggaaagatt cagggtcctt 180
cggtaccctc acatggcttg gctttggtag aacaagaaac taagctctga tttggcttta 240
aatgagagtg ctaaatttcc tttttctaat aaagaaccta gctaaacatt tatatatact 300
tttgaacact gaactttctt gttgcagagt taacagctgt tgggggtagc tgacagctgg 360
atcctggtgc tgttggtacc atggtacctg aagtgcacag gctggtagcc acacctgaca 420
ttaacaagtg agtggtaacc tctctgccgc tggctcacag ctactgtttc catagaaatg 480
gctgtcggga tcagtggaaa cgaggtaagt gaaagttttc gctgatcctt gtttccatca 540
agctgacgtc tgtttccctg gcaacagcag tggacagcag ccaggcgcta gcaacagatt 600
caggagagct ctcacttgtc agctgtggct atcatctgtt cctgaccaag ttcttttttt 660
tttttttaat aatggacaga aagacctctg aggacccagg aggcacctct gggcacatgt 720
gccctcctgg atgctccttt tgcagatgga gacctggggg ctgagttgac ttctctggcc 780

-continued

```
gcagttcccc ctccacctgg ggctcctggg tggtgagggg ccaggtaaaa aaagggaagg    840

tgtttgaggg tattaatggg tccccgggcg ggctgatcga atcctgggga ctccacgtcc    900

ctggggggac aagaatctct tcaacggggt tttccggccg ggagccggag ttttttattc    960

agcggg                                                               966
```

<210> SEQ ID NO 211
<211> LENGTH: 692
<212> TYPE: DNA
<213> ORGANISM: Homo sapiens

<400> SEQUENCE: 211

```
ttttttttt tttttttct tgtggaaaga tgataggttt atagtgactc aaaatatttt     60

agaaaaattt ctgtagtgtc aagttctttc aaacttaaaa ttttaacccc agaggatttt    120

cgctgaataa atgagaattg gctctatttc ttctacttct ggatagcccg agtaaaaata    180

ctaataattt ctagatttta gtggggaact acaattatta ggacccatgg atattgctgc    240

agttcaaata caatacagta attacaaaat atagaccatc tctttacaaa tacaaattat    300

agtatattac aagtcatgta cagtaaatct ataattttaa acaaactagt gtatctaagt    360

ttacctggtt gcgagtgcat tattattcca gtttacagtt gcccttagcg tgacagtcag    420

aaaccgacca tcggagtgat attctcttat gtaaactggc gtcacatcac agaaaacctt    480

atttatgagg tcccattgcc ctcgcaataa tcactggtag ctgggttctg acttacttac    540

acaccgtatt tcagaacagc taaacaggaa ccaggacgca gtgtatttgg gggaaagggt    600

ttacaaatgg atatgttggg cccagtgact gatatgctag accgatggct gaggtaacga    660

cacaggtgtg atgatcgtca tcacctttaa ct                                  692
```

<210> SEQ ID NO 212
<211> LENGTH: 595
<212> TYPE: DNA
<213> ORGANISM: Homo sapiens

<400> SEQUENCE: 212

```
tgcaaataag gacaagctca gcggctgaaa tctacaaatg gggactacca aaagcccacc     60

caatccagct cattttgcta tcgttttata acaattaatc tgcattatat ttggatccag    120

acaaataaag caattataaa tgtatctcac tttagaacag acaaaaaaag ggcatgctat    180

ggaaattgtt taaatctcaa gcaacaatgc tgattaattt ctggtcaata atcgttctat    240

agttctcctt catgaagcct ggtgaggttc caggaaacag cttgatttgg gaagcctcag    300

cagaaaagaa agcatctcag aggacacata aaatgtctgg caacccctct tggcggccct    360

catccagcaa agcttgtgtg gtcttggcaa ctgtcctcag gactctgctt tcaagatgaa    420

agaggtgtag cttacccgct caatacacca agtacaagat ttagtacgaa aaatgaccca    480

aagatgacga gactgacaaa atacacccag ggcaattcaa atcccatagc atcattcatc    540

tgcaagaaat aagatggtct cataggagtg ggttaataag aggatttaat aagga         595
```

<210> SEQ ID NO 213
<211> LENGTH: 999
<212> TYPE: DNA
<213> ORGANISM: Homo sapiens

<400> SEQUENCE: 213

```
ggcaaagtac ttccccacat ttagctggat tggtctttgg tttgaagagg ctaatacgtg     60
```

-continued

```
aaagatttgt tcacagttgg atgtcccctt ttctgaacca tgaagtaata ttgtgaatgg    120

agttgaatgc tgacggttag ggtgccggaa agattcaggg tccttcggta ccctcacatg    180

gcttggcttt ggtagaacaa gaaactaagc tctgatttgg ctttaaatga gagtgctaaa    240

tttccttttt ctaataaaga acctagctaa acatttatat atacttttga acactgaact    300

ttcttgtcag cagagttaac agctgtaggg ggtagctgac acggctggat cctggtgctg    360

ttggtaccat ggtacctgaa gtgcacaggc tggtagccac acctgacatt aacaacgtga    420

gtggtaacct ctctgccgct ggctcacagc tactgtttcc atcagaaatg gctgtcgggc    480

tcacgtggaa acgaggtaag tgaaagtacg ctagatcctt gttccatcac agctgacgct    540

ctgtttccca tggcaacacc cagcacggac aagccgccac gccgcataga caaccacaac    600

cacgtacagc tctccacaag tcagctcgtg gctatccatc atgtccctga acaagcccac    660

accacccccc cccaagcgac acagcaacga gcaccacccg gacgaaccaa aggacggacc    720

cccctgcccc aacctctcgc ccatccgcga cagacccgcc aagcaaacac gacaacctaa    780

caaagcagag ggacagaccc atagcgcccg ctaccggaag cgtacaccac ttcccaacag    840

taaggccaaa agagcgacgc ggagcacgtg aacggataag aaaacgagag aaggcacggc    900

cgcatggcaa acacaccagc aagcagcaga cagcacgtgg gcacgacaca ggacagaaag    960

cagcccacct cagaggggac caacgaagag tcgcacgac                           999


<210> SEQ ID NO 214
<211> LENGTH: 695
<212> TYPE: DNA
<213> ORGANISM: Homo sapiens
<220> FEATURE:
<221> NAME/KEY: misc_feature
<222> LOCATION: (695)..(695)
<223> OTHER INFORMATION: a or g or c or t/u

<400> SEQUENCE: 214

ctgggcccaa catatccatt tttaaaccct ttcccccaaa tacactgcgt cctggttcct     60

gtttagctgt tctgaaatac ggtgtgtaag taagtcagaa cccagctacc agtgattatt    120

gcgagggcaa tgggacctca taaataaggt tttctgtgat gtgacgccag tttacataag    180

agaatatcac tccggtggtc ggtttctgac tgtcacgcta agggcaactg taaactggaa    240

taataatgca ctcgcaacca ggtaaactta gatacactag tttgtttaaa attatagatt    300

tactgtacat gacttgtaat atactataat ttgtatttgt aaagagatgg tctatatttt    360

gtaattactg tattgtattt gaactgcagc aatatccatg ggtcctaata attgtagttc    420

cccactaaaa tctagaaatt attagtattt ttactcgggc tatccagaag tagaagaaat    480

agagccaatt ctcatttatt cagcgaaaat cctctggggt taaaatttta agtttgaaag    540

aacttgacac tacagaaatt tttctaaaat attttgagtc actataaacc tatcatcttt    600

ccacaagata taccagatga ctatttgcag tcttttcttt gggcaagagt tccatgattt    660

tgatactgta cctttggatc caccatgggt tgcan                               695


<210> SEQ ID NO 215
<211> LENGTH: 870
<212> TYPE: DNA
<213> ORGANISM: Homo sapiens

<400> SEQUENCE: 215

ggaaaagaaa tactgtttta gagaaataac attttcaaca aaacatccct ggagtcagat     60

tttgagttgg ggtgggctaa tcagggagtc ggggctctct gcgtgatgtc agttctatgg    120
```

-continued

```
ctaactggtt tttctaaacc agccagctgc ctatcaaaac agtacaactt ttctaggaaa    180

tgcaattggc aaagacactt acgatgctga gaagtacaca aggtgaaact gctccagttt    240

ttctcatagc agggtcagca ggaaagcaag tggtgcccct ggtcccatct cacacaggtg    300

agactgcacc gagaggtaac gtggccctca cagcccacca cgcctggcct tcgcccaatt    360

ctgaaacttc gtaggataga gctggaaagt gccacatggt gaagcgagat ccagctgtct    420

gggtggatgt cggagtccat aggctgagca gagatggttc ttagtgaggt tctcgctgcc    480

agttgacggt gaaatcatag ctgccattta catttgtga gattatgaaa aacataagac    540

taaagaaact aaatgtgtta ttcctgtgga cacaaaaatg tgtgtttttc agatggggag    600

gggaccaaaa aggaaaaaca tttcatctta aaactttcct aagacaaagg aaaacaaaaa    660

accatgctct acaacttcaa atttttctta caaagaaaaa tttaatattc gatgagcagg    720

ttgaaccagg cttaaagcag acatactagg aaatggtgca gcctgtaaga atgccagttt    780

gtaagtactg actttggaaa agatcatcgc tctatcagac acttagggtc ctggtctggc    840

cattttggcc tgatgtgatg ccaaaagacc                                      870
```

<210> SEQ ID NO 216
<211> LENGTH: 368
<212> TYPE: DNA
<213> ORGANISM: Homo sapiens

<400> SEQUENCE: 216

```
ttttatcgtg tggaaagatg ataggtttat agtgactcaa aatattttag aaaaatttct     60

gtagtgtcaa gttctttcaa acttaaaatt ttaaccccag aggattttcg ctgaataaat    120

gagaattggc tctatttctt ctacttctgg atagcccgag taaaaatact aataatttct    180

agattttagt ggggaactac aattattagg acccatggat attgctgcag ttcaaataca    240

atacagtaat tacaaaatat agaccatctc tttacaaata caaattatag tatattacaa    300

gtcatgtaca gtaaatctat tttaaacaaa ctagtgtatc taagtttacc tggttgcgag    360

tgcattat                                                              368
```

<210> SEQ ID NO 217
<211> LENGTH: 412
<212> TYPE: DNA
<213> ORGANISM: Homo sapiens

<400> SEQUENCE: 217

```
cttacaaaga aaaatttaat attcgatgag aggttgaacc aggcttaaag cagacatact     60

aggaaatggt gcagcctgta agaatgccag tttgtaagta ctgactttgg aaaagatcat    120

cgcctctatc agacacttag ggtcctggtc tggcaatttt ggcctgatgt gatgccacaa    180

gacccaacag agagagacac agagtccagg ataatgttga cagtggtgta gccctttagg    240

agaaatggcg ctccctgcgg ctggtattag gttaccattg gcaccgaaga gaccaggagg    300

ataagaatat ccataatttc agagctgccc tggcacagta cctgccccgt cggaggctct    360

cactggcaaa tgacagctct gtgcaaggag cactcccaag tataaaaatt at            412
```

<210> SEQ ID NO 218
<211> LENGTH: 610
<212> TYPE: DNA
<213> ORGANISM: Homo sapiens

<400> SEQUENCE: 218

-continued

```
ccgcgtccgg tcagatggta caagtttgtc tctataatta agacttttcc accatcacaa     60

actttaaaca caaagtctaa aatcttgggc agcatagaaa ataggttcta gctaagcagg    120

agttttgtcc tctaccaaga cctttcctga aaatcactta tcaagacagt ttcctgtaag    180

aaaaagccat atcccagctg attttccttc ctggggccaa aatctgctat tattcggcct    240

gaaagccttg atgactctgt gtgtgtgtgt gtgtgtgtgt gtgtgtgtgt gtgtgtgtgt    300

gtatggatgc ttgtgtgtgt gtatggggaa tatgtgatta atgtgtgttg gctgctgttg    360

tctctgattt ggctactgtt gtttctgatt taaatctaag taaatgttta attaaatgta    420

tagaatgctg tctctaatgt gaccctctct ccttattaaa tcctcttatt aacccactcc    480

tatgagacca tcttatttct tgcagatgaa tgatgctatg ggatttgaat tgccctgggt    540

gtattttgtc agtctcgtca tctttgggtc atttttcgta ctaaatcttg tacttggtgt    600

attgagcggg                                                           610
```

```
<210> SEQ ID NO 219
<211> LENGTH: 236
<212> TYPE: DNA
<213> ORGANISM: Homo sapiens
<220> FEATURE:
<221> NAME/KEY: misc_feature
<222> LOCATION: (195)..(195)
<223> OTHER INFORMATION: a or g or c or t/u

<400> SEQUENCE: 219

aatgcaaaat gttcttcaga ataaaactgt gtaataattt ttatacttgg gatgtgctcc     60

ttgcacagag ctgtcatttg ccagtgagag cctcgacagg caggtactgt gccagggcag    120

ctctgaaatt atggatattc ttatcctcct ggttccttct gtgctcaatg gtaacctaat    180

accagccgca ggacncgcca tttctcctaa agggctacac cactgtcaac attatc        236
```

```
<210> SEQ ID NO 220
<211> LENGTH: 427
<212> TYPE: DNA
<213> ORGANISM: Homo sapiens

<400> SEQUENCE: 220

tcagcgaaaa tcctctgggg ttaaaatttt aagtttgaaa gaacttgaca ctacagaaat     60

ttttctaaaa tattttgagt cactataaac ctatcatctt tccacaagat ataccagatg    120

actatttgca gtcttttctt tgggcaagag ttccatgatt ttgatactgt acctttggat    180

ccaccatggg ttgcaactgt ctttggtttt gtttgtttga cttgaaccac cctctggtaa    240

gtaagtaagt gaattacaga gcaggtccag ctggctgctc tgccccttgg gtatccatag    300

ttacggtttt ctctgtggcc cacccagggt gttttttgca tcgctggtgc agaaatgcat    360

aggtggatga gatatagctg ctcttgtcct ctggggactg gtggtgctgc ttaagaaata    420

aggggtg                                                              427
```

```
<210> SEQ ID NO 221
<211> LENGTH: 838
<212> TYPE: DNA
<213> ORGANISM: Homo sapiens

<400> SEQUENCE: 221

ttttgtcagt ctcgtcatct ttgggtcatt tttcgtacta aatcttgtac ttggtgtatt     60

gagcgggcac agtggctcac gcctataatc ccagcacttt cggaggccga ggcagctgga    120

ccacccgaga tcaggagttt gagaccagcc tgactaaggc agtgaaaccc tgtctctact    180
```

-continued

```
aaaaatacaa aaattagcca ggcatggtgg cgcatgcctg taatcccagc tacttgggag    240
gctgaggcag gagaatcact tgaaccaggg aggtggagat tgcagtgagc caagactgca    300
ccattgcatt ccagcctggg tgacaagagc aaaactccat ctcaaaaaaa aaaaaaaaaa    360
aaaaaaaaaa agacttttct ctcattcaac actttaccag catctactga cagaaaatgg    420
acaattgaat ttcctccaat atatatacct ctgatatgtc tgctttgtaa aagagtagtg    480
taattgctta caacattgaa aaggttgtta ttggggtcct ggggtagcca ggatatcggc    540
atgatttgtc accatattca gaataaaact gtactgcaat agtgagttaa ttccatatct    600
tggccaacag agaatttttg gccagtggct actaaggcac acggaagtcc agtctaaaag    660
ggacagggga ggactctttg tagatagttc ttatgattaa aaaataactt cctatgtgtt    720
gtagtgatga tttaagctga cagaatgcta aagacacccc ttatgattac ctggtagcaa    780
agtaccttcc ccacatttaa cctggatttg ccctttttggg tttgaaagag gctaaata      838
```

<210> SEQ ID NO 222
<211> LENGTH: 904
<212> TYPE: DNA
<213> ORGANISM: Homo sapiens

<400> SEQUENCE: 222

```
ggtgggattc ggcacgaggg caagacttcc ccacatttag ctggatttgt ctttggtttg     60
aagaggctaa tacgtgaaag atttgttcac agttggatgt cccctttttct gaaccatgaa    120
gtaatatttg tgatatggag ttcgaatggc tgaggtctag gtgtgccgag aaagattcag    180
ggtccttcgg taccctcaca tggcttggct ttggtagaac aagaaactaa gctctgattt    240
ggctttaaat gagagtgcta aatttccttt ttctaataaa gaacctagct aaacatttat    300
atatactttt gaacactgaa ctttcttgtt gcagagttaa cagctgttgg gggtagctga    360
cagctggatc ctggtgctgt tggtaccatg gtacctgaag tgcacaggct ggtagccaca    420
cctgacatta acaagtgagt ggtaacctct ctgccgctgg ctcacagcta ctgtttccat    480
agaaatggct gtcgggatca gtggaaacga ggtaagtgaa agttttcgct gatccttgtt    540
tccatcaagc tgacgtctgt ttccctggca acagcagtgg acagcagcca ggcgctagca    600
acagattcag tagagctctc acttgtcagc tgtggctatc atctgttcct gaccaagttc    660
ttttttttt ttttaataat gtacagaaag acctctgagg acccaggagg cacctctggc    720
cacatgtgcc ctcctggatg ctcgttttgc agatggagag ctgtgtgctg agttgacttc    780
tctgtccgca gttcccctc cacctgtgct ctgggttgtt gatgtgccag ttaaaacagg    840
gaggctgctt cagggtatta gtgttgccaa ggggaggctg ttgaaatctg gttgatccca    900
aatc                                                                  904
```

<210> SEQ ID NO 223
<211> LENGTH: 935
<212> TYPE: DNA
<213> ORGANISM: Homo sapiens

<400> SEQUENCE: 223

```
caaagtactt ccccacattt agctggattt gtctttggtt tgaagaggct aatacgtgaa     60
agatttgttc acagttggat gtccccttttt ctgaaccatg aagtaatatt gtgaatggag    120
ttgaatgctg aggttagggt gccggaaaga ttcagggtcc ttcggtaccc tcacatggct    180
tggctttggt agaacaagaa actaagctct gatttggctt taaatgagag tgctaaattt    240
```

-continued

```
ccttttttcta ataaagaacc tagctaaaca tttatatata cttttgaaca ctgaactttc    300

ttgttgcaga gttaacagct gttgggggta gctgacagct ggatcctggt gctgttggta    360

ccatggtacc tgaagtgcac aggctggtag ccacacctga cattaacaag tgagtggtaa    420

cctctctgcc gctggctcac agctactgtt tccatagaaa tggctgtcgg gatcagtgga    480

aacgaggtaa gtgaaagttt tcgctgatcc ttgtttccat caagctgacg tctgtttccc    540

tggcaacagc agtggacagc agccaggcgc tagcaacaga ttcagtagag ctctcacttg    600

tcagctgtgg ctatcatctg ttcctgacca agttcttttt tttttttta ataatgtaca    660

gaaagacctc tgaggaccca gggagcacct ctggccacat gtgccctcct gaatgctcgt    720

tttgcaaatg gagagctgtg tgctgagttg acttctctgt ccgcaggtcc ccctccaact    780

gtgctcctgg gttgtgatgt gcagggttaa accagggaag ctgttgaagg gtattagtgt    840

tgccagggaa aggctgttga attctggttg atcccaaatc cctaggggga agagaaatcc    900

cttacgagtg gtttttcatg gccaggaacc ctata                               935
```

<210> SEQ ID NO 224
<211> LENGTH: 382
<212> TYPE: DNA
<213> ORGANISM: Homo sapiens

<400> SEQUENCE: 224

```
tcagcgaaaa tcctctgggg ttaaaatttt aagtttgaaa gaacttgaca ctacagaaat     60

ttttctaaaa tattttgagt cactataaac ctatcatctt tccacaagat ataccagatg    120

actatttgca gtcttttctt tgggcaagag ttccatgatt ttgatactgt acctttggat    180

ccaccatggg ttgcaactgt ctttggtttt gtttgtttga cttgaaccac cctctggtaa    240

gtaagtaagt gaattacaga gcaggtccag ctggctgctc tgccccttgg gtatccatag    300

ttacggtttt ctctgtggcc cacccagggt gttttttgca tcgctggtgc agaaatgcat    360

aggtggatga gatatagctg ct                                             382
```

<210> SEQ ID NO 225
<211> LENGTH: 461
<212> TYPE: DNA
<213> ORGANISM: Homo sapiens

<400> SEQUENCE: 225

```
gtatatcttg tggaaagatg ataggtttat agtgactcaa aatattttag aaaaatttct     60

gtagtgtcaa gttctttcaa acttaaaatt ttaaccccag aggattttcg ctgaataaat    120

gagaattggc tctatttctt ctacttctgg atagcccgag taaaaatact aataatttct    180

agattttagt ggggaactac aattattagg acccatggat atagctgcag ttcaaataca    240

atacagtaat tacaaaatat agaccatctc tttacaaata caaattatag tatattacaa    300

gtcatgtaca gtaaatctat aattttaaac aaactagtgt atctaagttt accaggttgc    360

gagtgcatta ttattccagt ttacagttgc ccttagcgtg acagtcagaa accgaccatc    420

ggagtgatat tctcttatgt aaacaggcgt cacatcacag a                        461
```

<210> SEQ ID NO 226
<211> LENGTH: 557
<212> TYPE: DNA
<213> ORGANISM: Homo sapiens

<400> SEQUENCE: 226

```
ttttttttt tgtggaaaga tgataggttt atagtgactc aaaatatttt agaaaaattt     60
```

ctgtagtgtc aagttctttc aaacttaaaa ttttaacccc agaggatttt cgctgaataa 120
atgagaattg gctctatttc ttctacttct ggatagcccg agtaaaaata ctaataattt 180
ctagatttta gtggggaact acaattatta ggacccatgg atattgctgc agttcaaata 240
caatacagta attacaaaat atagaccatc tctttacaaa tacaaattat agtatattac 300
aagtcatgta cagtaaatct ataattttaa acaaactagt gtatctaagt ttacctggtt 360
gcgagtgcat tattattcca gtttacagtt gcccttagcg tgacagtcag aaaccgacca 420
tcggagtgat attctcttat gtaaactggc gtcacatcac agaaaacctt atttatgagg 480
tcccattgcc ctcgcaataa tcactggtag ctgggttctg acttacttac acaccgtatt 540
tcagaacagc taaacag 557

<210> SEQ ID NO 227
<211> LENGTH: 481
<212> TYPE: DNA
<213> ORGANISM: Homo sapiens

<400> SEQUENCE: 227
tttggtatat cttgtggaaa gatgataggt ttatagtgac tcaaaatatt ttagaaaaat 60
ttctgtagtg tcaagttctt tcaaacttaa aattttaacc ccagaggatt ttcgctgaat 120
aaatgagaat tggctctatt tcttctactt ctggatagcc cgagtaaaaa tactaataat 180
ttctagattt tagtggggaa ctacaattat taggacccat ggatattgct gcagttcaaa 240
tacaatacag taattacaaa atatagacca tctctttaca aatacaaatt atagtatatt 300
acaagtcatg tacagtaaat ctataatttt aaacaaacta gtgtatctaa gtttacctgg 360
ttgcgagtgc attattattc cagtttacag ttgcccttag cgtgacagtc agaaaccgac 420
catcggagtg atattctctt atgtaaactg gcgtcacatc acagaaaacc ttatttatga 480
g 481

<210> SEQ ID NO 228
<211> LENGTH: 466
<212> TYPE: DNA
<213> ORGANISM: Homo sapiens

<400> SEQUENCE: 228 ttttttgtg gaaagatgat aggtttatag tgactcaaaa tattttagaa aaatttctgt 60
agtgtcaagt tctttcaaac ttaaaatttt aaccccagag gattttcgct gaataaatga 120
gaattggctc tatttcttct acttctggat agcccgagta aaaatactaa taatttctag 180
attttagtgg ggaactacaa ttattaggac ccatggatat tgctgcagtt caaatacaat 240
acagtaatta caaaatatag accatctctt tacaaataca aattatagta tattacaagt 300
catgtacagt aaatctataa ttttaaacaa actagtgtat ctaagtttac ctggttgcga 360
gtgcattatt attccagttt acagttgccc ttagcgtgac agtcagaaac cgaccatcgg 420
agtgatattc tcttatgtaa actggcgtca catcacagaa aacctt 466

<210> SEQ ID NO 229
<211> LENGTH: 353
<212> TYPE: DNA
<213> ORGANISM: Homo sapiens

<400> SEQUENCE: 229
cggccgccaa ctttttgaa tgagtgaagt gccaggtacc atgagaaaac cctagctggt 60

-continued

```
aaagatcaaa cctgagttag ttctaaattc acatacggat ttttttgca tgacgaaatc    120

tattctcttt ttcctgacaa cttctccacc tagatgtttg ggaaagttgc catgagagat    180

aacaaccaga tcaataggaa caataacttc cagacgtttc cccaggcggt gctgctgctc    240

ttcaggtgac tgcaactggc ttgggcggtg ctcctgggca ggggggtccg ctaggcgtgg    300

gtccagaggg acggaggaca caggttatta aagcagtgtg cctttctcag ttg           353
```

<210> SEQ ID NO 230
<211> LENGTH: 526
<212> TYPE: DNA
<213> ORGANISM: Homo sapiens

<400> SEQUENCE: 230

```
taaataacta acaccatttt gttatgaaga ccttacaaac ctcttcttaa gacattctta     60

ctctgatcca ggcaaaaaca cttcaaggtt tgtaaatgac tctttcctga cataaatcct    120

ttttttatta aaatgcaaaa tgttcttcag aataaaactg tgtaataatt tttatacttg    180

ggagtgctcc ttgcacagag ctgtcatttg ccagtgagag cctccgacgg ggcaggtact    240

gtgccagggc agctctgaaa ttatggatat tcttatcctc ctggttcctt cggtgccaat    300

ggtaacctaa taccagccgc agggagcgcc atttctccta aagggctaca ccactgtcaa    360

cattatcctg gactctgtgt ctctctctgt tgggtcttgt ggcatcacat caggccaaaa    420

ttgccagacc aggaccctaa gtgtctgata gaggcgatga tcttttccaa agtcagtact    480

tacaaactgg cattcttaca ggctgcacca tttcctagta tgtctg                   526
```

<210> SEQ ID NO 231
<211> LENGTH: 750
<212> TYPE: DNA
<213> ORGANISM: Homo sapiens

<400> SEQUENCE: 231

```
acttttctag gaaatgcaat tggcaaagac acttacgatg ctgagaagta cacaaggtga     60

aactgctcca gtttttctca tagcagggtc agcaggaaag caagtggtgc ccctggtccc    120

atctcacaca ggtgagactg caccgagagg taacgtggcc ctcacagccc accacgcctg    180

gccttcgccc aattctgaaa cttcgtagga tagagctgga aagtgccaca tggtgaagcg    240

agatccagct gtctgggtgg atgtcggagt ccataggctg agcagagatg gttcttagtg    300

aggttctcgc tgccagttga cggtgaaatc atagctgcca tttacatttt gtgagattat    360

gaaaaacata agactaaaga aactaaatgt gttattcctg tggacacaaa aatgtgtgtt    420

tttcagatgg ggaggggacc aaaaaggaaa aacatttcat cttaaaactt tcctaagaca    480

aaggaaaaca aaaaaccatg ctctacaact tcaaattttt cttacaaaga aaaatttaat    540

attcgatgag aggttgaacc aggcttaaag cagacatact aggaaatggt gcagcctgta    600

agaatgccag tttgtaagta ctgactttgg aaaagatcat cgcctctatc agacacttag    660

ggtcctggtc tggcaatttt ggcctgatgt gatgccacaa gacccaacag agagagacac    720

agagtccagg ataatgttga cagtggtgta                                     750
```

<210> SEQ ID NO 232
<211> LENGTH: 432
<212> TYPE: DNA
<213> ORGANISM: Homo sapiens

<400> SEQUENCE: 232

```
ttttttttt ttttttaga agaaatagag ccaattctca tttattcagc gaaaatcctc     60
```

-continued

```
tggggttaaa attttaagtt tgaaagaact tgacactaca gaaatttttc taaaatattt    120

tgagtcacta taaacctatc atctttccac aagatatacc agatgactat ttgcagtctt    180

ttctttgggc aagagttcca tgattttgat actgtacctt tggatccacc atgggttgca    240

actgtctttg gttttgtttg tttgacttga accaccctct ggtaagtaag tgaattacag    300

agcaggtcca gctggctgct ctgccccttg ggtatccata gttacggttt tctctgtggc    360

ccacccaggg tgttttttgc atcgctggtg cagaaatgca caggtggatg agatatagct    420

gctcttgtcc tc                                                        432
```

<210> SEQ ID NO 233
<211> LENGTH: 502
<212> TYPE: DNA
<213> ORGANISM: Homo sapiens

<400> SEQUENCE: 233

```
ttatcttgtg gaaagatgat aggtttatag tgactcaaaa tattttagaa aaatttctgt     60

agtgtcaagt tctttcaaac ttaaaatttt aaccccagag gattttcgct gaataaatga    120

gaattggctc tatttcttct acttctggat agcccgagta aaaatactaa taatttctag    180

attttagtgg ggaactacaa ttattaggac ccatggatat tgctgcagtt caaatacaat    240

acagtaatta caaaatatag accatctctt tacaaataca aattatagta tattacaagt    300

catgtacagt aaatctataa ttttaaacaa actagtgtat ctaagtttac ctggttgcga    360

gtgcattatt attccagttt acagttgccc ttagcgtgac agtcagaaac cgaccatcgg    420

agtgatattc tcttatgtaa actggcgtca catcacagaa aaccttattt atgaggtccc    480

attgccctcg caataatcac tg                                             502
```

<210> SEQ ID NO 234
<211> LENGTH: 356
<212> TYPE: DNA
<213> ORGANISM: Homo sapiens

<400> SEQUENCE: 234

```
tttttcttgt ggaaagatga taggtttata gtgactcaaa atattttaga aaaatttctg     60

tagtgtcaag ttctttcaaa cttaaaattt taaccccaga ggattttcgc tgaataaatg    120

agaattggct ctatttcttc tacttctgga tagcccgagt aaaaatacta ataatttcta    180

gattttagtg gggaactaca attattagga cccatggata ttgctgcagt tcaaatacaa    240

tacagtaatt acaaaatata gaccatctct ttacaaatac aaattatagt atattacaag    300

tcatgtacag taaatctata attttaaaca aactagtgta tctaagttta cctggt        356
```

<210> SEQ ID NO 235
<211> LENGTH: 442
<212> TYPE: DNA
<213> ORGANISM: Homo sapiens

<400> SEQUENCE: 235

```
atcttgtgga aagatgatag gtttatagtg actcaaaata ttttagaaaa atttctgtag     60

tgtcaagttc tttcaaactt aaaattttaa ccccagagga ttttcgctga ataaatgaga    120

attggctcta tttcttctac ttctggatag cccgagtaaa aatactaata atttctagat    180

tttagtgggg aacctacaat tattaggacc catggatatt gctgcagttc aaatacaata    240

cagtaattac aaaatataga ccatctcttt acaaatacaa attatagtat attacaagtc    300
```

-continued atgtacagta aatctataat tttaaacaaa ctagtgtatc taagtttacc tggttgcgag 360
tgcattatta ttccagttta cagttgccct tagcgtgaca gtcagaaacc gaccatcgga 420
gtgatattct cttatgtaaa ct 442

<210> SEQ ID NO 236
<211> LENGTH: 552
<212> TYPE: DNA
<213> ORGANISM: Homo sapiens

<400> SEQUENCE: 236
ttttcttcaa ataattacaa gctcagcggc tgaaatctac aaatggggac taccaaaagc 60
ccacccaatc cagctcattt tgctatcgtt ttataacaat taatctgcat tatatttgga 120
tccagacaaa taaagcaatt ataaatgtat ctcactttag aacagacaaa aaaagggcat 180
gctatggaaa ttgtttaaat ctcaagcaac aatgctgatt aatttctggt caataatcgt 240
tctatagttc tccttcatga agcctggtga ggttccaggg aaacagcttg atttgggaag 300
cctcagcaga aaagaaagca tctcagagga cacataaaat gtctggcaac ccctcttggc 360
ggccctcatc cagcaaagct tgtgtggtct tggcaactgt cctcaggact ctgctttcaa 420
gatgaaagag gtgtagctta cccgctcaat acaccaagta caagatttag tacgaaaaat 480
gacccaaaga tgacgagact gacaaaatac acccagggca attcaaatcc catagcatca 540
ttcatctgca ag 552

<210> SEQ ID NO 237
<211> LENGTH: 491
<212> TYPE: DNA
<213> ORGANISM: Homo sapiens

<400> SEQUENCE: 237
tttgtaaata acaaacacca ctttgttatg aagaccttac aaacctcttc ttaagacatt 60
cttactctga tccaggcaaa aacacttcaa ggtttgtaaa tgactctttc ctgacataaa 120
tcctttttta ttaaaatgca aaatgttctt cagaataaaa ctgtgtaata atttttatac 180
ttgggagtgc tccttgcaca gagctgtcat ttgccagtga gagcctccga cggggcaggt 240
actgtgccag ggcagctctg aaattatgga tattcttatc ctcctggttc cttcggtgcc 300
aatggtaacc taataccagc cgcagggagc gccatttctc ctaaagggct acaccactgt 360
caacattatc ctggactctg tgtctctctc tgttgggtct tgtggcatca catcaggcca 420
aaattgccag accaggaccc taagtgtctg atagaggcga tgatcttttc caaagtcagt 480
acttacaaac t 491

<210> SEQ ID NO 238
<211> LENGTH: 401
<212> TYPE: DNA
<213> ORGANISM: Homo sapiens

<400> SEQUENCE: 238
tttttttttg gtccaaaatt tttaatagta tacagacaac ctgttaattt tttttttttt 60 ttttttgta aataacaaac accactttgt tatgaagacc ttacaaacct cttcttaaga 120
cattcttact ctgatccagg caaaaacact tcaaggtttg taaatgactc tttcctgaca 180
taaatccttt tttattaaaa tgcaaaatgt tcttcagaat aaaactgtgt aataattttt 240
atacttggga gtgctccttg cacagagctg tcatttgcca gtgagagcct ccgacggggc 300
aggtactgtg ccagggcagc tctgaaatta tggatattct tatcctcctg gttccttcgg 360

-continued tgccaatggt aacctaatac cagccgcagg gagcgccatt t 401

<210> SEQ ID NO 239
<211> LENGTH: 387
<212> TYPE: DNA
<213> ORGANISM: Homo sapiens

<400> SEQUENCE: 239
tcgacagcta ccagtgatta ttgcgagggc aatgggacct cataaataag gttttctgtg 60
atgtgacgcc atttacataa gagaatatca ctccgatggt cggtttctga ctgtcacgct 120
aagggcaact gtaaactgga ataataatgc actcgcaacc aggtaaactt agatacacta 180
gtttgtttaa aattatagat ttactgtaca tgacttgtaa tatactataa tttgtatttg 240
taaagagatg gtctatattt tgtaattact gtattgtatt tgaactgcag caatatccat 300
gggtcctaat aattgtagtt ccccactaaa atctagaaat tattagtatt tttactcggg 360
ctatccagaa gtagaagaaa tagagcc 387

<210> SEQ ID NO 240
<211> LENGTH: 474
<212> TYPE: DNA
<213> ORGANISM: Homo sapiens

<400> SEQUENCE: 240
gaatatgtga ttaatgtgtg ttggctgctg ttgtctctga tttggctact gttgtttctg 60
atttaaatct aagtaaatgt ttaattaaat gtatagaatg ctgtctctaa tgtgaccctc 120
tctccttatt aaatcctctt attaacccac tcctatgaga ccatcttatt tcttgcagat 180
gaatgatgct atgggatttg aattgccctg ggtgtatttt gtcagtctcg tcatctttgg 240
gtcatttttc gtactaaatc ttgtacttgg tgtattgagc gggtaagcta cacctctttc 300
atcttgaaag cagagtcctg aggacagttg ccaagaccac acaagctttg ctggatgagg 360
gccgccaaga ggggttgcca gacattttat gtgtcctctg agatgctttc ttttctgctg 420
aggcttccca aatcaagctg tttcctggaa cctcaccagg cttcatgaag gaga 474

<210> SEQ ID NO 241
<211> LENGTH: 594
<212> TYPE: DNA
<213> ORGANISM: Homo sapiens

<400> SEQUENCE: 241
tttgtaaata acaaacacca ctttgttatg aagaccttac aaacctcttc ttaagacatt 60
cttactctga tccaggcaaa aacacttcaa ggtttgtaaa tgactctttc ctgacataaa 120
tcctttttta ttaaaatgca aaatgttctt cagaataaaa ctgtgtaata atttttatac 180
ttgggagtgc tccttgcaca gagctgtcat ttgccagtga gagcctccga cggggcaggt 240
actgtgccag ggcagctctg aaattatgga tattcttatc ctcctggttc cttcggtgcc 300
aatggtaacc taataccagc cgcagggagc gccatttctc ctaaagggct acaccactgt 360
caacattatc ctggactctg tgtctctctc tgttgggtct tgtggcatca catcaggcca 420
aaattgccag accaggaccc taagtgtctg atagaggcga tgatcttttc caaagtcagt 480
acttacaaac tggcattctt acaggctgca ccatttccta gtatgtctgc tttaagcctg 540
gttcaacctc tcatcgaata ttaaattttt ctttgtaaga aaaaaaaaaa aaaa 594

<210> SEQ ID NO 242

-continued

<211> LENGTH: 548
<212> TYPE: DNA
<213> ORGANISM: Homo sapiens

<400> SEQUENCE: 242
tttgtaaata acaaacacca ctttgttatg aagaccttac aaacctcttc ttaagacatt 60
cttactctga tccaggcaaa aacacttcaa ggtttgtaaa tgactctttc ctgacataaa 120
tcctttttta ttaaaatgca aaatgttctt cagaataaaa ctgtgtaata atttttatac 180
ttgggagtgc tccttgcaca gagctgtcat ttgccagtga gagcctccga cagggcaggt 240
actgtgccag ggcagctctg aaattatgga tattcttatc ctcctggttc cttcggtgcc 300
aatggtaacc taataccagc cgcagggagc gccatttctc ctaaagggct acaccactgt 360
caacattatc ctggactctg tgtctctctc tgttgggtct tgtggcatca catcaggcca 420
aaattgccag accaggaccc taagtgtctg atagaggcga tgatcttttc caaagtcagt 480
acttacaaac tggcattctt acaggctgca ccatttccta gtatgtctgc tttaagcctg 540
gttcaacc 548

<210> SEQ ID NO 243
<211> LENGTH: 456
<212> TYPE: DNA
<213> ORGANISM: Homo sapiens
<220> FEATURE:
<221> NAME/KEY: misc_feature
<222> LOCATION: (57)..(57)
<223> OTHER INFORMATION: a or g or c or t/u
<220> FEATURE:
<221> NAME/KEY: misc_feature
<222> LOCATION: (324)..(324)
<223> OTHER INFORMATION: a or g or c or t/u
<220> FEATURE:
<221> NAME/KEY: misc_feature
<222> LOCATION: (396)..(396)
<223> OTHER INFORMATION: a or g or c or t/u

<400> SEQUENCE: 243
ggagaaagga gggaaaccag gagcagccgg catgggcagt ggcagaattg gccctgntag 60
agagcagagc tgatgccatc cttttggcaa atagctgaca ttttatggtg tggtgctggg 120 tgagcccccct gtgagggttg aacagatgtg gacaggactt gggtccaggc actagagtgg 180
tgcagcctgt aagaatgcca gtttgtaagt actgactttg gaaaagatca tcgcctctat 240
cagacactta gggtcctggt ctggcaattt tggcctgatg tgatgccaca agacccaaca 300
gagagagaca cagagtccag gatnaatgtt gacagtggtg tagcctttag gaagaaatgg 360
cgctccctgc ggctggtatt aggttaccat tggcanccga aggaacccag gaggattaag 420
aatttcccta atttcagaac ttgccctggc acagta 456

<210> SEQ ID NO 244
<211> LENGTH: 434
<212> TYPE: DNA
<213> ORGANISM: Homo sapiens
<220> FEATURE:
<221> NAME/KEY: misc_feature
<222> LOCATION: (194)..(194)
<223> OTHER INFORMATION: a or g or c or t/u
<220> FEATURE:
<221> NAME/KEY: misc_feature
<222> LOCATION: (351)..(351)
<223> OTHER INFORMATION: a or g or c or t/u
<220> FEATURE:
<221> NAME/KEY: misc_feature
<222> LOCATION: (401)..(401)
<223> OTHER INFORMATION: a or g or c or t/u
<220> FEATURE:
<221> NAME/KEY: misc_feature
<222> LOCATION: (426)..(426)
<223> OTHER INFORMATION: a or g or c or t/u

<400> SEQUENCE: 244
ggtccaaaat ttttaatagt atacagacaa cctgttaatt tttttttttt ttttttttgt 60
aaataacaaa caccactttg ttatgaagac cttacaaacc tcttcttaag acattcttac 120
tctgatccag gcaaaaacac ttcaaggttt gtaaatcgac tctttcctga cataaatcct 180
tttttattaa aatngcaaaa ttgttcttca gaataaaact gtgtaataat ttttatactt 240
gggagtgctc cttgcacaga gctgtcattt gccagtgaga gcctccgacg gggcaggtac 300
tgtgccaggg cagctctgaa attatggaaa ttcttatccc cctggttcct ncggtggcca 360
atgggtaacc taataccagc ccgcgggaag cgccaatttc ncccaaaagg gggtaaacca 420
ctggtnaaac atta 434

<210> SEQ ID NO 245
<211> LENGTH: 199
<212> TYPE: DNA
<213> ORGANISM: Homo sapiens
<220> FEATURE:
<221> NAME/KEY: misc_feature
<222> LOCATION: (187)..(187)
<223> OTHER INFORMATION: a or g or c or t/u
<220> FEATURE:
<221> NAME/KEY: misc_feature
<222> LOCATION: (195)..(195)
<223> OTHER INFORMATION: a or g or c or t/u

<400> SEQUENCE: 245
tttttctttt gtaaataaca aacaccactt tgttatgaag accttacaaa cctcttctta 60
agacattctt actctgatcc aggcaaaaac acttcaaggt ttgtaaatga ctctttcctg 120
acataaatcc tttttttatta aaatgcaaaa tgttcttcag aataaaactg tgtaataatt 180
tttatangtg ggggngctc 199

<210> SEQ ID NO 246
<211> LENGTH: 459
<212> TYPE: DNA
<213> ORGANISM: Homo sapiens
<220> FEATURE:
<221> NAME/KEY: misc_feature
<222> LOCATION: (405)..(405)
<223> OTHER INFORMATION: a or g or c or t/u
<220> FEATURE:
<221> NAME/KEY: misc_feature
<222> LOCATION: (456)..(456)
<223> OTHER INFORMATION: a or g or c or t/u

<400> SEQUENCE: 246
acaaagaaaa atttaatatt cgatgagagg ttgaaccagg cttaaagcag acatactagg 60
aaatggtgca gcctgtaaga atgccagttt gtaagtactg actttggaaa agatcatcgc 120
ctctatcaga cacttagggt cctggtctgg caattttggc ctgatgtgat gccacaagac 180
ccaacagaga gagacacaga gtccaggata atgttgacag tggtgtagcc ctttaggaga 240
aatggcgctc cctgcggctg gtattaggtt accattggca ccgaagaacc aggaggataa 300
gaatatccat aatttcagag cttgccctgg cacagtacct gccccgtcgg aggctctcac 360
tgggcaaatg gacagctctg tgcaaggagc actcccaagt ataanaatta ttacacagtt 420
ttattctgaa gaacattttg cattttaata aaaaangga 459

-continued

<210> SEQ ID NO 247
<211> LENGTH: 443
<212> TYPE: DNA
<213> ORGANISM: Homo sapiens

<400> SEQUENCE: 247 ttttttttt ttttgggcca aaatttttaa tagtatacag acaacctgtt aatttttttt 60 ttttttttt ttgtaaataa caaacaccac tttgttatga agaccttaca aacctctttt 120
taagacattc ttactctgat ccaggcaaaa acacttcaag gtttgtaaat gactttttcc 180
tgacataaat cctttttat taaaatgcaa aatgttcttc agaataaaac tgtgtaataa 240
tttttatact tgggagtgct ccttgcacag agctgtcatt tgccagtgag agcctccgac 300
ggggcaggta ctgtgccagg gcagctctga aattatggat attcttatcc tcctggttcc 360
ttcggtgcca atggtaacct aataccagcc gcagggagcg ccatttctcc taaagggcta 420
caccactgtc aacattatcc tgg 443

<210> SEQ ID NO 248
<211> LENGTH: 442
<212> TYPE: DNA
<213> ORGANISM: Homo sapiens

<400> SEQUENCE: 248 ttttttttg gtccaaaatt tttaatagta tacagacaac ctgttaattt ttttttttt 60 ttttttgta aataacaaac accactttgt tatgaagacc ttacaaacct cttcttaaga 120
cattcttact ctgatccagg caaaaacact tcaaggtttg taaatgactc tttcctgaca 180
taaatccttt tttattaaaa tgcaaaatgt tcttcagaat aaaactgtgt aataattttt 240
atacttggga gtgctccttg cacagagctg tcatttgcca gtgagagcct ccgacggggc 300
aggtactgtg ccagggcagc tctgaaatta tggatattct tatcctcctg gttccttcgg 360
tgccaatggt aacctaatac cagccgcagg gagcgccatt tctcctaaag ggctacacca 420
ctgtcaacat tatcctggac tc 442

<210> SEQ ID NO 249
<211> LENGTH: 471
<212> TYPE: DNA
<213> ORGANISM: Homo sapiens

<400> SEQUENCE: 249
tttgtggaaa gatgataggt ttatagtgac tcaaaatatt ttagaaaaat ttctgtagtg 60
tcaagttctt tcaaacttaa aattttaacc ccagaggatt ttcgctgaat aaaatgagaa 120
ttggctctat ttcttctact tctggatagc ccgagtaaaa atactaataa tttctagatt 180
ttagtgggga actacaatta ttaggaccca tggatattgc tgcagttcaa atacaataca 240
gtaattacaa aatatagacc atctctttac aaatacaaat tatagtatat tacaagtcat 300
gtacagtaaa tctataattt taaacaaact agtgtatcta agtttacctg gttgcgagtg 360
cattattatt ccagtttaca gttgccctta gcgtgacagt cagaaaccga ccatcggagt 420
gatattctct tatgtaaact ggcgtcacat cacagaaaac cttatttatg a 471

<210> SEQ ID NO 250
<211> LENGTH: 7635
<212> TYPE: DNA
<213> ORGANISM: Homo sapiens

<400> SEQUENCE: 250

-continued

```
gggcgagcgc ctccgtcccc ggatgtgagc tccggctgcc cgcggtcccg agccagcggc     60
gcgcgggcgg cggcggcggg caccgggcac cgcggcgggc gggcagacgg gcgggcatgg    120
ggggagcgcc gagcggcccc ggcggccggg ccggcatcac cgcggcgtct ctccgctaga    180
ggaggggaca agccagttct cctttgcagc aaaaaattac atgtatatat tattaagata    240
atatatacat tggattttat ttttttaaaa agtttatttt gctccatttt tgaaaaagag    300
agagcttggg tggcgagcgg ttttttttta aaatcaatta tccttatttt ctgttatttg    360
tccccgtccc tccccacccc cctgctgaag cgagaataag ggcagggacc gcggctccta    420
cctcttggtg atccccttcc ccattccgcc cccgccccaa cgcccagcac agtgccctgc    480
acacagtagt cgctcaataa atgttcgtgg atgatgatga tgatgatgat gaaaaaaatg    540
cagcatcaac ggcagcagca agcggaccac gcgaacgagg caaactatgc aagaggcacc    600
agacttcctc tttctggtga aggaccaact tctcagccga atagctccaa gcaaactgtc    660
ctgtcttggc aagctgcaat cgatgctgct agacaggcca aggctgccca aactatgagc    720
acctctgcac ccccacctgt aggatctctc tcccaaagaa aacgtcagca atacgccaag    780
agcaaaaaac agggtaactc gtccaacagc cgacctgccc gcgccctttt ctgtttatca    840
ctcaataacc ccatccgaag agcctgcatt agtatagtgg aatggaaacc atttgacata    900
tttatattat tggctatttt tgccaattgt gtggccttag ctatttacat cccattccct    960
gaagatgatt ctaattcaac aaatcataac ttggaaaaag tagaatatgc cttcctgatt   1020
atttttacag tcgagacatt tttgaagatt atagcgtatg gattattgct acatcctaat   1080
gcttatgtta ggaatggatg gaatttactg gattttgtta tagtaatagt aggattgttt   1140
agtgtaattt tggaacaatt aaccaaagaa acagaaggcg ggaaccactc aagcggcaaa   1200
tctggaggct ttgatgtcaa agccctccgt gcctttcgag tgttgcgacc acttcgacta   1260
gtgtcaggag tgcccagttt acaagttgtc ctgaactcca ttataaaagc catggttccc   1320
ctccttcaca tagccctttt ggtattattt gtaatcataa tctatgctat tataggattg   1380
gaacttttta ttggaaaaat gcacaaaaca tgttttttTg ctgactcaga tatcgtagct   1440
gaagaggacc cagctccatg tgcgttctca gggaatggac gccagtgtac tgccaatggc   1500
acggaatgta ggagtggctg ggttggcccg aacggaggca tcaccaactt tgataacttt   1560
gcctttgcca tgcttactgt gtttcagtgc atcaccatgg agggctggac agacgtgctc   1620
tactggatga atgatgctat gggatttgaa ttgccctggg tgtattttgt cagtctcgtc   1680
atctttgggt catttttcgt actaaatctt gtacttggtg tattgagcgg agaattctca   1740
aaggaaagag agaaggcaaa agcacgggga gatttccaga agctccggga gaagcagcag   1800
ctggaggagg atctaaaggg ctacttggat tggatcaccc aagctgagga catcgatccg   1860
gagaatgagg aagaaggagg agaggaaggc aaacgaaata ctagcatgcc caccagcgag   1920
actgagtctg tgaacacaga gaacgtcagc ggtgaaggcg agaaccgagg ctgctgtgga   1980
agtctctgtc aagccatctc aaaatccaaa ctcagccgac gctggcgtcg ctggaaccga   2040
ttcaatcgca gaagatgtag ggccgccgtg aagtctgtca cgttttactg gctggttatc   2100
gtcctggtgt ttctgaacac cttaaccatt tcctctgagc actacaatca gccagattgg   2160
ttgacacaga ttcaagatat tgccaacaaa gtcctcttgg ctctgttcac ctgcgagatg   2220
ctggtaaaaa tgtacagctt gggcctccaa gcatatttcg tctctctttt caaccggttt   2280
gattgcttcg tggtgtgtgg tggaatcact gagacgatct tggtggaact ggaaatcatg   2340
```

-continued

```
tctcccctgg ggatctctgt gtttcggtgt gtgcgcctct taagaatctt caaagtgacc   2400
aggcactgga cttccctgtg caacttagtg gcatccttat taaactccat gaagtccagt   2460
gcttcgctgt tgcttctgct ttttctcttc attatcatct tttccttgct tgggatgcag   2520
ctgtttggcg gcaagtttaa ttttgatgaa acgcaaacca agcggagcac ctttgacaat   2580
ttccctcaag cacttctcac agtgttccag atcctgacag gcgaagactg gaatgctgtg   2640
atgtacgatg gcatcatggc ttacgggggc ccatcctctt caggaatgat cgtctgcatc   2700
tacttcatca tcctcttcat ttgtggtaac tatattctac tgaatgtctt cttggccatc   2760
gctgtagaca atttggctga tgctgaaagt ctgaacactg ctcagaaaga agaagcggaa   2820
gaaaaggaga ggaaaaagat tgccagaaaa gagagcctag aaaataaaaa gaacaacaaa   2880
ccagaagtca accagatagc caacagtgac aacaaggtta caattgatga ctatagagaa   2940
gaggatgaag acaaggaccc ctatccgcct tgcgatgtgc cagtagggga agaggaagag   3000
gaagaggagg aggatgaacc tgaggttcct gccggacccc gtcctcgaag gatctcggag   3060
ttgaacatga aggaaaaaat tgcccccatc cctgaaggga gcgctttctt cattcttagc   3120
aagaccaacc cgatccgcgt aggctgccac aagctcatca accaccacat cttcaccaac   3180
ctcatccttg tcttcatcat gctgagcagt gctgccctgg ccgcagagga ccccatccgc   3240
agccactcct tccggaacac gatactgggt tactttgact atgccttcac agccatcttt   3300
actgttgaga tcctgttgaa gatgacaact tttggagctt tcctccacaa aggggccttc   3360
tgcaggaact acttcaattt gctggatatg ctggtggttg gggtgtctct ggtgtcattt   3420
gggattcaat ccagtgccat ctccgttgtg aagattctga gggtcttaag ggtcctgcgt   3480
cccctcaggg ccatcaacag agcaaaagga cttaagcacg tggtccagtg cgtcttcgtg   3540
gccatccgga ccatcggcaa catcatgatc gtcaccaccc tcctgcagtt catgtttgcc   3600
tgtatcgggg tccagttgtt caaggggaag ttctatcgct gtacggatga agccaaaagt   3660
aaccctgaag aatgcagggg acttttcatc ctctacaagg atggggatgt tgacagtcct   3720
gtggtccgtg aacggatctg gcaaaacagt gatttcaact tcgacaacgt cctctctgct   3780
atgatggcgc tcttcacagt ctccacgttt gagggctggc ctgcgttgct gtataaagcc   3840
atcgactcga atggagagaa catcggccca atctacaacc accgcgtgga gatctccatc   3900
ttcttcatca tctacatcat cattgtagct ttcttcatga tgaacatctt tgtgggcttt   3960
gtcatcgtta catttcagga acaaggagaa aaagagtata agaactgtga gctggacaaa   4020
aatcagcgtc agtgtgttga atacgccttg aaagcacgtc ccttgcggag atacatcccc   4080
aaaaacccct accagtacaa gttctggtac gtggtgaact cttcgccttt cgaatacatg   4140
atgtttgtcc tcatcatgct caacacactc tgcttggcca tgcagcacta cgagcagtcc   4200
aagatgttca atgatgccat ggacattctg aacatggtct tcaccggggt gttcaccgtc   4260
gagatggttt tgaaagtcat cgcatttaag cctaaggggt attttagtga cgcctggaac   4320
acgtttgact ccctcatcgt aatcggcagc attatagacg tggccctcag cgaagcagac   4380
ccaactgaaa gtgaaaatgt ccctgtccca actgctacac ctgggaactc tgaagagagc   4440
aatagaatct ccatcacctt tttccgtctt ttccgagtga tgcgattggt gaagcttctc   4500
agcagggggg aaggcatccg gacattgctg tggactttta ttaagttctt tcaggcgctc   4560
ccgtatgtgg ccctcctcat agccatgctg ttcttcatct atgcggtcat tggcatgcag   4620
atgtttggga aagttgccat gagagataac aaccagatca ataggaacaa taacttccag   4680
acgtttcccc aggcggtgct gctgctcttc aggtgtgcaa caggtgaggc ctggcaggag   4740
```

-continued

```
atcatgctgg cctgtctccc agggaagctc tgtgaccctg agtcagatta caaccccggg   4800
gaggagcata catgtgggag caactttgcc attgtctatt tcatcagttt ttacatgctc   4860
tgtgcatttc tgatcatcaa tctgtttgtg gctgtcatca tggataattt cgactatctg   4920
acccgggact ggtctatttt ggggcctcac catttagatg aattcaaaag aatatggtca   4980
gaatatgacc ctgaggcaaa gggaaggata aaacaccttg atgtggtcac tctgcttcga   5040
cgcatccagc ctcccctggg gtttgggaag ttatgtccac acagggtagc gtgcaagaga   5100
ttagttgcca tgaacatgcc tctcaacagt gacgggacag tcatgtttaa tgcaaccctg   5160
tttgctttgg ttcgaacggc tcttaagatc aagaccgaag ggaacctgga gcaagctaat   5220
gaagaacttc gggctgtgat aaagaaaatt tggaagaaaa ccagcatgaa attacttgac   5280
caagttgtcc ctccagctgg tgatgatgag gtaaccgtgg ggaagttcta tgccactttc   5340
ctgatacagg actactttag gaaattcaag aaacggaaag aacaaggact ggtgggaaag   5400
taccctgcga agaacaccac aattgcccta caggcgggat taaggacact gcatgacatt   5460
gggccagaaa tccggcgtgc tatatcgtgt gatttgcaag atgacgagcc tgaggaaaca   5520
aaacgagaag aagaagatga tgtgttcaaa agaaatggtg ccctgcttgg aaaccatgtc   5580
aatcatgtta atagtgatag gagagattcc cttcagcaga ccaataccac ccaccgtccc   5640
ctgcatgtcc aaaggccttc aattccacct gcaagtgata ctgagaaacc gctgtttcct   5700
ccagcaggaa attcggtgtg tcataaccat cataaccata attccatagg aaagcaagtt   5760
cccacctcaa caaatgccaa tctcaataat gccaatatgt ccaaagctgc ccatggaaag   5820
cggcccagca ttgggaacct tgagcatgtg tctgaaaatg ggcatcattc ttcccacaag   5880
catgaccggg agcctcagag aaggtccagt gtgaaaagaa cccgctatta tgaaacttac   5940
attaggtccg actcaggaga tgaacagctc ccaactattt gccgggaaga cccagagata   6000
catggctatt tcagggaccc ccactgcttg ggggagcagg agtatttcag tagtgaggaa   6060
tgctacgagg atgacagctc gcccacctgg agcaggcaaa actatggcta ctacagcaga   6120
tacccaggca gaaacatcga ctctgagagg ccccgaggct accatcatcc ccaaggattc   6180
ttggaggacg atgactcgcc cgtttgctat gattcacgga gatctccaag gagacgccta   6240
ctacctccca ccccagcatc ccaccggaga tcctccttca actttgagtg cctgcgccgg   6300
cagagcagcc aggaagaggt cccgtcgtct cccatcttcc cccatcgcac ggccctgcct   6360
ctgcatctaa tgcagcaaca gatcatggca gttgccggcc tagattcaag taaagcccag   6420
aagtactcac cgagtcactc gacccggtcg tgggccaccc ctccagcaac ccctccctac   6480
cgggactgga caccgtgcta caccccccctg atccaagtgg agcagtcaga ggccctggac   6540
caggtgaacg gcagcctgcc gtccctgcac cgcagctcct ggtacacaga cgagcccgac   6600
atctcctacc ggactttcac accagccagc ctgactgtcc ccagcagctt ccggaacaaa   6660
aacagcgaca agcagaggag tgcggacagc ttggtggagg cagtcctgat atccgaaggc   6720
ttgggacgct atgcaaggga cccaaaattt gtgtcagcaa caaaacacga aatcgctgat   6780
gcctgtgacc tcaccatcga cgagatggag agtgcagcca gcaccctgct taatgggaac   6840
gtgcgtcccc gagccaacgg ggatgtgggc cccctctcac accggcagga ctatgagcta   6900
caggactttg gtcctggcta cagcgacgaa gagccagacc ctgggaggga tgaggaggac   6960
ctggcggatg aaatgatatg catcaccacc ttgtagcccc cagcgagggg cagactggct   7020
ctggcctcag gtggggcgca ggagagccag ggaaaagtg cctcatagtt aggaaagttt   7080
```

-continued

```
aggcactagt tgggagtaat attcaattaa ttagactttt gtataagaga tgtcatgcct   7140

caagaaagcc ataaacctgg taggaacagg tcccaagcgg ttgagcctgg cagagtacca   7200

tgcgctcggc cccagctgca ggaaacagca ggcccgccc tctcacagag gatgggtgag   7260

gaggccagac ctgccctgcc ccattgtcca gatgggcact gctgtggagt ctgcttctcc   7320

catgtaccag ggcaccaggc ccacccaact gaaggcatgg cggcggggtg caggggaaag   7380

ttaaaggtga tgacgatcat cacacctgtg tcgttacctc agccatcggt ctagcatatc   7440

agtcactggg cccaacatat ccatttttaa accctttccc ccaaatacac tgcgtcctgg   7500

ttcctgttta gctgttctga aatacggtgt gtaagtaagt cagaacccag ctaccagtga   7560

ttattgcgag ggcaatggga cctcataaat aaggttttct gtgatgtgac gccagtttac   7620

ataagagaat atcac                                                    7635
```

<210> SEQ ID NO 251
<211> LENGTH: 637
<212> TYPE: DNA
<213> ORGANISM: Homo sapiens

<400> SEQUENCE: 251

```
ttttttttt cttacaaaga aaaatttaat attcgatgag aggttgaacc aggcttaaag     60

cagacatact aggaaatggt gcagcctgta agaatgccag tttgtaagta ctgactttgg    120

aaaagatcat cgcctctatc agacacttag ggtcctggtc tggcaatttt ggcctgatgt    180

gatgccacaa gacccaacag agagagacac agagtccagg ataatgttga cagtggtgta    240

gccctttagg agaaatggcg ctccctgcgg ctggtattag gttaccattg gcaccgaagg    300

aaccaggagg ataagaatat ccataatttc agagctgccc tggcacagta cctgccccgt    360

cggaggctct cactggcaaa tgacagctct gtgcaaggag cactcccaag tataaaaatt    420

attacacagt tttattctga agaacatttt gcattttaat aaaaaaggat ttatgtcagg    480

aaagagtcat ttacaaacct tgaagtgttt ttgcctggat cagagtaaga atgtcttaag    540

aagaggtttg taaggtcttc ataacaaagt ggtgtttgtt atttacaaaa aaaaaaaaaa    600

aaaaaaatta acaggttgtc tgtatactat taaaaat                             637
```

<210> SEQ ID NO 252
<211> LENGTH: 7193
<212> TYPE: DNA
<213> ORGANISM: Homo sapiens

<400> SEQUENCE: 252

```
agaataaggg cagggaccgc ggctcctatc tcttggtgat ccccttcccc attccgcccc     60

cgcctcaacg cccagcacag tgccctgcac acagtagtcg ctcaataaat gttcgtggat    120

gatgatgatg atgatgatga aaaaaatgca gcatcaacgg cagcagcaag cggaccacgc    180

gaacgaggca aactatgcaa gaggcaccag acttcctctt tctggtgaag gaccaacttc    240

tcagccgaat agctccaagc aaactgtcct gtcttggcaa gctgcaatcg atgctgctag    300

acaggccaag gctgcccaaa ctatgagcac ctctgcaccc ccacctgtag gatctctctc    360

ccaaagaaaa cgtcagcaat acgccaagag caaaaaacag ggtaactcgt ccaacagccg    420

acctgcccgc gccctttct gtttatcact caataacccc atccgaagag cctgcattag     480

tatagtggaa tggaaaccat ttgacatatt tatattattg gctatttttg ccaattgtgt    540

ggccttagct atttacatcc cattccctga agatgattct aattcaacaa atcataactt    600

ggaaaaagta gaatatgcct tcctgattat ttttacagtc gagacatttt tgaagattat    660
```

-continued

```
agcgtatgga ttattgctac atcctaatgc ttatgttagg aatggatgga atttactgga    720
ttttgttata gtaatagtag gattgtttag tgtaattttg gaacaattaa ccaaagaaac    780
agaaggcggg aaccactcaa gcggcaaatc tggaggcttt gatgtcaaag ccctccgtgc    840
ctttcgagtg ttgcgaccac ttcgactagt gtcaggggtg cccagtttac aagttgtcct    900
gaactccatt ataaaagcca tggttcccct ccttcacata gccctttttgg tattatttgt    960
aatcataatc tatgctatta taggattgga actttttatt ggaaaaatgc acaaaacatg   1020
tttttttgct gactcagata tcgtagctga agaggaccca gctccatgtg cgttctcagg   1080
gaatggacgc cagtgtactg ccaatggcac ggaatgtagg agtggctggg ttggcccgaa   1140
cggaggcatc accaactttg ataactttgc ctttgccatg cttactgtgt ttcagtgcat   1200
caccatggag ggctggacag acgtgctcta ctgggtaaat gatgcgatag gatgggaatg   1260
gccatgggtg tattttgtta gtctgatcat ccttggctca tttttcgtcc ttaacctggt   1320
tcttggtgtc cttagtggag aattctcaaa ggaaagagag aaggcaaaag cacggggaga   1380
tttccagaag ctccgggaga agcagcagct ggaggaggat ctaaagggct acttggattg   1440
gatcacccaa gctgaggaca tcgatccgga gaatgaggaa gaaggaggag aggaaggcaa   1500
acgaaatact agcatgccca ccagcgagac tgagtctgtg aacacagaga acgtcagcgg   1560
tgaaggcgag aaccgaggct gctgtggaag tctctggtgc tggtggagac ggagaggcgc   1620
ggccaaggcg gggccctctg ggtgtcggcg gtggggtcaa gccatctcaa aatccaaact   1680
cagccgacgc tggcgtcgct ggaaccgatt caatcgcaga agatgtaggg ccgccgtgaa   1740
gtctgtcacg ttttactggc tggttatcgt cctggtgttt ctgaacacct taaccatttc   1800
ctctgagcac tacaatcagc cagattggtt gacacagatt caagatattg ccaacaaagt   1860
cctcttggct ctgttcacct gcgagatgct ggtaaaaatg tacagcttgg gcctccaagc   1920
atatttcgtc tctcttttca accggtttga ttgcttcgtg gtgtgtggtg gaatcactga   1980
gacgatcctg gtggaactgg aaatcatgtc tcccctgggg atctctgtgt ttcggtgtgt   2040
gcgcctctta agaatcttca aagtgaccag gcactggact tccctgagca acttagtggc   2100
atccttatta aactccatga agtccatcgc ttcgctgttg cttctgcttt ttctcttcat   2160
tatcatcttt tccttgcttg ggatgcagct gtttggcggc aagtttaatt ttgatgaaac   2220
gcaaaccaag cggagcacct ttgacaattt ccctcaagca cttctcacag tgttccagat   2280
cctgacaggc gaagactgga atgctgtgat gtacgatggc atcatggctt acggggggccc   2340
atcctcttca ggaatgatcg tctgcatcta cttcatcatc ctcttcattt gtggtaacta   2400
tattctactg aatgtcttct tggccatcgc tgtagacaat ttggctgatg ctgaaagtct   2460
gaacactgct cagaaagaag aagcggaaga aaaggagagg aaaaagattg ccagaaaaga   2520
gagcctagaa aataaaaaga acaacaaacc agaagtcaac cagatagcca acagtgacaa   2580
caaggttaca attgatgact atagagaaga ggatgaagac aaggacccct atccgccttg   2640
cgatgtgcca gtaggggaag aggaagagga agaggaggag gatgaacctg aggttcctgc   2700
cggaccccgt cctcgaagga tctcggagtt gaacatgaag gaaaaaattg cccccatccc   2760
tgaagggagc gctttcttca ttcttagcaa gaccaacccg atccgcgtag gctgccacaa   2820
gctcatcaac caccacatct tcaccaacct catccttgtc ttcatcatgc tgagcagcgc   2880
tgccctggcc gcagaggacc ccatccgcag ccactccttc cggaacacga tactgggtta   2940
ctttgactat gccttcacag ccatctttac tgttgagatc ctgttgaaga tgacaacttt   3000
```

-continued

```
tggagctttc ctccacaaag gggccttctg caggaactac ttcaatttgc tggatatgct   3060
ggtggttggg gtgtctctgg tgtcatttgg gattcaatcc agtgccatct ccgttgtgaa   3120
gattctgagg gtcttaaggg tcctgcgtcc cctcagggcc atcaacagag caaaaggact   3180
taagcacgtg gtccagtgcg tcttcgtggc catccggacc atcggcaaca tcatgatcgt   3240
cactaccctc ctgcagttca tgtttgcctg tatcggggtc cagttgttca aggggaagtt   3300
ctatcgctgt acggatgaag ccaaaagtaa ccctgaagaa tgcaggggac ttttcatcct   3360
ctacaaggat ggggatgttg acagtcctgt ggtccgtgaa cggatctggc aaaacagtga   3420
tttcaacttc gacaacgtcc tctctgctat gatggcgctc ttcacagtct ccacgtttga   3480
gggctggcct gcgttgctgt ataaagccat cgactcgaat ggagagaaca tcggcccaat   3540
ctacaaccac cgcgtggaga tctccatctt cttcatcatc tacatcatca ttgtagcttt   3600
cttcatgatg aacatctttg tgggctttgt catcgttaca tttcaggaac aaggagaaaa   3660
agagtataag aactgtgagc tggacaaaaa tcagcgtcag tgtgttgaat acgccttgaa   3720
agcacgtccc ttgcggagat acatccccaa aaacccctac cagtacaagt tctggtacgt   3780
ggtgaactct tcgcctttcg aatacatgat gtttgtcctc atcatgctca acacactctg   3840
cttggccatg cagcactacg agcagtccaa gatgttcaat gatgccatgg acattctgaa   3900
catggtcttc accggggtgt tcaccgtcga gatggttttg aaagtcatcg catttaagcc   3960
taaggggtat tttagtgacg cctggaacac gtttgactcc ctcatcgtaa tcggcagcat   4020
tatagacgtg gccctcagcg aagcggaccc aactgaaagt gaaaatgtcc ctgtcccaac   4080
tgctacacct gggaactctg aagagagcaa tagaatctcc atcacctttt tccgtctttt   4140
ccgagtgatg cgattggtga agcttctcag caggggggaa ggcatccgga cattgctgtg   4200
gacttttatt aagtcctttc aggcgctccc gtatgtggcc ctcctcatag ccatgctgtt   4260
cttcatctat gcggtcattg gcatgcagat gtttgggaaa gttgccatga gagataacaa   4320
ccagatcaat aggaacaata acttccagac gtttccccag gcggtgctgc tgctcttcag   4380
gtgtgcaaca ggtgaggcct ggcaggagat catgctggcc tgtctcccag ggaagctctg   4440
tgaccctgag tcagattaca accccgggga ggagtataca tgtgggagca actttgccat   4500
tgtctatttc atcagttttt acatgctctg tgcatttctg atcatcaatc tgtttgtggc   4560
tgtcatcatg gataatttcg actatctgac ccgggactgg tctattttgg ggcctcacca   4620
tttagatgaa ttcaaaagaa tatggtcaga atatgaccct gaggcaaagg gaaggataaa   4680
acaccttgat gtggtcactc tgcttcgacg catccagcct cccctggggt ttgggaagtt   4740
atgtccacac agggtagcgt gcaagagatt agttgccatg aacatgcctc tcaacagtga   4800
cgggacagtc atgtttaatg caaccctgtt tgctttggtt cgaacggctc ttaagatcaa   4860
gaccgaaggg aacctggagc aagctaatga agaacttcgg gctgtgataa agaaaatttg   4920
gaagaaaacc agcatgaaat tacttgacca agttgtccct ccagctggtg atgatgaggt   4980
aaccgtgggg aagttctatg ccactttcct gatacaggac tactttagga aattcaagaa   5040
acggaaagaa caaggactgg tgggaaagta ccctgcgaag aacaccacaa ttgccctaca   5100
ggcgggatta aggacactgc atgacattgg gccagaaatc cggcgtgcta tatcgtgtga   5160
tttgcaagat gacgagcctg aggaaacaaa acgagaagaa gaagatgatg tgttcaaaag   5220
aaatggtgcc ctgcttggaa accatgtcaa tcatgttaat agtgatagga gagattccct   5280
tcagcagacc aataccaccc accgtcccct gcatgtccaa aggccttcaa ttccacctgc   5340
aagtgatact gagaaaccgc tgtttcctcc agcaggaaat tcggtgtgtc ataaccatca   5400
```

-continued

```
taaccataat tccataggaa agcaagttcc cacctcaaca aatgccaatc tcaataatgc   5460
caatatgtcc aaagctgccc atggaaagcg gcccagcatt gggaaccttg agcatgtgtc   5520
tgaaaatggg catcattctt cccacaagca tgaccgggag cctcagagaa ggtccagtgt   5580
gaaaagaacc cgctattatg aaacttacat taggtccgac tcaggagatg aacagctccc   5640
aactatttgc cgggaagacc cagagataca tggctatttc agggaccccc actgcttggg   5700
ggagcaggag tatttcagta gtgaggaatg ctacgaggat gacagctcgc ccacctggag   5760
caggcaaaac tatggctact acagcagata cccaggcaga aacatcgact ctgagaggcc   5820
ccgaggctac catcatcccc aaggattctt ggaggacgat gactcgcccg tttgctatga   5880
ttcacggaga tctccaagga gacgcctact acctcccacc ccagcatccc accggagatc   5940
ctccttcaac tttgagtgcc tgcgccggca gagcagccag gaagaggtcc cgtcgtctcc   6000
catcttcccc catcgcacgg ccctgcctct gcatctaatg cagcaacaga tcatggcagt   6060
tgccggccta gattcaagta aagcccagaa gtactcaccg agtcactcga cccggtcgtg   6120
ggccacccct ccagcaaccc ctccctaccg ggactggaca ccgtgctaca ccccccctgat   6180
ccaagtggag cagtcagagg ccctggacca ggtgaacggc agcctgccgt ccctgcaccg   6240
cagctcctgg tacacagacg agcccgacat ctcctaccgg actttcacac cagccagcct   6300
gactgtcccc agcagcttcc ggaacaaaaa cagcgacaag cagaggagtg cggacagctt   6360
ggtggaggca gtcctgatat ccgaaggctt gggacgctat gcaagggacc caaaatttgt   6420
gtcagcaaca aaacacgaaa tcgctgatgc ctgtgacctc accatcgacg agatggagag   6480
tgcagccagc accctgctta atgggaacgt gcgtccccga gccaacgggg atgtgggccc   6540
cctctcacac cggcaggact atgagctaca ggactttggt cctggctaca gcgacgaaga   6600
gccagaccct gggagggatg aggaggacct ggcggatgaa atgatatgca tcaccacctt   6660
gtagccccca gcgaggggca gactggctct ggcctcaggt ggggcgcagg agagccaggg   6720
gaaaagtgcc tcatagttag gaaagtttag gcactagttg ggagtaatat tcaattaatt   6780
agacttttgt ataagagatg tcatgcctca agaaagccat aaacctggta ggaacaggtc   6840
ccaagcggtt gagcctggca gagtaccatg cgctcggccc cagctgcagg aaacagcagg   6900
ccccgccctc tcacagagga tgggtgagga ggccagacct gccctgcccc attgtccaga   6960
tgggcactgc tgtggagtct gcttctccca tgtaccaggg caccaggccc acccaactga   7020
aggcatggcg gcggggtgca ggggaaagtt aaaggtgatg acgatcatca cacctcgtgt   7080
cgttacctca gccatcggtc tagcatatca gtcactgggc ccaacatatc catttttaaa   7140
ccctttcccc caaatacact gcgtcctggt tcctgtttag ctgttctgaa ata          7193
```

```
<210> SEQ ID NO 253
<211> LENGTH: 243
<212> TYPE: DNA
<213> ORGANISM: Homo sapiens

<400> SEQUENCE: 253

gtactgtgcc ggggcagctc tgaaattatg gatattctta tcctcctggt tccttcggtg     60
ccaatggtaa cctaatacca gccgcaggga gcgccatttc tcctaaaggg ctacaccact    120
gtcaacatta tcctggactc tgtgtctctc tctgttgggt cttgtggcat cacatcaggc    180
caaaattgcc agaccaggac cctaagtgtc tgatagaggc gatgatcttt tcaaagtcag    240
tac                                                                  243
```

-continued

<210> SEQ ID NO 254
<211> LENGTH: 341
<212> TYPE: DNA
<213> ORGANISM: Homo sapiens
<220> FEATURE:
<221> NAME/KEY: misc_feature
<222> LOCATION: (9)..(9)
<223> OTHER INFORMATION: a or g or c or t/u

<400> SEQUENCE: 254
tgcagcaant ggcacggaat gtaggagtgg gtgggtggga ccgaacggag gcatcaccaa 60
ctttgataac ttggcctatg ccatgcttac ggtgtttcag tgcatcacca tggagggctg 120
gacagatgtg ctctactggg taaatgatgc gataggatgg gaatggccat gggcgtattt 180
tgttagtctg atcatccttg gctcattttt cgtccttaac ctggttcttg gtgtccttag 240
tggagaattc tcaaaggaaa gagagaaggc aaaagcacgg ggagatttcc agaagctccg 300
ggagaagcag cagctggagg aggatctaaa gggctacttg g 341

<210> SEQ ID NO 255
<211> LENGTH: 406
<212> TYPE: DNA
<213> ORGANISM: Homo sapiens
<220> FEATURE:
<221> NAME/KEY: misc_feature
<222> LOCATION: (332)..(332)
<223> OTHER INFORMATION: a or g or c or t/u

<400> SEQUENCE: 255
atgactacgg gggaagttca ttctgacctt ccagactagc tagtactata tgaaatccga 60
gagacggaat gaacacggac tgatgggaaa gtaccctgcg aagaacacca caattgccct 120
acaggcgtga ttaaggacac tgcatgatag ttgctccaga atgccggcgt gctatatcgt 180
gtgatttgca agatgacgag cgtgaggaaa caaaacgaga agaagaagat gatgtgttca 240
aaagaaatgg tgccctgctt ggaaaccatg tcaatcatgt taatagtgat aggagagatt 300
cccttcagca gaccaatacc acccaccgtc cnctgcatgt ccaaaggcct tcaattccac 360
ctgcaagtga tactgagaaa ccgctgttcc tccagcagga aattcg 406

<210> SEQ ID NO 256
<211> LENGTH: 236
<212> TYPE: DNA
<213> ORGANISM: Homo sapiens

<400> SEQUENCE: 256
tacatctccg ctatctgtgc cgtgtaacac ggtgtccagt ctcgttaggg aggggctgct 60
ggaggggtgg cccacgaccg ggtcgagtga ctcggtgagc acttctgtgc tttacttgaa 120
tctaggccgg caactgccat gatctgttgc tgcattagat gcagaggcag tgccgcgcga 180
tggtgaagat gggagacgac gggacctctt gctggctgct ctgccggcgc aggcac 236

<210> SEQ ID NO 257
<211> LENGTH: 586
<212> TYPE: DNA
<213> ORGANISM: Homo sapiens

<400> SEQUENCE: 257
tgtcgtgact ggcgatacct ggcgttagtg tgtacatggt gttcataatt gctgctgcat 60
aacattttgt gagaattaat gtgacaatgt atgtgcagtg cttagcacat agcaagtgct 120
catgaatggt agccaccaag atggctgttg tcattttagt ttgcagcagt tccacttgtc 180

-continued

```
atcattgagt tcccagggag tcccctcttc tttgggaaca gacttgctct ctgtagctcc    240

attgcggtaa aaacagatga ggttaatccc tgtcccaatc attttggaga tggcgtcgtt    300

tgtattccaa ttccacagcc cagttcttgt ctttgtcttc cttttattta agcagcagcc    360

acacagaatt agccctttc aaaaataaat aagattatca tcctgttttg cgtccctggg     420

gtaacagact ctaacatttc tttctctttc tcttctttca gattgtctag tgtaattttg    480

gaacaattaa ccaaagaaac agaaggcggg aaccactcac gcggcaaatc tggaggcttt    540

gatgtcaaag ccctccgtgc ctttcgagtg ttgcgaccac ttcgaa                   586
```

<210> SEQ ID NO 258
<211> LENGTH: 549
<212> TYPE: DNA
<213> ORGANISM: Homo sapiens

<400> SEQUENCE: 258

```
agttcccacc tcaacaaatg ccaatctcaa taatgccaat atgtccaaag ctgcccatgg     60

aaagcggccc agcattggga accttgagca tgtgtctgaa aatgggcatc attcttccca    120

caagcatgac cgggagcctc agagaaggtc cagtgtgaaa aggtccgact caggagatga    180

acagctccca actatttgcc gggaagaccc agagatacat ggctatttca gggacccccca   240

ctgcttgggg gagcaggagt atttcagtag tgaggaatgc tacgaggatg acagctcgcc    300

cacctggagc aggcaaaact atggctacta cagcagatac ccaggcagaa acatcgactc    360

tgagaggccc cgaggctacc atcatcccca aggattcttg gaggacgatg actcgcccgt    420

ttgctatgat tcacggagat ctccaaggag acgcctacta cctcccaccc cagcatgtga    480

ggccagattt tttgtttttg ggtggaacct cccggggaac agtgtacctt tcccccaacc    540

cccgctctg                                                            549
```

<210> SEQ ID NO 259
<211> LENGTH: 595
<212> TYPE: DNA
<213> ORGANISM: Homo sapiens

<400> SEQUENCE: 259

```
attcggcacg agcctccttc aactttgagt gctctgcccc ttgggtatcc atagttacgg     60

ttttctctgt ggcccaccca gggtgttttt tgcatcgctg gtgcagaaat gcacaggtgg    120

atgagatata gctgctcttg tcctctgggg actggtggtg ctgcttaaga aataaggggt    180

gctggggaca gaggagcaac gtggtgatct ataggattgg agtgtcgggg tctgtacaaa    240

tcgtattgtt gccttttaca aaactgctgt actgtatgtt ctctttgagg gcttttatat    300

gcaattgact gagggctgaa gttttcatta gaatgcactc acactctgac tgtacgtcct    360

gatgaaaacc cacttttgga taattagaac cgtcaaggct tcattttctg tcaacagaat    420

taggccgact gtcaggttac cttggcaggg attccctgca atcaaaaaga tagatgatag    480

gtagcaattt tggtccaaaa tttttaatag tatacagaca acctgttaat ttttttttt     540

ttttttttg taaataacaa acaccacttt gttatgaaga ccttacaaac ctctt          595
```

<210> SEQ ID NO 260
<211> LENGTH: 209
<212> TYPE: DNA
<213> ORGANISM: Homo sapiens

<400> SEQUENCE: 260

-continued

```
ggaaaactca agtccagagc aatactacgt aaaattcaga agtgagaaca tacaaaggca      60

acacacaggc tgacgaagaa acagaaagaa gatactgacc tgagtttgga ttttgagatg     120

gcttgactga aagaaagaca aaaagtgtta agattctggt tccgagggct tgagcacaca     180

ctccccatca tttcagctgg agatttcat                                       209
```

<210> SEQ ID NO 261
<211> LENGTH: 687
<212> TYPE: DNA
<213> ORGANISM: Homo sapiens
<220> FEATURE:
<221> NAME/KEY: misc_feature
<222> LOCATION: (632)..(632)
<223> OTHER INFORMATION: a or g or c or t/u

<400> SEQUENCE: 261

```
ttttttttt ttttttttat tctgaagaac attttgcatt ttaataaaaa aggatttatg       60

tcaggaaaga gtcatttaca aaccttgaag tgtttttgcc tggatcagag taagaatgtc     120

ttaagaagag gtttgtaagg tcttcataac aaagtggtgt ttgttattta caaaaaaaaa     180

aaaaaaaaat taacaggttg tctgtatact attaaaaatt ttggaccaaa attgctacct     240

atcatctatc tttttgattg cagggaatcc ctgccaaggt aacttgacag tcggcctaat     300

tctgttgaca gaaaatgaag ccttgacggt tctaattatc caaaagtggg ttttcatcag     360

gacgtacagt cagagtgtga gtgcattcta atgaaaactt cttcagccct cattcaattg     420

catacaaaag ccctcaaaga gaacatacag tacagcagtt ttgtaaaagg caacaatacg     480

atttgtacag accccgacac tccaatccta tagatcacca cgttgctcct ctgtccccag     540

caccccttat ttcttaagca gcaccaccag tccccagagg acaagagcag ctatatctca     600

tccacctgtg catttctgca ccagcgatgc anaaaacacc ctggggtggg ccacagagaa     660

aaccgtaact atggataccc aaggggc                                         687
```

<210> SEQ ID NO 262
<211> LENGTH: 573
<212> TYPE: DNA
<213> ORGANISM: Homo sapiens

<400> SEQUENCE: 262

```
taaataacaa acaccacttt gttatgaaga ccttacaaac ctcttcttaa gacattctta      60

ctctgatcca ggcaaaaaca cttcaaggtt tgtaaatgac tctttcctga cataaatcct     120

tttttattaa aatgcaaaat gttcttcaga ataaaactgt gtaataattt ttatacttgg     180

gagtgctcct tgcacagagc tgtcatttgc cagtgagagc ctccgacggg gcaggtactg     240

tgccagggca gctctgaaat tatggatatt cttatcctcc tggttccttc ggtgccaatg     300

gtaacctaat accagccgca gggagcgcca tttctcctaa agggctacac cactgtcaac     360

attatcctgg actctgtgtc tctctctgtt gggtcttgtg gcatcacatc aggccaaaat     420

tgccagacca ggaccctaag tgtctgatag aggcgatgat cttttccaaa gtcagtactt     480

acaaactggc attcttacag gctgcaccat ttcctagtat gtctgcttta agcctggttc     540

aacctctcat cgaatattaa atttttcttt gta                                  573
```

<210> SEQ ID NO 263
<211> LENGTH: 453
<212> TYPE: DNA
<213> ORGANISM: Homo sapiens

<400> SEQUENCE: 263

-continued

```
ttttttttt tttttcttgg ggaaagatga taggtttata gtgactcaaa atattttaaa      60

aaaatttctg tagggtcaag ttctttcaaa cttaaaattt taaccccaga ggattttcgc    120

tgaataaatg aaaattggct ctatttcttc aacttcggga tagcccgagt aaaaatacta    180

ataatttcta aattttaggg gggaactaca attattagga cccatggata ttgctgcagt    240

tcaaatacaa tacagtaatt acaaaatata gaccatctct ttacaaatac aaattatagt    300

atattacaag tcatgtacag taaatctata attttaaaca aactagtgta tctaagttta    360

cctggttgcg agtgcattat tattccagtt tacagttgcc cttagcgtga cagtcagaaa    420

ccgaccatcg gagtgatatt ctcttatgta aac                                 453
```

<210> SEQ ID NO 264
<211> LENGTH: 415
<212> TYPE: DNA
<213> ORGANISM: Homo sapiens
<220> FEATURE:
<221> NAME/KEY: misc_feature
<222> LOCATION: (311)..(311)
<223> OTHER INFORMATION: a or g or c or t/u

<400> SEQUENCE: 264

```
tgattacttg tagcaaagta cttccccaca tttagctgga tttgtctttg gtttgaagag     60

gctaatacgt gaaagatttg ttcacagttg gatgtcccct tttctgaacc atgaagtaat    120

attgtgaatg gagttgaatg ctgaggttag ggtgccggaa agattcaggg tccttcggta    180

ccctcacatg gcttggcttt ggtagaacaa gaaactaagc tctgatttgg ctttaaatga    240

gagtgctaaa tttccttttt ctaataaaga acctagctaa acatttatat atacttttga    300

acactgaact ntcttgttgc agagttaaca gctgttgggg gtagctgaca gctggatcct    360

ggtgctgttg gtaccatggt acctgaagtg cacaggctgg tagccacacc tgaca         415
```

<210> SEQ ID NO 265
<211> LENGTH: 646
<212> TYPE: DNA
<213> ORGANISM: Homo sapiens
<220> FEATURE:
<221> NAME/KEY: misc_feature
<222> LOCATION: (43)..(43)
<223> OTHER INFORMATION: a or g or c or t/u
<220> FEATURE:
<221> NAME/KEY: misc_feature
<222> LOCATION: (573)..(573)
<223> OTHER INFORMATION: a or g or c or t/u

<400> SEQUENCE: 265

```
ttttttttt tttttcttac aaagaaaaat ttaatattcg atngagaggt tgaaccaggc      60

ttaaagcaga catactagga aatggtgcag cctgtaagaa tgccagtttg taagtactga    120

ctttggaaaa gatcatcgcc tctatcagac acttagggtc ctggtctggc aattttggcc    180

tgatgtgatg ccacaagacc caacagagag agacacagag tccaggataa tgttgacagt    240

ggtgtagccc tttaggagaa atggcgctcc ctgcggctgg tattaggtta ccattggcac    300

cgaaggaacc aggaggataa gaatatccat aatttcagag ctgccctggc acagtacctg    360

ccccgtcgga ggctctcact ggcaaatgac agctctgtgc aaggagcact cccaagtata    420

aaaattatta cacagtttta ttctgaagaa cattttgcat tttaataaaa aaggatttat    480

gtcaggaaag agtcatttac aaaccttgaa gtgtttttgc ctggatcaga gtaagaatgt    540

cttaagaaga ggtttgtaag gtcttcataa canagtggtg tttgttattt acaaaaaaaa    600
```

-continued aaaaaaaaaa aataaaaaaa aaaaaaaaaa cctcgtgccg aattct 646

<210> SEQ ID NO 266
<211> LENGTH: 668
<212> TYPE: DNA
<213> ORGANISM: Homo sapiens

<400> SEQUENCE: 266
tttttttttt ttttttgtaa ataacaaaca ccactttggt tatgaagacc ttacaaacct 60
cttcttaaga cattcttact ctgatccagg caaaaacact tcaaggtttg taaatgactc 120
tttcctgaca taaatccttt tttattaaaa tgcaaaatgt tcttcagaat aaaactgtgt 180
aataattttt atacttggga gtgctccttg cacagagctg tcatttgcca gtgagagcct 240
ccgacagggc aggtactgtg ccagggcagc tctgaaatta tggatattct tatcctcctg 300
gttccttcgg tgccaatggt aacctaatac cagccgcagg gagcgccatt tctcctaaag 360
ggctacacca ctgtcaacat tatcctggac tctgtgtctc tctctgttgg gtcttgtggc 420
atcacatcag gccaaaattg ccagaccagg accctaagtg tctgatagag gcgatgatct 480
tttccaaagt cagtacttac aaactggcat tcttacaggc tgcaccattt cctagtatgt 540
ctgctttaag cctggttcaa cctctcatcg aatattaaat ttttctttgt aagaaaaatt 600
tgaagttgta gagcatggtt ttttgttttc ccttgtctta ggaaagtttt aagatgaaat 660
gtttttcc 668

<210> SEQ ID NO 267
<211> LENGTH: 496
<212> TYPE: DNA
<213> ORGANISM: Homo sapiens

<400> SEQUENCE: 267
agtacacaag gtgaaactgc tccagttttt ctcatagcag ggtcagcagg aaagcaagtg 60
gtgcccctgg tcccatctca cacaggtgag actgcaccga gaggtaacgt ggccctcaca 120
gcccaccacg cctggccttc gcccaattct gaaacttcgt aggatagagc tggaaagtgc 180
cacatggtga agcgagatcc agctgtctgg gtggatgtcg gagtccatag gctgagcaga 240
gatggttctt agtgaggttc tcgctgccag ttgacggtga aatcatagct gccatttaca 300
ttttgtgaga ttatgaaaaa cataagacta aagaaactaa atgtgttatt cctgtggaca 360
caaaaatgtg tgtttttcag atggggaggg gaccaaaaag gaaaaacatt tcatcttaaa 420
acttccctaa gacaaaggaa aacaaaaaac catgctctac aacttcaaat ttttcttaca 480
aagaaaaatt taatat 496

<210> SEQ ID NO 268
<211> LENGTH: 701
<212> TYPE: DNA
<213> ORGANISM: Homo sapiens

<400> SEQUENCE: 268
agctgaggaa acaaaacgag agaagaagat gatgtgttca aaagaaatgg tgccctgctt 60
ggaaaccatg tcaatcatgt taatagtgat aggagagatt cccttcagca gaccaatacc 120
acccaccgtc ccctgcatgt ccaaaggcct tcaattccac ctgcaagtga tactgagaaa 180
ccgctgtttc ctccagcagg aaattcggtg tgtcataacc atcataacca taattccata 240
ggaaagcaag ttcccacctc aacaaatgcc aatctcaata atgccaatat gtccaaagct 300
gcccatggaa agcggcccag catagggaac cttgagcatg tgtctgaaaa tgggcatcat 360

-continued

```
tcttcccaca agcatgaccg ggagcctcag agaaggtcca gtgtgaaaag gtccgactca    420

ggagatgaac agctcccaac tattggccgg gaagacccag agatacatgg ctatttcagg    480

cacccccacg gcttggggga gcaggagtat ttcagtagtg aggaatgcta cgaggatgac    540

agctcgccca cctggagcag gcaaaactat ggctactaca gcagataccc aggcagaaac    600

atcgactctg agaggcgcga ggctacatca tcccaagatt ctggaggaga tgactcgccg    660

tttgtatgat cacgagatct caagagagct atactcccac c                        701
```

<210> SEQ ID NO 269
<211> LENGTH: 515
<212> TYPE: DNA
<213> ORGANISM: Homo sapiens

<400> SEQUENCE: 269

```
tcttgtggaa agatgatagg tttatagtga ctcaaaatat tttagaaaaa tttctgtagg     60

gtcaagttct ttcaaactta aaattttaac cccagaggat tttcgctgaa taaatgaaaa    120

ttggctctat ttcttctact tctggatagc ccgagtaaaa atactaataa tttctagatt    180

ttagtgggga actacaatta ttaggaccca tggatattgc tgcagttcaa atacaataca    240

gtaattacaa aatatagacc atctctttac aaatccaaat tatagtatat tacaagtcat    300

gtaccgtaaa tctattttaa acaaactagg gtatctaagt ttacctggtt gcaagtgcat    360

tattattcca gtttacagtt gcccttagcg tgacagtcag aaaccgacca tcggagtgat    420

attctcttat gtaaactggc gtcacatcac agaaaacctt atttatttgg gggaaagggt    480

ttaaaaatgg atatgttggg cccagtgact gatac                              515
```

<210> SEQ ID NO 270
<211> LENGTH: 258
<212> TYPE: DNA
<213> ORGANISM: Homo sapiens

<400> SEQUENCE: 270

```
ggaaaagatc atcgcctcta tcagacactt agggtcctgg tctggcaatt ttggcctgat     60

gtgatgccac aagacccaac agagagagac acagagtcca ggataatgtt gacagtggtg    120

tagcccttta ggagaaatgg cgctccctgc ggctggtatt aggttaccat tggcaccgaa    180

ggaaccagga ggataagaat atccataatt tcagagctgc cctggcacgg tacctgcccc    240

gtcggaggct ctcactgg                                                 258
```

<210> SEQ ID NO 271
<211> LENGTH: 510
<212> TYPE: DNA
<213> ORGANISM: Homo sapiens

<400> SEQUENCE: 271

```
gatgcgtgat ggctgatcta gaggtatccc atggactctc atcgcagctc ctggtacaca     60

gacgagcccg acatctccta ccggactttc acaccagcca gcctgactgt ccccagcagc    120

ttccggaaca aaaacagcga caagcagagg agtgcggaca gcttggtgga ggcagtcctg    180

atatccgaag gcttgggacg ctatgcaagg gacccaaaat ttgtgtcagc aacaaaacac    240

gagatcgctg atgcctgtga cctcaccatc gacgagatgg agagtgcagc cagcaccctg    300

cttaatggga acgtgcgtcc ccgagccaac ggggatgtgg gccccctctc acaccggcag    360

gactatgagc tacaggactt tggtcctggc tacagcgacg aagggccaga ccctgggagg    420
```

-continued gatgaggagg acctggcgga tgaaatgata tgcatcacca ccttgtagcc cccagcgagg 480
ggcagactgg ctctggcctc aggtggggcg 510

<210> SEQ ID NO 272
<211> LENGTH: 405
<212> TYPE: DNA
<213> ORGANISM: Homo sapiens
<220> FEATURE:
<221> NAME/KEY: misc_feature
<222> LOCATION: (75)..(75)
<223> OTHER INFORMATION: a or g or c or t/u
<220> FEATURE:
<221> NAME/KEY: misc_feature
<222> LOCATION: (142)..(142)
<223> OTHER INFORMATION: a or g or c or t/u

<400> SEQUENCE: 272
cgctcgttcg ctgtgccagg acaaagtcct gtagctcata gtcctgccgt gtgagagggg 60
gccacatccc cgttnctcgg gacgcacgac ccattaagca gggtgctggc tgccccctcc 120
atctcgtcga tggagaggtc ancaggcatc agcgatttcg tgttttgtgt gcgtgacaca 180
aattttgggt cccttgcata cgcgtcccac agccttacgg agtatcagcg actgctctcc 240
accaatgctg cccgcgactc ctactgcttg tccgctgttt ttggttccgg aagctgctgg 300
ggacagtcag gctggctggt gtgaaagtcc ggtaggagat gtcgggctcg tctgtgtacc 360
aggagctgcg gtgcagggac ggcaggctgc cgttcacctg gtccg 405

<210> SEQ ID NO 273
<211> LENGTH: 892
<212> TYPE: DNA
<213> ORGANISM: Homo sapiens
<220> FEATURE:
<221> NAME/KEY: misc_feature
<222> LOCATION: (27)..(27)
<223> OTHER INFORMATION: a or g or c or t/u
<220> FEATURE:
<221> NAME/KEY: misc_feature
<222> LOCATION: (35)..(35)
<223> OTHER INFORMATION: a or g or c or t/u
<220> FEATURE:
<221> NAME/KEY: misc_feature
<222> LOCATION: (42)..(42)
<223> OTHER INFORMATION: a or g or c or t/u
<220> FEATURE:
<221> NAME/KEY: misc_feature
<222> LOCATION: (49)..(49)
<223> OTHER INFORMATION: a or g or c or t/u
<220> FEATURE:
<221> NAME/KEY: misc_feature
<222> LOCATION: (831)..(831)
<223> OTHER INFORMATION: a or g or c or t/u
<220> FEATURE:
<221> NAME/KEY: misc_feature
<222> LOCATION: (835)..(835)
<223> OTHER INFORMATION: a or g or c or t/u

<400> SEQUENCE: 273
gagtttcgag cttctctttt cctaagngaa aaaanaaaga ancacaagna aaccaaataa 60
ccatgttact ctgtataaaa atgctaatca gggaattctg aatcaataat gctccaatga 120
aggacagaat ttaattagaa acaacactaa ccacaagagc ctagcacaac ccaaactcag 180
agcttcctgg taatctcaat gcgatggatt cattacacag accatcttat taaaattctc 240
atctgagagc taatcagcat tgaatgcatc atttatttta tgacaccaaa attaactgca 300
gtgattcttt aagcatgggg acacgtgact cccactctca gccccgaggg atgacagcca 360
agagcctggc ttctgcccaa gattccatcc gttttggtct gcagtgcatg gtcaaccatg 420

-continued

```
atccacaaag cagcaacccg ggggctgtag ctgccgtgat gcgggggtaa gcctggcagg    480

ctgcaactgt tgcagggctc ccaacacagc ccctggacaa acgcgtcagg ggaaaatagg    540

gttacctggc aatctttttc ctctcctttt cttccgcttc ttctttctga gcagtgttca    600

gactttcagc atcagccaaa gtgtctacag cgatggccaa gaagacattc agtagaatat    660

ctaattacaa ctttttaagg gcacaacaca ctactaaatg caactacgtg cggccaacaa    720

tggcaacgcc acacacctct gcatcccggg aagctgggta gtaggtgacg tccccaagtg    780

ttatactcac acagcaaacc tagagtacca gagccctgct tttcaaacaa nacanaacaa    840

acaaacaacc caaagtaaaa cctggtaagg gacgtcttca gaagtaaatt ac            892
```

<210> SEQ ID NO 274
<211> LENGTH: 425
<212> TYPE: DNA
<213> ORGANISM: Homo sapiens

<400> SEQUENCE: 274

```
ctggctttcc catagcacgc tcggcaggaa agcaagtgat gcccctggct cccatctcac     60

acaggtgaca ctgcaccgag aggtaacgtg gccctcacag cccaccacgc ctggccttcg    120

cccaattctg aaacttcgta ggatagagct ggaaagtggc acatggtgaa gcgagatcca    180

gctgtctggg tggatgtcgg agctccatag gctgagcaga gatggttctt agtgaggttc    240

tcgctgccag ttgacggtga aatcatagct gccatttaca ttttgtgaga ttatgaaaaa    300

cataagacta aagaaactaa atgtgttatt cctgtggaca caaaaatgtg tgtttttcag    360

atggggaggg gaccaaaaag gaaaaacatt tcatcttaaa actttcctaa gacaaaggaa    420

aacaa                                                                425
```

<210> SEQ ID NO 275
<211> LENGTH: 441
<212> TYPE: DNA
<213> ORGANISM: Homo sapiens
<220> FEATURE:
<221> NAME/KEY: misc_feature
<222> LOCATION: (10)..(10)
<223> OTHER INFORMATION: a or g or c or t/u

<400> SEQUENCE: 275

```
ctcagcatgn atgaaacagg atgaggttgg tgaagatgtg gtggttgatg agcttgtggc     60

agcctacgcg gatcgggttg gtcttgctaa gaatgaagaa agcgctccct tcagggatgg    120

gggcaatttt ttccttcatg ttcaactccg agatccttcg aggacggggt ccggcaggaa    180

cctcaggttc atcctcctcc tcttcctctt cctcttcccc tacgggcaca tcgcaaggcg    240

gataggggtc cttgtcttca tcctcttctc tatagtcatc aattgtaacc ttgttgtcac    300

tgttggctat ctggttgact tctggtttgt tgttcttttt attttctagg ctctcttttc    360

tggcaatctt tttcctctcc ttttcttccg cttcttcttt ctgagcagtg ttcagacttt    420

cagcatcagc caaatggtct a                                              441
```

<210> SEQ ID NO 276
<211> LENGTH: 165
<212> TYPE: DNA
<213> ORGANISM: Homo sapiens

<400> SEQUENCE: 276

```
tcaaagtcga aggaggatct ccgcgtggga tgctggggtg ggaggtagta ggcgtctcct     60
```

-continued

```
tggagatctc cgtgaatcat agcaaacggg cgagtcatcg tcctacaaga atcctagtgg    120

atgatggtag cctcggggcc tctcagagtc gatgtttctg cctgg                    165


<210> SEQ ID NO 277
<211> LENGTH: 330
<212> TYPE: DNA
<213> ORGANISM: Homo sapiens

<400> SEQUENCE: 277

ctcgcccgtt tgctatgagt cacggagatc tccaaggaga cgcctactac ctcccacccc     60

agcatcccac cggagatcct ccttcaactt tgagtgcctg cgccggcaga gcagccagga    120

agaggtcccg tcgtctccca tcttccccca tcgcacggcc ctgcctctgc atctaatgca    180

gcaacagatc atggcagttg ccggcctaga ttcaagtaaa gcccagaagt actcaccgag    240

tcactcgacc cggccgtggg ccacccctcc agcaacccct ccctaccggg actggacacc    300

gtgctacacc ccccagatga cgccgatgta                                     330


<210> SEQ ID NO 278
<211> LENGTH: 401
<212> TYPE: DNA
<213> ORGANISM: Homo sapiens

<400> SEQUENCE: 278

ccaggcagaa acatcgactc tgagaggccc cgaggctacc atcatcccca aggattcttg     60

gaggacgatg actcgcccgt ttgctatgat tcacggagat ctccaaggag acgcctacta    120

cctcccaccc cagcatccca ccggagatcc tccttcaact ttgagtgcct gcgccggcag    180

agcagccagg aagaggtccc gtcgtctccc atcttccccc atcgcacggc cctgcctctg    240

catctaatgc agcaacagat catggcagtt gccggcctag attcaagtaa agcccagaag    300

tactcaccga gtcactcgac ccggtcgtgg gccacccctc cagcaacccc tccctaccgg    360

gactggacac cgtgctacac cccccagatg acgccgatgt a                        401


<210> SEQ ID NO 279
<211> LENGTH: 431
<212> TYPE: DNA
<213> ORGANISM: Homo sapiens
<220> FEATURE:
<221> NAME/KEY: misc_feature
<222> LOCATION: (321)..(321)
<223> OTHER INFORMATION: a or g or c or t/u
<220> FEATURE:
<221> NAME/KEY: misc_feature
<222> LOCATION: (354)..(355)
<223> OTHER INFORMATION: a or g or c or t/u
<220> FEATURE:
<221> NAME/KEY: misc_feature
<222> LOCATION: (373)..(373)
<223> OTHER INFORMATION: a or g or c or t/u
<220> FEATURE:
<221> NAME/KEY: misc_feature
<222> LOCATION: (401)..(401)
<223> OTHER INFORMATION: a or g or c or t/u

<400> SEQUENCE: 279

tacatcggcg tcatctgggg ggtgtagcac ggtgtccagt cccggtaggg aggggttgct     60

ggaggggtgg cccacgaccg ggtcgagtga ctcggtgagt acttctgggc tttacttgaa    120

tctaggccgg caactgccat gatctgttgc tgcattagat gcagaggcag ggccgtgcga    180

tgggggaaga tgggagacga cgggacctct tcctggctgc tctgccggcg caggcactca    240

aagttgaagg aggatctccg gtgggatgct ggggtgggag gtagtaggcg tctccttgga    300
```

-continued

```
gatctccgtg aatcatagca nacgggcgag tcatcgtcct ccaagaatcc ttgnngatga    360

tggtagcctc ggngcctctc agagtcgatg tttctgcctg ngtatctgct cgggcgagcc    420

ggtaccgagc t                                                          431


<210> SEQ ID NO 280
<211> LENGTH: 330
<212> TYPE: DNA
<213> ORGANISM: Homo sapiens

<400> SEQUENCE: 280

tacatcggcg tcatctgggg ggtgtagcac ggtgtccagt cccggtaggg aggggttgct     60

ggaggggtgg cccacgaccg ggtcgagtga ctcggtgagt acttctgggc tttacttgaa    120

tctaggccgg caactgccat gatctgttgc tgcattagat gcagaggcag ggccgtgcga    180

tgggggaaga tgggagacga cgggacctct tcctggctgc tctgccggcg caggcactca    240

aagttgaagg aggatctccg gtgggatgct ggggtgggag gtagtaggcg tctccttgga    300

gatctccgtg aatcatagca aacgggcgag                                      330


<210> SEQ ID NO 281
<211> LENGTH: 183
<212> TYPE: DNA
<213> ORGANISM: Homo sapiens
<220> FEATURE:
<221> NAME/KEY: misc_feature
<222> LOCATION: (42)..(42)
<223> OTHER INFORMATION: a or g or c or t/u
<220> FEATURE:
<221> NAME/KEY: misc_feature
<222> LOCATION: (70)..(70)
<223> OTHER INFORMATION: a or g or c or t/u
<220> FEATURE:
<221> NAME/KEY: misc_feature
<222> LOCATION: (133)..(133)
<223> OTHER INFORMATION: a or g or c or t/u

<400> SEQUENCE: 281

gcggacagct tggtggaggc agtcctgata tccgaagcct tnggacgcta tgcaagggac     60

ccaaaatttn tttcagcaac aaaacacgaa atcgctgatg cctgtaacct caccatcgac    120

gagatggaga gtncagccag caccctgctt aatgggaacg tgcgtccccg agccaacggg    180

gat                                                                   183


<210> SEQ ID NO 282
<211> LENGTH: 132
<212> TYPE: DNA
<213> ORGANISM: Homo sapiens

<400> SEQUENCE: 282

aagaaatagg aggataagaa tatcatattt cagagctgcc ctggcacagt acctgccccg     60

tcggaggctc tcactggcaa atgacagctc tgtgcaagga gcactcccaa gtataaaaat    120

tattacacag tt                                                         132


<210> SEQ ID NO 283
<211> LENGTH: 358
<212> TYPE: DNA
<213> ORGANISM: Homo sapiens

<400> SEQUENCE: 283

ccattggtac gagagaaatt aggaggataa gattatctat tattctgagc tgccctggca     60
```

-continued

```
cagtacctgc cccgtcggag gctctcactg gcaaatgaca gctctgtgca aggagcactc    120

ccaagtataa aaattattac atagttttat tctgaagaac attttgcatt ttaataaaaa    180

aggatttatg tcaggaaaga gtcatttaca taccttgaat tgtttttgcc tggatcagag    240

taagaatgtc ttaagaagag gtttgtaagg tcttcataac aaagtggtgt ttgttattta    300

caaaaaaaaa aaaaaaaaaa atttttatac cgggtttgtc tgtatacaaa tttctctg      358
```

```
<210> SEQ ID NO 284
<211> LENGTH: 289
<212> TYPE: DNA
<213> ORGANISM: Homo sapiens

<400> SEQUENCE: 284

tccagagtag aagaaatcag ccaagtatca tttattcagc gaaaatcctc tggggattaa     60

aattttaagt ttgaaagaac ttgacactac agaaattttt ctaaaatatt ttgagtcact    120

ataaacctat catctttcca caagatatac cagatgacta tttgcagtct tttctttggg    180

caagagttcc atgattttga tactgtacct ttggatccac catgggttgc aactgtcttt    240

ggttttgttt gtttgacttg aaccaccctc tggaaagcta ctctggaaa                 289
```

```
<210> SEQ ID NO 285
<211> LENGTH: 889
<212> TYPE: DNA
<213> ORGANISM: Homo sapiens

<400> SEQUENCE: 285

gggattcccc cggctgggtg gggagagcga gctgggtgcc cccatagatt cccctgcccg     60

aacctcatga gccgaccctc ggctccatgg agcccggaaa ttatgccacc ttggatggag    120

ccaaggatat cgaaggcttg ttgggagcgg gagggggcg gaatctggtc gcccactccc    180

tctctgacca gccacccagc gcgctacgct tgatgcctgt gtcaatatgc ccccttgatc    240

tgccaggctc ggggagcggc caaaagcaat gcccacccta tgctctgggg gtgcccaggg    300

gactgtcccc ggctccgtgc cttatggtta ctgtggggcg gggtacatac tcctgcagag    360

ttgtcccgga gctcgttgaa accttgtgcc gaggagagcc accctggcgg tacccgggaa    420

gactccccag ggcgggaaga gtaccccagc ggcccaatga gttgtgcttc tatcgggata    480

tccgggacct accaggccta tgtgcaggta ctggacgtgt cctgtgctgc agactctggg    540

tgtccgtgga gcaccggaca ttggctcgct gtggcctgtg gccggtacca gtcttgggct    600

ctcggtgtgt ggctggacac gccggttgtg ttcgcgggag accgcaccca ccaggttcct    660

ttgggagggc cgctttgcag actccggggg aggcccctct gaggcggggc cttttcgggg    720

gggcgaagaa agctttccga cgcaggcgct tgcggagctg gcgggacatc gggacacttc    780

acccagcgaa gcgcggcttg gggcccctct gggcgcggtc tcggttgaca ccggcgaaga    840

gtttcgggag aggcccatat cttctgggga gggcgttgcg tcgcccccg                 889
```

```
<210> SEQ ID NO 286
<211> LENGTH: 1356
<212> TYPE: DNA
<213> ORGANISM: Homo sapiens

<400> SEQUENCE: 286

ggattccccc ggcctgggtg gggagagcga gctgggtgcc ccctagattc cccgcccccg     60

cacctcatga gccgaccctc ggctccatgg agcccggcaa ttatgccacc ttggatggag    120

ccaaggatat cgaaggcttg ctgggagcgg gagggggcg gaatctggtc gcccactccc    180
```

-continued

```
ctctgaccag ccacccagcg gcgcctacgc tgatgcctgc tgtcaactat gccccccttgg    240
atctgccagg ctcggcggag ccgccaaagc aatgccaccc atgccctggg gtgccccagg    300
ggacgtcccc agctcccgtg ccttatggtt actttggagg cgggtactac tcctgccgag    360
tgtcccggag ctcgctgaaa ccctgtgccc aggcagccac cctggccgcg taccccgcgg    420
agactcccac ggccggggaa gagtacccca gccgccccac tgagtttgcc ttctatccgg    480
gatatccggg aacctaccag cctatggcca gttacctgga cgtgtctgtg gtgcagactc    540
tgggtgctcc tggagaaccg cgacatgact ccctgttgcc tgtggacagt taccagtctt    600
gggctctcgc tggtggctgg aacagccaga tgtgttgcca gggagaacag aacccaccag    660
gtccctttttg gaaggcagca tttgcagact ccagcgggca gcaccctcct gacgcctgcg    720
cctttcgtcg cggccgcaag aaacgcattc cgtacagcaa ggggcagttg cgggagctgg    780
agcgggagta tgcggctaac aagttcatca ccaaggacaa gaggcgcaag atctcggcag    840
ccaccagcct ctcggagcgc cagattacca tctggtttca gaaccgccgg gtcaaagaga    900
agaaggttct cgccaaggtg aagaacagcg ctacccctta agagatctcc ttgcctgggt    960
gggaggagcg aaagtggggg tgtcctgggg agaccaggaa cctgccaagc ccaggctggg   1020
gccaaggact ctgctgagag gcccctagag acaacaccct tcccaggcca ctggctgctg   1080
gactgttcct caggagcggc ctgggtaccc agtatgtgca gggagacgga accccatgtg   1140
acagcccact ccaccagggt tcccaaagaa cctggcccag tcataatcat tcatcctgac   1200
agtggcaata atcacgataa ccagtactag ctgccatgat cgttagcctc atattttcta   1260
tctagagctc tgtagagcac tttagaaacc gctttcatga attgagctaa ttatgaataa   1320
atttggaaaa aaaaaaaaaa aaaaaaaaaa aaaaaa                              1356
```

<210> SEQ ID NO 287
<211> LENGTH: 727
<212> TYPE: DNA
<213> ORGANISM: Homo sapiens

<400> SEQUENCE: 287

```
attcccccgg cctgggtggg gagagcgagc tgggtgcccc ctagattccc cgcccccgca     60
cctcatgagc cgaccctcgg ctccatggag cccggcaatt atgccacctt ggatggagcc    120
aaggatatcg aaggcttgct gggagcggga ggggggcgga atctggtcgc ccactcccct    180
ctgaccagcc acccagcggc gcctacgctg atgcctgctg tcaactatgc cccccttggat    240
ctgccaggct cggcggagcc gccaaagcaa tgccacccat gccctggggt gccccagggg    300
acgtccccag ctcccgtgcc ttatggttac tttggaggcg ggtactactc ctgccgagtg    360
tcccggagct cgctgaaacc ctgtgcccag gcagccaccc tggccgcgta ccccgcggag    420
actcccacgg ccggggaaga gtaccccagc cgccccactg agtttgcctt ctatccggga    480
tatccgggaa cctaccagcc tatggccagt tacctggacg tgtctgtggt gcagactctg    540
ggtgctcctg gagaaccgcg acatgactcc ctgttgcctg tggacagtta ccagtcctgg    600
gctctcgctg gtggctggaa cagccagatg tgttgccagg gagaacagaa cccaccaggt    660
ccccttttgg aaggcagcat ttgcagactc cagcgggcag caccctcctg acgcctgcgc    720
ctttcgt                                                              727
```

<210> SEQ ID NO 288
<211> LENGTH: 793
<212> TYPE: DNA

-continued

<213> ORGANISM: Homo sapiens

<400> SEQUENCE: 288
gcaggcgact tgcgagctgg gagcgattta aaacgctttg gattccccg gcctgggtgg 60 ggagagcgag ctgggtgccc cctagattcc ccgcccccgc acctcatgag ccgaccctcg 120
gctccatgga gcccggcaat tatgccacct tggatggagc caaggatatc gaaggcttgc 180
tgggagcggg aggggggcgg aatctggtcg cccactcccc tctgaccagc cacccagcgg 240
cgcctacgct gatgcctgct gtcaactatc ccccttgga tctgccaggc tcggcggagc 300
cgccaaagca atgccaccca tgccctgggg tgccccaggg gacgtcccca gctcccgtgc 360
cttatggtta ctttggaggc gggtactact cctgccgagt gtcccggagc tcgctgaaac 420
cctgtgccca ggcagccacc ctggccgcgt accccgcgga gactcccacg gccggggaag 480
agtaccccag ccgccccact gagtttgcct tctatccggg atatccggga acctaccagc 540
ctatggccag ttacctggac gtgtctgtgg tgcagactct gggtgctcct ggagaaccgc 600
gacatgactc cctgttgcct gtggacagtt accagtcttg ggctctcgct ggtggctgga 660
acagccagat gtgttgccag ggagaacaga agccaccagg tcccttttgg aaggcagcat 720
ctgcagactc cagcgggcag gacctcctga cgcctgcggc ctttcgtcgc gagcgcaaga 780
aacgcattcc gta 793

<210> SEQ ID NO 289
<211> LENGTH: 759
<212> TYPE: DNA
<213> ORGANISM: Homo sapiens

<400> SEQUENCE: 289
ggatttaaaa cgctttggat tccccggcc tgggtgggga gagcgagctg ggtgccccct 60
agattccccg cccccgcacc tcatgagccg accctcggct ccatggagcc cggcaattat 120
gccaccttgg atggagccaa ggatatcgaa ggcttgctgg gagcgggagg ggggcggaat 180
ctggtcgccc actcccctct gaccagccac ccagcggcgc ctacgctgat gcctgctgtc 240
aactatgccc ccttggatct gccaggctcg gcggagccgc caaagcaatg ccacccatgc 300
cctggggtgc cccagggacg tccccagctc ccgtgcctta tggttacttt ggaggcgggt 360
actactcctg ccgagtgtcc cggagctcgc tgaaaccctg tgcccaggca gccaccctgg 420
ccgcgtaccc cgcggagact cccacggccg gggaagagta ccccagccgc cccactgagt 480
ttgccttcta tccgggatat ccgggaacct accagcctat ggccagttac ctggacgtgt 540
ctgtggtgca gactctgggt gctcctggag aaccgcgaca tgactccctg ttgcctgtgg 600
acagttacca gtcttgggct ctcgctggtg ggctggaaca gccagatgtg ttgccagcgc 660
agaacagaac ccaccaggtc ccttttggaa ggcagcattt gcagactcca gcgggcagaa 720
ccctcctgac gcctgcgcct ttcgttcgcg ggcgaaaaa 759

<210> SEQ ID NO 290
<211> LENGTH: 614
<212> TYPE: DNA
<213> ORGANISM: Homo sapiens

<400> SEQUENCE: 290
aagaaacgca ttccgtacag caaggggcag ttgcgggagc tggagcggga gtatgcggct 60
aacaagttca tcaccaagga caagaggcgc aagatctcgg cagccaccag cctctcggag 120
cgccagatta ccatctggtt tcagaaccgc cgggtcaaag agaagaaggt tctcgccaag 180

-continued gtgaagaaca gcgctacccc ttaagagatc tccttgcctg ggtgggagga gcgaaagtgg 240
gggtgtcctg gggagaccag gaacctgcca agcccaggct ggggccaagg actctgctga 300
gaggccccta gagacaacac ccttcccagg ccactggctg ctggactgtt cctcaggagc 360
ggcctgggta cccagtatgt gcagggagac ggaaccccat gtgacagccc actccaccag 420
ggttcccaaa gaacctggcc cagtcataat cattcatcct gacagtggca ataatcacga 480
taaccagtac tagctgccat gatcgttagc ctcatatttt ctatctagag ctctgtagag 540
cactttagaa accgctttca tgaattgagc taattatgaa taaatttgga aggcgaaaaa 600
aaaaacctcg tgcc 614

<210> SEQ ID NO 291
<211> LENGTH: 318
<212> TYPE: DNA
<213> ORGANISM: Homo sapiens

<400> SEQUENCE: 291
attcggcacg aggttttttt tttcgccttc caaatttatt cataattagc tcaattcatg 60
aaagcggttt ctaaagtgct ctacagagct ctagatagaa aatatgaggc taacgatcat 120
ggcagctagt actggttatc gtgattattg ccactgtcag gatgaatgat tatgactggg 180
ccaggttctt tgggaaccct ggtggagtgg gctgtcacat ggggttccgt ctccctgcac 240
atactgggta cccaggccgc tcctgaggaa cagtccagca accagtggcc tgggaagggt 300
gttgtctcta ggggcctc 318

<210> SEQ ID NO 292
<211> LENGTH: 1483
<212> TYPE: DNA
<213> ORGANISM: Homo sapiens

<400> SEQUENCE: 292
gggtggggag agcgagctgg gtgcccccta gattccccgc ccccgcacct catgagccga 60
ccctcggctc catggagccc ggcaattatg ccaccttgga tggagccaag gatatcgaag 120
gcttgctggg agcgggaggg gggcggaatc tggtcgccca ctcccctctg accagccacc 180
cagcggcgcc tacgctgatg cctgctgtca actatgcccc cttggatctg ccaggctcgg 240
cggagccgcc aaagcaatgc cacccatgcc ctggggtgcc ccaggggacg tccccagctc 300
ccgtgcctta tggttacttt ggaggcgggt actactcctg ccgagtgtcc cggagctcgc 360
tgaaaccctg tgccaggcag ccaccctggc cgcgtaaccc gacggagact ctcacgtgcg 420
gggaagagta cccctagcgc cccacatgag tttgccttct atccgggata tccgggaccg 480
taccagccta tggcagttac ctggacgtgt ctgtggtgcc gactctgggt gctcctggag 540
aaccgcggac atgactcctt gtttgctgtg cgacgctcac cagtctgggc tcctcgtcgg 600
tggtcgcact cccacttttt gccgggcgac atccccgggg gccccttccg gaacagcgac 660
cttgcgagcc cccggggaca cacccccgta agcggcctat catcgctgat aaacctcatc 720
agagggcacc gaaagccgcg actctaaccc ccccactacg actcacgacc gcacaggtac 780
tcgaaccgcc caatatctgg ttctaaccca tggcgcatct cagccgctag agagccaacc 840
aaacgcgcca cgcgcaacca cactacacca cggcacccct ttcatctcac tcccacgccg 900
atcactcttc accctccaga atcattcccc tcgcacatcc tacctatctc atgcctccca 960
gttcacccca ttccctcccc taatctcacc cacacattca cgcacgttct cactacgctt 1020

-continued

```
cgctccgacc cacatcctca cccccacatt cataccactt caccatcacg acccccccct   1080

ctcatcgact cctgtctcat tctcaaccac agtactacca gctccaacac accactcacc   1140

ccaagctatc catcacctac acgctttcac ccctcaccgc tcccaagtaa ttcagatcac   1200

tcaaacacaa tctgctacat actcatccct cccccactcc cagtacagtc caaccaccga   1260

ccaactacct ccgcgccacc cgcgccgccc cacctcaccg gccccaaccg cccgcacagg   1320

gcacgcaccc cccggcaacc gcgcgatccg gccgtacaca ctcttgggcg gcacgcagct   1380

gaggacattc cgcgggagcg ccccaccgtg ggctacgtgg gtcgcgaccc ggcggggcgc   1440

gtgcggcgtc gcccgcccgc ccgccgactg cgacccagtc gag                     1483
```

```
<210> SEQ ID NO 293
<211> LENGTH: 758
<212> TYPE: DNA
<213> ORGANISM: Homo sapiens
<220> FEATURE:
<221> NAME/KEY: misc_feature
<222> LOCATION: (561)..(561)
<223> OTHER INFORMATION: a or g or c or t/u
<220> FEATURE:
<221> NAME/KEY: misc_feature
<222> LOCATION: (656)..(656)
<223> OTHER INFORMATION: a or g or c or t/u

<400> SEQUENCE: 293

ggggctttgg attcccccgg cctgggtggg gagagcgagc tgggtgcccc ctagattccc     60

cgcccccgca cctcatgagc cgaccctcgg ctccatggag cccggcaatt atgccacctt    120

ggatggagcc aaggatatcg aaggcttgct gggagcggga ggggggcgga atctggtcgc    180

ccactcccct ctgaccagcc acccagcggc gcctacgctg atgcctgctg tcaactatgc    240

ccccttggat ctgccaggct cggcggagcc gccaaagcaa tgccacccat gccctggggt    300

gccccagggg acgtccccag ctcccgtgcc ttatggttac tttggaggcg ggtactactc    360

ctgccgagtg tcccggagct cgctgaaacc ctgtgcccag gcagccaccc tggccgcgta    420

ccccgcggag actcccacgg ccggggaaga gtaccccagc cgccccactg agtttgcctt    480

ctatccggga tatccgggaa cctaccagcc tatggccagt tacctggacg tgtctgtggt    540

gcagactctg ggtgctcctg nagaaccgcg acatgactcc ctgttgcctg tggacagtta    600

ccagtcttgg gctctcgctg gtggcctgga acagcccaga tgtgtttgcc cagggnagaa    660

cacgaacccc acccggttcc cccttttggg aaagggcagc cattttggcc agccttccaa    720

gcggggccaa ccacccccctc ccctggacag gccctggt                           758
```

```
<210> SEQ ID NO 294
<211> LENGTH: 476
<212> TYPE: DNA
<213> ORGANISM: Homo sapiens

<400> SEQUENCE: 294

gcggccgcaa gaaacgcatt ccgtacagca aggggcagtt gcgggactgg agcgggagta     60

tgcggctaac aagttcatca ccaaggacaa gaggcgcaag atctcggcag ccaccagcct    120

ctcggagcgc cagattacca tctggtttca gaaccgccgg gtcaaagaga agaaggttct    180

cgccaaggtg aagaacagcg ctacccctta agagatctcc ttgcctgggt gggaggagcg    240

aaagtggggg tgtcctgggg agaccaggaa cctgccaagc ccaggctggg gccaaggact    300

ctgctgagag gcccctagag acaacaccct tcccaggcca ctggctgctg gactgttcct    360

caggagcggc ctgggtaccc agtatgtgca gggagacgga accccatgtg acagcccatt    420
```

-continued ccaccagggt tcccaaagaa cctggcccag tcataatcat tcatcctgac agtggc 476

<210> SEQ ID NO 295
<211> LENGTH: 552
<212> TYPE: DNA
<213> ORGANISM: Homo sapiens

<400> SEQUENCE: 295
agcggccgca agaaacgcat tccgtacagc aaggggcagt tgcgggagct ggagcgggag 60
tatgcggcta acaagttcat caccaaggac aagaggcgca agatctcggc agccaccagc 120
ctctcggagc gccagattac catctggttt cagaaccgcc gggtcaaaga gaagaaggtt 180
ctcgccaagg tgaagaacag cgctacccct taagagatct ccttgcctgg gtgggaggag 240
cgaaagtggg ggtgtcctgg ggagaccagg aacctgccaa gcccaggctg gggccaagga 300
ctctgctgag aggcccctag agacaacacc cttcccaggc cactggctgc tggactgttc 360
ctcaggagcg gcctgggtac ccagtatgtg cagggagacg gaaccccatg tgacagccca 420
ctccaccagg gttcccaaag aacctggccc agtcataatc attcatcctg acagtggcaa 480
taatcacgat aaccagtact agctgccatg atcgttagcc tcatattttc tatctagagc 540
tctgtagagc ac 552

<210> SEQ ID NO 296
<211> LENGTH: 447
<212> TYPE: DNA
<213> ORGANISM: Homo sapiens

<400> SEQUENCE: 296
gcggccgcaa gaaacgcatt ccgtacagca aggggcagtt gcgggactgg agcgtgagta 60
tgcggctaac aagttcatca ccaaggacaa gaggcgcaag atctcggcag ccaccagcct 120
ctcggagcgc cagattacca tctggtttca gaaccgccgg gtcaaagaga agaaggttct 180
cgccaaggtg aagaacagcg ctacccctta agagatctcc ttgcctgggt gggaggagcg 240
aaagtggggg tgtcctgggg agaccaggaa cctgccaagc ccaggctggg gccaaggact 300
ctgctgagag gcccctagag acaacaccct tcccaggcca ctggctgctg gactgttcct 360
caggagcggc ctgggtaccc agtatgtgca gggagacgga accccatgtg acagcccact 420
ccaccagggt tcccaaagaa cctggcc 447

<210> SEQ ID NO 297
<211> LENGTH: 418
<212> TYPE: DNA
<213> ORGANISM: Homo sapiens

<400> SEQUENCE: 297
tttttttttt ttttttttc gccttccaaa tttattcata attagctcaa ttcatgaaag 60
cggtttctaa agtgctctac aaagctctaa ataaaaaata tgaggctaac gatcatggca 120
gctagtactg gttatcggga ttattgccac tgtcaggatg aatgattatg actgggccag 180
gttctttggg aaccctggtg gagtgggctg tcacatgggg ttccgtctcc ctgcacatac 240
tgggtaccca ggccgttcct gaggaacagt ccaccaccca gtggcctggg aagggtgttg 300
tctctagggg cctctcaaca aagtccttgg ccccagcctg ggcttggcag gttcctggtc 360
tccccaggac acccccactt tcgctcctcc cacccaggca aggagatctc ttaagggg 418

<210> SEQ ID NO 298

-continued

<211> LENGTH: 405
<212> TYPE: DNA
<213> ORGANISM: Homo sapiens
<220> FEATURE:
<221> NAME/KEY: misc_feature
<222> LOCATION: (6)..(6)
<223> OTHER INFORMATION: a or g or c or t/u
<220> FEATURE:
<221> NAME/KEY: misc_feature
<222> LOCATION: (380)..(380)
<223> OTHER INFORMATION: a or g or c or t/u

<400> SEQUENCE: 298
gacgcnaggt atgcggctaa caagttcatc accaaggaca agaggcgcaa gatctcggca 60
gccaccagcc tctcggagcg ccagattacc atctggtttc agaaccgccg ggtcaaagag 120
aagaaggttc tcgccaaggt gaagaacagc gctacccctt aagagatctc cttgcctggg 180
tgggaggagc gaaagtgggg gtgtcctggg gagaccagga acctgccaag cccaggctgg 240
ggccaaggac tctgctgaga ggcccctaga gacaacaccc ttcccaggcc actggctgct 300
ggactgttcc tcaggagcgg cctgggtacc catgtatgtg cagggagacg gaaccccatg 360
tgacagccca ctccaccagn gttcctaaag aaccctggcc agtca 405

<210> SEQ ID NO 299
<211> LENGTH: 369
<212> TYPE: DNA
<213> ORGANISM: Homo sapiens
<220> FEATURE:
<221> NAME/KEY: misc_feature
<222> LOCATION: (301)..(301)
<223> OTHER INFORMATION: a or g or c or t/u
<220> FEATURE:
<221> NAME/KEY: misc_feature
<222> LOCATION: (318)..(318)
<223> OTHER INFORMATION: a or g or c or t/u

<400> SEQUENCE: 299
gcaggcgact tgcgagctgg gagcggttta aaacgctttg gattccccg gcctgggtgg 60 ggagagcgag ctgggtgccc cctagattcc ccgcccccgc acctcatgag ccgaccctcg 120
gtccatggac acggcaatta tgccaccttg gatggagcca aggatatcga aggcttgctg 180
ggagcgggag gggggcggaa tctggtcgcc cactcccctc tgaccagcca cccagcggcg 240
cctacgctga tgcctgctgt caactatgcc cccttggatc tgccaggctc ggcggactct 300
naaagcatat gccacccnat gccctggggt gccccagggg aacgtcccca gctcccgtgc 360
cttatggtt 369

<210> SEQ ID NO 300
<211> LENGTH: 374
<212> TYPE: DNA
<213> ORGANISM: Homo sapiens

<400> SEQUENCE: 300
gcggccgcaa gaaacgcatt ccgtacagca aggggcagtt gcgggagctg gagcgggagt 60
atgcggctaa caagttcatc accaaggaca agaggcgcaa gatctcggca gccaccagcc 120
tctcggagcg ccagattacc atctggtttc agaaccgccg ggtcaaagag aagaaggttc 180
tcgccaaggt gaagaacagc gctacccctt aagagatctc cttgcctggg tgggaggagc 240
gaaagtgggg gtgtcctggg gagaccagga acctgccaag cccaggctgg ggccaaggac 300
tctgctgaga ggcccctaga gacaacaccc ttcccaggcc actggctgct ggactgttcc 360
tcaggagcgg cctg 374

-continued

<210> SEQ ID NO 301
<211> LENGTH: 337
<212> TYPE: DNA
<213> ORGANISM: Homo sapiens

<400> SEQUENCE: 301
gtcgacgaac agcgctaccc cttaagagat ctccttgcct gggtgggagg agcgaaagtg 60
ggggtgtcct ggggagaccg ggaactgcca agcccaggct ggggcaagga ctctgctgag 120
aggcccctag agacaacacc cttcccaggc cactgctgct ggactgttcc tcaggagcgg 180
cctgggtacc cagtatgtgc agggagacgg aaccccatgt gacagcccac tccaccaggg 240
ttcccaaaga acctggccca gtcataatca ttcatcctga cagtggcaat aatcacgata 300
accagtactc agctgccatg atcgttagcc tcatatt 337

<210> SEQ ID NO 302
<211> LENGTH: 452
<212> TYPE: DNA
<213> ORGANISM: Homo sapiens

<400> SEQUENCE: 302
gcgtcgaccc cttgaagaga tctccttgcc tgggtgggag gagcgaaagt gggggtgtcc 60
tggggagacc aggaacctgc caagcccagg ctggggccaa ggactctgct gagaggcccc 120
tagagacaac acccttccca ggccactggc tgctggactg ttcctcagga gcggcctggg 180
tacccagtat gtgcagggag acggaacccc atgtgacagc ccactccacc agggttccca 240
aagaacctgg cccagtcata atcattcatc ctgacagtgg caataatcac gataaccagt 300
actagctgcc atgatcgtta gcctcatatt ttctatctag agctctgtag agcacttgta 360
gaaaccgctt tcatgaattg agctaattat gaatagattt ggaaggggaa aaaagtggaa 420
aaagttttgc ccaaagtggg tcgtttacgt cg 452

<210> SEQ ID NO 303
<211> LENGTH: 358
<212> TYPE: DNA
<213> ORGANISM: Homo sapiens

<400> SEQUENCE: 303
ctccctggca acacatctgg ctgttccagc accagcgaga cccaagactg gtaactgtcc 60
acaggcaaca gggagtcatg tcgcggttct ccaggagcac ccagagtctg caccacagac 120
acgtccaggt aactggccat agctgagtag gttcccggat atcccggata gaaggcaaac 180
tcagtggggc ggctggggta ctcttccccg gccgtggaga gtctccgcgg ggtacggccc 240
agggtggctg cctgggcatc agggtttcag cgagctccgg gacactcggc aggagtagta 300
cccgcctcca aagtaaccat aaggcacggg agctggggac gtccctgggg caccccag 358

<210> SEQ ID NO 304
<211> LENGTH: 474
<212> TYPE: DNA
<213> ORGANISM: Homo sapiens

<400> SEQUENCE: 304
tttaaaacgc tttggattcc cccggcctgg gtggggagag cgagctgggt gccccctaga 60
ttccccgccc ccgcacctca tgagccgacc ctcggtccat ggagccggcg aattatgcca 120
ccttggatgg agccaaggat atcgaaggct tgctgggagc gggagggggg cggaatctgg 180

-continued

```
tcgcccactc ccctctgacc agccacccag cggcgctacg tgatgcctgc tgtcaactat    240

gcccttggat ctgccagctc gcggagccaa agcaatgcca cccatgccct ggggtgcccc    300

aggtgacgtc cccagctccc gtgccttatg gttactttgg aggcgggtac tactcctgcc    360

gagtgtcccg gagctcgctg aaaccctgtg cccaggcagc caccctggcc gcgtaccccg    420

cgatgactcc cacggccggg gaagagtacc ccagccgccc cactgagttt gcct          474
```

```
<210> SEQ ID NO 305
<211> LENGTH: 739
<212> TYPE: DNA
<213> ORGANISM: Homo sapiens
<220> FEATURE:
<221> NAME/KEY: misc_feature
<222> LOCATION: (616)..(616)
<223> OTHER INFORMATION: a or g or c or t/u
<220> FEATURE:
<221> NAME/KEY: misc_feature
<222> LOCATION: (678)..(678)
<223> OTHER INFORMATION: a or g or c or t/u
<220> FEATURE:
<221> NAME/KEY: misc_feature
<222> LOCATION: (730)..(730)
<223> OTHER INFORMATION: a or g or c or t/u

<400> SEQUENCE: 305

caggcgactt gcgagtctgg gagcgattta aaacgctttg gattccccg gcctgggtgg     60

ggagagcgag ctgggtgccc cctagattcc ccgcccccgc acctcatgag ccgaccctcg    120

gctccatgga gcccggcaat tatgccacct tggatggagc caaggatatc gaaggcttgc    180

tgggagcggg aggggggcgg aatctggtcg cccactcccc tctgaccagc cacccagcgg    240

cgcctacgct gatgcctgct gtcaactatg ccccttgga tctgccaggc tcggcggagc     300

cgccaaagca atgccaccca tgccctgggg tgccccaggg gacgtcccca gctcccgtgc    360

cttatggtta ctttggaggc gggtactact cctgccgagt gtcccggagc tcgctgaaac    420

cctgtgccca ggcagccacc ctggccgcgt accccgcgga gactcccacg gccggggaag    480

agtaccccag ccgccccact gagtttgcct tctatccggg atatccggga acctaccagc    540

ctatggccag ttaccttgga cgtgtctgtg gtgcagactc tgggtgctcc tggagaaccg    600

cgacatgact ccctgntgcc tgtggacagt taccagtctt gggctctcgc tggtggctgg    660

aacagccaga tgtgttgnca gggagaacag aacccaccag gtcccttttg gaaggcagat    720

ttgcagactn cagcgggca                                                 739
```

```
<210> SEQ ID NO 306
<211> LENGTH: 924
<212> TYPE: DNA
<213> ORGANISM: Homo sapiens

<400> SEQUENCE: 306

aggcagccac cctggccgcg taccccgcgg agactcccac ggccggggaa gagtacccca     60

gccgccccac tgagtttgcc ttctatccgg gatatccggg aacctaccag cctatggcca    120

gttaccttgga cgtgtctgtg gtgcagactc tgggtgctcc tggagaaccg cgacatgact   180

ccctgttgcc tgtggacagt taccagtctt gggctctcgc tggtggctgg aacagccaga    240

tgtgttgcca gggagaacag aacccaccag gtcccttttg gaaggcagca tttgcagact    300

ccagcgggca gcaccctcct gacgcctgcg cctttcgtcg cggccgcaag aaacgcattc    360

cgtacagcaa ggggcagttg cgggagctgg agcgggagta tgcggctaac aagttcatca    420

ccaaggacaa gaggcgcaag atctcggcag ccaccagcct ctcggagcgc cagattacca    480
```

-continued

```
tctggtttca gaaccgccgg gtcaaagaga agaaggttct cgccaaggtg aagaacagcg    540

ctacccctta agagatctcc ttgcctgggt gggaggagcg aaagtggggg tgtcctgggg    600

agaccaggaa cctgccaagc cccaggctgg ggccaaggac tctgctgaga ggcccctaga    660

gacaacaccc ttcccaggcc actggctgct ggactgttcc tcaggagcgg cctgagtacc    720

ccgtatgtgc aggggagacg gaaccccctg tgaccagccc ccctccaccc gtggtctccc    780

agataacctg gcccccactc ataaatcatt tcttcccggg ccgggggcca atcattcccc    840

gaactacccc ggtaccttat acaattagat tggacatgaa tcctctcggg ggcattccct    900

atggcgctga ggcccctcac acct                                            924
```

<210> SEQ ID NO 307
<211> LENGTH: 566
<212> TYPE: DNA
<213> ORGANISM: Homo sapiens
<220> FEATURE:
<221> NAME/KEY: misc_feature
<222> LOCATION: (421)..(421)
<223> OTHER INFORMATION: a or g or c or t/u
<220> FEATURE:
<221> NAME/KEY: misc_feature
<222> LOCATION: (541)..(541)
<223> OTHER INFORMATION: a or g or c or t/u

<400> SEQUENCE: 307

```
gggtgctgtc ctctggagtc tgcaaatgct gccttccaaa agggacctgg tgggttctgt     60

tctccctggc aacacatctg gctgttccag ccaccagcga gagcccaaga ctggtaactg    120

tccacaggca acagggagtc atgtcgcggt tctccaggag cacccagagt ctgcaccaca    180

gacacgtcca ggtaactggc cataggctgg taggttcccg gatatcccgg atagaaggca    240

aactcaatgg ggcggctggg gtactcttcc ccggccgtgg gagtctccgc ggggtacgcg    300

gccagggtgg ctgcctgggc acagggtttc agcgagctcc gggacactcg gcaggagtag    360

tacccgcctc caaagtaacc ataaggcacg ggagctgggg acgtcccctg ggcaccccca    420

nggcatgggt ggcattgctt tggcggctcc gccgagcctg gcagatccaa gggggcatag    480

ttgacagcag gcatcagcgt aggcgccgct gggtggctgg tcaaaaggga gtggcgacca    540

nattccgccc ccctcccgct tcccag                                          566
```

<210> SEQ ID NO 308
<211> LENGTH: 526
<212> TYPE: DNA
<213> ORGANISM: Homo sapiens
<220> FEATURE:
<221> NAME/KEY: misc_feature
<222> LOCATION: (472)..(472)
<223> OTHER INFORMATION: a or g or c or t/u
<220> FEATURE:
<221> NAME/KEY: misc_feature
<222> LOCATION: (501)..(501)
<223> OTHER INFORMATION: a or g or c or t/u

<400> SEQUENCE: 308

```
gggtgctgcc cgctggagtc tgcaaatgct gccttccaaa agggacctgg tgggttctgt     60

tctccctggc aacacatctg gctgttccag ccaccagcga gagcccagga ctggtaactg    120

tccacaggca acagggagtc atgtcgcggt tctccaggag cacccagagt ctgcaccaca    180

gacacgtcca ggtaactggc cataggctgg taggttcccg gatatcccgg atagaaggca    240

aactcagtgg ggcggctggg gtactcttcc ccgccgtggg agtctccgcg gggtacgcgg    300
```

-continued

```
ccagggtggc tgcctgggca cagggtttca gcgagctccg ggacactcgg caggagtagt    360

acccgcctcc aaagtaacca taaggcacgg gagctgggga cgtcccctgg ggcaccccag    420

ggcatgggtg gcattgcttt ggcggctccg ccgagcctgg cagatccaag gnggcatagt    480

tgacagcagg catcagcgta ngcgccgctg ggtggctgtc aagagg                   526
```

<210> SEQ ID NO 309
<211> LENGTH: 471
<212> TYPE: DNA
<213> ORGANISM: Homo sapiens

<400> SEQUENCE: 309

```
tcgacgttac ctggacgtgt ctgtggtgca gactctgggt gctcctggag aaccgcgaca     60

tgactccctg ttgcctgtgg acagttacca gtcttgggct ctcgctggtg gctggaacag    120

cagatgtgtt gccagggaga acagaaccca ccaggtccct tttggaaggc agcatttgca    180

gactccagcg ggcagcaccc tcctgacgcc tgcgcctttc gtcgcggccg caagaaacgc    240

attccgtaca gcaaggggca gttgcgggac tggagcggga gtatgcggct aacaagttca    300

tcaccaagga caagaggcgc aagatctcgg cagccaccag cctctcggag cgccagatta    360

ccatctggtt tcagaaccgc cgggtcaaag agaagaaggt tctcgccaag gtgaagaaca    420

gcgctacccc ttaagagatc tccttgcctg ggtgggagga gcgaaagtgt g             471
```

<210> SEQ ID NO 310
<211> LENGTH: 545
<212> TYPE: DNA
<213> ORGANISM: Homo sapiens
<220> FEATURE:
<221> NAME/KEY: misc_feature
<222> LOCATION: (427)..(427)
<223> OTHER INFORMATION: a or g or c or t/u

<400> SEQUENCE: 310

```
gtcaggaggg tgctgcccgc tggagtctgc aaatgctgcc ttccaaaagg gacctggtgg     60

gttctgttct ccctggcaac acatctggct gttccagcca ccagcgagag cccaggactg    120

gtaactgtcc acaggcaaca gggagtcatg tcgcggttct ccaggagcac ccagagtctg    180

caccacagac acgtccaggt aactggccat aggctggtag gttcccggat atcccggata    240

gaaggcaaac tcagtggggc ggctggggta ctcttccccg gccgtgggag tctccgcggg    300

gtacgcggcc agggtggctg cctgggcaca gggtttcagc gagctccggg acactcggca    360

tgagtagacc cgccttccaa gtaaccataa ggcacgggag ctggtaacgt cccctggggc    420

accccanggc catgggtgca ttgctttggc ggctccgccg agccctgcag atccaaggtg    480

ggcatattga cagcaggcat tcacgtatgc gccccctggg tggctgtcat attggggatt    540

gcgac                                                                545
```

<210> SEQ ID NO 311
<211> LENGTH: 438
<212> TYPE: DNA
<213> ORGANISM: Homo sapiens
<220> FEATURE:
<221> NAME/KEY: misc_feature
<222> LOCATION: (366)..(366)
<223> OTHER INFORMATION: a or g or c or t/u
<220> FEATURE:
<221> NAME/KEY: misc_feature
<222> LOCATION: (375)..(375)
<223> OTHER INFORMATION: a or g or c or t/u
<220> FEATURE:
<221> NAME/KEY: misc_feature -continued
<222> LOCATION: (415)..(415)
<223> OTHER INFORMATION: a or g or c or t/u
<220> FEATURE:
<221> NAME/KEY: misc_feature
<222> LOCATION: (419)..(420)
<223> OTHER INFORMATION: a or g or c or t/u

<400> SEQUENCE: 311
gcaggcgtca ggagggtgct gcccgctgga gtctgcaaat gctgccttcc aaaagggacc 60
tggtgggttc tgttctccct ggcaacacat ctggctgttc cagccaccag cgagagccca 120
agactggtaa ctgtccacag gcaacaggga gtcatgtcgc ggttctccag gagcacccag 180
agtctgcacc acagacacgt ccaggtaact ggccataggc tggtaggttc ccggatatcc 240
cggatagaag gcaaactcag tggggcgact ggggtactct tcccggccgt ggggagtctc 300
cgcggggtac gcggccaggg gtggctgcct gggcaccagg ggtttcagcg agctccggga 360
cactcngcag gaaantagta cccgcctccc aaagtaacca taagcaccgg actgngggnn 420
ggacgtcccc tggggcac 438

<210> SEQ ID NO 312
<211> LENGTH: 370
<212> TYPE: DNA
<213> ORGANISM: Homo sapiens

<400> SEQUENCE: 312
gcgaccggac gaaaggaggc gtcaggaggg tgctgcccgc tggagtctgc aaatgctgcc 60
ttccaaaagg gacctggtgg gttctgttct ccctggcaac acatctggct gttccagcac 120
cagcgagacc caagactggt aactgtccac aggcaacagg gagtcatgtc gcggttctcc 180
aggagcaccc agagtctgca ccacagacac gtccaggtaa ctggccatag ctaggtaggt 240
tcccggatat cccggataga aggcaaactc agtggggcga ctggggtact cttccccggc 300
cgtgggagtc tccgcggggt acgcccatgg gtggctgcct gggcacaggg tttcagcgag 360
ctccgggaca 370

<210> SEQ ID NO 313
<211> LENGTH: 495
<212> TYPE: DNA
<213> ORGANISM: Homo sapiens

<400> SEQUENCE: 313
gcaggcgtca ggagggtgct gcccgctgga gtctgcaaat gctgccttcc aaaagggacc 60
tggtgggttc tgttctccct ggcaacacat ctggctgttc cagccaccag cgagagccca 120
agactggtaa ctgtccacag gcaacaggga gtcatgtcgc ggttctccag gagcacccag 180
agtctgcacc acagacacgt ccaggtaact ggccataggc tggtaggttc ccggatatcc 240
cggatagaag gcaaactcag tggggcgact ggggtactct tccccggccg tgggagtctc 300
cgcggggtac gcggccaggg tggctgcctg ggcacagggt ttcagcgagc tccgggacac 360
tcggcaggag tagtacccgc ctccaaagta accataaggc acgggagctg gatgcgtccc 420
ctagggcacc ccatggcatg ggtggcattg ctttggcggc tccgccgagc ctggcagatc 480
caaggaggca ctgtt 495

<210> SEQ ID NO 314
<211> LENGTH: 408
<212> TYPE: DNA
<213> ORGANISM: Homo sapiens -continued

<400> SEQUENCE: 314
gggtgctgcc cgctggagtc tgcaaatgct gccttccaaa agggacctgg tgggttctgt 60
tctccctggc aacacatctg gctgttccag ccaccagcga gacccaagac tggtaactgt 120
ccacaggcaa cagggagtca tgtcgcggtt ctccaggagc acccagagtc tgcaccacag 180
acacgtccag gtaactggcc ataggctggt aggttcccgg atatcccgga tagaaggcaa 240
actcagtggg gcggctgggg tactcttccc cggccgtggg agtctccgcg gggtacgcgt 300
ccagggtggc tgcctgggca cagggtttca gcgagctccg ggacactcgg caggagtagt 360
acccgcctcc aaagtaacca taaggcacgg gagctgggga cgtccctg 408

<210> SEQ ID NO 315
<211> LENGTH: 344
<212> TYPE: DNA
<213> ORGANISM: Homo sapiens

<400> SEQUENCE: 315
gggtgctgcc cgctggagtc tgcaaatgct gccttccaaa agggacctgg tgggttctgt 60
tctccctggc aacacatctg gctgttccag ccaccagcga gacccaagac tggtaactgt 120
ccacaggcaa cagggagtca tgtcgcggtt ctccaggagc acccagagtc tgcaccacag 180
acacgtccag gtaactggcc ataggtggta ggttcccgga tatcccggat agaaggcaaa 240
ctcagtgggg cggctggggt actcttcccc ggccgtggga gtctccgcgg ggtacgcggc 300
cagggtggct gcctgggcac agggtttcag cgagctccgg gaca 344

<210> SEQ ID NO 316
<211> LENGTH: 334
<212> TYPE: DNA
<213> ORGANISM: Homo sapiens

<400> SEQUENCE: 316
gggtgctgcc cgctggagtc tgcaaatgct gccttccaaa agggacctgg tgggttctgt 60
tctccctggc aacacatctg gctgttcctg ccaccagcga gagcccaaga ctggtaactg 120
tccacaggca acagggagtc atgtcgcggt tctccaggag cacccagagt ctgcaccaca 180
gacacgtcca ggtaactggc cataggctgg taggttcccg gatatcccgg atagaaggca 240
aactcagtgg ggcggctggg gtactcttcc ccggccgtgg gagtctccgc ggggtacgcg 300
gccagggtgg ctgcctgggc acagggtttc agcg 334

<210> SEQ ID NO 317
<211> LENGTH: 288
<212> TYPE: DNA
<213> ORGANISM: Homo sapiens
<220> FEATURE:
<221> NAME/KEY: misc_feature
<222> LOCATION: (207)..(207)
<223> OTHER INFORMATION: a or g or c or t/u

<400> SEQUENCE: 317
gggtgctgcc cgctggagtc tgcaaatgct gccttccaaa agggacctgg tgggttctgt 60
tctccctggc aacacatctg gctgttccag ccaccagcga gacccaagac tggtaactgt 120
ccacaggcaa cagggagtca tgtcgcggtt ctccaggagc acccagagtc tgcaccacag 180
acacgtccag gtaactggcc ataggtnggt aggttcccgg atatcccgga tagaaggcaa 240
actcagtggg gcggctgggg tactcttccc cggccgtggg agtctccg 288

-continued

<210> SEQ ID NO 318
<211> LENGTH: 343
<212> TYPE: DNA
<213> ORGANISM: Homo sapiens
<220> FEATURE:
<221> NAME/KEY: misc_feature
<222> LOCATION: (238)..(238)
<223> OTHER INFORMATION: a or g or c or t/u
<220> FEATURE:
<221> NAME/KEY: misc_feature
<222> LOCATION: (300)..(300)
<223> OTHER INFORMATION: a or g or c or t/u
<220> FEATURE:
<221> NAME/KEY: misc_feature
<222> LOCATION: (321)..(321)
<223> OTHER INFORMATION: a or g or c or t/u

<400> SEQUENCE: 318
ctccctggca acacatctgg ctgttccagc accagcgaga gccaagactg gtaactgtcc 60
acaggcaaca gggagtcatg tcgcggttct ccaggagcac ccagagtctg caccacagac 120
acgtccaggt aactggccat aggtcggtag gttcccggat atcccggata gaaggcaaac 180
tcagtggggc gactggggta ctcttccccg gccgtgggag tctccgcggg gtacggcnac 240
agggtggctg cctgggcaca gggtttcagc gagctccggg acactcggca ggagtagtan 300
ccgcctcaaa gtaaccataa ngcacgggag ctggggacgt ccc 343

<210> SEQ ID NO 319
<211> LENGTH: 441
<212> TYPE: DNA
<213> ORGANISM: Homo sapiens
<220> FEATURE:
<221> NAME/KEY: misc_feature
<222> LOCATION: (379)..(379)
<223> OTHER INFORMATION: a or g or c or t/u

<400> SEQUENCE: 319
acgaaaggcg caggcgtcag gagggtgctg cccgctggag tctgcaaatg ctgccttcca 60
aaagggacct ggtgggttct gttctccctg gcaacacatc tggctgttcc agccaccagc 120
gagagcccaa gactggtaac tgtccacagg caacagggag tcatgtcgcg gttctccagg 180
agcacccaga gtctgcacca cagacacgtc caggtaactg gccataggct ggtaggttcc 240
cggatatccc ggatagaagg caaactcagt ggggcgactg gggtactctt ccccggcccg 300
gggagtctcc gcggggtacg cggccagggt ggctgcctgg gcacagggtt tcagcgagct 360
ccgggacact cggcggagnt agtacccgcc tccaaagtaa ccataaggca cgggagctgg 420
ggaaccgtcc cctggggcac c 441

<210> SEQ ID NO 320
<211> LENGTH: 729
<212> TYPE: DNA
<213> ORGANISM: Homo sapiens

<400> SEQUENCE: 320
gagcgagctg ggtgccccct agattccccg cccccgcacc tcatgagccg accctcggct 60
ccatggagcc cggcaattat gccaccttgg atggagccaa ggatatcgaa ggcttgctgg 120
gagcgggagg ggggcggaat ctggtcgccc actcccctct gaccagccac ccagcggcgc 180
ctacgctgat gcctgctgtc aactatgccc ccttggatct gccaggctcg gcggagccgc 240
caaagcaatg ccacccatgc cctggggtgc cccagggacg tccccagctc ccgtgcctta 300
tggttacttt ggaggcgggt actactcctg ccgagtgtcc cggagctcgc tgaaaccctg 360

-continued

```
tgcccaggca gccaccctgg ccgcgtaccc cgcggagact cccacggccg gggaagagta    420

ccccagccgc cccactgagt ttgccttcta tccgggatat ccgggaacct accagcctat    480

ggccagttac ctggacgtgt ctgtggtgca gactctgggt gctcctggag aaccgcgaca    540

tgactccctg ttgcctgtgg acagttacca gtcttgggct ctcgctggtg gctggaacag    600

ccagatgtgt tgccagggag aacagaaccc accaggtccc tttttggaag gcagcatttg    660

cagactccag cggcaggacc tcctgaacgc ctgcgccttt cgtcgcggcg tctaaagtaa    720

tcctcgagg                                                              729
```

<210> SEQ ID NO 321
<211> LENGTH: 502
<212> TYPE: DNA
<213> ORGANISM: Homo sapiens
<220> FEATURE:
<221> NAME/KEY: misc_feature
<222> LOCATION: (301)..(301)
<223> OTHER INFORMATION: a or g or c or t/u
<220> FEATURE:
<221> NAME/KEY: misc_feature
<222> LOCATION: (479)..(479)
<223> OTHER INFORMATION: a or g or c or t/u

<400> SEQUENCE: 321

```
gcggccgcgg cccaccacca actgctcgcc accgacccca ctactcgcca ccgacccgct     60

gctcggagct tcggttctgc gggttgtcca gacttcaggc ctgtgcgctc aatcgtggag    120

aatgcgccgg caggcccccc acccccagcc taaggtgcag gaaggaccag cacgaacccg    180

ctggctttgc tgcgcggcca ggagatgagt cccaccgggc actgagccca ggtacaggac    240

atcagagaat gaacacagag gcagaggccc tcatgtccct ctcagagtcc cggctctgca    300

nagagcccgt ctgtctccag cttccagaat tccgcactgt gaatctgtct acgtggactg    360

ggaaaacagg gttggcacca ctctgccact ccgtttgtgc ctgggaaggg ctaagtatgc    420

aaggctacaa acatctactt cactgggatc ccaaatgctc aacaaaccat gacctgctnt    480

ggtcagaacc accagaaata tt                                               502
```

<210> SEQ ID NO 322
<211> LENGTH: 282
<212> TYPE: DNA
<213> ORGANISM: Homo sapiens

<400> SEQUENCE: 322

```
gcaggcgact tgcgagctgg gagcacttta aaacgctttg gattcccccg gcctgggtgg     60

ggagagcgag ctgggtgccc cctagattcc ccgcccccgc acctcatgag ccgaccctcg    120

gctccatgga gcctggcata ttatgccacc ttggtatgga gccaaggata tcgaaggctt    180

gctgggagcg ggagggggc ggaatctggt cgcccactcc cctctgacca gccacccagc     240

ggcgcctacg ctgatgcctg ctgtcaacta tgcccccttg ga                         282
```

<210> SEQ ID NO 323
<211> LENGTH: 381
<212> TYPE: DNA
<213> ORGANISM: Homo sapiens
<220> FEATURE:
<221> NAME/KEY: misc_feature
<222> LOCATION: (201)..(201)
<223> OTHER INFORMATION: a or g or c or t/u

<400> SEQUENCE: 323

```
gcccgctgga gtctgcaaat gctgccttcc aaaagggacc tggtgggttc tgttctccct     60
```

-continued

```
ggcaacacat ctggctgttc cagccaccag cgagacgcca agactggtaa ctgtccacag    120

gcaacaggga gtcatgtcgc ggttctccag gagcacccag agtctgcacc acagacacgt    180

ccaggtaact ggccataggt nggtaggttc ccggatatcc cggatagaag gcaaactcag    240

tggggcggct ggggtactct tccccggccg tgggagtctc cgcggggtac gcgcacaggg    300

tggctgcctg ggcacagggt ttcagcgagc tccgggacac tcggcaggag tagtacccgc    360

ctccaaagta accataaggc a                                              381
```

<210> SEQ ID NO 324
<211> LENGTH: 405
<212> TYPE: DNA
<213> ORGANISM: Homo sapiens

<400> SEQUENCE: 324

```
aactgctcgc caccgacccc actactcgcc accgacccgc tgctcggagc ttcggttctg     60

cgggttgtcc agacttcagg cctgtgcgct caatcgtgga gaatgcgccg gcagcccccca   120

cccccagcct aaggtgcagg aaggaccagc acgaacccgc tggctttgct gcgcggccag    180

gagatgagtc ccaccgggca ctgagcccag gtacaggaca tcagagaatg aacacagagg    240

cagaggccct catgtccctc tcagagtccc ggctctgcaa agagcccgtc tgtctccagc    300

ttccagaatt ccgcactgtg aatctgtcta cgtggactgg gaaaacaggg ttggcaccac    360

tctgccactc cgtttgtgcc tgggaagggc taagtatgca aggct                    405
```

<210> SEQ ID NO 325
<211> LENGTH: 328
<212> TYPE: DNA
<213> ORGANISM: Homo sapiens

<400> SEQUENCE: 325

```
gatccctttg cagggaagct ttctctcaga ccccccttcca ttacacctct caccctggta    60

acagcaggaa gactgaggag aggggaacgg gcagattcgt tgtgtggctg tgatgtccgt    120

ttagcatttt tctcagctga cagctgggta ggtggacaat tgtagaggct gtctcttcct    180

ccctccttgt ccaccccata gggtgtaccc actggtcttg gaagcaccca tccttaatac    240

gatgattttt ctgtcgtgtg aaaatgaagc cagcaggctg cccctagtca gtccttcctt    300

ccagagaaaa agagatttga gaaagtga                                       328
```

<210> SEQ ID NO 326
<211> LENGTH: 320
<212> TYPE: DNA
<213> ORGANISM: Homo sapiens

<400> SEQUENCE: 326

```
tttttttttt tttttttttt ctttttcact ttctcaaatc tctttttctc tggaaggaag     60

gactgactag gggcagcctg ctggcttcat tttcacacga caaaaaaatc atcgtattaa    120

ggatgggtgc ttccaaaacc agtgggtaca ccctatgggg gggacaagga gggaggaaga    180

gacagcctct acaattgtcc acctacccag ctgtcagctg agaaaaatgc taaacggaca    240

tcacagccac acaacgaatc tgcccgttcc cctctcctca gtcttcctgc tgttaccagg    300

gtgagaggtg taatggaagg                                                320
```

<210> SEQ ID NO 327
<211> LENGTH: 321
<212> TYPE: DNA

-continued

<213> ORGANISM: Homo sapiens

<400> SEQUENCE: 327
tttttttttt tttttttttt ctttttcact ttcccaaatc tctttttctc tggaaggaag 60
gactgactag gggcagcctg ctggcttcat tttcacacga cagaaaaatc atcgtattaa 120
ggatgggtgc ttccaagacc agtgggtaca ccctatgggg tggacacagg agggaggaag 180
agacagcctc tacaattgtc cacctaccca gctgtcagct gagaaaaatg ctaaacggac 240
atcacagcca cacaacgaat ctgcccgttc ccctctcctc agtcttcctg ctgttaccag 300
ggtgagaggt gtaatggaag g 321

<210> SEQ ID NO 328
<211> LENGTH: 354
<212> TYPE: DNA
<213> ORGANISM: Homo sapiens

<400> SEQUENCE: 328
gcggccgcgg cccaccacca actgctcgcc accgacccca ctactcgcca ccgacccgct 60
gctcggagct tcggttctgc gggttgtcca gacttcaggc ctgtgcgctc aatcttggag 120
aatgcgccgg caggcccccc accccccagcc taaggtgcag gaaggaccag cacgaacccg 180
ctggctttgc tgcgcggcca ggagatgagt cccaccgggc actgagccca ggtacaggac 240
atcagagaat gaacacagag gcagaggccc tcatgtccct ctcagagtcc cggctctgca 300
aagagcccgt ctgtctccag cttccagaat tccgcactgt gaatctgtct acgt 354

<210> SEQ ID NO 329
<211> LENGTH: 448
<212> TYPE: DNA
<213> ORGANISM: Homo sapiens

<400> SEQUENCE: 329
cacgcgtcga tcccagtgaa gtagatgttt gtagccttgc atacttagtc cttcccaggc 60
acaaacggag tggcagagtg gtgccaaccc tgttttccca gtccacgtag acagattcac 120
agtgcggaat tctggaagct ggagacagac gggctctttg cagagccggg actctgagag 180
ggacatgagg gcctctgcct ctgtgttcat tctctgatgt cctgtacctg ggctcagtgc 240
ccggtgggac tcatctcctg gccgcgcagc aaagccagcg ggttcgtgct ggtccttcct 300
gcaccttagg ctgggggtgg ggggcctgcc ggcgcattct ccacgattga gcgcacaggc 360
ctgaagtctg gacaacccgc agaaccgaag ctccgagcag cgggtcggtg gcgagtagtg 420
gggtcggtgg cgagcagttg gtggtggg 448

<210> SEQ ID NO 330
<211> LENGTH: 223
<212> TYPE: DNA
<213> ORGANISM: Homo sapiens

<400> SEQUENCE: 330
tcgacctcgc caaggtgaag aacaacgcta ccccttaaga gatctccttg cctgggtggg 60
aggagcgaaa gtgggggtgt cctggggaga ccaggaacct gccaagccca ggctggggcc 120
aaggactctg ctgagaggcc cctagagaca acacccttcc caggccactg gctgctggac 180
tgttcctcag gagcggcctg ggtacccagt atgtgcaggg aga 223

<210> SEQ ID NO 331
<211> LENGTH: 157

-continued

<212> TYPE: DNA
<213> ORGANISM: Homo sapiens

<400> SEQUENCE: 331 tttttactg gttatcgtgg ttattgccac tgtcaggatg aatgattatg actgggccag 60
gttctttggg aaccctggtg gagtgggctg tcacatgggg ttccgtctcc ctgcacatac 120
tgggtaccca ggccgctcct gaggaacagt ccagcag 157

<210> SEQ ID NO 332
<211> LENGTH: 344
<212> TYPE: DNA
<213> ORGANISM: Homo sapiens

<400> SEQUENCE: 332
ggcccaccac caactgctcg ccaccgaccc cactactcgc caccgacccg ctgctcggag 60
cttcggttct gcgggttgtc cagacttcag gcctgtgcgc tcaatcgtgg agaatgcgcc 120
ggcaggcccc ccacccccag cctaaggtgc aggaaggacc agcacgaacc cgctggcttt 180
gctgcgcggc caggagatga gtcccaccgg gcactgagcc caggtacagg acatcagaga 240
atgaacacag aggcagaggc cctcatgtcc ctctcagagt cccggctctg caaagagccc 300
gtctgtctcc agcttccaga attccgcact gtgaacctcg tgcc 344

<210> SEQ ID NO 333
<211> LENGTH: 344
<212> TYPE: DNA
<213> ORGANISM: Homo sapiens

<400> SEQUENCE: 333
ggcacgaggt tcacagtgcg gaattctgga agctggagac agacgggctc tttgcagagc 60
cgggactctg agagggacat gagggcctct gcctctgtgt tcattctctg atgtcctgta 120
cctgggctca gtgcccggtg ggactcatct cctggccgcg cagcaaagcc agcgggttcg 180
tgctggtcct tcctgcacct taggctgggg gtggggggcc tgccggcgca ttctccacga 240
ttgagcgcac aggcctgaag tctggacaac ccgcagaacc gaagctccga gcagcgggtc 300
ggtggcgagt agtggggtcg gtggcgagca gttggtggtg ggcc 344

<210> SEQ ID NO 334
<211> LENGTH: 305
<212> TYPE: DNA
<213> ORGANISM: Homo sapiens

<400> SEQUENCE: 334
gctgctcgga gcttcggttc tgcgggttgt ccagacttca ggcctgtgcg ctcaatcgtg 60
gagaatgcgc cggcagcccc cacccccagc ctaaggtgca ggaaggacca gcacgaaccc 120
gctggctttg ctgcgcggcc aggagatgag tcccaccggc actgagccag gtacaggaca 180
tcagagaatg aacacagagg cagaggcctc atgtccctct cagagtcccg gctctgcaaa 240
gagccgtact gtctccagct tccagaattc cgcactgtga atctgtctac gtggactggg 300
aaaac 305

<210> SEQ ID NO 335
<211> LENGTH: 687
<212> TYPE: DNA
<213> ORGANISM: Homo sapiens

<400> SEQUENCE: 335

-continued

```
cacgaggatt ttctatctag agctctgtag agcactttag aaaccgcttt catgaattga     60

gctaattatg aataaatttg gaaggcgatc cctttgcagg gaagctttct ctcagacccc    120

cttccattac acctctcacc ctggtaacag caggaagact gaggagaggg gaacgggcag    180

attcgttgtg tggctgtgat gtccgtttag catttttctc agctgacagc tgggtaggtg    240

gacaattgta gaggctgtct cttcctccct ccttgtccac cccatagggt gtacccactg    300

gtcttggaaa cacccatcct taatacgatg atttttctgt cgtgtgaaaa tgaagccagc    360

aggctgcccc tagtcagtcc ttccttccag agaaaaagag atttgagaaa gtgcctgggt    420

aattcaccat taatttcctc ccccaaactc tctgagtctt cccttaatat ttctggtggt    480

tctgaccaaa gcaggtcatg gtttgttgag catttgggat cccagtgaag tagatgtttg    540

tagccttgca tacttagccc ttcccaggca caaacggagt ggcagagtgg tgccaaccct    600

gttttcccag tccacgtaga cagattcaca gtgcggaatt ctggaagctg gagacagacg    660

ggctctttgc agagccggga ctctgag                                       687
```

<210> SEQ ID NO 336
<211> LENGTH: 687
<212> TYPE: DNA
<213> ORGANISM: Homo sapiens
<220> FEATURE:
<221> NAME/KEY: misc_feature
<222> LOCATION: (17)..(17)
<223> OTHER INFORMATION: a or g or c or t/u
<220> FEATURE:
<221> NAME/KEY: misc_feature
<222> LOCATION: (42)..(42)
<223> OTHER INFORMATION: a or g or c or t/u

<400> SEQUENCE: 336

```
cacgaggatt ttctatncta gagctctggt agagcacttt anaaaccgct ttcatgaatt     60

gagctaatta tgaataaatt tggaaggcga tccctttgca gggaagcttt ctctcagacc    120

cccttccatt acacctctca ccctggtaac agcaggaaga ctgaggagag gggaacgggc    180

agattcgttg tgtggctgtg atgtccgttt agcatttttc tcagctgaca gctgggtagg    240

tggacaattg tagaggctgt ctcttcctcc ctccttgtcc accccatagg gtgtacccac    300

tggtcttgga aacacccatc cttaatacga tgatttttct gtcgtgtgaa aatgaagcca    360

gcaggctgcc cctagtcagt ccttccttcc agagaaaaag agattgagaa agtgcctggg    420

taattcacca ttaatttcct cccccaaact ctctgagtct tcccttaata tttctggtgg    480

ttctgaccaa agcaggtcat ggtttgttga gcatttggga tcccagtgaa gtagatgttt    540

gtagccttgc atacttagcc cttcccaggc acaaacggag tggcagagtg gtgccaaccc    600

tgttttccca gtccacgtag acagattcac agtgcggaat tctggaagct ggagacagac    660

gggctctttg cagagccggg actctga                                       687
```

<210> SEQ ID NO 337
<211> LENGTH: 473
<212> TYPE: DNA
<213> ORGANISM: Homo sapiens

<400> SEQUENCE: 337

```
cacgagggaa gccagcaggc tgcccctagt cagtccttcc ttccagagaa aaagagattt     60

gagaaagtgc ctgggtaatt caccattaat ttcctccccc aaactctctg agtcttccct    120

taatatttct ggtggttctg accaaagcag gtcatggttt gttgagcatt tgggatccca    180

gtgaagtaga tgtttgtagc cttgcatact tagcccttcc caggcacaaa cggagtggca    240
```

-continued gagtggtgcc aaccctgttt tcccagtcca cgtagacaga ttcacagtgc ggaattctgg 300
aagctggaga cagacgggct ctttgcagag ccgggactct gagagggaca tgagggcctc 360
tgcctctgtg ttcattctct gatgtcctgt acctgggctc agtgcccggt gggactcatc 420
tcctgggcgc gcagcaaagc cagcgggttc gtgctggtcc ttcctgcacc tta 473

<210> SEQ ID NO 338
<211> LENGTH: 514
<212> TYPE: DNA
<213> ORGANISM: Homo sapiens

<400> SEQUENCE: 338
cacgaggcct ggtaacagca ggaagactga ggagagggga acgggcagat tcgttgtgtg 60
gctgtgatgt ccgtttagca tttttctcag ctgacagctg ggtaggtgga caattgtaga 120
ggctgtctct tcctccctcc ttgtccaccc catagggtgt acccactggt cttggaaaca 180
cccatcctta atacgatgat ttttctgtcg tgtgaaaatg aagccagcag gctgccccta 240
gtcagtcctt ccttccagag aaaaagagat ttgagaaagt gcctgggtaa ttcaccatta 300
atttcctccc ccaaactctc tgagtcttcc cttaatattt ctggtggttc tgaccaaagc 360
aggtcatggt ttgttgagca tttgggatcc cagtgaagta gatgtttgta gccttgcata 420
cttagccctt cccaggcaca aacggagtgg cagagtggtg ccaaccctgt tttcccagtc 480
cacgtagaca gattcacagt gcggaattct ggaa 514

<210> SEQ ID NO 339
<211> LENGTH: 477
<212> TYPE: DNA
<213> ORGANISM: Homo sapiens

<400> SEQUENCE: 339
cacgaggtct tcccttaata tttctggtgg ttctgaccaa agcaggtcat ggtttgttga 60
gcatttggga tcccagtgaa gtagatgttt gtagccttgc atacttagcc cttcccaggc 120
acaaacggag tggcagagtg gtgccaaccc tgttttccca gtccacgtag acagattcac 180
agtgcggaat tctggaagct ggagacagac gggctctttg cagagccggg actctgagag 240
ggacatgagg gcctctgcct ctgtgttcat tctctgatgt cctgtacctg ggctcagtgc 300
ccggtgggac tcatctcctg gccgcgcagc aaagccagcg ggttcgtgct ggtccttcct 360
gcaccttagg ctgggggtgg ggggcctgcc ggcgcattct ccacgattga gcgcacaggc 420
ctgaagtctg gacaacccgc agaaccgaag ctccgagcag cgggtcggtg gcgagta 477

<210> SEQ ID NO 340
<211> LENGTH: 355
<212> TYPE: DNA
<213> ORGANISM: Homo sapiens

<400> SEQUENCE: 340
cacgaggatt tctggtggtt ctgaccaaag caggtcatgg tttgttgagc atttgggatc 60
ccagtgaagt agatgtttgt agccttgcat acttagccct tcccaggcac aaacggagtg 120
gcagagtggt gccaaccctg ttttcccagt ccacgtagac agattcacag tgcggaattc 180
tggaagctgg agacagacgg gctctttgca gagccgggac tctgagaggg acatgagggc 240
ctctgcctct gtgttcattc tctgatgtcc tgtacctggg ctcagtgccc ggtgggactc 300
atctcctggc cgcgcagcaa agccagcggg ttcgtgctgg tccttcctgc acctt 355

-continued

<210> SEQ ID NO 341
<211> LENGTH: 490
<212> TYPE: DNA
<213> ORGANISM: Homo sapiens

<400> SEQUENCE: 341
cacgaggaag gcgatccctt tgcagggaag ctttctctca gacccccttc cattacacct 60
ctcaccctgg taacagcagg aagactgagg agaggggaac gggcagattc gttgtgtggc 120
tgtgatgtcc gtttagcatt tttctcagct gacagctggg taggtggaca attgtagagg 180
ctgtctcttc ctccctcctt gtccacccca tagggtgtac ccactggtct tggaaacacc 240
catccttaat acgatgattt ttctgtcgtg tgaaaatgaa gccagcaggc tgcccctagt 300
cagtccttcc ttccagagaa aaagagattt gagaaagtgc ctgggtaatt caccattaat 360
ttcctccccc aaactctctg agtcttccct taatatttct ggtggttctg accaaagcag 420
gtcatggttt gttgagcatt tgggatccca gtgaagtaga tgtttgtagc cttgcatact 480
tagcccttcc 490

<210> SEQ ID NO 342
<211> LENGTH: 403
<212> TYPE: DNA
<213> ORGANISM: Homo sapiens

<400> SEQUENCE: 342
cacgaggtgg attcccccgg cctgggtggg gagagcgagc tgggtgcccc ctagattccc 60
cgcccccgca cctcatgagc cgaccctcgg ctccatggag cccggcaatt atgccacctt 120
ggatggagcc aaggatatcg aaggcttgct gggagcggga ggggggcgga atctggtcgc 180
ccactcccct ctgagcagcc acccagcggc gcctacgctg atgcctgctg tcaactatgc 240
ccccttggat ctgccaggct cggcggagcc gccaaagcaa tgccacccat gccctggggt 300
gccccagggg acgtccccag ctcccgtgcc ttatggttac tttggaggcg ggtactactc 360
ctgccgagtg tcgcggagct cgctgaaacc ctgtgcccag gca 403

<210> SEQ ID NO 343
<211> LENGTH: 562
<212> TYPE: DNA
<213> ORGANISM: Homo sapiens
<220> FEATURE:
<221> NAME/KEY: misc_feature
<222> LOCATION: (533)..(533)
<223> OTHER INFORMATION: a or g or c or t/u

<400> SEQUENCE: 343
cacgaggatt ttctatctag agctctgtag agcactttag aaaccgcttt catgaattga 60
gctaattatg aataaatttg gaaggcgatc cctttgcagg gaagctttct ctcagacccc 120
cttccattac acctctcacc ctggtaacag caggaagact gaggagaggg gaacgggcag 180
attcgttgtg tggctgtgat gtccgtttag catttttctc agctgacagc tgggtaggtg 240
gacaattgta gaggctgtct cttcctccct ccttgtccac cccatagggt gtacccactg 300
gtcttggaaa cacccatcct taatacgatg atttttctgt cgtgtgaaaa tgaagccagc 360
aggctgcccc tagtcagtcc ttccttccag agaaaaagag atttgagaaa gtgcctgggt 420
aattcaccat taatttcctc ccccaaactc tctgagtctt cccttaatat ttctggtggt 480
tctgaccaaa gcaggtcatg gtttgttgag catttgggat cccagtgaag tanatgtttg 540
tagccttgca tacttagccc tt 562

<210> SEQ ID NO 344
<211> LENGTH: 463
<212> TYPE: DNA
<213> ORGANISM: Homo sapiens

<400> SEQUENCE: 344
cattttcaca cgactgtaaa atcatcgtat taaggatggg tgcttccaag accagtgggt 60
acaccctatg gggtggacaa ggagggagga agagacagcc tctacaattg tccacctacc 120
cagctgtcag ctgagaaaaa tgctaaacgg acatcacagc cacacaacga atctgcccgt 180
tcccctctcc tcagtcttcc tgctgttacc agggtgagag gtgtaatgga agggggtctg 240
agagaaagct tccctgcaaa gggatcgcct tccaaattta ttcataatta gctcaattca 300
tgaaagcggt ttctaaagtg ctctacagag ctctagatag aaaatatgag gctaacgatc 360
atggcagcta gtactggtta tcgtgattat tgccactgtc aggatgaatg attatgactg 420
ggccaggttc tttgggaacc ctggtggagt gggctgtcac atg 463

<210> SEQ ID NO 345
<211> LENGTH: 198
<212> TYPE: DNA
<213> ORGANISM: Homo sapiens

<400> SEQUENCE: 345
tgcagctagt actggttatc gtgattattg ccactgtcag gatgaatgat tatgactggg 60
ccaggttctt tgggaaccct ggtggagtgg gctgtcacat ggggttccgt ctccctgcac 120
atactgggta cccaggccgc tcctgaggaa cagtccagca cagggtttca gcgagctccg 180
ggacactcgg cctcgtgc 198

<210> SEQ ID NO 346
<211> LENGTH: 320
<212> TYPE: DNA
<213> ORGANISM: Homo sapiens

<400> SEQUENCE: 346
tttttttttt tttttttttt ctttttcact ttctcaaatc tctttttctc tggaaggaag 60
gactgactag gggcagcctg ctggcttcat tttcacacca caaaaaaatc atcgtattaa 120
ggatgggtgc ttccaaaacc agtgggtaca ccctatgggg tggacaagga gggaggaaaa 180
aacagcctct acaattgtcc acctacccag ctgtcagctg aaaaaaatgc taaacggaca 240
tcacagccac acaacgaatc tgcccgttcc cctctcctca gtcttcctgc tgttaccagg 300
gtgaaaggtg taatggaagg 320

<210> SEQ ID NO 347
<211> LENGTH: 421
<212> TYPE: DNA
<213> ORGANISM: Homo sapiens

<400> SEQUENCE: 347
accgacccca ctacttgcca ccgacccgct gctcggagct tcggttctgc gggttgtcca 60
gacttcaggc ctgtgcgctc aatcgtggag aatgcgccgg caggcccccc acccccagcc 120
taaggtgcag gaaggaccag cacgaacccg ctggctttgc tgcgcggcca ggagatgagt 180
cccaccgggc actgagccca ggtacaggac atcagagaat gaacacagag gcagaggccc 240
tcatgtccct ctcagagtcc cggctctgca aagagcccgt ctgtctccag cttccagaat 300

-continued

```
tccgcactgt gaatctgtct acgtggactg ggaaaacagg gttggcacca ctctgccact    360

ccgtttgtgc ctgggaaggg ctaagtatgc aaggctacaa acatctactt cactgggatc    420

c                                                                    421
```

<210> SEQ ID NO 348
<211> LENGTH: 272
<212> TYPE: DNA
<213> ORGANISM: Homo sapiens

<400> SEQUENCE: 348

```
tttttttttt tttttccctg caaagggatc gccttccaaa tttattcata attagctcaa     60

ttcatgaaag cggtttctaa agtgctctac agagctctag atagaaaata tgaggctaac    120

gatcatggca gctagtactg gttatcgtga ttattgccac tgtcaggatg aatgattatg    180

actgggccag gttctttggg aaccctggtg gagtgggctg tcacatgggg ttccgtctcc    240

ctgcacatac tgggtaccca ggccgctcct ga                                  272
```

<210> SEQ ID NO 349
<211> LENGTH: 679
<212> TYPE: DNA
<213> ORGANISM: Homo sapiens

<400> SEQUENCE: 349

```
cacgaggcga cttgcgagct gggagcgatt taaaacgctt tggattcccc ggcctgggtg     60

gggagagcga gctgggtgcc ccctagattc cccgccccg cacctcatga gccgaccctc     120

ggctccatgg agcccggcaa ttatgccacc ttggatggag ccaaggatat cgaaggcttg    180

ctgggagcgg gaggggggcg gaatctggtc gcccactccc ctctgaccag ccacccagcg    240

gcgcctacgc tgatgcctgc tgtcaactat gccccccttgg atctgccagg ctcggcggag   300

ccgccaaagc aatgccaccc atgccctggg gtgccccagg ggacgtcccc agctcccgtg    360

ccttatggtt actttggagg cgggtactac tcctgccgag tgtcccggag ctcgctgaaa    420

ccctgtgccc aggcagccac cctggccgcg taccccgcgg agactcccac ggccggggaa    480

gagtacccca gccgccccac tgagtttgcc ttctatccgg gatatccggg aacctaccag    540

cctatggcca gttacctgga cgtgtctgtg gtgcagactc tgggtgctcc tggagaacgc    600

gacatgactc cctgttgcct gtggacagtt accagtcttg ggctctcgct ggtggctgga    660

acagccagat gtgttgcca                                                 679
```

<210> SEQ ID NO 350
<211> LENGTH: 393
<212> TYPE: DNA
<213> ORGANISM: Homo sapiens

<400> SEQUENCE: 350

```
gcggccgcgg cccaccacca actgctcgcc attcgacccc actactcgcc accgacccgc     60

tgctcggagc ttcggttctg cgggttgtcc agacttcagg cctgtgcgct caatcgtgga    120

gaatgcgccg gcaggccccc cacccccagc ctaaggtgca ggaaggacca gcacgaaccc    180

gctggctttg ctgcgcggcc aggagatgag tcccaccggg cactgagccc aggtacagga    240

catcagagaa tgaacacaga ggcagaggcc ctcatgtccc tctcagagtc ccggctctgc    300

aaagagcccg tctgtctcca gcttccagaa ttccgcactg tgaatctgtc tacgtggact    360

gggaaaacag ggttggcacc actctgccac tcc                                 393
```

-continued

<210> SEQ ID NO 351
<211> LENGTH: 504
<212> TYPE: DNA
<213> ORGANISM: Homo sapiens
<220> FEATURE:
<221> NAME/KEY: misc_feature
<222> LOCATION: (479)..(479)
<223> OTHER INFORMATION: a or g or c or t/u

<400> SEQUENCE: 351
gcggccgcgg cccaccacca actgctcgcc accgacccca ctactcgcca ccgacccgct 60
gctcggagct tcggttctgc gggttgtcca gacttcaggc ctgtgcgctc aatcgtggag 120
aatgcgccgg caggcccccc acccccagcc taaggtgcag gaaggaccag cacgaacccg 180
ctggctttgc tgcgcggcca ggagatgagt cccaccgggc actgagccca ggtacaggac 240
atcagagaat gaacacagag gcagaggccc tcatgtccct ctcagagtcc cggctctgca 300
aagagcccgt ctgtctccag cttccagaat tccgcactgt gaatctgtct acgtggactg 360
ggaaaacagg gttggcacca ctctgccact ccgtttgtgc ctgggaaggg ctaagtatgc 420
aaggctacaa acatctactt cactgggatc ccaaatgctc aacaaaccat gacctgctnt 480
ggtcagaacc accagaaata ttaa 504

<210> SEQ ID NO 352
<211> LENGTH: 451
<212> TYPE: DNA
<213> ORGANISM: Homo sapiens

<400> SEQUENCE: 352
gcggccgcgg cccaccacca actgctcgcc accgacccca ctactcgcca ccgacccgct 60
gctcggagct tcggttctgc gggttgtcca gacttcaggc ctgtgcgctc aatcgtggag 120
aatgcgccgg caggcccccc acccccagcc taaggtgcag gaaggaccag cacgaacccg 180
ctggctttgc tgcgcggcca ggagatgagt cccaccgggc actgagccca ggtacaggac 240
atcagagaat gaacacagag gcagaggccc tcatgtccct ctcagagtcc cggctctgca 300
aagagcccgt ctgtctccag cttccagaat tccgcactgt gaatctgtct acgtggactg 360
ggaaaacagg gttggcacca ctctgccact ccgtttgtgc ctgggaaggg ctaagtatgc 420
aaggctacaa acatctactt cactgggatc c 451

<210> SEQ ID NO 353
<211> LENGTH: 219
<212> TYPE: DNA
<213> ORGANISM: Homo sapiens

<400> SEQUENCE: 353
tcctccctct aagaaaggcg caagcgtcaa gagggtgctg cccgctggtt tctgcaaatg 60
ctgccttcca aaaaggacct ggtgggttct gttctccctg gcaacacatc tggctgttcc 120
agccaccagc gagagcccaa gactggtaac tgtccacagg caacagggag tcatgtcgcg 180
gttctccagg agcacccaga gtctgcacca cagacacgt 219

<210> SEQ ID NO 354
<211> LENGTH: 699
<212> TYPE: DNA
<213> ORGANISM: Homo sapiens

<400> SEQUENCE: 354
ttaatacgat gatttttctg tcgtgtgaaa atgaagccag caggctgccc ctagtcagtc 60

-continued

```
cttccttcca gagaaaaaga gatttgagaa agtgcctggg taattcacca ttaatttcct    120

cccccaaact ctctgagtct tcccttaata tttctggtgg ttctgaccaa agcaggtcat    180

ggtttgttga gcatttggga tcccagtgaa gtagatgttt gtagccttgc atacttagcc    240

cttcccaggc acaaacggag tggcagagtg gtgccaaccc tgttttccca gtccacgtag    300

acagattcac agtgcggaat tctggaagct ggagacagac gggctctttg cagagccggg    360

actctgagag ggacatgagg gcctctgcct ctgtgttcat tctctgatgt cctgtacctg    420

ggctcagtgc ccggtgggac tcatctcctg gccgcgcagc aaagccagcg ggttcgtgct    480

ggtccttcct gcaccttagg ctgggggtgg ggggcctgcc ggcgcattct ccacgattga    540

gcgcacaggc ctgaagtctg gacaacccgc agaaccgaag ctccgagcag cgggtcggtg    600

gcgagtagtg gggtcggtg gcgaacaagt ggtggtgggc cggggccgca taactcgagg    660

actttcctcc cggagcagtc cctaaaaacc cgggggcgc                           699
```

<210> SEQ ID NO 355
<211> LENGTH: 575
<212> TYPE: DNA
<213> ORGANISM: Homo sapiens

<400> SEQUENCE: 355

```
gacgaggaca attgtagagg ctgtctcttc ctccctcctt gtcaccccat agggtgtacc     60

actggtcttg gaagcaccca tccttaatac gatgattttt ctgtcgtgtg aaaatgaagc    120

cagcaggctg cccctagtca gtccttcctt ccagagaaaa agagatttga gaaagtgcct    180

gggtaattca ccattaattt cctcccccaa actctctgag tcttccctta atatttctgg    240

tggttctgac caaagcaggt catggtttgt tgagcatttg ggatcccagt gaagtagatg    300

tttgtagcct tgcatactta gcccttccca ggcacaaacg gagtggcaga gtggtgccaa    360

ccctgttttc ccagtccacg tagacagatt cacagtgcgg aattctggaa gctggagaca    420

gacgggctct ttgcagagcc gggactctga gagggacatg agggcctctg cctctgtgtt    480

cattctctga tgtcctgtac ctgggctcag tgcccggtgg gactcatctc ctggccgcgc    540

agcaaagcca gcgggttcgt gctggtcctt cctgc                               575
```

<210> SEQ ID NO 356
<211> LENGTH: 684
<212> TYPE: DNA
<213> ORGANISM: Homo sapiens

<400> SEQUENCE: 356

```
cacgaggcga cttgcgagct gggagcgatt taaaacgctt tggattcccc cggcctgggt     60

ggggagagcg agctgggtgc cccctagatt ccccgccccc gcacctcatg agccgaccct    120

cggctccatg gagcccggca attatgccac cttggatgga gccaaggata tcgaaggctt    180

gctgggagcg ggagggggc ggaatctggt cgcccactcc cctctgacca gccacccagc    240

ggcgcctacg ctgatgcctg ctgtcaacta tgccccccttg gatctgccag gctcggcgga    300

gccgccaaag caatgccacc catgccctgg ggtgccccag gggacgtccc cagctcccgt    360

gccttatggt tactttggag gcgggtacta ctcctgccga gtgtcccgga gctcgctgaa    420

accctgtgcc caggcagcca ccctggccgc gtaccccgcg gagactccca cggccgggga    480

agagtaccca gccgccccac tgagtttgcc ttctatccgg gatatccggg aacctaccag    540

cctatggcca gttacctgga cgtgtctgtg gtgcagactc tgggtgctcc tggagaacgc    600

gacatgactc cctgttgcct gtggacagtt accaatcttg ggctctcgct ggtggctgga    660
```

-continued acagccagat gtgttgccag ggag 684

<210> SEQ ID NO 357
<211> LENGTH: 855
<212> TYPE: DNA
<213> ORGANISM: Homo sapiens

<400> SEQUENCE: 357
atggagcccg gcaattatgc caccttggat ggagccaagg atatcgaagg cttgctggga 60
gcgggagggg ggcggaatct ggtcgcccac tcccctctga ccagccaccc agcggcgcct 120
acgctgatgc ctgctgtcaa ctatgccccc ttggatctgc caggctcggc ggagccgcca 180
aagcaatgcc acccatgccc tggggtgccc caggggacgt ccccagctcc cgtgccttat 240
ggttactttg gaggcgggta ctactcctgc cgagtgtccc ggagctcgct gaaaccctgt 300
gcccaggcag ccaccctggc cgcgtacccc gcggagactc ccacggccgg ggaagagtac 360
cccagccgcc ccactgagtt tgccttctat ccgggatatc cgggaaccta ccagcctatg 420
gccagttacc tggacgtgtc tgtggtgcag actctgggtg ctcctggaga accgcgacat 480
gactccctgt tgcctgtgga cagttaccag tcttgggctc tcgctggtgg ctggaacagc 540
cagatgtgtt gccagggaga acagaaccca ccaggtccct tttggaaggc agcatttgca 600
gactccagcg ggcagcaccc tcctgacgcc tgcgcctttc gtcgcggccg caagaaacgc 660
attccgtaca gcaaggggca gttgcgggag ctggagcggg agtatgcggc taacaagttc 720
atcaccaagg acaagaggcg caagatctcg gcagccacca gcctctcgga gcgccagatt 780
accatctggt ttcagaaccg ccgggtcaaa gagaagaagg ttctcgccaa ggtgaagaac 840
agcgctaccc cttag 855

<210> SEQ ID NO 358
<211> LENGTH: 1356
<212> TYPE: DNA
<213> ORGANISM: Homo sapiens

<400> SEQUENCE: 358
ggattccccc ggcctgggtg gggagagcga gctgggtgcc ccctagattc cccgcccccg 60
cacctcatga gccgaccctc ggctccatgg agcccggcaa ttatgccacc ttggatggag 120
ccaaggatat cgaaggcttg ctgggagcgg gagggggggcg gaatctggtc gcccactccc 180
ctctgaccag ccacccagcg gcgcctacgc tgatgcctgc tgtcaactat gccccccttgg 240 atctgccagg ctcggcggag ccgccaaagc aatgccaccc atgccctggg gtgccccagg 300
ggacgtcccc agctcccgtg ccttatggtt actttggagg cgggtactac tcctgccgag 360
tgtcccggag ctcgctgaaa ccctgtgccc aggcagccac cctggccgcg taccccgcgg 420
agactcccac ggccggggaa gagtacccca gccgccccac tgagtttgcc ttctatccgg 480
gatatccggg aacctaccag cctatggcca gttacctgga cgtgtctgtg gtgcagactc 540
tgggtgctcc tggagaaccg cgacatgact ccctgttgcc tgtggacagt taccagtctt 600
gggctctcgc tggtggctgg aacagccaga tgtgttgcca gggagaacag aacccaccag 660
gtcccttttg gaaggcagca tttgcagact ccagcgggca gcaccctcct gacgcctgcg 720
cctttcgtcg cggccgcaag aaacgcattc cgtacagcaa ggggcagttg cgggagctgg 780
agcgggagta tgcggctaac aagttcatca ccaaggacaa gaggcgcaag atctcggcag 840
ccaccagcct ctcggagcgc cagattacca tctggtttca gaaccgccgg gtcaaagaga 900

-continued

```
agaaggttct cgccaaggtg aagaacagcg ctacccctta agagatctcc ttgcctgggt    960

gggaggagcg aaagtggggg tgtcctgggg agaccaggaa cctgccaagc ccaggctggg   1020

gccaaggact ctgctgagag gcccctagag acaacaccct tcccaggcca ctggctgctg   1080

gactgttcct caggagcggc ctgggtaccc agtatgtgca gggagacgga accccatgtg   1140

acagcccact ccaccagggt tcccaaagaa cctggcccag tcataatcat tcatcctgac   1200

agtggcaata atcacgataa ccagtactag ctgccatgat cgttagcctc atattttcta   1260

tctagagctc tgtagagcac tttagaaacc gctttcatga attgagctaa ttatgaataa   1320

atttggaaaa aaaaaaaaaa aaaaaaaaaa aaaaaa                             1356
```

<210> SEQ ID NO 359
<211> LENGTH: 1026
<212> TYPE: DNA
<213> ORGANISM: Homo sapiens

<400> SEQUENCE: 359

```
cgggtgcccc ctagattccc cgccccegca cctcatgagc cgaccctcgg ctccatggag     60

cccggcaatt atgccacctt ggatggagcc aaggatatcg aaggcttgct gggagcggga    120

ggggggcgga atctggtcgc ccactcccct ctgaccagcc acccagcggc gcctacgctg    180

atgcctgctg tcaactatgc cccccttggat ctgccaggct cggcggagcc gccaaagcaa    240

tgccacccat gccctggggt gccccagggg acgtccccag ctcccgtgcc ttatggttac    300

tttggaggcg ggtactactc ctgccgagtg tcccggagct cgctgaaacc ctgtgcccag    360

gcagccaccc tggccgcgta ccccgcggag actcccacgg ccggggaaga gtaccccagc    420

cgccccactg agtttgcctt ctatccggga tatccgggaa cctaccacgc tatggccagt    480

tacctggacg tgtctgtggt gcagactctg ggtgctcctg gagaaccgcg acatgactcc    540

ctgttgcctg tggacagtta ccagtcttgg gctctcgctg gtggctggaa cagccagatg    600

tgttgccagg gagaacagaa cccaccaggt cccttttgga aggcagcatt tgcagactcc    660

agcgggcagc accctcctga cgcctccgcc tttcgtcgcg gccgcaagaa acgcattccg    720

tacagcaagg ggcagttgcg ggagctggag cgggagtatg cggctaacaa gttcatcacc    780

aaggacaaga ggcgcaagat ctcggcagcc accagcctct cggagcgcca gattaccatc    840

tggtttcaga accgccgggt caaagagaag aaggttctcg ccaaggtgaa gaacagcgct    900

accccttaag agatctcctt gcctgggtgg gaggagcgaa agtgggggtg tcctggggag    960

accaggaacc tgccaagccc aggctggggc caaggactct gctgagaggc ccctagagac   1020

aacacc                                                              1026
```

<210> SEQ ID NO 360
<211> LENGTH: 1316
<212> TYPE: DNA
<213> ORGANISM: Homo sapiens

<400> SEQUENCE: 360

```
tcctaatacg actcactata gggctcgagc ggccgcccgg gcaggtcgaa tgcaggcgac     60

ttgcgagctg ggagcgattt aaaacgcttt ggattccccc ggcctgggtg gggagagcga    120

gctgggtgcc ccctagattc cccgcccccg cacctcatga gccgaccctc ggctccatgg    180

agcccggcaa ttatgccacc ttggatggag ccaaggatat cgaaggcttg ctgggagcgg    240

gagggggggcg gaatctggtc gcccactccc ctctgaccag ccacccagcg gcgcctacgc    300

tgatgcctgc tgtcaactat gccccccttgg atctgccagg ctcggcggag ccgccaaagc    360
```

-continued aatgccaccc atgccctggg gtgccccagg ggacgtcccc agctcccgtg ccttatggtt 420
actttggagg cgggtactac tcctgccgag tgtcccggag ctcgctgaaa ccctgtgccc 480
aggcagccac cctggccgcg taccccgcgg agactcccac ggccggggaa gagtacccca 540
gtcgccccac tgagtttgcc ttctatccgg gatatccggg aacctaccac gctatggcca 600
gttacctgga cgtgtctgtg gtgcagactc tgggtgctcc tggagaaccg cgacatgact 660
ccctgttgcc tgtggacagt taccagtctt gggctctcgc tggtggctgg aacagccaga 720
tgtgttgcca gggagaacag aacccaccag gtcccttttg gaaggcagca tttgcagact 780
ccagcgggca gcaccctcct gacgcctgcg cctttcgtcg cggccgcaag aaacgcattc 840
cgtacagcaa ggggcagttg cgggagctgg agcgggagta tgcggctaac aagttcatca 900
ccaaggacaa gaggcgcaag atctcggcag ccaccagcct ctcggagcgc cagattacca 960
tctggtttca gaaccgccgg gtcaaagaga agaaggttct cgccaaggtg aagaacagcg 1020
ctacccctta agagatctcc ttgcctgggt gggaggagcg aaagtggggg tgtcctgggg 1080
agaccagaaa cctgccaagc ccaggctggg gccaaggact ctgctgagag gcccctagag 1140
acaacaccct tcccaggcca ctggctgctg gactgttcct caggagcggc ctgggtaccc 1200
agtatgtgca gggagacgga accccatgtg acaggcccac tccaccaggg ttcccaaaga 1260
acctggccca gtcataatca ttcatcctca cagtggcaat aatcacgata accagt 1316

<210> SEQ ID NO 361
<211> LENGTH: 506
<212> TYPE: DNA
<213> ORGANISM: Homo sapiens

<400> SEQUENCE: 361
atttttctgt cgtgtgaaaa tgaagccagc aggctgcccc tagtcagtcc ttccttccag 60
agaaaaagag atttgagaaa gtgcctgggt aattcaccat taatttcctc ccccaaactc 120
tctgagtctt cccttaatat ttctggtggt tctgaccaaa gcaggtcatg gtttgttgag 180
catttgggat cccagtgaag tagatgtttg tagccttgca tacttagccc ttcccaggca 240
caaacggagt ggcagagtgg tgccaaccct gttttcccag tccacgtaga cagattcaca 300
gtgcggaatt ctggaagctg gagacagacg ggctctttgc agagccggga ctctgagagg 360
gacatgaggg cctctgcctc tgtgttcatt ctctgatgtc ctgtacctgg gctcagtgcc 420
cggtgggact catctcctgg ctgcgcagca aagccagcgg gttcgtgctg gtccttcctg 480
caccttaggc tgggggtggg gggcct 506

<210> SEQ ID NO 362
<211> LENGTH: 597
<212> TYPE: DNA
<213> ORGANISM: Homo sapiens

<400> SEQUENCE: 362
atttttctgt cgtgtgaaaa tgaagccagc aggctgcccc tagtcagtcc ttccttccag 60
agaaaaagag atttgagaaa gtgcctgggt aattcaccat taatttcctc ccccaaactc 120
tctgagtctt cccttaatat ttctggtggt tctgaccaaa gcaggtcatg gtttgttgag 180
catttgggat cccagtgaag tagatgtttg tagccttgca tacttagccc ttcccaggca 240
caaacggagt ggcagagtgg tgccaaccct gttttcccag tccacgtaga cagattcaca 300
gtgcggaatt ctggaagctg gagacagacg ggctctttgc agagccggga ctctgagagg 360

-continued

```
gacatgaggg cctctgcctc tgtgttcatt ctctgatgtc ctgtacctgg gctcagtgcc    420

cggtgggact catctcctgg ctgcgcagca aagccagcgg gttcgtgctg gtccttcctg    480

caccttaggc tgggggtggg gggggcctgc cggcgcattc tccacgattg agcgcacagg    540

cctgaagtct ggacaacccg cagaaccgaa gctccgagca gcgggtcggt ggcgagt       597


<210> SEQ ID NO 363
<211> LENGTH: 300
<212> TYPE: DNA
<213> ORGANISM: Homo sapiens

<400> SEQUENCE: 363

atttaaaacg ctttggattc tttcgtcctg cgtggggaga gcgagctggg tgccccctag     60

attccccgcc cccgcacctc atgagccgac cctcggctcc atggagcccg gcacttatgc    120

caccttggat ggagccaagg atatcgaagg cttgctggga gcgggagggg ggcggaatct    180

ggtcgcccac tcccctctga ccagccaccc agcggcgcct acgctgatgc ctgctgtcaa    240

ttatgccccc ttgcatctgc caggctcggc ggagccgcca aagcaatgcc acccatgccc    300


<210> SEQ ID NO 364
<211> LENGTH: 508
<212> TYPE: DNA
<213> ORGANISM: Homo sapiens

<400> SEQUENCE: 364

atttttctgt cgtgtgaaaa tgaagccagc aggctgcccc tagtcagtcc ttccttccag     60

agaaaaagag atttgagaaa gtgcctgggt aattcaccat taatttcctc ccccaaactc    120

tctgagtctt cccttaatat ttctggtggt tctgaccaaa gcaggtcatg gtttgttgag    180

catttgggat cccagtgaag tagatgtttg tagccttgca tacttagccc ttcccaggca    240

caaacggagt ggcagagtgg tgccaaccct gttttcccag tccacgtaga cagattcaca    300

gtgcggaatt ctggaagctg gagacagacg ggctctttgc agagccggga ctctgagagg    360

gacatgaggg cctctgcctc tgtgttcatt ctctgatgtc ctgtacctgg gctcagtgcc    420

cggtgggact catctcctgg ctgcgcagca aagccagcgg gttcgtgctg gtccttcctg    480

caccttaggc tgggggtggg gggcctgc                                       508


<210> SEQ ID NO 365
<211> LENGTH: 284
<212> TYPE: DNA
<213> ORGANISM: Homo sapiens
<220> FEATURE:
<221> NAME/KEY: misc_feature
<222> LOCATION: (227)..(227)
<223> OTHER INFORMATION: a or g or c or t/u
<220> FEATURE:
<221> NAME/KEY: misc_feature
<222> LOCATION: (269)..(269)
<223> OTHER INFORMATION: a or g or c or t/u

<400> SEQUENCE: 365

aggccgcacc cagtcttaag gtgcagtgaa ggacagcacg aacccgctgt gctttgctgc     60

gcggcaggag atgagtccca ccgggcactg agcccaggta caggacatca gagaatgaac    120

acagaggcag aggccctcat gtccctctca gagtcccggc tctgcaaaga gcccgtctgt    180

ctccagcttc cagaattccg cactgtgaat ctgtctacgt ggactgngaa aacagggttg    240

gcaccactct gccactccgt ttgtgcctng gggcgggcag aggg                     284
```

-continued

<210> SEQ ID NO 366
<211> LENGTH: 651
<212> TYPE: DNA
<213> ORGANISM: Homo sapiens

<400> SEQUENCE: 366
aaaaacgctt tggattcccc cggcctgggt ggggagagcg agctgggtgc cccctagatt 60
ccccgccccc gcacctcatg agccgaccct cggctccatg gagcccggca attatgccac 120
cttggatgga gccaaggata tcgaaggctt gctgggagcg ggagggggc ggaatctggt 180 cgcccactcc cctctgacca gccacccagc ggcgcctacg ctgatgcctg ctgtcaacta 240 tgccccttg gatctgccag gctcggcgga gccgccaaag caatgccacc catgccctgg 300
ggtgccccag gggacgtccc cagctcccgt gccttatggt tactttggag gcgggtacta 360
ctcctgccga gtgtcccgga gctcgctgaa accctgtgcc caggcagcca ccctggccgc 420
gtaccccgcg gagactccca cggccgggga agagtacccc agccgcccca ctgagtttgc 480
cttctatccg ggatatccgg gaacctacca gcctatggcc agttacctgg acgtgtctgt 540
ggtgcagact ctgggtgctc ctggagaacc gcgacatgac tccctgttgc ctgtggacag 600
ttaccagtct tgggctctcg ctggtggctg gaacagccag atgtgttgcc a 651

<210> SEQ ID NO 367
<211> LENGTH: 498
<212> TYPE: DNA
<213> ORGANISM: Homo sapiens

<400> SEQUENCE: 367
gcagactctg ggtgctcctg gagaaccgcg acgtgactcc ctgttgcctg tggacagtta 60
ccactcttgg gctctcgctg gtggctggaa cagccagatg tgttgccagg gagaacagaa 120
cccaccaggt cccttttgga aggcagcatt tgcagactcc agcgggcagc accctcctga 180
cgcctgcgcc tttcgtcgcg gccgcaagaa acgcattccg tacagcaagg ggcagttgcg 240
ggagctggag cgggagtatg cggctaacaa gttcatcacc aaggacaaga ggcgcaagat 300
ctcggcagcc accagcctct cggagcgcca gattaccatc tggtttcaga accgccgggt 360
caaagagaag aaggttctcg ccaaggtgaa gaacagcgct accccttaag agatctcctt 420
gcctgggtgg gaggatctaa agtgggggtg tcctggggag accaggaacc tgccaagccc 480
aggctggggc caaggact 498

<210> SEQ ID NO 368
<211> LENGTH: 233
<212> TYPE: DNA
<213> ORGANISM: Homo sapiens

<400> SEQUENCE: 368
acgctgcact gcgtttcaaa gagaagaagg ttctcgccaa ggtgaagaac agcgctaccc 60
cttaagagat ctccttgctt gggtgggagg agcgaaagtg ggggtgtcct ggggagacca 120
ggaacctgcc atcaccaggc tgggcccaag gactctgctg agaggcccct agagacaaca 180
cccttcccag gccattgctt gctggactgt gcctcaggag cggcctgggt acc 233

<210> SEQ ID NO 369
<211> LENGTH: 539
<212> TYPE: DNA
<213> ORGANISM: Homo sapiens

<400> SEQUENCE: 369

-continued

```
gagttttcca atttccaaag aaaaatttag gtttcctgca gccgtgacat atgtgtgtgc     60

actgggatgg gttaatgtgt gtgtgtgtgt gtgtatgcgc atgtattggg agtgggggca    120

gaaacgtgtt tccagaattt gcctgtagaa tctaaaagag tggccaagag tctggaaatg    180

catgaagact ggacgtatgt gatggtgggc aaaggcctga ctgtgtgtgg tgtgtgggta    240

tgtttgcaga ttcgcgggtg tgagagcagt gatgggtgag ggtggccttc aggagccaag    300

gctgatcggt ggtgagagaa caagccggaa gccagggtgc tgtcctggta tgctttggag    360

gaacaggatt gcacgtgcgc ctgtagggtg acctgtgtgc acctgtgaga tgacttagct    420

tggggcttgc aaggcctggg tctgcatggg tgggtatctg accatgcctt ttcctccctc    480

cctttcacgc cgcgcagact ccagcgggca gcaccctcct gacgcctgcg cctttcgtc     539
```

<210> SEQ ID NO 370
<211> LENGTH: 240
<212> TYPE: DNA
<213> ORGANISM: Homo sapiens

<400> SEQUENCE: 370

```
ccggcctggg tggggagagc gagctgggtg ccccctagat tccccgcccc cgcacctcat     60

gagccgaccc tcggctccat ggagcccggc aattatgcca ccttggatgg agccaaggat    120

atcgaaggct tgctgggagc gggagggggg cggaatctgg tcgcccactc ccctctgacc    180

agccacccag cggcgcctac gcttgatgcc tgcttgtcaa ctatgccccc ttggatctgc    240
```

<210> SEQ ID NO 371
<211> LENGTH: 469
<212> TYPE: DNA
<213> ORGANISM: Homo sapiens

<400> SEQUENCE: 371

```
accgcgggtc aaatttattc ataattagct caatcatgaa agcggttcta aagtgctcta     60

cagagctcta gatagaaaat atgaggctaa cgatcatggc agctagtact ggttatcgtg    120

attatggcca ctgtcaggat gaatgataat gactgggcca ggtcctttgg aaaccctggt    180

ggagtgggct gtcacatggg gtcccgtctc cctgcacata ctgggtaccc aggccgctcc    240

tgaggaacag tccagcagcc agtggcctgg gaagggtgtg gtctctaggg gcctctcagc    300

agagtccttg gccccagcct gggcttggca ggtccctggt ctccccagga cacccccact    360

ttcgctcctc ccacccaggc aaggagatct cttaaggggt agcgctgttc ttcaccttgg    420

cgagaacctt cttctctttg aaccggcggt gcggcgtggg gtaccgagc                469
```

<210> SEQ ID NO 372
<211> LENGTH: 472
<212> TYPE: DNA
<213> ORGANISM: Homo sapiens

<400> SEQUENCE: 372

```
atttttctgt cgtgtgaaaa tgaagccagc aggctgcccc tagtcagtcc ttccttccag     60

agaaaaagag atttgagaaa gtgcctgggt aattcaccat taatttcctc ccccaaactc    120

tctgagtctt cccttaatat ttctggtggt tctgaccaaa gcaagtcatg gtttgttgag    180

catttgggat cccagtgaag tagatgtttg tagccttgca tacttagccc ttcccaggca    240

caaacggagt ggcagagtgg tgccaaccct gttttcccag tccacgtaga cagattcaca    300

gtgcggaatt ctggaagctg gagacagacg ggctctttgc agagccggga ctctgagagg    360

gacatgaagg cctctgcctc tgtgttcatt ctctgatgtc ctgtacctgg gctcagtgcc    420
```

-continued

```
cggtgggact catctcctgg ctgcgcagca aagccagcgg gttcgtgctg gt           472


<210> SEQ ID NO 373
<211> LENGTH: 450
<212> TYPE: DNA
<213> ORGANISM: Homo sapiens

<400> SEQUENCE: 373

ccaacgagaa gaaggttctc gcaaggtgaa gaacagcgct accccttaag agatctcctt     60

gcgtgggtgg gaggagcgaa agtgggggtg tcctggggag accaggaacc tgccagccca    120

ggctgaggcc aaggactctg ctgagaggcc cctagagaca acacccttcc caggccactg    180

gatgctgaac tgtccctcag gagcggcctg ggtacccagt atgtgcaggg agacggaacc    240

ccatgtgaca gcccactcca ccagggttcc caaagaacct ggccccagtc ataatcattc    300

atcctgacag tggcaataat cacgataacc agtactagct gccatgatcg taagcctcat    360

atttgctatc tagagctctg tagagcactt tagaaaccgc tttcatgaat tgagctaatt    420

atgactcaat ttgaaccggc gtccggcgtg                                     450


<210> SEQ ID NO 374
<211> LENGTH: 472
<212> TYPE: DNA
<213> ORGANISM: Homo sapiens

<400> SEQUENCE: 374

acgcgcaccg cggtcaagag aagaaggttc tcgcaaggtg aagaacagcg ctacccctta     60

agagatctcc ttgcgtgggt gggaggagcg aaagtggggg tgtcctgggg agaccaggaa    120

cctgccaagc ccaggctgtg gccaaggact ctgctgagag gcccctatga gacaacaccc    180

ttcccaggcc actggctgct gggactgttc ctcaggagcg gcctgggtac ccgagtaatg    240

tgcaggggag acggaacccc atgtgacagc ccactccacc agggttccca aaagaaccct    300

ggcccagtca taatcattca tcctgacagt ggcaataatc acgataacca gtactagctg    360

ccatgatcgt aagcctcata tttgctatct agagctctgt agagcccttt agaaaccgct    420

ttcatgaatg gagctaaatt atgaatacat ttgaaccggc gatccgacgt ga           472


<210> SEQ ID NO 375
<211> LENGTH: 320
<212> TYPE: DNA
<213> ORGANISM: Homo sapiens

<400> SEQUENCE: 375

ctagaggatc ccggaagcaa ctgcaacagg ttcccaaaga accgggccag tcataatcat     60

tcatcctgac agggcaataa tcacgataac cagtactagc tgccatgatc gttagcctca    120

tattttctat ctagagctct gtagagcact ttagaaaccg ctttcatgaa tggagctaat    180

tatgaataaa tttggaaggc gatcccttgg cagggaagct ttctctcaga ccccccttcca    240

ttacacctct caccctggta acagcaggaa gactgaggag aggggaacgg gcagattcgt    300

ggtgttgcag tgtgcttccg                                                320


<210> SEQ ID NO 376
<211> LENGTH: 459
<212> TYPE: DNA
<213> ORGANISM: Homo sapiens
<220> FEATURE:
<221> NAME/KEY: misc_feature
<222> LOCATION: (393)..(393)
```

<223> OTHER INFORMATION: a or g or c or t/u
<220> FEATURE:
<221> NAME/KEY: misc_feature
<222> LOCATION: (439)..(440)
<223> OTHER INFORMATION: a or g or c or t/u
<220> FEATURE:
<221> NAME/KEY: misc_feature
<222> LOCATION: (443)..(443)
<223> OTHER INFORMATION: a or g or c or t/u
<220> FEATURE:
<221> NAME/KEY: misc_feature
<222> LOCATION: (459)..(459)
<223> OTHER INFORMATION: a or g or c or t/u

<400> SEQUENCE: 376
gagcgaatgc aggcgacttg cgagctggga gcgatttaaa acgctttgga ttcccccggc 60
ctgggtgggg agagcgagct gggtgccccc tagattcccc gcccccgcac ctcatgagcc 120
gaccctcggc tccatggagc ccggcaatta tgccaccttg gatggagcca aggatatcga 180
agacttgctg ggagcgggag gggggcggaa tctggtcgcc cactcccctc tgaccagcca 240
cccagcggcg cctacgctga tgcctgctgt caactatgcc cccttggatc tgccaggctc 300
ggcggagccg ccaaagcaat gccacccatg ccctggggtg ccccagggga cgtccccagc 360
tcccgtgcct tatggttact ttggaggcgg gtnctactcc tgccgagtgt cccggagctc 420
gctgaaaccc tgtgcccann canccaccct ggccgcgtn 459

<210> SEQ ID NO 377
<211> LENGTH: 156
<212> TYPE: DNA
<213> ORGANISM: Homo sapiens

<400> SEQUENCE: 377
ctctgcctct gtgttcattc tctgatgtcc tgtacctgtg ctcagtgccc ggtgggactc 60
atctcctggc tgcgcagcaa agccagcggg ttcgtgctgg tccttcctgc accttcggct 120
gggggtgggg ggcctgccgg cgcattctcc acgatt 156

<210> SEQ ID NO 378
<211> LENGTH: 467
<212> TYPE: DNA
<213> ORGANISM: Homo sapiens
<220> FEATURE:
<221> NAME/KEY: misc_feature
<222> LOCATION: (233)..(233)
<223> OTHER INFORMATION: a or g or c or t/u

<400> SEQUENCE: 378
acgctgcacc gccggtccaa gagaagaagg ttctcgccaa ggtgaagaac agcgctaccc 60
ctttaagaga tctccttgct ggggtgggag gagcgaaagt gggggtgtct ggggagacca 120
ggaacctgcc agccccaggc tgggcccaag gactctgctg agaggcccct agagacaaca 180
cccttcccag gccactgtct gctggactgt tcctcaggag cggcctgggt acncagtatg 240
tgcagggaga cggaacccca tgtgacagcc cactccacca gggttcccaa agaacctggc 300
ccagtcataa tcattcatcc tgacagtggc aataatcacg ataaccagta ctagctgcca 360
tgatcgttag cctcatattt tctatctaga gctctgtaga gcactttaga aaccgctttc 420
atgaattgag ctacttatga atcactttga accggcggtg cggcgtg 467

<210> SEQ ID NO 379
<211> LENGTH: 666
<212> TYPE: DNA
<213> ORGANISM: Homo sapiens -continued
<220> FEATURE:
<221> NAME/KEY: misc_feature
<222> LOCATION: (594)..(594)
<223> OTHER INFORMATION: a or g or c or t/u

<400> SEQUENCE: 379
gggggagagc gagctgggtg cccccctagat tccccgcccc cgcacctcat gagccgaccc 60
tcggctccat ggagcccggc aattatgcca ccttggatgg agccaaggat atcgaaggct 120
tgctgggagc gggagggggg cggaatctgg tcgcccactc ccctctgacc agccacccag 180
cggcgcctac gctgacgcct gctgtcaact atgcccccttt ggatctgcca ggctcggcgg 240
agccgccaaa gcaatgccac ccatgccctg ggtgccccca ggggacgtcc ccagctcccg 300
tgccttatgg ttactttgga ggcgggtact actcctgccg agtgtcccgg agctcgctga 360
aaccctgtgc ccaggcagcc accctggccg cgtaccccgc ggagactccc acggccgggg 420
aagagtaccc cagccgcccc actgagtttg ccttctatcc gggatatccg ggaacctacc 480
agcctatggc cagttacctg gacgtgtctg tggtgcagac tctgggtgct cctggagaac 540
cgcgacatga ctccctgttg cctgtggaca gttaccagtc ttgggctctc gctngtggct 600
ggaacagcca gatgtgttgc cagggagaac agaacccacc aggtcccttt tggaaggcag 660
catttg 666

<210> SEQ ID NO 380
<211> LENGTH: 664
<212> TYPE: DNA
<213> ORGANISM: Homo sapiens

<400> SEQUENCE: 380
gctgagttct gaagcttctg agttctgcag cctcacctct gagaaaacct cttttccacc 60
aataccatga agctctgcgt gactgtcctg tctctcctca tgctagtagc tgccttctgc 120
tctctagcgc tctcagcacc aatgggctca gaccctccca ccgcctgctg cttttcttac 180
accgcgagga agcttcctcg caactttgtg gtagattact atgagaccag cagcctctgc 240
tcccagccag ctgtggtatt ccaaaccaaa agaagcaagc aagtctgtgc tgatcccagt 300
gaatcctggg tccaggagta cgtgtatgac ctggaactga actgagctgc tcagagacag 360
gaagtcttca gggaaggtca cctgagcccg gatgcttctc catgagacac atctcctcca 420
tactcaggac tcctctccgc agttcctgtc ccttctctta atttaatctt ttttatgtgc 480
cgtgttattg tattaggtgt catttccatt atttatatta gtttagccaa aggataagtg 540
tcccctatgg ggatggtcca ctgtcactgt ttctctgctg ttgcaaatac atggataaca 600
catttgattc tgtgtgtttt cataataaaa ctttaaaata aaatgcaaaa aaaaaaaaaa 660
aaaa 664

<210> SEQ ID NO 381
<211> LENGTH: 1308
<212> TYPE: DNA
<213> ORGANISM: Homo sapiens

<400> SEQUENCE: 381
gccacgtgct gctgggtctc agtcctccac ttcccgtgtc ctctggaagt tgtcaggagc 60
aatgttgcgc ttgtacgtgt tggtaatggg agtttctgcc ttcacccttc agcctgcggc 120
acacacaggg gctgccagaa gctgccggtt tcgtgggagg cattacaagc gggagttcag 180
gctggaaggg gagcctgtag ccctgaggtg cccccaggtg ccctactggt tgtgggcctc 240

-continued

```
tgtcagcccc cgcatcaacc tgacatggca taaaaatgac tctgctagga cggtcccagg    300
agaagaagag acacggatgt gggcccagga cggtgctctg tggcttctgc cagccttgca    360
ggaggactct ggcacctacg tctgcactac tagaaatgct tcttactgtg acaaaatgtc    420
cattgagctc agagtttttg agaatacaga tgctttcctg ccgttcatct catacccgca    480
aattttaacc ttgtcaacct ctggggtatt agtatgccct gacctgagtg aattcacccg    540
tgacaaaact gacgtgaaga ttcaatggta caaggattct cttcttttgg ataaagacaa    600
tgagaaattt ctaagtgtga gggggaccac tcacttactc gtacacgatg tggccctgga    660
agatgctggc tattaccgct gtgtcctgac atttgcccat gaaggccagc aatacaacat    720
cactaggagt attgagctac gcatcaagaa aaaaaaagaa gagaccattc ctgtgatcat    780
ttccccctc aagaccatat cagcttctct ggggtcaaga ctgacaatcc cgtgtaaggt     840
gtttctggga accggcacac ccttaaccac catgctgtgg tggacggcca atgacaccca    900
catagagagc gcctacccgg gaggccgcgt gaccgagggg ccacgccagg aatattcaga    960
aaataatgag aactacattg aagtgccatt gatttttgat cctgtcacaa gagaggattt   1020
gcacatggat tttaaatgtg ttgtccataa taccctgagt tttcagacac tacgcaccac   1080
agtcaaggaa gcctcctcca cgttctcctg ggcattgtg ctggccccac tttcactggc    1140
cttcttggtt ttggggggaa tatggatgca cagacggtgc aaacacagaa ctggaaaagc   1200
agatggtctg actgtgctat ggcctcatca tcaagacttt caatcctatc ccaagtgaaa   1260
taaatggaat gaaataattc aaacacaaaa aaaaaaaaaa aaaaaaaa                1308
```

<210> SEQ ID NO 382
<211> LENGTH: 2110
<212> TYPE: DNA
<213> ORGANISM: Homo sapiens

<400> SEQUENCE: 382

```
ggatccaagc tattgtcctg cccatggctt cccatctcag gacgctctct ggccgctatc     60
atcccagcag tggagttcag cccactactc tgaaccagcc gcaggtggct gctatgggac    120
tgaagccatg aatggtgccg gccctggccc cgccgcagcc gccccggtcc cagtcccggt    180
cccggtcccg gactggcggc agttctgcga gctgcatgcg caggcggccg ccgtggactt    240
tgcgcacaag ttctgccgtt tcctgcggga caacccagct tacgacacgc ccgacgccgg    300
cgcctccttc tcccgccact tcgccgccaa cttcctggac gtcttcggcg aggaggtgcg    360
ccgcgtgctg gtggctgggc cgacgactcg gggcgcggcc gtgagcgcag aggccatgga    420
gccggagctc gcggacacct ctgcactcaa ggcggcgtcc tacggccact cgcggagctc    480
ggaggacgtg tccacgcacg cggccaccaa ggcccgcgtt cgcaagggct tctcgctgcg    540
caacatgagc ctgtgcgtgg tggacggcgt gcgcgacatg tggcaccggc gcgcctcgcc    600
cgagcccgac gcggcagctg ccccgcgcac cgccgagccc cgcgacaagt ggacgcggcg    660
cctgaggctg tcgcggacgc tggctgccaa ggtggagctg gtggacattc aacgcgaggg    720
ggcgctgcgc ttcatggtgg ccgacgacgc ggccgcgggc tccgggggct cggctcagtg    780
gcagaagtgc cgcctgctcc tgcgcagggc tgtggccgag gaacgcttcc gcctggagtt    840
cttcgtgccg cccaaagcct ccaggcccaa ggtcagcatc ccactgtcag ccatcattga    900
ggtccgcacc accatgcccc tggaaatgcc agagaaggat aacacattcg tcctcaaggt    960
agagaatgga gccgaataca tcttggagac catcgactct ctgcagaagc actcgtgggt   1020
agctgacatc cagggctgcg tggaccccgg tgacagtgag gaagacaccg agctctcctg   1080
```

-continued tacccgagga ggctgtctgg ccagccgcgt ggcctcctgc agctgtgagc tcctgactga 1140
tgcagtcgac ctgccccgcc ccccagagac gacagccgtg ggtgcagtgg tgacagcccc 1200
ccacagccga ggtcgagatg ccgtcagaga atccctgatc cacgtcccgc tagagacctt 1260
tctgcagacc ctggaatccc cgggcggcag cggcagtgac agcaataaca caggggaaca 1320
gggtgcagag acggatcccg aggctgaacc cgagctggag ctatccgact acccatggtt 1380
ccacgggaca ctgtcccggg tcaaggctgc tcaactggtt ctggcagggg ggccccggaa 1440
ccacggcctc ttcgtgatcc gccaaagtga gactcggcct ggggagtacg tgctgacctt 1500
caacttccag ggcaaggcca agcacctgcg cctgtccctg aacggccacg gccagtgtca 1560
cgtacagcat ctgtggttcc agtctgtgct tgacatgctc cgccacttcc acacacaccc 1620
catcccactg gagtcagggg gctcggccga catcaccctt cgcagctatg tgcgggccca 1680
ggacccccca ccagagccgg gccccacgcc ccctgccgcg cccgcgtccc cggcctgctg 1740
gagcgactcg cccggccagc actacttctc cagcctcgcc gcggccgcct gcccgcctgc 1800
ctcgccctcc gacgccgccg gcgcctcctc gtcttccgcc tcgtcgtcct ctgccgcgtc 1860
ggggcccgcc cccccgcgcc ccgtcgaggg ccagctcagc gcgcggagcc gcagcaacag 1920
cgccgagcgc ctgctggagg ccgtggccgc caccgccgcc gaggagcccc cggaggccgc 1980
gcccggccgc gcgcgcgccg tggagaacca gtactccttc tactagcccg cggcgccgcc 2040
cgggtgggac acgccaagct cttcagtgaa gacacgatgt tattaaaagc ctgttttagg 2100
gactgcaaaa 2110

<210> SEQ ID NO 383
<211> LENGTH: 496
<212> TYPE: DNA
<213> ORGANISM: Homo sapiens

<400> SEQUENCE: 383
gattccagca cgggcttcgc agactgcagg acacagaggc acgcgtgcac atcatgtctt 60
ctaaggaatt tgaacactgt tgagaagact gtgtacaaga gagatgtgcc atgtcagcct 120
tgcaagggac agcgtgaaaa ctacccatct ccggtcacca agttgcagga ggccaggagc 180
caggagggga aaccgctcag tttgcaaaac gtcgcttcca caagcctgat ggctgaaact 240
gctcactgta ccctgaaacc agctttacct acagcttctg agataaactg ctgcaactct 300
gggacccacg atgcctatca cagtggctca tcaatggaac ctgccggctc ccaacccttc 360
ctagggccca tgaactctct gaaaagagga acagaaatat ttctcctttt tgtaaaatct 420
ttaaccttcc ctttgttctt catgtacacg ctgaactgca attcttcttc ccaaataaaa 480
cattaaattt aaaaaa 496

<210> SEQ ID NO 384
<211> LENGTH: 824
<212> TYPE: DNA
<213> ORGANISM: Homo sapiens

<400> SEQUENCE: 384
ggccccggag ggagagtaac ccggcccatc catccgtcgc ccggttcttg gggaactact 60
ttcaggggct tcttgccgtc ccctcatcag ctctgtgcga accctctgtc ggcagccatt 120
gaggagaccc tgcccccctgg accctgacca catatagatt gaggccgagg agtggctgcc 180
ctgtcccttt tatgacagcc cgcagaagcc ccggggtgag gcatggagga ggcaggcgac 240

-continued

```
agctgacagg gaccctgttg gcctccagca tgtccagcca gccgggcagg atttctctgc    300

ttctggctgg cagccaggaa ctgagtatga caatgttgta ctaaagaaag gcccaaagtg    360

acagaggcag cagagggatg gtccaccgcc ccttggcttc tgctggtgac tcctcctggc    420

cactgcatca gaagaacctc ctctgcccct tctggagccc gaggcctggc ctgtcttcgt    480

tggggctgat aaattgcctc tcccagggcc tgctgggtga gtcaccatcc caaagcagga    540

agggtgccct ggagagaacc accctcctcc tactcttttt ccacttcctc ctctttcttt    600

ccccagctga ggaggaacct ggggcattta gggcagagga caaaaggatg tcagcaattg    660

cttgggctgc ttggctatgc aagcctcctg cctgctgatg gccacttcag ggacagcctg    720

ggcccaggca cccaggggga tggcggcagc ttcctgcacc tttcagattt cttggtggca    780

ttaaagcatt ttcagaacaa aaaaaaaaaa aaaaaaaaaa aaaa                     824
```

<210> SEQ ID NO 385
<211> LENGTH: 2429
<212> TYPE: DNA
<213> ORGANISM: Homo sapiens

<400> SEQUENCE: 385

```
ggcgggcctg gacggccgcg tgctgtactg gccacgcggc cgcgtctggg gtggctcctc     60

atccctcaat gccatggtct acgtccgtgg gcacgccgag gactacgagc gctggcagcg    120

ccagggcgcc cgcggctggg actacgcgca ctgcctgccc tacttccgca aggcgcaggg    180

ccacgagctg ggcgccagcc ggtaccgggg cgccgatggc ccgctgcggg tgtcccgggg    240

caagaccaac cacccgctgc actgcgcatt cctggaggcc acgcagcagg ccggctaccc    300

gctcaccgag gacatgaatg gcttccagca ggagggcttc ggctggatgg acatgaccat    360

ccatgaaggc aaacggtgga gcgcggcctg tgcctacctg cacccagcac tgagccgcac    420

caacctcaag gccgaggccg agacgcttgt gagcagggtg ctatttgagg gcacccgtgc    480

agtgggcgtg gagtatgtta agaatggcca gagccacagg gcttatgcca gcaaggaggt    540

gattctgagt ggaggtgcca tcaactctcc acagctgctc atgctctctg gcatcgggaa    600

tgctgatgac ctcaagaaac tgggcatccc tgtggtgtgc cacctacctg ggggttggcca   660

gaacctgcaa gaccacctgg agatctacat tcagcaggca tgcacccgcc ctatcaccct    720

ccattcagca cagaagcccc tgcggaaggt ctgcattggt ctggagtggc tctggaaatt    780

cacaggggag ggagccactg cccatctgga aacaggtggg ttcatccgca gccagcctgg    840

ggtcccccac ccggacatcc agttccattt cctgccatcc caagtgattg accacgggcg    900

ggtccccacc cagcaggagg cttaccaggt acatgtgggg cccatgcggg gcacgagtgt    960

gggctggctc aaactgagaa gtgccaatcc ccaagaccac cctgtgatcc agcccaacta   1020

cttgtcaaca gaaactgata ttgaggattt ccgtctgtgt gtgaagctca ccagagaaat   1080

ttttgcacag gaagccctgg ctccgttccg agggaaagag ctccagccag gaagccacat   1140

tcagtcagat aaagagatag atgcctttgt gcgggcaaaa gccgacagcg cctaccaccc   1200

ctcgtgcacc tgtaagatgg gccagccctc cgatcccact gccgtggtgg atccgcagac   1260

aagggtcctc ggggtggaaa acctcagggt cgtcgatgcc tccatcatgc ctagcatggt   1320

cagcggcaac ctgaacgccc ccacaatcat gatcgcagag aaggcagctg acattatcaa   1380

ggggcagcct gcactctggg acaaagatgt ccctgtctac aagcccagga cgctggccac   1440

ccagcgctaa gacagttgct gctggaggat gaccagggaa gccccctgat aagccaagag   1500

ggccagcaca gcccttgctc ccaggctcct gcctgaaact atctagcaca ctaggaccca   1560
```

-continued

```
ggtggtaccc tactcagtgg ctgagaattg gataaagtct tkgggaaatg agacaagtac   1620

tgggcagtga atccagctcc ttttccccag cctttccctg tgggccattt ggggaaggcc   1680

agcattycag cctgagatgt tcctccctgc ctcctggggg ggcaraaggg vtaggwtggt   1740

taactcctgc cgcatccttc cctgcctcct ggagggacag aaggggagga tggttaactc   1800

ctgccgcatc ctttttcttg tgttcacgtg gcattctcta acccagggca gtggttcctt   1860

cccaggccat gcacagaggc tgggtgcctg ccagacccac ggagggttcg cgaaggaagg   1920

ggcatcctcc ttcttgagct gcaagcttta gctgaggcag taagtcacac agtagttagt   1980

tcagcctggg ctggcacata agtccccagt gtccctgttg agaggggaaa gttgcctgct   2040

ggttgaaaaa ctggcttttc ctttctcgct gcctaatttc actctcagag tgaggcaggt   2100

aactggggct ccactgggtc actctgagag ggttgtggct ctggttctta ttaaaccagg   2160

gccaggtgca gggctcacac ctgtaatccc agcactttgg gaaggtcact tgagctcagg   2220

agttcaagac cagcctgggc aacatagtga gaccttgtct ctggaaaaca attagctggg   2280

catggtggta cacacctgta gtcccagcta cttgggaggc tgaggcggga ggatggcttt   2340

agcccaggag gttgaggctc ctgtgaaccc tgatggcacc actgcactcc agcctgggtg   2400

acagggtgag accctgtctc aaaaaaaaa                                     2429


<210> SEQ ID NO 386
<211> LENGTH: 626
<212> TYPE: DNA
<213> ORGANISM: Homo sapiens
<220> FEATURE:
<221> NAME/KEY: misc_feature
<222> LOCATION: (10)..(10)
<223> OTHER INFORMATION: a or g or c or t/u
<220> FEATURE:
<221> NAME/KEY: misc_feature
<222> LOCATION: (39)..(39)
<223> OTHER INFORMATION: a or g or c or t/u
<220> FEATURE:
<221> NAME/KEY: misc_feature
<222> LOCATION: (77)..(77)
<223> OTHER INFORMATION: a or g or c or t/u
<220> FEATURE:
<221> NAME/KEY: misc_feature
<222> LOCATION: (83)..(83)
<223> OTHER INFORMATION: a or g or c or t/u
<220> FEATURE:
<221> NAME/KEY: misc_feature
<222> LOCATION: (102)..(102)
<223> OTHER INFORMATION: a or g or c or t/u
<220> FEATURE:
<221> NAME/KEY: misc_feature
<222> LOCATION: (121)..(121)
<223> OTHER INFORMATION: a or g or c or t/u

<400> SEQUENCE: 386

ccgccgttgn caaagggccc agaatatggg ccatggacna tctccatgcc tggggaaatt     60

ccctcgggtc ttttggntaa ccnccttata gaaaggtaat gncatggagt ctctacaggg    120

ngcacaaggt ggactaattg atacgaagag ccctgtaaat atgtgggcag cggcagattt    180

tgaccatttg gaccgaactg tatttgacac agcgcaatat ctggaactgg ttggtcaaaa    240

acctgcttgt cttgttaaat ttcctctgtc caaggacatg gaatctctct ctaattttac    300

ttcaaatttc cctttccttc atttctctaa aaacgttaaa taagaaagaa gattgtaaag    360

ccagcatttg aagcctaagt attgaaagtc tttgacaatt tctgaaatca gacttgacat    420

ctttcccccg ccttgcaaat ttcttgaaga aataagaagc tacatgtaag catcatcatg    480
```

-continued

```
tttattaaat tacaatgaga actctcactc aatcttgacc agagcagact cttaacttgg    540

aagcagagtc cctctaaagg taactcttgt ggtcactcaa tattgtattg gcatttgcat    600

attaaataga catttcagta gcattt                                         626
```

<210> SEQ ID NO 387
<211> LENGTH: 691
<212> TYPE: DNA
<213> ORGANISM: Homo sapiens

<400> SEQUENCE: 387

```
tggcccgcgg tcgcggtggg atcctagccc tgtctcctct cctgggaagg agtgagggtg     60

ggacgtgact tagacaccta caaatctatt taccaaagag gagcccggga ctgagggaaa    120

aggccaaaga gtgtgagtgc atgcggactg gggttcagg ggaagaggac gaggaggagg     180

aagatgaggt cgatttcctg atttaaaaaa tcgtccaagc cccgtggtcc agcttaaggt    240

cctcggttac atgcgccgct cagagcaggt cactttctgc cttccacgtc ctccttcaag    300

gaagccccat gtgggtagct ttcaatatcg caggttctta ctcctctgcc tctataagct    360

caaacccacc aacgatcggg caagtaaacc ccctccctcg ccgacttcgg aactggcgag    420

agttcagcgc agatgggcct gtggggaggg ggcaagatag atgaggggga gcggcatggt    480

gcggggtgac cccttggaga gaggaaaaag gccacaagag gggctgccac cgccactaac    540

ggagatggcc ctggtagaga cctttggggg tctggaacct ctggactccc catgctctaa    600

ctcccacact ctgctatcag aaacttaaac ttgaggattt tctctgtttt tcactcgcaa    660

taaattcaga gcaaacaaaa aaaaaaaaaa a                                   691
```

<210> SEQ ID NO 388
<211> LENGTH: 1824
<212> TYPE: DNA
<213> ORGANISM: Homo sapiens

<400> SEQUENCE: 388

```
caataggccg gcttttgaac tgcttcgcag gggacttgga acagctggac cagctcttgc     60

ccatcttttc agagcagttc ctggtcctgt ccttaatggt gatcgccgtc ctgttgattg    120

tcagtgtgct gtctccatat atcctgttaa tgggagccat aatcatggtt atttgcttca    180

tttattatat gatgttcaag aaggccatcg gtgtgttcaa gagactggag aactatagcc    240

ggtctccttt attctcccac atcctcaatt ctctgcaagg cctgagctcc atccatgtct    300

atggaaaaac tgaagacttc atcagccagt ttaagaggct gactgatgcg cagaataact    360

acctgctgtt gtttctatct tccacacgat ggatggcatt gaggctggag atcatgacca    420

accttgtgac cttggctgtt gccctgttcg tggcttttgg catttcctcc accccctact    480

cctttaaagt catggctgtc aacatcgtgc tgcagctggc gtccagcttc caggccactg    540

cccggattgg cttggagaca gaggcacagt tcacggctgt agagaggata ctgcagtaca    600

tgaagatgtg tgtctcggaa gctcctttac acatggaagg cacaagttgt ccccaggggt    660

ggccacagca tggggaaatc atatttcagg attatcacat gaaatacaga gacaacacac    720

ccaccgtgct tcacggcatc aacctgacca tccgcggcca cgaagtggtg ggcatcgtgg    780

gaaggacggg ctctgtaggt ttttactgag cacctactat gtgcctggga accgaaaggg    840

aagtcctcct tgggcatggc tctcttccgc ctggtggagc ccatggcagg ccggattctc    900

attgacggcg tggacatttg cagcatcggc ctggaggact tgcggtccaa gctctcagtg    960

atccctcaag atccagtgct gctctcagga accatcagat tcaacctaga tccctttgac   1020
```

-continued cgtcacactg accagcagat ctgggatgcc ttggagagga cattcctgac caaggccatc 1080
tcaaagttcc ccaaaaagct gcatacagat gtggtggaaa acggtggaaa cttctctgtg 1140
ggggagaggc agctgctctg cattgccagg gctgtgcttc gcaactccaa gatcatcctt 1200
atcgatgaag ccacagcctc cattgacatg gagacagaca ccctgatcca gcgcacaatc 1260
cgtgaagcct tccagggctg caccgtgctc gtcattgccc accgtgtcac cactgtgctg 1320
aactgtgacc acatcctggt tatgggcaat gggaaggtgg tagaatttga tcggccggag 1380
gtactgcgga agaagcctgg gtcattgttc gcagccctca tggccacagc cacttcttca 1440
ctgagataag gagatgtgga gacttcatgg aggctggcag ctgagctcag aggttcacac 1500
aggtgcagct tcgaggccca cagtctgcga ccttcttgtt tggagatgag aacttctcct 1560
ggaagcaggg gtaaatgtag ggggggtggg gattgctgga tggaaaccct ggaataggct 1620
acttgatggc tctcaagacc ttagaacccc agaaccatct aagacatggg attcagtgat 1680
catgtggttc tccttttaac ttacatgctg aataatttta taataaggta aaagcttata 1740
gttttctgat ctgtgttaga agtgttgcaa atgctgtact gactttgtaa aatataaaac 1800
taaggaaaac tcaaaaaaaa aaaa 1824

<210> SEQ ID NO 389
<211> LENGTH: 3621
<212> TYPE: DNA
<213> ORGANISM: Homo sapiens

<400> SEQUENCE: 389
cccacagggg gaccggccct gtgacccctc accggggccg tgggcccgag ccccggactt 60
ccctaagccg gcaatgaccg cctgcgcccg ccgagcgggt gggcttccgg accccgggct 120
ctgcggtccc gcgtggtggg ctccgtccct gccccgcctc ccccgggccc tgccccggct 180
cccgctcctg ctgctcctgc ttctgctgca gccccccgcc ctctccgccg tgttcacggt 240
gggggtcctg ggcccctggg cttgcgaccc catcttctct cgggctcgcc cggacctggc 300
cgcccgcctg gccgccgccc gcctgaaccg cgaccccggc ctggcaggcg gtccccgctt 360
cgaggtagcg ctgctgcccg agccttgccg gacgccgggc tcgctggggg ccgtgtcctc 420
cgcgctggcc cgcgtgtcgg gcctcgtggg tccggtgaac cctgcggcct gccggccagc 480
cgagctgctc gccgaagaag ccgggatcgc gctggtgccc tggggctgcc cctggacgca 540
ggcggagggc accacggccc ctgccgtgac ccccgccgcg gatgccctct acgccctgct 600
tcgcgcattc ggctgggcgc gcgtggccct ggtcaccgcc ccccaggacc tgtgggtgga 660
ggcgggacgc tcactgtcca cggcactcag ggcccggggg ctgcctgtcg cctccgtgac 720
ttccatggag cccttggacc tgtctggagc ccgggaggcc ctgaggaagg ttcgggacgg 780
gcccagggtc acagcagtga tcatggtgat gcactcggtg ctgctgggtg gcgaggagca 840
gcgctacctc ctggaggccg cagaggagct gggcctgacc gatggctccc tggtcttcct 900
gcccttcgac acgatccact acgccttgtc cccaggcccg gaggccttgg ccgcactcgc 960
caacagctcc cagcttcgca gggcccacga tgccgtgctc accctcacgc gccactgtcc 1020
ctctgaaggc agcgtgctgg acagcctgcg cagggctcaa gagcgccgcg agctgccctc 1080
tgacctcaat ctgcagcagg tctccccact ctttggcacc atctatgacg cggtcttctt 1140
gctggcaagg ggcgtggcag aagcgcgggc tgccgcaggt ggcagatggg tgtccggagc 1200
agctgtggcc cgccacatcc gggatgcgca ggtccctggc ttctgcgggg acctaggagg 1260

-continued

```
agacgaggag cccccattcg tgctgctaga cacggacgcg gcgggagacc ggctttttgc   1320
cacatacatg ctggatcctg cccggggctc cttcctctcc gccggtaccc ggatgcactt   1380
cccgcgtggg ggatcagcac ccggacctga cccctcgtgc tggttcgatc caaacaacat   1440
ctgcggtgga ggactggagc cgggcctcgt ctttcttggc ttcctcctgg tggttgggat   1500
ggggctggct ggggccttcc tggcccatta tgtgaggcac cggctacttc acatgcaaat   1560
ggtctccggc cccaacaaga tcatcctgac cgtggacgac atcacctttc tccacccaca   1620
tgggggcacc tctcgaaagg tggcccaggg gagtcgatca agtctgggtg cccgcagcat   1680
gtcagacatt cgcagcggcc ccagccaaca cttggacagc cccaacattg gtgtctatga   1740
gggagacagg gtttggctga agaaattccc aggggatcag cacatagcta tccgcccagc   1800
aaccaagacg gccttctcca agctccagga gctccggcat gagaacgtgg ccctctacct   1860
ggggcttttc ctggctcggg gagcagaagg ccctgcggcc ctctgggagg gcaacctggc   1920
tgtggtctca gagcactgca cgcggggctc tcttcaggac ctcctcgctc agagagaaat   1980
aaagctggac tggatgttca agtcctccct cctgctggac cttatcaagg gaataaggta   2040
tctgcaccat cgaggcgtgg ctcatgggcg gctgaagtca cggaactgca tagtggatgg   2100
cagattcgta ctcaagatca ctgaccacgg ccacgggaga ctgctggaag cacagaaggt   2160
gctaccggag cctcccagag cggaggacca gctgtggaca gccccggagc tgcttaggga   2220
cccagccctg gagcgccggg gaacgctggc cggcgacgtc tttagcttgg ccatcatcat   2280
gcaagaagta gtgtgccgca gtgcccctta tgccatgctg gagctcactc ccgaggaagt   2340
ggtgcagagg gtgcggagcc cccctccact gtgtcggccc ttggtgtcca tggaccaggc   2400
acctgtcgag tgtatcctcc tgatgaagca gtgctgggca gagcagccgg aacttcggcc   2460
ctccatggac cacaccttcg acctgttcaa gaacatcaac aagggccgga agacgaacat   2520
cattgactcg atgcttcgga tgctggagca gtactctagt aacctggagg atctgatccg   2580
ggagcgcacg gaggagctgg agctggaaaa gcagaagaca gaccggctgc ttacacagat   2640
gctgcctccg tctgtggctg aggccttgaa gacggggaca ccagtggagc ccgagtactt   2700
tgagcaagtg acactgtact ttagtgacat tgtgggcttc accaccatct ctgccatgag   2760
tgagcccatt gaggttgtgg acctgctcaa cgatctctac acactctttg atgccatcat   2820
tggttcccac gatgtctaca aggtggagac aatagggggac gcctatatgg tggcctcggg   2880
gctgccccag cggaatgggc agcgacacgc ggcagagatc gccaacatgt cactggacat   2940
cctcagtgcc gtgggcactt tccgcatgcg ccatatgcct gaggttcccg tgcgcatccg   3000
cataggcctg cactcgggtc catgcgtggc aggcgtggtg ggcctcacca tgccgcggta   3060
ctgcctgttt ggggacacgg tcaacaccgc ctcgcgcatg gagtccaccg ggctgcctta   3120
ccgcatccac gtgaacttga gcactgtggg gattctccgt gctctggact cgggctacca   3180
ggtggagctg cgaggccgca cggagctgaa gggcaagggc gccgaggaca ctttctggct   3240
agtgggcaga cgcggcttca acaagcccat ccccaaaccg cctgacctgc aaccggggtc   3300
cagcaaccac ggcatcagcc tgcaggagat cccacccgag cggcgacgga agctggagaa   3360
ggcgcggccg ggccagttct cttgagaagt gaggcccggc cccggacagg gtctgggccc   3420
tgctccctgt cccatctgca gtggacccca ggcacccccc tttgaggagg tggggtgaac   3480
tgctccttgg cagggatttg tgacactgca ttgctgggct gtgttcctcg ggctcttctg   3540
gaccttgcac cgtggatacc aggccatgtg ccatggtatt tgggtcctgg gagggtgggt   3600
gaaataaagg catactgtct t                                               3621
```

<210> SEQ ID NO 390
<211> LENGTH: 1284
<212> TYPE: DNA
<213> ORGANISM: Homo sapiens

<400> SEQUENCE: 390

```
ctttcacaga aagaaagtaa caggcataat tcctgttgat gaggctggga ttgtttttaa     60

gaggagagat aataacttca tatttttaaa gtgccagtag cctaatatgt gaaacagatc    120

agaatctgtt gtgtagtaag tctgctttgt tgaagaattt attatgggag taaagataag    180

aaggaaagag atcaccatca gaaacaagtc agccttttca tgctttttttg agcatttttg    240

gagatgattc cacttctcaa gttattatca tttgtgcatc tcttcaatgc tattgttaaa    300

tgctttagaa ttagaatatt ttgatccttt aattaaagta agccaaacgt ctaggcaaaa    360

acagccaatc attaaacttt aatagtaatt caaatataga tttctcatac agttttccat    420

gtctgtagaa atcaaagttg taatgttaag cagagggaaa tgcgtgtgat ttactaatac    480

acttcaacgt tctactttttg aaaggatact catgtgggtg gggcagagaa catagaaaaa    540

gatatgatgg aaaacctgtc cattttctac ctgttaacct tcatcatttt gtgcaggccc    600

tggaagcaaa gagaggaagg gaccgactgc atttatcttt gaacacttga gcatcagtag    660

tactactgag tggccagggg tcttgtctgt caaagcaaat gataagttca ctcaggccat    720

tattgactgc tgaactctct tccttcccaa ctcttccttg aaagagaaaa aaatactttg    780

ccttcttgct ctccttatca aatgtttttg tacaaatagt gtaagcctgt ttaagcaaac    840

caattaaaat aggcactgat tattttgatc tgtttgtaac aaatgaatgt aagtactatt    900

tacatggtgt gcctaggagg agctgaaatc attggcactt taatccatat tgtaaagatc    960

agtatcaaaa gcatagtgtt cttcacctct cctcctcagc atccatctct atatacttga   1020

ttaaatggaa aagtctcttt tatcacctct atgtaaagtt ttatgggtag ttatcgtcag   1080

tgtatttaaa tatatcttct agtatgtttt aaaggctggt cttcaatact gtggagacaa   1140

aaaataaaag agcgtatgaa aagtacgtta gacttttgct ggcattcaag tcatggctag   1200

tctgtgtatt taataaatgt gtgttattta tgtcgtgttt gtcaatggaa aataaagttg   1260

aatattctga aaaaaaaaaa aaaa                                           1284
```

<210> SEQ ID NO 391
<211> LENGTH: 547
<212> TYPE: DNA
<213> ORGANISM: Homo sapiens
<220> FEATURE:
<221> NAME/KEY: misc_feature
<222> LOCATION: (5)..(5)
<223> OTHER INFORMATION: a or g or c or t/u
<220> FEATURE:
<221> NAME/KEY: misc_feature
<222> LOCATION: (10)..(10)
<223> OTHER INFORMATION: a or g or c or t/u
<220> FEATURE:
<221> NAME/KEY: misc_feature
<222> LOCATION: (42)..(42)
<223> OTHER INFORMATION: a or g or c or t/u
<220> FEATURE:
<221> NAME/KEY: misc_feature
<222> LOCATION: (49)..(49)
<223> OTHER INFORMATION: a or g or c or t/u
<220> FEATURE:
<221> NAME/KEY: misc_feature
<222> LOCATION: (80)..(80)
<223> OTHER INFORMATION: a or g or c or t/u
<220> FEATURE:

-continued

<221> NAME/KEY: misc_feature
<222> LOCATION: (115)..(115)
<223> OTHER INFORMATION: a or g or c or t/u

<400> SEQUENCE: 391
cctanaagtn ccattttggc aaggataaac tcccatgaca anctcccant actgcatgtg 60
aatgaataag aaacaagaan tgaccacacc aaagcctccc tggctggtgt tacangggat 120
caggtccaca gtggtgcaga ttcaaccacc acccagggag tgcttgcaga ctctgcatag 180
atgttgctgc atgcgtccca tgtgcctgtc agaatggcag tgtttaattc tcttgaaaga 240
aagttatttg ctcactatcc ccagcctcaa ggagccaagg aagagtcatt cacatggaag 300
gtccgggact ggtcagccac tctgactttt ctaccacatt aaattctcca ttacatctca 360
ctattggtaa tggcttaagt gtaaagagcc atgatgtgta tattaagcta tgtgccacat 420
atttattttt agactctcca cagcattcat gtcaatatgg gattaatgcc taaactttgt 480
aaatattgta cagtttgtaa atcaatgaat aaaggttttg agtgtaaaaa aaaaaaaaaa 540
aaaaaaa 547

<210> SEQ ID NO 392
<211> LENGTH: 784
<212> TYPE: DNA
<213> ORGANISM: Homo sapiens

<400> SEQUENCE: 392
ggcacgaggg caaagagtag tcagtccctt cttggctctg ctgacactcg agcccacatt 60
ccatcacctg ctcccaatca tgcaggtctc cactgctgcc cttgccgtcc tcctctgcac 120
catggctctc tgcaaccagg tcctctctgc accacttgct gctgacacgc cgaccgcctg 180
ctgcttcagc tacacctccc ggcagattcc acagaatttc atagctgact actttgagac 240
gagcagccag tgctccaagc ccagtgtcat cttcctaacc aagagaggcc ggcaggtctg 300
tgctgacccc agtgaggagt gggtccagaa atacgtcagt gacctggagc cgagtgcctg 360
aggggtccag aagcttcgag gcccagcgac ctcagtgggc ccagtgggga ggagcaggag 420
cctgagcctt gggaacatgc gtgtgacctc cacagctacc tcttctatgg actggttatt 480
gccaaacagc cacactgtgg gactcttctt aacttaaatt ttaatttatt tatactattt 540
agtttttata atttattttt gatttcacag tgtgtttgtg attgtttgct ctgagagttc 600
cccctgtccc ctccaccttc cctcacagtg tgtctggtga caaccgagtg gctgtcatcg 660
gcctgtgtag gcagtcatgg caccaaagcc accagactga caaatgtgta tcagatgctt 720
ttgttcaggg ctgtgatcgg cctggggaaa taataaagat gttcttttaa acggtaaaaa 780
aaaa 784

<210> SEQ ID NO 393
<211> LENGTH: 1216
<212> TYPE: DNA
<213> ORGANISM: Homo sapiens

<400> SEQUENCE: 393
agaaaactat tttctaaata ttaacactga aaatgttttg ttagcttttc cttctttctc 60
tccagaagaa acatggatag atgatagctg tttcattgtt tgtttttgtc aagcatattc 120
actttcctcc ttgtcctctg attctgagca aagggcctca gactctgaac ttccctcaag 180
tgccgttgtt atgtgaactc ttccattcag attccagaga ggttctcatg ctcccccccc 240
ctccttattt gtagcaatcg tagcaactaa ttccactaag tacaagggag ntttttacac 300
tcctccattt ttatagcatc tgcatttttt ttttttgtta ggtacatgta tacacctgcc 360
tgagtataaa tactctctct acctaataat aacatcaacc aacatctttt ccaaattagg 420
gccacagaac agcaacattt gtctgacagt agtataaaga ataatgatag ctctatcctt 480
aagaagtatt tcctttcctt tttatatagt cccgttaggg tttaaaacca tattgatcaa 540
ctagaaagaa aaatatgaaa agagaaaaat attttaattt aaaaattgta atacattgat 600
ttataaaatg ccttctctga tacttttgaa acagatgtga aaaacagaaa aagaaaaaat 660
tgtctgaaat gtttattttg caaaacagtg caatagaatc tagttatgcc ttcatcactg 720
ttgacagtaa atactgacag ccccttgcag tgtgttagtt ttagatcact ctgttttagt 780
tgagagaaat gttttatatc atggttttta tatgaataca aattatttct caaagattta 840
tagcacacac tattctcagg aattctgtat tacatgaatg ctgcttatat attttcatat 900
tctaacttgt cttttcaagc aaataactaa tatatatgtg catgcagtct gccttgacaa 960
gttgttccaa gctgaagagc tttcactgta caatgtgtgg aaaatcacca tagatcatgg 1020
ctgaaatagt ttgtaattgt ctgagtctgt gcacgtactt ttagataaaa tgctgctgag 1080
tgactgcatg atgagataca acttctgaat gctgcacatt cttccaaaat gatccttagc 1140
acaatctatt gtatgatgga atgaatagaa aactttttca ctcaataaat tattatttga 1200
tatggtaaaa aaaaaa 1216

<210> SEQ ID NO 394
<211> LENGTH: 993
<212> TYPE: DNA
<213> ORGANISM: Homo sapiens

<400> SEQUENCE: 394
cccaaggttg ttatatcttc atgtcctcat ttcttaggga ggtaccttca gaaccaatag 60
tgacccctaa cttctctggt ggtcggttcc atgaaaggca aaggagtgtg agagaggagt 120
ggatggtcaa cctcccactg ccatggtaac atgggtgctg gctgatggga gcagaaaata 180
atttagtgaa agtctgtggg ggcagtcaca agatgtctga gaaaactggc gagccagctg 240
ctgaaaacag ggacaaggaa gcctccgtgg ctggagccca aatcacactg cagacccaga 300
caccgtgacc accaccatgg actccagaga gagcagctta tagtactcaa tcagctgcca 360
ctaccaccat ccagaacacc agatgttgta gccatggctg cagcaggaat ggatgtccca 420
ctgtccctgc tcctcggtgt gacttgctcc caagttcagg gcaggtccat ctgattggct 480
gagtctggaa tgtctgcctg tgcctcagct gtgagggagg cagggaaagt aagccttttc 540
agcttctgtc gtgggaggtg ggctctgcct cctaccaaga atcaaagggt ggaggatctt 600
caaacacagg aaaagaaccc ggatcctggc acccccaaat tttcagagtc catttcagag 660
cataagaaat tgagggtcca agatcattca tgtaagaagt ttagaggggg aagaaaagaa 720
tgataaacga aaagaacagc aatagtaaag gatcttttct ttgtttcagt aagatgaaga 780
ggcctgagca gtttcgtgga ggggaagaaa caggaaaacc tcttcaaaag acaaaaagct 840
ggcactgcat tctctctctg tagcaggaca gaactgtcta aagacaagac ccctttggcc 900
aaaataaagg aacctgaaac attaaaaaaa aaaaaaaaaa aaaaaaaaaa aaaaaaaaaa 960
aaaaaaaaaa aaaaaaaaaa aaaaaacctc ggg 993

<210> SEQ ID NO 395
<211> LENGTH: 2214
<212> TYPE: DNA

-continued

<213> ORGANISM: Homo sapiens

<400> SEQUENCE: 395

```
aaatttaatt aattataaac tcagtctctt ggttgcacca gccacatttc agatgctcaa     60
tagccacatg tggctagtgg gtaccatatt ggacagggca gctatagaat atttccatca    120
ttgcagaaag ttctattgga tagtaccata atctttttat agtaacttgg aaatactatt    180
tgatattaga tgttagacca caaaaagaag aaaaatgtta ggactatttc agatataaaa    240
aggaactgaa ttgtgacata attagcatct tacattccat acagttgaat accttatgct    300
gtgacaacca tagttaatca tttcagtgct gttcaacata catacctatc agcagtgtgt    360
ttagaccagg ggtctgcaaa ctttctgtga atggacaaag agtaaatact ttagtaaatg    420
tcttaggctt tgtggcctac atgatctttg ttgcaagtac tcaactctgc cattatagag    480
ttaaagcagc catacacaat atataaacaa aatgggcata gttgtatttc agtaaaactt    540
tatttacaaa gacaggcggt aggccagatt tggcttgcat gctgtagagc tgtggtctaa    600
attttattca tagactttct ttgcaaatac agtgtgagta ttgttccatt tacagtatta    660
ttatttttta gatacctggt ttttagattc ttgcctggta actttttact gaaaatacaa    720
gaatttcgta ctgcatttgc atctccgaga ttagggagca cctgtcagga tatgttgttc    780
tatcagggtt acttctgttg actacctctt agattttgat acagttatat tgttgagttt    840
cattttcata tattcttgta gtgtctgctt gcctgtgact tctggtaaaa taaaataagc    900
ctttgaaaat attttagcat ggtatttaac attttctaaa tattatggca ttttgacata    960
ttttagtcag cgaagacatc tgcccctttg gtgtttctac ttgcttatga ttgagatttt   1020
acaagccctt caaactccgt tttaaaggaa tttattgtaa aacattaact ttaataaatt   1080
agtgttttca cagatcagat cattatactt ggaacttcta aatcatgcaa tttctgaata   1140
aggacataag gctagattca tttttcttaa tagagaaaaa ggaaatttct gatttatcac   1200
ttttctagtt gataagtagg attcaaaacg tttgatatgt aagtatttat ataagactaa   1260
tgtaatttaa agttctgtat tattgtgatt aatcatacag aaattcagga actgatcaga   1320
agtgagattc ttttccacat ctggttaatg tagtgagttg acaccctgtg ggtggtaaag   1380
cattataaac atttcatctt gaaccatgat ttatacacat ctgtgttata agggaggctt   1440
gagtacatat accaatgaag agatattcag catttgtcta tttgataagg aattaaatgt   1500
cctagtgatt ataaagtaaa accacagacc aatttgcaaa tgatcttcaa tgttaagcac   1560
ttgctctaag attaaaattc cttttctttt taaggttaag ggtgtgtacg tatggcagtg   1620
atgtctatgt tgagattaac ttatgtattg aggaaaattt gaagtttatt ttttcgatga   1680
ataaggctgt caaatgattt agtatagatt aatgacatct tttttagaaa tattaaagtg   1740
agtattcctc attatgtcat catttctgat aattagagtg ctaatttgaa tgttagataa   1800
tgtttccaca tctataccta tttctttcta gggcacttct gaccctgggg cttggggatg   1860
gcctttaggc cacagtagtg tctgtgttaa gttcactaaa tgtgtattta atgagaaaca   1920
ttcctatgta aaaatgtgtg tatgtgaacg tatgcataca tttttattgt gcacctgtac   1980
attgtgaaga agtagtttgg aaatttgtaa agcacaaacc ataaaagagt gtggagttat   2040
taaatgatgt agcacaaatg taatgtttag cttataaaag gtcctttcta ttttctatgg   2100
caaagacttt gacacttgaa aaataaaacc aatatttgat ttatttttgt aagtatttag   2160
gatattattt taaataaatg attgtccatt atcaataaaa aaaaaaaaaa aaaa         2214
```

-continued

<210> SEQ ID NO 396
<211> LENGTH: 1182
<212> TYPE: DNA
<213> ORGANISM: Homo sapiens

<400> SEQUENCE: 396
gtcctgagca gccaacacac cagcccagac agctgcaagt caccatggac gctgaaggcc 60
tggcgctgct gctgccgccc gtcaccctgg cagccctggt ggacagctgg ctccgagagg 120
actgcccagg gctcaactac gcagccttgg tcagcggggc aggcccctcg caggcggcgc 180
tgtgggccaa atcccctggg gtactggcag ggcagccttt cttcgatgcc atatttaccc 240
aactcaactg ccaagtctcc tggttcctcc ccgagggatc gaagctggtg ccggtggcca 300
gagtggccga ggtccggggc cctgcccact gcctgctgct gggggaacgg gtggccctca 360
acacgctggc ccgctgcagt ggcattgcca gtgctgccgc cgctgcagtg gaggccgcca 420
ggggggccgg ctggactggg cacgtggcag gcacgaggaa gaccacgcca ggcttccggc 480
tggtggagaa gtatgggctc ctggtgggcg gggccgcctc gcaccgctac gacctgggag 540
ggctggtgat gttgaaggat aaccatgtgg tgccccccgg tggcgtggag aaggcggtgc 600
gggcggccag acaggcggct gacttcgctc tgaaggtgga agtggaatgc agcagcctgc 660
aggaggtcgt ccaggcagct gaggctggcg ccgaccttgt cctgctggac aacttcaagc 720
cagaggagct gcaccccacg gccaccgcgc tgaaggccca gttcccgagt gtggctgtgg 780
aagccagtgg gggcatcacc ctggacaacc tcccccagtt ctgcgggccg cacatagacg 840
tcatctccat ggggatgctg acccaggcgg tcccagccct tgatttctcc ctcaagctgt 900
ttgccaaaga ggtggctcca gtgcccaaaa tccactagtc ctaaaccgga agaggatgac 960
accggccatg ggttaacgtg gctcctcagg accctctggg tcacacatct ttagggtcag 1020
tgaacaatgg ggcacatttg gcactagctt gagcccaact ctggctctgc cacctgctgc 1080
tcctgtgacc tgtcagggct gacttcacct ctgctcatct cagtttccta atctgtaaaa 1140
tgggtctaat aaaggatcaa ccaaaaaaaa aaaaaaaaaa aa 1182

<210> SEQ ID NO 397
<211> LENGTH: 2630
<212> TYPE: DNA
<213> ORGANISM: Homo sapiens

<400> SEQUENCE: 397
cggggcatgc tgcttccctt caccttccac catgattgta agtttcctga ggcctcccca 60
ggtgtgcttc tgtacagcct gtggaatgtt accaaagacg ttggaagagg tggctatggg 120
acatcacctg ggagaagtgg aagcaaatgg acactgttca gaagtccata tacagaaaca 180
tacttggaaa aatatagaaa cctggttttg ctagatggga agcttgcagc tggggccaag 240
acatcaagag tagagcagca ggacatttca aaagaagatt aactcaaaga ttagagatgg 300
aagaacttgc aaagagaaag tctgtaccgg aagaaatctg gaaatctaga ggccagttta 360
agaatcagca gctaaacaag gagaataatc tagggcaaga gatagctacc tgcacaaaaa 420
ttcctaccag aaaaagagac atagaatcta atgaatttgt gaaaaatttt actgtaagat 480
caatacttgt tgcagaacag atagatccta tggaagagaa ttgtcataaa tatggtacat 540
gttgaaagat gctcaaacaa aactcagatt taattataca aagaaagtat gatggaaaaa 600
aaaaaacctt gtaaatatag tgaatgtggg agaaccttca gaggccacat cactcttgtt 660
cagcatcaaa taactcattg tggagagaga ccctgtaaat gtactgagtg tagaaaggga 720

-continued

```
tttaatcaga gttcccactt aagaaataat cagagaaaaa ctctttcagg agaaaagccc    780
tacaaatgca gtgagtgtgg gaaggccttc agttattgct tagttcttaa tcaacaccag    840
agaattcaca gtggagagaa accttatgag ggtactgaat gtggcaagac attcattcag    900
tcgtacatac cttactcagc atcaaagaat tcacacactg gtgagaagcc ctatacatgt    960
cttgaatgtg gaaggctttt tagtcagaac acacatctta ctctacatca gagaatccat   1020
actggagaga aaccttatga atgcaatgaa tgtggtaggt cctttagtca gactgcacat   1080
cttactcaac atcaaagaat gtatacagga gaaaaactct atgaatgtaa tgaatgtgag   1140
aaagccttcc atgatcactc agctcttatt caacatcata ttgtccatac tgcagagaaa   1200
ccctatgata tcatgactgg gaaaactttc agttactgtt cagacctcat tcaacatcag   1260
agaatgcaca ctggagagaa accatacaaa tgcaatgaat gtgggaatgc ctttagtgat   1320
tgttcatccc ttattcagca tcaaagaact cacactggag aagagcctta tgaatgtaag   1380
caatgtggaa aagcctttag cagaagcaca taccttactc aacatcagag aagtcacgca   1440
ggagagaaac agtataaatg caatgaatgt gagaaaactt tcagcctgag ttcattcctt   1500
acacagcata tgagggttca gactggagaa aaaccctaca aatataatga atatggaaaa   1560
gcttttagtg actgctcagg acattttcag agaactcaca ctggagagaa gccctgtgaa   1620
tgtaatgact gtgggaaacc tttcagtttc tgttcagccc taattcaaca taagagaatt   1680
cataccagaa agaagccctg actgtacctt cataccagta aatgcactga ctgtggaaaa   1740
gccttcagtg attggttagc acttgttcaa catcagataa ctcaacactg gagaaaaacc   1800
gtataaatgt actgaatgtg gaaaagcctt cagttggagt acagacctca aaaatcacca   1860
gaaaactcat actagtgaaa aatcctataa atgtaatgaa tgtagaaagg cctttagtta   1920
ctgctctggt cttattcaat gtcaggtcat tcatactata gaaaaacctt atgaatacgg   1980
taaatgtggc aaagccttta ggcagaggac agaccttaaa aaacatcaga aaatgcatac   2040
cgaagagaaa ccctatgaat gtaatgaatg tgggaaagcc tttagccaga gcacatatct   2100
tacaaaacac caaaaaattc atagtgaaga gaaatcaaat atacatactg agtgtgggga   2160
aaccattaga caaaactctt ctttttacaa caataaaacc tcacactgga gagttctctg   2220
aatgccttaa gaatttggtt aatatggaga cccttcccag ggaaacagaa ggaggatcgt   2280
gaaaaccgtt gactacttga atgatcacat ggtttagtgg agagagcatg attctgggtt   2340
ttaaaagtca tggatctcaa tctcagctcc tattactaac tagatctttt actttggggt   2400
aagtcacttc atatctttag gccttaattt cctcatctga aaactggaag gcctgacttg   2460
acttgttgag cttaagatcc tcaattatta tatttactag gaattcaagt ttctatagat   2520
gtggttcaga attgtgactt atttattgta catcaggtgt gattcacaag tgagcttgta   2580
gtagttatta aggagtcaat aaagatatga tataaaaaaa aaaaaaaaaa              2630
```

<210> SEQ ID NO 398
<211> LENGTH: 551
<212> TYPE: DNA
<213> ORGANISM: Homo sapiens

<400> SEQUENCE: 398

```
catttcatct tcattggata gtgttacata gtaatatatt tatgttttct tttaatcatt     60
tcataacttg gaaaatacta acatagtcaa aactctaggg taggtgatac atgagtttct    120
gtagtaatct ggttggagac atgttgtaat tctgtatata tatgtacatt tatcccatgc    180
atgttatgcc taaactaaga cggataccc  tgaattaaga ggtgctgtta tacattgacc    240
```

-continued aggcttaaga atatctcttt aaagtgtgtc gacatttaat tgacctttgg aagttcattc 300
tgttaatcat actcaaagtg ctaaagctat ggttgactgc tctggtgttt ttatattcat 360
tcgtgcttta gcatataaat tcttcagcat aattgctact tatttagcaa gagtttcctt 420
tatttgaaaa tgtgagttgt gcttgtattt ttgtgtcttt ctttctttct ttcttttttt 480
aaactttgct tcaggctggg tagtggtaga ggtttgaatt aaaatgtttt cctgtcagta 540
aaaaaaaaaa a 551

<210> SEQ ID NO 399
<211> LENGTH: 2390
<212> TYPE: DNA
<213> ORGANISM: Homo sapiens

<400> SEQUENCE: 399
gagcgagccc agcagcttgc ccttgacagg tgggggctgg ctggggcctt aatgtgaaaa 60
gacagtggca ggcagctgga gtagagcgag cccagcagcc ctaaaaggct gccttcatgg 120
ccatctagcc ccagttcagg gcagcatcca tagcccacaa gccagcgtgg gtggggcggg 180
ggtggtccca cagctgggtt ccacctgaag agcctccgtg cctcggagca ggagaggcag 240
gctatggctg tcaccctccc tcctgcctgt gtcccagtga gaactgacct gagtcccctt 300
ccaaacccag acccacctcc tgccccaggc ccactgaagc atgttccatt tctaaaaagc 360
ccagagttca gtgtgtccca aggaaaaccc aaagtggagg tgctcaggtc caggggagtc 420
cagtgggcag gacccttggc aggcaagccc ctcccttcac tcccaggacc taccttctgc 480
tagtaaagga ctggcttcat tctaattatg gcccacagac tgccccggag acctggagga 540
cagcagtgct ggcacttggg tgtccatggg cccgtctgcc ggctctgcct gtgctgcaag 600
tgttggccgt gggtccagcc aacaactccc tacgtcctgt gtggggccct gcccaagtgg 660
atgaggcatt ccttgaggag tatcattttc cctgacaatc cccatcacct ttaggggttc 720
cctgcttggc tcctttccag ctgaaaaact agacctgtgc cattggggaa gctggacaaa 780
gtctaggggg cccgcctggt agagggtccc gggaagctgg atctgtcagc ctcggccctg 840
aggcccctgt taactcaaga ctgtgagctg cctctaggtg gtcacgtctg ggagctagct 900
tgtatggctt ctgaccagta tcaggatttc tgttctgaga gcagcgtggg cagcaaggca 960
gggcagccca gaggtggcag cggcaggcaa tctggtcact aggtctttgt gatgccaaaa 1020
ataaaagagg gtggggtggg tgctttctgt tcctctgatt ggatggagtc cgccagcagg 1080
catggggcta cattccagtg cctgactata gggaggcact cctgattcca tggagcagcc 1140
cggactttga gaatgggctc tggtttgcgg ggggcaggcg taccagactg caagaccccc 1200
cagtacctca ccgtgccaaa taggaagagg tggccttggt gtagccaaat ggatcttttt 1260
aacagtgtgc ctttggggag ggacccatgt ccatggcttc gttgagggcc atccatatgc 1320
cagctggggg ccagcccaca gtggccatat tggctgcagc aggaatggtg cccacctcgg 1380
cgaattgaag ggctaagagt cccagatagc taggccagag ctggaagcag acagtaaggg 1440
gaagagctgc tcccacagga gagggagaga ttccagctca ctgcgcagcc tgggaggagg 1500
cgtggatcct ggcacgctga gcctcaggca ccagcctccc tgtgctcgac agcaaagtct 1560
tgactccttc ctgctgagca ctgtgctacc ttcactgctc caaagccaga ctaacagctc 1620
tccaagccct tggggtgact cggcttccag gagctgttgg agaaatgagg atgtctgtcc 1680
ctgtctgcct gggcaggcca gattcctccc cagcagccgg gtctctccag accctgattc 1740

-continued

```
ggtgcctttc tgtttaccag ctacttcaat cccaaagttt gaatctgcag ataccttact   1800

cccagccact ttgccttctt actgtgttgt gtgtttttcc tggtgcttca agagcgtgtg   1860

cagggcaagt gccgtcactg ggaactgcac cagatgctca gacttggttg tcttatgttt   1920

accaataaat aaaagtagac tttttctatt tttatttgct gctatttgtg tgtgtgtttg   1980

tgtttgtgta gctaggtatc tggcacttct gacgatgcat tgttgctttt ttcccgaagg   2040

tcccgcagga actgtggcaa tggtgtgtgt gtgaaatggt gtgttaaccg cgttttgttt   2100

gctcctgtat tgaataggaa gcagtggcca gtctgtcttc cttagagatg ttagcatatt   2160

tttatatgta tatattttgt accaaaaaag agtgttcctt gttttggtta cactcgaaat   2220

tctgacctag ctggagaggg ctctgggccg agagctttca ctaaggggag acttcagggg   2280

aggatcaagc tttgaaccaa agccaatcac tggcttgatt tgtgtttttt aattaaaaaa   2340

aaaatcattc atgtatgcca cttctaaaaa aaaaaaaaaa aaaaaaaaaa              2390
```

<210> SEQ ID NO 400
<211> LENGTH: 1303
<212> TYPE: DNA
<213> ORGANISM: Homo sapiens

<400> SEQUENCE: 400

```
ggcacgaggc tgagaccggt gcgccgcgcg ctagtggccg ctcttccgcg ggctagcggg     60

cggtgggggc gccagcagcg cggaaggcgg gcacgcgggc catggctccc tgggcggagg    120

ccgagcactc ggcgctgaac ccgctgcgcg cggtgtggct cacgctgacc gccgccttcc    180

tgctgaccct actgctgcag ctcctgccgc ccggcctgct cccgggctgc gcgatcttcc    240

aggacctgat ccgctatggg aaaaccaagt gtggggagcc gtcgcgcccc gccgcctgcc    300

gagcctttga tgtccccaag agatattttt cccactttta tatcatctca gtgctgtgga    360

atggcttcct gctttggtgc cttactcaat ctctgttcct gggagcacct tttccaagct    420

ggcttcatgg tttgctcaga attctcgggg cggcacagtt ccagggaggg gagctggcac    480

tgtctgcatt cttagtgcta gtatttctgt ggctgcacag cttacgaaga ctcttcgagt    540

gcctctacgt cagtgtcttc tccaatgtca tgattcacgt cgtgcagtac tgttttggac    600

ttgtctatta tgtccttgtt ggcctaactg tgctgagcca agtgccaatg gatggcagga    660

atgcctacat aacagggaaa aatctattga tgcaagcacg gtggttccat attcttggga    720

tgatgatgtt catctggtca tctgcccatc agtataagtg ccatgttatt ctcggcaatc    780

tcaggaaaaa taaagcagga gtggtcattc actgtaacca caggatccca tttggagact    840

ggtttgaata tgtttcttcc cctaactact tagcagagct gatgatctac gtttccatgg    900

ccgtcacctt tgggttccac aacttaactt ggtggctagt ggtgacaaat gtcttcttta    960

atcaggccct gtctgccttt ctcagccacc aattctacaa aagcaaattt gtctcttacc   1020

cgaagcatag gaaagctttc ctaccatttt tgttttaagt taacctcagt catgaagaat   1080

gcaaaccagg tgatggtttc aatgcctaag gacagtgaag tctggagccc aaagtacagt   1140

ttcagcaaag ctgtttgaaa ctctccattc catttctata ccccacaagt tttcactgaa   1200

tgagcatggc agtgccactc aagaaaatga atctccaaag tatcttcaaa gaataaatac   1260

taatggcaga aaaaaaaaaa aaaaaaaaaa aaaaaaaaaa aaa                     1303
```

PREDICTING OUTCOME WITH TAMOXIFEN IN BREAST CANCER

RELATED APPLICATIONS

This application claims benefit of priority from U.S. Provisional Patent Application 60/504,087, filed Sep. 19, 2003, which is hereby incorporated by reference in its entirety as if fully set forth.

FIELD OF THE INVENTION

The invention relates to the identification and use of gene expression profiles, or patterns, with clinical relevance to the treatment of breast cancer using tamoxifen. In particular, the invention provides the identities of genes that are correlated with patient survival and breast cancer recurrence in women treated with tamoxifen. The gene expression profiles, whether embodied in nucleic acid expression, protein expression, or other expression formats, may be used to select subjects afflicted with breast cancer who will likely respond positively to tamoxifen treatment as well as those who will likely be non-responsive and thus candidates for other treatments. The invention also provides the identities of three sets of sequences from three genes with expression patterns that are strongly predictive of responsiveness to tamoxifen.

BACKGROUND OF THE INVENTION

Breast cancer is by far the most common cancer among women. Each year, more than 180,000 and 1 million women in the U.S. and worldwide, respectively, are diagnosed with breast cancer. Breast cancer is the leading cause of death for women between ages 50-55, and is the most common non-preventable malignancy in women in the Western Hemisphere. An estimated 2,167,000 women in the United States are currently living with the disease (National Cancer Institute, Surveillance Epidemiology and End Results (NCI SEER) program, *Cancer Statistics Review* (CSR), www-seer-.ims.nci.nih.gov/Publications/CSR1973 (1998)). Based on cancer rates from 1995 through 1997, a report from the National Cancer Institute (NCI) estimates that about 1 in 8 women in the United States (approximately 12.8 percent) will develop breast cancer during her lifetime (NCI's Surveillance, Epidemiology, and End Results Program (SEER) publication *SEER Cancer Statistics Review* 1973-1997). Breast cancer is the second most common form of cancer, after skin cancer, among women in the United States. An estimated 250,100 new cases of breast cancer are expected to be diagnosed in the United States in 2001. Of these, 192,200 new cases of more advanced (invasive) breast cancer are expected to occur among women (an increase of 5% over last year), 46,400 new cases of early stage (in situ) breast cancer are expected to occur among women (up 9% from last year), and about 1,500 new cases of breast cancer are expected to be diagnosed in men (Cancer Facts & Figures 2001 American Cancer Society). An estimated 40,600 deaths (40,300 women, 400 men) from breast cancer are expected in 2001. Breast cancer ranks second only to lung cancer among causes of cancer deaths in women. Nearly 86% of women who are diagnosed with breast cancer are likely to still be alive five years later, though 24% of them will die of breast cancer after 10 years, and nearly half (47%) will die of breast cancer after 20 years.

Every woman is at risk for breast cancer. Over 70 percent of breast cancers occur in women who have no identifiable risk factors other than age (U.S. General Accounting Office. Breast Cancer, 1971-1991: Prevention, Treatment and Research. GAO/PEMD-92-12; 1991). Only 5 to 10% of breast cancers are linked to a family history of breast cancer (Henderson I C, Breast Cancer. In: Murphy G P, Lawrence W L, Lenhard R E (eds). *Clinical Oncology*. Atlanta, Ga.: American Cancer Society; 1995:198-219).

Each breast has 15 to 20 sections called lobes. Within each lobe are many smaller lobules. Lobules end in dozens of tiny bulbs that can produce milk. The lobes, lobules, and bulbs are all linked by thin tubes called ducts. These ducts lead to the nipple in the center of a dark area of skin called the areola. Fat surrounds the lobules and ducts. There are no muscles in the breast, but muscles lie under each breast and cover the ribs. Each breast also contains blood vessels and lymph vessels. The lymph vessels carry colorless fluid called lymph, and lead to the lymph nodes. Clusters of lymph nodes are found near the breast in the axilla (under the arm), above the collarbone, and in the chest.

Breast tumors can be either benign or malignant. Benign tumors are not cancerous, they do not spread to other parts of the body, and are not a threat to life. They can usually be removed, and in most cases, do not come back. Malignant tumors are cancerous, and can invade and damage nearby tissues and organs. Malignant tumor cells may metastasize, entering the bloodstream or lymphatic system. When breast cancer cells metastasize outside the breast, they are often found in the lymph nodes under the arm (axillary lymph nodes). If the cancer has reached these nodes, it means that cancer cells may have spread to other lymph nodes or other organs, such as bones, liver, or lungs.

Major and intensive research has been focused on early detection, treatment and prevention. This has included an emphasis on determining the presence of precancerous or cancerous ductal epithelial cells. These cells are analyzed, for example, for cell morphology, for protein markers, for nucleic acid markers, for chromosomal abnormalities, for biochemical markers, and for other characteristic changes that would signal the presence of cancerous or precancerous cells. This has led to various molecular alterations that have been reported in breast cancer, few of which have been well characterized in human clinical breast specimens. Molecular alterations include presence/absence of estrogen and progesterone steroid receptors, HER-2 expression/amplification (Mark H F, et al. HER-2/neu gene amplification in stages I-IV breast cancer detected by fluorescent in situ hybridization. Genet Med; 1(3):98-103 1999), Ki-67 (an antigen that is present in all stages of the cell cycle except G0 and used as a marker for tumor cell proliferation, and prognostic markers (including oncogenes, tumor suppressor genes, and angiogenesis markers) like p53, p27, Cathepsin D, pS2, multi-drug resistance (MDR) gene, and CD31.

Adjuvant tamoxifen (TAM) is the most effective systemic treatment for estrogen receptor positive (ER+) breast cancer. ER and progesterone receptor (PR) expression have been the major clinicopathological predictor for response to TAM. However, up to 40% of ER+ tumors fail to respond or develop resistance to TAM. Therefore, better predictive biomarkers for TAM response may be able to identify patients who are unlikely to benefit from TAM so that additional or alternative therapies may be sought.

van't Veer et al. (Nature 415:530-536, 2002) describe gene expression profiling of clinical outcome in breast cancer. They identified genes expressed in breast cancer tumors, the expression levels of which correlated either with patients afflicted with distant metastases within 5 years or with patients that remained metastasis-free after at least 5 years.

Ramaswamy et al. (Nature Genetics 33:49-54, 2003) describe the identification of a molecular signature of metastasis in primary solid tumors. The genes of the signature were identified based on gene expression profiles of 12 metastatic adenocarcinoma nodules of diverse origin (lung, breast, prostate, colorectal, uterus) compared to expression profiles of 64 primary adenocarcinomas representing the same spectrum of tumor types from different individuals. A 128 gene set was identified.

Both of the above described approaches, however, utilize heterogeneous populations of cells found in a tumor sample to obtain information on gene expression patterns. The use of such populations may result in the inclusion or exclusion of multiple genes that are differentially expressed in cancer cells. The gene expression patterns observed by the above described approaches may thus provide little confidence that the differences in gene expression are meaningfully associated with breast cancer recurrence or survival.

Citation of documents herein is not intended as an admission that any is pertinent prior art. All statements as to the date or representation as to the contents of documents is based on the information available to the applicant and does not constitute any admission as to the correctness of the dates or contents of the documents.

SUMMARY OF THE INVENTION

The present invention relates to the identification and use of gene expression patterns (or profiles or "signatures") which are clinically relevant to breast cancer. In particular, the identities of genes that are correlated with patient survival and breast cancer recurrence are provided. The gene expression profiles, whether embodied in nucleic acid expression, protein expression, or other expression formats, may be used to predict survival of subjects afflicted with breast cancer and the likelihood of breast cancer recurrence.

The invention thus provides for the identification and use of gene expression patterns (or profiles or "signatures") which correlate with (and thus able to discriminate between) patients with good or poor survival outcomes. In one embodiment, the invention provides patterns that are able to distinguish patients with estrogen receptor positive (ER+) breast tumors into those with that are responsive, or likely to be responsive, to tamoxifen (TAM) treatment and those that are non-responsive, or likely to be non-responsive, to TAM treatment. Responsiveness may be viewed in terms of better survival outcomes over time. These patterns are thus able to distinguish patients with ER+ breast tumors into at least two subtypes.

In a first aspect, the present invention provides a non-subjective means for the identification of patients with ER+ breast cancer as likely to have a good or poor survival outcome following TAM treatment by assaying for the expression patterns disclosed herein. Thus where subjective interpretation may have been previously used to determine the prognosis and/or treatment of breast cancer patients, the present invention provides objective gene expression patterns, which may used alone or in combination with subjective criteria to provide a more accurate assessment of ER+ breast cancer patient outcomes or expected outcomes, including survival and the recurrence of cancer, following treatment with TAM. The expression patterns of the invention thus provide a means to determine ER+ breast cancer prognosis. Furthermore, the expression patterns can also be used as a means to assay small, node negative tumors that are not readily assayed by other means.

The gene expression patterns comprise one or more than one gene capable of discriminating between breast cancer outcomes with significant accuracy. The gene(s) are identified as correlated with ER+ breast cancer outcomes such that the levels of their expression are relevant to a determination of the preferred treatment protocols for a patient. Thus in one embodiment, the invention provides a method to determine the outcome of a subject afflicted with ER+ breast cancer by assaying a cell containing sample from said subject for expression of one or more than one gene disclosed herein as correlated with ER+ breast cancer outcomes following TAM treatment.

Gene expression patterns of the invention are identified as described below. Generally, a large sampling of the gene expression profile of a sample is obtained through quantifying the expression levels of mRNA corresponding to many genes. This profile is then analyzed to identify genes, the expression of which are positively, or negatively, correlated, with ER+ breast cancer outcome with TAM treatment. An expression profile of a subset of human genes may then be identified by the methods of the present invention as correlated with a particular outcome. The use of multiple samples increases the confidence which a gene may be believed to be correlated with a particular survival outcome. Without sufficient confidence, it remains unpredictable whether expression of a particular gene is actually correlated with an outcome and also unpredictable whether expression of a particular gene may be successfully used to identify the outcome for a ER+ breast cancer patient.

A profile of genes that are highly correlated with one outcome relative to another may be used to assay an sample from a subject afflicted with ER+ breast cancer to predict the likely responsiveness (or lack thereof) to TAM in the subject from whom the sample was obtained. Such an assay may be used as part of a method to determine the therapeutic treatment for said subject based upon the breast cancer outcome identified.

The correlated genes may be used singly with significant accuracy or in combination to increase the ability to accurately correlating a molecular expression phenotype with an ER+ breast cancer outcome. This correlation is a way to molecularly provide for the determination of survival outcomes as disclosed herein. Additional uses of the correlated gene(s) are in the classification of cells and tissues; determination of diagnosis and/or prognosis; and determination and/or alteration of therapy.

The ability to discriminate is conferred by the identification of expression of the individual genes as relevant and not by the form of the assay used to determine the actual level of expression. An assay may utilize any identifying feature of an identified individual gene as disclosed herein as long as the assay reflects, quantitatively or qualitatively, expression of the gene in the "transcriptome" (the transcribed fraction of genes in a genome) or the "proteome" (the translated fraction of expressed genes in a genome). Identifying features include, but are not limited to, unique nucleic acid sequences used to encode (DNA), or express (RNA), said gene or epitopes specific to, or activities of, a protein encoded by said gene. All that is required is the identity of the gene(s) necessary to discriminate between ER+ breast cancer outcomes and an appropriate cell containing sample for use in an expression assay.

In another embodiment, the invention provides for the identification of the gene expression patterns by analyzing global, or near global, gene expression from single cells or homogenous cell populations which have been dissected away from, or otherwise isolated or purified from, contaminating cells beyond that possible by a simple biopsy. Because the expression of numerous genes fluctuate between cells from different patients as well as between cells from the same patient sample, multiple data from expression of individual genes and gene expression patterns are used as reference data to generate models which in turn permit the identification of individual gene(s), the expression of which are most highly correlated with particular ER+ breast cancer outcomes.

In additional embodiments, the invention provides physical and methodological means for detecting the expression of gene(s) identified by the models generated by individual expression patterns. These means may be directed to assaying one or more aspects of the DNA template(s) underlying the expression of the gene(s), of the RNA used as an intermediate to express the gene(s), or of the proteinaceous product expressed by the gene(s).

In a further embodiments, the gene(s) identified by a model as capable of discriminating between ER+ breast cancer outcomes may be used to identify the cellular state of an unknown sample of cell(s) from the breast. Preferably, the sample is isolated via non-invasive means. The expression of said gene(s) in said unknown sample may be determined and compared to the expression of said gene(s) in reference data of gene expression patterns correlated with ER+ breast cancer outcomes. Optionally, the comparison to reference samples may be by comparison to the model(s) constructed based on the reference samples.

One advantage provided by the present invention is that contaminating, non-breast cells (such as infiltrating lymphocytes or other immune system cells) are not present to possibly affect the genes identified or the subsequent analysis of gene expression to identify the survival outcomes of patients with breast cancer. Such contamination is present where a biopsy is used to generate gene expression profiles.

In a second aspect, the invention provides a non-subjective means based on the expression of three genes, or combinations thereof, for the identification of patients with ER+ breast cancer as likely to have a good or poor survival outcome following TAM treatment. These three genes are members of the expression patterns disclosed herein which have been found to be strongly predictive of clinical outcome following TAM treatment of ER+ breast cancer.

The present invention thus provides gene sequences identified as differentially expressed in ER+ breast cancer in correlation to TAM responsiveness. The sequences of two of the genes display increased expression in ER+ breast cells that respond to TAM treatment (and thus decreased expression in nonresponsive cases). The sequences of the third gene display decreased expression in ER+ breast cells that respond to TAM treatment (and thus increased expression in nonresponsive cases).

The first set of sequences found to be more highly expressed in TAM responsive, ER+ breast cells are those of interleukin 17 receptor B (IL17RB), which has been mapped to human chromosome 3 at 3p21.1. IL17RB is also referred to as interleukin 17B receptor (IL17BR) and sequences corresponding to it, and thus may be used in the practice of the instant invention, are identified by UniGene Cluster Hs.5470.

The second set of sequences found to be more highly expressed in TAM responsive, ER+ breast cells are those of the calcium channel, voltage-dependent, L type, alpha 1D subunit (CACNA1D), which has been mapped to human chromosome 3 at 3p14.3. Sequences corresponding to CACNA1D, and thus may be used in the practice of the instant invention, are identified by UniGene Cluster Hs.399966.

The set of sequences found to be expressed at lower levels in TAM responsive, ER+ breast cells are those of homeobox B13 (HOXB13), which has been mapped to human chromosome 17 at 17q21.2. Sequences corresponding to HOXB13, and thus may be used in the practice of the instant invention, are identified by UniGene Cluster Hs.66731.

The identified sequences may thus be used in methods of determining the responsiveness of a subject's ER+ breast cancer to TAM treatment via analysis of breast cells in a tissue or cell containing sample from a subject. The present invention provides an non-empirical means for determining TAM responsiveness in ER+ patients. This provides advantages over the use of a "wait and see" approach following treatment with TAM. The expression levels of these sequences may also be used as a means to assay small, node negative tumors that are not readily assessed by conventional means.

The expression levels of the identified sequences may be used alone or in combination with other sequences capable of determining responsiveness to TAM treatment. Preferably, the sequences of the invention are used alone or in combination with each other, such as in the format of a ratio of expression levels that can have improved predictive power over analysis based on expression of sequences corresponding to individual genes.

The present invention provides means for correlating a molecular expression phenotype with a physiological response in a subject with ER+ breast cancer. This correlation provides a way to molecularly diagnose and/or determine treatment for a breast cancer afflicted subject. Additional uses of the sequences are in the classification of cells and tissues; and determination of diagnosis and/or prognosis. Use of the sequences to identify cells of a sample as responsive, or not, to TAM treatment may be used to determine the choice, or alteration, of therapy used to treat such cells in the subject, as well as the subject itself, from which the sample originated.

An assay of the invention may utilize a means related to the expression level of the sequences disclosed herein as long as the assay reflects, quantitatively or qualitatively, expression of the sequence. Preferably, however, a quantitative assay means is preferred. The ability to determine TAM responsiveness and thus outcome of treatment therewith is provided by the recognition of the relevancy of the level of expression of the identified sequences and not by the form of the assay used to determine the actual level of expression. Identifying features of the sequences include, but are not limited to, unique nucleic acid sequences used to encode (DNA), or express (RNA), the disclosed sequences or epitopes specific to, or activities of, proteins encoded by the sequences. Alternative means include detection of nucleic acid amplification as indicative of increased expression levels (IL17RB and CACNA1D sequences) and nucleic acid inactivation, deletion, or methylation, as indicative of decreased expression levels (HOXB13 sequences). Stated differently, the invention may be practiced by assaying one or more aspect of the DNA template(s) underlying the expression of the disclosed sequence(s), of the RNA used as an intermediate to express the sequence(s), or of the proteinaceous product expressed by the sequence(s). As such, the detection of the amount of, stability of, or degradation (including rate) of, such DNA, RNA and proteinaceous molecules may be used in the practice of the invention.

The practice of the present invention is unaffected by the presence of minor mismatches between the disclosed sequences and those expressed by cells of a subject's sample. A non-limiting example of the existence of such mismatches are seen in cases of sequence polymorphisms between individuals of a species, such as individual human patients within *Homo sapiens*. Knowledge that expression of the disclosed sequences (and sequences that vary due to minor mismatches)

is correlated with the presence of non-normal or abnormal breast cells and breast cancer is sufficient for the practice of the invention with an appropriate cell containing sample via an assay for expression.

In one embodiment, the invention provides for the identification of the expression levels of the disclosed sequences by analysis of their expression in a sample containing ER+ breast cells. In one preferred embodiment, the sample contains single cells or homogenous cell populations which have been dissected away from, or otherwise isolated or purified from, contaminating cells beyond that possible by a simple biopsy. Alternatively, undissected cells within a "section" of tissue may be used. Multiple means for such analysis are available, including detection of expression within an assay for global, or near global, gene expression in a sample (e.g. as part of a gene expression profiling analysis such as on a microarray) or by specific detection, such as quantitative PCR (Q-PCR), or real time quantitative PCR.

Preferably, the sample is isolated via non-invasive means. The expression of the disclosed sequence(s) in the sample may be determined and compared to the expression of said sequence(s) in reference data of non-normal breast cells. Alternatively, the expression level may be compared to expression levels in normal cells, preferably from the same sample or subject. In embodiments of the invention utilizing Q-PCR, the expression level may be compared to expression levels of reference genes in the same sample.

When individual breast cells are isolated in the practice of the invention, one benefit is that contaminating, non-breast cells (such as infiltrating lymphocytes or other immune system cells) are not present to possibly affect detection of expression of the disclosed sequence(s). Such contamination is present where a biopsy is used to generate gene expression profiles. However, analysis of differential gene expression and correlation to ER+ breast cancer outcomes with both isolated and non-isolated samples, as described herein, increases the confidence level of the disclosed sequences as capable of having significant predictive power with either type of sample.

While the present invention is described mainly in the context of human breast cancer, it may be practiced in the context of breast cancer of any animal known to be potentially afflicted by breast cancer. Preferred animals for the application of the present invention are mammals, particularly those important to agricultural applications (such as, but not limited to, cattle, sheep, horses, and other "farm animals"), animal models of breast cancer, and animals for human companionship (such as, but not limited to, dogs and cats).

MODES OF PRACTICING THE INVENTION

Figure 1:
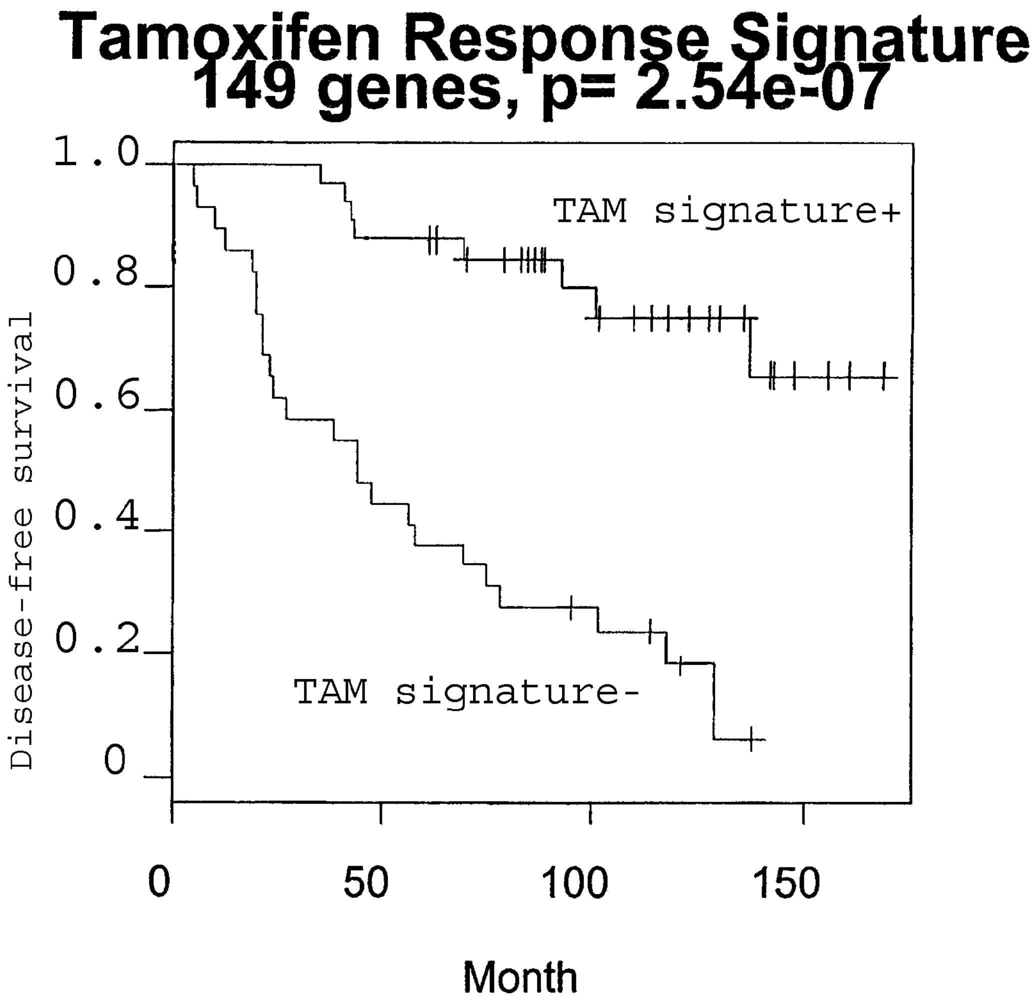
FIG. 1 shows the survival curves for two groups of breast cancer patients defined by expression signatures based on 149 genes as described herein.

Definitions of terms as used herein:

A gene expression "pattern" or "profile" or "signature" refers to the relative expression of genes correlated with responsiveness to TAM treatment of ER+ breast cancer. Responsiveness or lack thereof may be expressed as survival outcomes which are correlated with an expression "pattern" or "profile" or "signature" that is able to distinguish between, and predict, said outcomes.

A "gene" is a polynucleotide that encodes a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis.

A "sequence" or "gene sequence" as used herein is a nucleic acid molecule or polynucleotide composed of a discrete order of nucleotide bases. The term includes the ordering of bases that encodes a discrete product (i.e. "coding region"), whether RNA or proteinaceous in nature, as well as the ordered bases that precede or follow a "coding region". Non-limiting examples of the latter include 5' and 3' untranslated regions of a gene. It is appreciated that more than one polynucleotide may be capable of encoding a discrete product. It is also appreciated that alleles and polymorphisms of the disclosed sequences may exist and may be used in the practice of the invention to identify the expression level(s) of the disclosed sequences or the allele or polymorphism. Identification of an allele or polymorphism depends in part upon chromosomal location and ability to recombine during mitosis.

The terms "correlate" or "correlation" or equivalents thereof refer to an association between expression of one or more genes and a physiological response of a breast cancer cell and/or a breast cancer patient in comparison to the lack of the response. A gene may be expressed at higher or lower levels and still be correlated with responsiveness or breast cancer survival or outcome. The invention provides for the correlation between increases in expression of IL 17RB and CACNA1D sequences and TAM responsiveness in ER+ breast cells. Similarly, the invention provides for the correlation between decreases in expression of HOXB13 sequences and TAM responsiveness in ER+ breast cells. Increases and decreases may be readily expressed in the form of a ratio between expression in a non-normal cell and a normal cell such that a ratio of one (1) indicates no difference while ratios of two (2) and one-half indicate twice as much, and half as much, expression in the non-normal cell versus the normal cell, respectively. Expression levels can be readily determined by quantitative methods as described below.

For example, increases in IL17RB expression can be indicated by ratios of or about 1.1, of or about 1.2, of or about 1.3, of or about 1.4, of or about 1.5, of or about 1.6, of or about 1.7, of or about 1.8, of or about 1.9, of or about 2, of or about 2.5, of or about 3, of or about 3.5, of or about 4, of or about 4.5, of or about 5, of or about 5.5, of or about 6, of or about 6.5, of or about 7, of or about 7.5, of or about 8, of or about 8.5, of or about 9, of or about 9.5, of or about 10, of or about 15, of or about 20, of or about 30, of or about 40, of or about 50, of or about 60, of or about 70, of or about 80, of or about 90, of or about 100, of or about 150, of or about 200, of or about 300, of or about 400, of or about 500, of or about 600, of or about 700, of or about 800, of or about 900, or of or about 1000. A ratio of 2 is a 100% (or a two-fold) increase in expression. Similar ratios can be used with respect to increases in CACNA1D expression. Decreases in HOXB13 expression can be indicated by ratios of or about 0.9, of or about 0.8, of or about 0.7, of or about 0.6, of or about 0.5, of or about 0.4, of or about 0.3, of or about 0.2, of or about 0.1, of or about 0.05, of or about 0.01, of or about 0.005, of or about 0.001, of or about 0.0005, of or about 0.0001, of or about 0.00005, of or about 0.00001, of or about 0.000005, or of or about 0.000001.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

The term "amplify" is used in the broad sense to mean creating an amplification product can be made enzymatically with DNA or RNA polymerases. "Amplification," as used herein, generally refers to the process of producing multiple copies of a desired sequence, particularly those of a sample. "Multiple copies" mean at least 2 copies. A "copy" does not necessarily mean perfect sequence complementarity or identity to the template sequence. Methods for amplifying mRNA are generally known in the art, and include reverse transcription PCR (RT-PCR) and those described in U.S. patent application Ser. No. 10/062,857 (filed on Oct. 25, 2001), as well as U.S. Provisional Patent Application No. 60/298,847 (filed Jun. 15, 2001) and 60/257,801 (filed Dec. 22, 2000), all of which are hereby incorporated by reference in their entireties as if fully set forth. Another method which may be used is quantitative PCR (or Q-PCR). Alternatively, RNA may be directly labeled as the corresponding cDNA by methods known in the art.

By "corresponding", it is meant that a nucleic acid molecule shares a substantial amount of sequence identity with another nucleic acid molecule. Substantial amount means at least 95%, usually at least 98% and more usually at least 99%, and sequence identity is determined using the BLAST algorithm, as described in Altschul et al. (1990), J. Mol. Biol. 215:403-410 (using the published default setting, i.e. parameters w=4, t=17).

A "microarray" is a linear or two-dimensional array of preferably discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, preferably at least about 50/$cm^2$, more preferably at least about 100/$cm^2$, even more preferably at least about 500/$cm^2$, but preferably below about 1,000/$cm^2$. Preferably, the arrays contain less than about 500, about 1000, about 1500, about 2000, about 2500, or about 3000 immobilized polynucleotides in total. As used herein, a DNA microarray is an array of oligonucleotides or polynucleotides placed on a chip or other surfaces used to hybridize to amplified or cloned polynucleotides from a sample. Since the position of each particular group of primers in the array is known, the identities of a sample polynucleotides can be determined based on their binding to a particular position in the microarray.

Because the invention relies upon the identification of genes that are over- or under-expressed, one embodiment of the invention involves determining expression by hybridization of mRNA, or an amplified or cloned version thereof, of a sample cell to a polynucleotide that is unique to a particular gene sequence. Preferred polynucleotides of this type contain at least about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. Even more preferred are polynucleotides of at least or about 50, at least or about 100, at least about or 150, at least or about 200, at least or about 250, at least or about 300, at least or about 350, at least or about 400, at least or about 450, or at least or about 500 consecutive bases of a sequence that is not found in other gene sequences. The term "about" as used in the preceding sentence refers to an increase or decrease of 10% from the stated numerical value. Longer polynucleotides may of course contain minor mismatches (e.g. via the presence of mutations) which do not affect hybridization to the nucleic acids of a sample. Such polynucleotides may also be referred to as polynucleotide probes that are capable of hybridizing to sequences of the genes, or unique portions thereof, described herein. Such polynucleotides may be labeled to assist in their detection. Preferably, the sequences are those of mRNA encoded by the genes, the corresponding cDNA to such mRNAs, and/or amplified versions of such sequences. In preferred embodiments of the invention, the polynucleotide probes are immobilized on an array, other solid support devices, or in individual spots that localize the probes.

In another embodiment of the invention, all or part of a disclosed sequence may be amplified and detected by methods such as the polymerase chain reaction (PCR) and variations thereof, such as, but not limited to, quantitative PCR (Q-PCR), reverse transcription PCR (RT-PCR), and real-time PCR, optionally real-time RT-PCR. Such methods would utilize one or two primers that are complementary to portions of a disclosed sequence, where the primers are used to prime nucleic acid synthesis. The newly synthesized nucleic acids are optionally labeled and may be detected directly or by hybridization to a polynucleotide of the invention. The newly synthesized nucleic acids may be contacted with polynucleotides (containing sequences) of the invention under conditions which allow for their hybridization.

Alternatively, and in yet another embodiment of the invention, gene expression may be determined by analysis of expressed protein in a cell sample of interest by use of one or more antibodies specific for one or more epitopes of individual gene products (proteins) in said cell sample. Such antibodies are preferably labeled to permit their easy detection after binding to the gene product.

The term "label" refers to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

As used herein, a "breast tissue sample" or "breast cell sample" refers to a sample of breast tissue or fluid isolated from an individual suspected of being afflicted with, or at risk of developing, breast cancer. Such samples are primary isolates (in contrast to cultured cells) and may be collected by any non-invasive means, including, but not limited to, ductal lavage, fine needle aspiration, needle biopsy, the devices and methods described in U.S. Pat. No. 6,328,709, or any other suitable means recognized in the art. Alternatively, the "sample" may be collected by an invasive method, including, but not limited to, surgical biopsy.

"Expression" and "gene expression" include transcription and/or translation of nucleic acid material.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because the present invention is based on the relative level of gene expression, mutations in non-coding regions of genes as disclosed herein may also be assayed in the practice of the invention.

"Detection" includes any means of detecting, including direct and indirect detection of gene expression and changes therein. For example, "detectably less" products may be observed directly or indirectly, and the term indicates any reduction (including the absence of detectable signal). Similarly, "detectably more" product means any increase, whether observed directly or indirectly.

Increases and decreases in expression of the disclosed sequences are defined in the following terms based upon percent or fold changes over expression in normal cells. Increases may be of 10, 20, 30, 40, 50, 60, 70, 80, 90, 100, 120, 140, 160, 180, or 200% relative to expression levels in normal cells. Alternatively, fold increases may be of 1, 1.5, 2, 2.5, 3, 3.5, 4, 4.5, 5, 5.5, 6, 6.5, 7, 7.5, 8, 8.5, 9, 9.5, or 10 fold over expression levels in normal cells. Decreases may be of 10, 20, 30, 40, 50, 55, 60, 65, 70, 75, 80, 82, 84, 86, 88, 90, 92, 94, 96, 98, 99 or 100% relative to expression levels in normal cells.

Unless defined otherwise all technical and scientific terms used herein have the same meaning as commonly understood to one of ordinary skill in the art to which this invention belongs.

EMBODIMENTS OF THE INVENTION

In a first aspect, the disclosed invention relates to the identification and use of gene expression patterns (or profiles or "signatures") which discriminate between (or are correlated with) breast cancer survival in a subject treated with tamoxifen (TAM). Such patterns may be determined by the methods of the invention by use of a number of reference cell or tissue samples, such as those reviewed by a pathologist of ordinary skill in the pathology of breast cancer, which reflect breast cancer cells as opposed to normal or other non-cancerous cells. The outcomes experienced by the subjects from whom the samples may be correlated with expression data to identify patterns that correlate with the outcomes following TAM treatment. Because the overall gene expression profile differs from person to person, cancer to cancer, and cancer cell to cancer cell, correlations between certain cells and genes expressed or underexpressed may be made as disclosed herein to identify genes that are capable of discriminating between breast cancer outcomes.

The present invention may be practiced with any number of the genes believed, or likely to be, differentially expressed with respect to breast cancer outcomes, particularly in cases of ER+ breast cancer. The identification may be made by using expression profiles of various homogenous breast cancer cell populations, which were isolated by microdissection, such as, but not limited to, laser capture microdissection (LCM) of 100-1000 cells. The expression level of each gene of the expression profile may be correlated with a particular outcome. Alternatively, the expression levels of multiple genes may be clustered to identify correlations with particular outcomes.

Genes with significant correlations to breast cancer survival when the subject is treated with tamoxifen may be used to generate models of gene expressions that would maximally discriminate between outcomes where a subject responds to tamoxifen treatment and outcomes where the tamoxifen treatment is not successful. Alternatively, genes with significant correlations may be used in combination with genes with lower correlations without significant loss of ability to discriminate between outcomes. Such models may be generated by any appropriate means recognized in the art, including, but not limited to, cluster analysis, supported vector machines, neural networks or other algorithm known in the art. The models are capable of predicting the classification of a unknown sample based upon the expression of the genes used for discrimination in the models. "Leave one out" cross-validation may be used to test the performance of various models and to help identify weights (genes) that are uninformative or detrimental to the predictive ability of the models. Cross-validation may also be used to identify genes that enhance the predictive ability of the models.

The gene(s) identified as correlated with particular breast cancer outcomes relating to tamoxifen treatment by the above models provide the ability to focus gene expression analysis to only those genes that contribute to the ability to identify a subject as likely to have a particular outcome relative to another. The expression of other genes in a breast cancer cell would be relatively unable to provide information concerning, and thus assist in the discrimination of, a breast cancer outcome.

As will be appreciated by those skilled in the art, the models are highly useful with even a small set of reference gene expression data and can become increasingly accurate with the inclusion of more reference data although the incremental increase in accuracy will likely diminish with each additional datum. The preparation of additional reference gene expression data using genes identified and disclosed herein for discriminating between different tamoxifen treatment outcomes in breast cancer is routine and may be readily performed by the skilled artisan to permit the generation of models as described above to predict the status of an unknown sample based upon the expression levels of those genes.

To determine the (increased or decreased) expression levels of genes in the practice of the present invention, any method known in the art may be utilized. In one preferred embodiment of the invention, expression based on detection of RNA which hybridizes to the genes identified and disclosed herein is used. This is readily performed by any RNA detection or amplification+detection method known or recognized as equivalent in the art such as, but not limited to, reverse transcription-PCR, the methods disclosed in U.S. patent application Ser. No. 10/062,857 (filed on Oct. 25, 2001) as well as U.S. Provisional Patent Applications No. 60/298,847 (filed Jun. 15, 2001) and 60/257,801 (filed Dec. 22, 2000), and methods to detect the presence, or absence, of RNA stabilizing or destabilizing sequences.

Alternatively, expression based on detection of DNA status may be used. Detection of the DNA of an identified gene as methylated or deleted may be used for genes that have decreased expression in correlation with a particular breast cancer outcome. This may be readily performed by PCR based methods known in the art, including, but not limited to, Q-PCR. Conversely, detection of the DNA of an identified gene as amplified may be used for genes that have increased expression in correlation with a particular breast cancer outcome. This may be readily performed by PCR based, fluorescent in situ hybridization (FISH) and chromosome in situ hybridization (CISH) methods known in the art.

Expression based on detection of a presence, increase, or decrease in protein levels or activity may also be used. Detection may be performed by any immunohistochemistry (IHC) based, blood based (especially for secreted proteins), antibody (including autoantibodies against the protein) based, exfoliate cell (from the cancer) based, mass spectroscopy based, and image (including used of labeled ligand) based method known in the art and recognized as appropriate for the detection of the protein. Antibody and image based methods are additionally useful for the localization of tumors after determination of cancer by use of cells obtained by a non-invasive procedure (such as ductal lavage or fine needle aspiration), where the source of the cancerous cells is not known. A labeled antibody or ligand may be used to localize the carcinoma(s) within a patient.

A preferred embodiment using a nucleic acid based assay to determine expression is by immobilization of one or more sequences of the genes identified herein on a solid support, including, but not limited to, a solid substrate as an array or to beads or bead based technology as known in the art. Alternatively, solution based expression assays known in the art may also be used. The immobilized gene(s) may be in the form of polynucleotides that are unique or otherwise specific to the gene(s) such that the polynucleotide would be capable of hybridizing to a DNA or RNA corresponding to the gene(s). These polynucleotides may be the full length of the gene(s) or be short sequences of the genes (up to one nucleotide shorter than the full length sequence known in the art by deletion from the 5' or 3' end of the sequence) that are optionally minimally interrupted (such as by mismatches or inserted non-complementary basepairs) such that hybridization with a DNA or RNA corresponding to the gene(s) is not affected. Preferably, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

The immobilized gene(s) may be used to determine the state of nucleic acid samples prepared from sample breast cell(s) for which the outcome of the sample's subject (e.g. patient from whom the sample is obtained) is not known or for confirmation of an outcome that is already assigned to the sample's subject. Without limiting the invention, such a cell may be from a patient with ER+ breast cancer. The immobilized polynucleotide(s) need only be sufficient to specifically hybridize to the corresponding nucleic acid molecules derived from the sample under suitable conditions. While even a single correlated gene sequence may to able to provide adequate accuracy in discriminating between two breast cancer outcomes, two or more, three or more, four or more, five or more, six or more, seven or more, eight or more, nine or more, ten or more, or eleven or more of the genes identified herein may be used as a subset capable of discriminating may be used in combination to increase the accuracy of the method. The invention specifically contemplates the selection of more than one, two or more, three or more, four or more, five or more, six or more, seven or more, eight or more, nine or more, ten or more, or eleven or more of the genes disclosed in the tables and figures herein for use as a subset in the identification of breast cancer survival outcome.

Of course 15 or more, 20 or more, 30 or more, 40 or more, 50 or more, 60 or more, 70 or more, 80 or more, 90 or more, 100 or more, 110 or more, 120 or more, 130 or more, 140 or more, or all the genes provided in Tables 1 and/or 2 below may be used. "Accession" as used in the context of the Tables herein as well as the present invention refers to the GenBank accession number of a sequence of each gene, the sequences of which are hereby incorporated by reference in their entireties as they are available from GenBank as accessed on the filing date of the present application. P value refers to values assigned as described in the Examples below. The indications of "E-xx" where "xx" is a two digit number refers to alternative notation for exponential figures where "E-xx" is "$10^{-xx}$". Thus in combination with the numbers to the left of "E-xx", the value being represented is the numbers to the left times $10^{-xx}$. "Description" as used in the Tables provides a brief identifier of what the sequence/gene encodes.

Genes with a correlation identified by a p value below or about 0.02, below or about 0.01, below or about 0.005, or below or about 0.001 are preferred for use in the practice of the invention. The present invention includes the use of gene (s) the expression of which identify different ER+ breast cancer outcomes after TAM treatment to permit simultaneous identification of breast cancer survival outcome of a patient based upon assaying a breast cancer sample from said patient.

In a second aspect, the present invention relates to the identification and use of three sets of sequences for the determination of responsiveness to TAM treatment in ER+ breast cancer. The differential expression of these sequences in breast cancer relative to normal breast cells is used to predict TAM responsiveness in a subject. The identity of the sets of sequences were determined by use of ER+ primary breast cancers from 60 patients uniformly treated with adjuvant TAM. The cancers were analyzed using high-density oligonucleotide microarrays to identify gene expression patterns highly correlated with treatment outcome. Expression levels of IL17BR, CACNA1D, and HOXB13 were strongly predictive of clinical outcome. In contrast, a previously reported 70-gene prognosis signature was not a significant predictor of clinical outcome in these patients. Validation in an independent cohort of 31 TAM treated patients confirmed the predictive utility of these three genes.

In comparison with existing biomarkers, including ESR1, PGR, ERBB2 and EGFR, these genes are significantly more predictive of TAM response. Multivariate analysis indicated that these three genes were significant predictors of clinical outcome independent of tumor size, nodal status and tumor grade. TAM is the most effective systemic treatment for ER+ breast cancer. ER and progesterone receptor (PR) expression have been the major clinicopathological predictors for response to TAM. However, up to 40% of ER+ tumors fail to respond or develop resistance to TAM. The invention thus provides for the use of the identified biomarkers to allow better patient management by identifying patients who are more likely to benefit from TAM or other endocrine therapy and those who are likely to develop resistance and tumor recurrence.

As noted herein, the sequences(s) identified by the present invention are expressed in correlation with ER+ breast cells. For example, IL17RB, identified by I.M.A.G.E. Consortium Clusters NM_018725 and NM_172234 ("The I.M.A.G.E. Consortium: An Integrated Molecular Analysis of Genomes and their Expression," Lennon et al., 1996, Genomics 33:151-152; see also image.11n1.gov) has been found to be useful in predicting responsiveness to TAM treatment.

In preferred embodiments of the invention, any sequence, or unique portion thereof, of the IL17RB sequences of the cluster, as well as the UniGene *Homo sapiens* cluster Hs.5470, may be used. Similarly, any sequence encoding all or a part of the protein encoded by any IL17RB sequence disclosed herein may be used. Consensus sequences of I.M.A.G.E. Consortium clusters are as follows, with the assigned coding region (ending with a termination codon) underlined and preceded by the 5' untranslated and/or non-coding region and followed by the 3' untranslated and/or non-coding region:

SEQ ID NO:1 (consensus sequence for IL17RB, transcript variant 1, identified as NM_018725 or NM_018725.2)

agcgcagcgt gcgggtggcc tggatcccgc gcagtggccc ggcgatgtcg ctcgtgctgc taagcctggc cgcgctgtgc aggagcgccg taccccgaga gccgaccgtt caatgtggct ctgaaactgg gccatctcca gagtggatgc tacaacatga tctaatcccc ggagacttga gggacctccg agtagaacct gttacaacta gtgttgcaac aggggactat tcaattttga tgaatgtaag ctgggtactc cgggcagatg ccagcatccg cttgttgaag gccaccaaga tttgtgtgac gggcaaaagc aacttccagt cctacagctg tgtgaggtgc aattacacag aggccttcca gactcagacc agaccctctg gtggtaaatg gacattttcc tacatcggct tccctgtaga gctgaacaca gtctatttca ttggggccca taatattcct aatgcaaata tgaatgaaga tggcccttcc atgtctgtga atttcacctc accaggctgc ctagaccaca taatgaaata taaaaaaaag tgtgtcaagg ccggaagcct gtgggatccg aacatcactg cttgtaagaa gaatgaggag acagtagaag tgaacttcac aaccactccc ctgggaaaca gatacatggc tcttatccaa cacagcacta tcatcgggtt ttctcaggtg tttgagccac accagaagaa acaaacgcga gcttcagtgg tgattccagt gactggggat agtgaaggtg ctacggtgca gctgactcca tattttccta cttgtggcag cgactgcatc cgacataaag gaacagttgt gctctgccca caaacaggcg tccctttccc tctggataac aacaaaagca agccgggagg ctggctgcct ctcctcctgc tgtctctgct ggtggccaca tgggtgctgg tggcagggat ctatctaatg tggaggcacg aaaggatcaa gaagacttcc ttttctacca ccacactact gcccccatt aaggttcttg tggtttaccc atctgaaata tgtttccatc acacaatttg ttacttcact gaatttcttc aaaaccattg cagaagtgag gtcatccttg aaaagtggca gaaaaagaaa atagcagaga tgggtccagt gcagtggctt gccactcaaa agaaggcagc agacaaagtc gtcttccttc tttccaatga cgtcaacagt gtgtgcgatg gtacctgtgg caagagcgag ggcagtccca gtgagaactc tcaagacctc ttcccccttg cctttaacct tttctgcagt gatctaagaa gccagattca tctgcacaaa tacgtggtgg tctactttag agagattgat acaaaagacg attacaatgc tctcagtgtc tgccccaagt accacctcat gaaggatgcc actgctttct gtgcagaact tctccatgtc aagcagcagg -continued tgtcagcagg aaaaagatca caagcctgcc acgatggctg ctgctccttg tagcccaccc atgagaagca agagacctta aaggcttcct atcccaccaa ttacagggaa aaaacgtgtg atgatcctga agcttactat gcagcctaca aacagcctta gtaattaaaa cattttatac caataaaatt ttcaaatatt gctaactaat gtagcattaa ctaacgattg gaaactacat ttacaacttc aaagctgttt tatacataga aatcaattac agttttaatt gaaaactata accattttga taatgcaaca ataaagcatc ttcagccaaa catctagtct tccatagacc atgcattgca gtgtacccag aactgtttag ctaatattct atgtttaatt aatgaatact aactctaaga acccctcact gattcactca atagcatctt aagtgaaaaa ccttctatta catgcaaaaa atcattgttt ttaagataac aaaagtaggg aataaacaag ctgaacccac ttttaaaaaa aaaaaaaaaa aaaaaaaaaa aaaaaaa SEQ ID NO:2 (consensus sequence for IL17RB, transcript variant 2, identified as NM_172234 or NM_172234.1)

agcgcagcgt gcgggtggcc tggatcccgc gcagtggccc ggcgatgtcg ctcgtgctgc taagcctggc cgcgctgtgc aggagcgccg taccccgaga gccgaccgtt caatgtggct ctgaaactgg gccatctcca gagtggatgc tacaacatga tctaatcccc ggagacttga gggacctccg agtagaacct gttacaacta gtgttgcaac aggggactat tcaattttga tgaatgtaag ctgggtactc cgggcagatg ccagcatccg cttgttgaag gccaccaaga tttgtgtgac gggcaaaagc aacttccagt cctacagctg tgtgaggtgc aattacacag aggccttcca gactcagacc agaccctctg gtggtaaatg gacattttcc tacatcggct tccctgtaga gctgaacaca gtctatttca ttggggccca taatattcct aatgcaaata tgaatgaaga tggcccttcc atgtctgtga atttcacctc accaggctgc ctagaccaca taatgaaata taaaaaaaag tgtgtcaagg ccggaagcct gtgggatccg aacatcactg cttgtaagaa gaatgaggag acagtagaag tgaacttcac aaccactccc ctgggaaaca gatacatggc tcttatccaa cacagcacta tcatcgggtt ttctcaggtg tttgagccac accagaagaa acaaacgcga gcttcagtgg tgattccagt gactggggat agtgaaggtg ctacggtgca ggtaaagttc agtgagctgc tctggggagg gaagggacat agaagactgt tccatcattc attgctttta aggatgagtt ctctcttgtc aaatgcactt ctgccagcag acaccagtta agtggcgttc atgggggctc tttcgctgca gcctccaccg tgctgaggtc aggaggccga cgtggcagtt gtggtccctt ttgcttgtat taatggctgc tgaccttcca aagcactttt tattttcatt ttctgtcaca gacactcagg gatagcagta ccattttact tccgcaagcc tttaactgca agatgaagct gcaaagggtt tgaaatggga aggtttgagt tccaggcagc gtatgaactc tggagagggg ctgccagtcc tctctgggcc gcagcggacc cagctggaac acaggaagtt ggagcagtag gtgctccttc acctctcagt atgtctcttt caactctagt ttttgaggtg gggacacagg aggtccagtg ggacacagcc actccccaaa gagtaaggag cttccatgct tcattccctg gcataaaaag tgctcaaaca caccagaggg ggcaggcacc agccagggta tgatggctac taccctttc tggagaacca tagacttccc ttactacagg gacttgcatg tcctaaagca ctggctgaag gaagccaaga ggatcactgc tgctcctttt ttctagagga aatgtttgtc tacgtggtaa gatatgacct agcccttta ggtaagcgaa ctggtatgtt agtaacgtgt acaaagttta ggttcagacc ccgggagtct tgggcacgtg ggtctcgggt cactggtttt gactttaggg ctttgttaca gatgtgtgac caaggggaaa atgtgcatga caacactaga ggtatgggcg aagccagaaa gaagggaagt -continued

```
tttggctgaa gtaggagtct tggtgagatt ttgctctgat gcatggtgtg aactttctga
gcctcttgtt tttcctcagc tgactccata ttttcctact tgtggcagcg actgcatccg
acataaagga acagttgtgc tctgcccaca aacaggcgtc cctttccctc tggataacaa
caaaagcaag ccgggaggct ggctgcctct cctcctgctg tctctgctgg tggccacatg
ggtgctggtg gcagggatct atctaatgtg gaggcacgaa aggatcaaga agacttcctt
ttctaccacc acactactgc cccccattaa ggttcttgtg gtttacccat ctgaaatatg
tttccatcac acaatttgtt acttcactga atttcttcaa aaccattgca gaagtgaggt
catccttgaa aagtggcaga aaaagaaaat agcagagatg ggtccagtgc agtggcttgc
cactcaaaag aaggcagcag acaaagtcgt cttccttctt tccaatgacg tcaacagtgt
gtgcgatggt acctgtggca agagcgaggg cagtcccagt gagaactctc aagacctctt
ccccccttgcc tttaaccttt tctgcagtga tctaagaagc cagattcatc tgcacaaata
cgtggtggtc tactttagag agattgatac aaaagacgat tacaatgctc tcagtgtctg
ccccaagtac cacctcatga aggatgccac tgctttctgt gcagaacttc tccatgtcaa
gcagcaggtg tcagcaggaa aaagatcaca agcctgccac gatggctgct gctccttgta
gcccacccat gagaagcaag agaccttaaa ggcttcctat cccaccaatt acagggaaaa
aacgtgtgat gatcctgaag cttactatgc agcctacaaa cagccttagt aattaaaaca
ttttatacca ataaaatttt caaatattgc taactaatgt agcattaact aacgattgga
aactacattt acaacttcaa agctgtttta tacatagaaa tcaattacag ttttaattga
aaactataac cattttgata atgcaacaat aaagcatctt cagccaaaca tctagtcttc
catagaccat gcattgcagt gtacccagaa ctgtttagct aatattctat gtttaattaa
tgaatactaa ctctaagaac ccctcactga ttcactcaat agcatcttaa gtgaaaaacc
ttctattaca tgcaaaaaat cattgttttt aagataacaa aagtagggaa taaacaagct
gaacccactt ttaaaaaaaa aaaaaaaaaa aaaaaaaaaa aaaaa
```

I.M.A.G.E. Consortium Clone ID numbers and the corresponding GenBank accession numbers of sequences identified as belonging to the I.M.A.G.E. Consortium and UniGene clusters, are listed below. Also included are sequences that are not identified as having a Clone ID number but still identified as being those of IL17RB. The sequences include those of the "sense" and complementary strands sequences corresponding to IL17RB. The sequence of each GenBank accession number is presented in the Sequence Listing.

Table (i)

| Clone ID numbers | GenBank accession numbers |
|---|---|
| 2985728 | AW675096, AW673932, BC000980 |
| 5286745 | BI602183 |
| 5278067 | BI458542 |
| 5182255 | BI823321 |
| 924000 | AA514396 |
| 3566736 | BF110326 |
| 3195409 | BE466508 |
| 3576775 | BF740045 |
| 2772915 | AW299271 |
| 1368826 | AA836217 |
| 1744837 | AI203628 |
| 2285564 | AI627783 |
| 2217709 | AI744263 |
| 2103651 | AI401622 |

-continued

| Clone ID numbers | GenBank accession numbers |
|---|---|
| 2419487 | AI826949 |
| 3125592 | BE047352 |
| 2284721 | AI911549 |
| 3643302 | BF194822 |
| 1646910 | AI034244 |
| 1647001 | AI033911 |
| 3323709 | BF064177 |
| 1419779 | AA847767 |
| 2205190 | AI538624 |
| 2295838 | AI913613 |
| 2461335 | AI942234 |
| 2130362 | AI580483 |
| 2385555 | AI831909 |
| 2283817 | AI672344 |
| 2525596 | AW025192 |
| 454687 | AA677205 |
| 1285273 | AA721647 |
| 3134106 | BF115018 |
| 342259 | W61238, W61239 |
| 1651991 | AI032064 |
| 2687714 | AW236941 |
| 3302808 | BG057174 |
| 2544461 | AW058532 |
| 122014 | T98360, T98361 |
| 2139250 | AI470845 |
| 2133899 | AI497731 |

-continued

| Clone ID numbers | GenBank accession numbers |
|---|---|
| 121300 | T96629, T96740 |
| 162274 | H25975, H25941 |
| 3446667 | BE539514, BX282554 |
| 156864 | R74038, R74129 |
| 4611491 | BG433769 |
| 4697316 | BG530489 |
| 429376 | AA007528, AA007529 |
| 5112415 | BI260259 |
| 701357 | AA287951, AA287911 |
| 121909 | T97852, T97745 |
| 268037 | N40294 |
| 1307489 | AA809841 |
| 1357543 | AA832389 |
| 48442 | H14692 |
| 1302619 | AA732635 |
| 1562857 | AA928257 |
| 1731938 | AI184427 |
| 1896025 | AI298577 |
| 2336350 | AI692717 |
| 1520997 | AA910922 |
| 240506 | H90761 |
| 2258560 | AI620122 |
| 1569921 | AI793318, AA962325, AI733290 |
| 6064627 | BQ226353 |
| 299018 | W04890 |
| 5500181 | BM455231 |
| 2484011 | BI492426 |
| 4746376 | BG674622 |
| 233783 | BX111256 |
| 1569921 | BX117618 |

-continued

| Clone ID numbers | GenBank accession numbers |
|---|---|
| 450450 | AA682806 |
| 1943085 | AI202376 |
| 2250390 | AI658949 |
| 4526156 | BG403405 |
| 3249181 | BE673417 |
| 2484395 | AW021469 |
| 30515867 | CF455736 |
| 2878155 | AW339874 |
| 4556884 | BG399724 |
| 3254505 | BF475787 |
| 3650593 | BF437145 |
| 233783 | H64601 |
| None (mRNA sequences) | AF212365, AF208110, AF208111, AF250309, AK095091 |
| None | BM983744, CB305764, BM715988, BM670929, BI792416, BI715216, N56060, CB241389, AV660618, BX088671, CB154426, CA434589, CA412162, CA314073, BF921554, BF920093, AV685699, AV650175, BX483104, CD675121, BE081436, AW970151, AW837146, AW368264, D25960, AV709899, BX431018, AL535617, AL525465, BX453536, BX453537, AV728945, AV728939, AV727345 |

In one preferred embodiment, any sequence, or unique portion thereof, of the following IL17RB sequence, identified by AF208111 or AF208111.1, may be used in the practice of the invention.

```
SEQ ID NO:3 (sequence for IL17RB):
CGGCGATGTCGCTCGTGCTGATAAGCCTGGCCGCGCTGTGCAGGAGCGCCGTACCCCGAG
AGCCGACCGTTCAATGTGGCTCTGAAACTGGGCCATCTCCAGAGTGGATGCTACAACATG
ATCTAATCCCCGGAGACTTGAGGGACCTCCGAGTAGAACCTGTTACAACTAGTGTTGCAA
CAGGGGACTATTCAATTTTGATGAATGTAAGCTGGGTACTCCGGGCAGATGCCAGCATCC
GCTTGTTGAAGGCCACCAAGATTTGTGTGACGGGCAAAAGCAACTTCCAGTCCTACAGCT
GTGTGAGGTGCAATTACACAGAGGCCTTCCAGACTCAGACCAGACCCTCTGGTGGTAAAT
GGACATTTTCCTATATCGGCTTCCCTGTAGAGCTGAACACAGTCTATTTCATTGGGGCCC
ATAATATTCCTAATGCAAATATGAATGAAGATGGCCCTTCCATGTCTGTGAATTTCACCT
CACCAGGCTGCCTAGACCACATAATGAAATATAAAAAAAAGTGTGTCAAGGCCGGAAGCC
TGTGGGATCCGAACATCACTGCTTGTAAGAAGAATGAGGAGACAGTAGAAGTGAACTTCA
CAACCACTCCCCTGGGAAACAGATACATGGCTCTTATCCAACACAGCACTATCATCGGGT
TTTCTCAGGTGTTTGAGCCACACCAGAAGAAACAAACGCGAGCTTCAGTGGTGATTCCAG
TGACTGGGGATAGTGAAGGTGCTACGGTGCAGGTAAAGTTCAGTGAGCTGCTCTGGGGAG
GGAAGGGACATAGAAGACTGTTCCATCATTCATTGCTTTTAAGGATGAGTTCTCTCTTGT
CAAATGCACTTCTGCCAGCAGACACCAGTTAAGTGGCGTTCATGGGGGTTCTTTCGCTGC
AGCCTCCACCGTGCTGAGGTCAGGAGGCCGACGTGGCAGTTGTGGTCCCTTTTGCTTGTA
TTAATGGCTGCTGACCTTCCAAAGCACTTTTTATTTTCATTTTCTGTCACAGACACTCAG
GGATAGCAGTACCATTTTACTTCCGCAAGCCTTTAACTGCAAGATGAAGCTGCAAAGGGT
TTGAAATGGGAAGGTTTGAGTTCCAGGCAGCGTATGAACTCTGGAGAGGGGCTGCCAGTC
CTCTCTGGGCCGCAGCGGACCCAGCTGGAACACAGGAAGTTGGAGCAGTAGGTGCTCCTT
CACCTCTCAGTATGTCTCTTTCAACTCTAGTTTTTGAAGTGGGGACACAGGAAGTCCAGT
GGGGACACAGCCACTCCCCAAAGAATAAGGAACTTCCATGCTTCATTCCCTGGCATAAAA
AGTGNTCAAACACACCAGAGGGGGCAGGCACCAGCCAGGGTATGATGGGTACTACCCTTT
TCTGGAGAACCATAGACTTCCCTTACTACAGGGACTTGCATGTCCTAAAGCACTGGCTGA
AGGAAGCCAAGAGGATCACTGCTGCTCCTTTTTTGTAGAGGAAATGTTTGTGTACGTGGT
AAGATATGACCTAGCCCTTTTAGGTAAGCGAACTGGTATGTTAGTAACGTGTACAAAGTT
TAGGTTCAGACCCCGGGAGTCTTGGGCATGTGGGTCTCGGGTCACTGGTTTTGACTTTAG
GGCTTTGTTACAGATGTGTGACCAAGGGGAAAATGTGCATGACAACACTAGAGGTAGGGG
CGAAGCCAGAAAGAAGGGAAGTTTTGGCTGAAGTAGGAGTCTTGGTGAGATTTTGCTGTG
ATGCATGGTGTGAACTTTCTGAGCCTCTTGTTTTTCCTCAGCTGACTCCATATTTTCCTA
CTTGTGGCAGCGACTGCATCCGACATAAAGGAACAGTTGTGCTCTGCCCACAAACAGGCG
TCCCTTTCCCTCTGGATAACAACAAAAGCAAGCCGGGAGGCTGGCTGCCTCTCCTCCTGC
TGTCTCTGCTGGTGGCCACATGGGTGCTGGTGGCAGGGATCTATCTAATGTGGAGGCACG
AAAGGATCAAGAAGACTTCCTTTTCTACCACCACACTACTGCCCCCCATTAAGGTTCTTG
TGGTTTACCCATCTGAAATATGTTTCCATCACACAATTTGTTACTTCACTGAATTTCTTC
AAAACCATTGCAGAAGTGAGGTCATCCTTGAAAAGTGGCAGAAAAAGAAAATAGCAGAGA
TGGGTCCAGTGCAGTGGCTTGCCACTCAAAAGAAGGCAGCAGACAAAGTCGTCTTCCTTC
TTTCCAATGACGTCAACAGTGTGTGCGATGGTACCTGTGGCAAGAGCGAGGGCAGTCCCA
GTGAGAACTCTCAAGACCTCTTCCCCCTTGCCTTTAACCTTTTCTGCAGTGATCTAAGAA
GCCAGATTCATCTGCACAAATACGTGGTGGTCTACTTTAGAGAGATTGATACAAAAGACG
ATTACAATGCTCTCAGTGTCTGCCCCAAGTACCACTTCATGAAGGATGCCACTGCTTTCT
```

-continued

```
GTGCAGAACTTCTCCATGTCAAGCAGCAGGTGTCAGCAGGAAAAAGATCACAAGCCTGCC
ACGATGGCTGCTGCTCCTTGTAGCCCACCCATGAGAAGCAAGAGACCTTAAAGGCTTCCT
ATCCCACCAATTACAGGGAAAAAACGTGTGATGATCCTGAAGCTTACTATGCAGCCTACA
AACAGCCTTAGTAATTAAAACATTTTATACCAATAAAATTTTCAAATATTACTAACTAAT
GTAGCATTAACTAACGATTGGAAACTACATTTACAACTTCAAAGCTGTTTTATACATAGA
AATCAATTACAGCTTTAATTGAAAACTGTAACCATTTTGATAATGCAACAATAAAGCATC
TTCCAAAAAAAAAAAAAAAAAAAAAAAAAAAAAAA
```

In another set of preferred embodiments of the invention, any sequence, or unique portion thereof, of the CACNA1D sequences of the I.M.A.G.E. Consortium cluster NM_000720, as well as the UniGene *Homo sapiens* cluster Hs.399966, may be used. Similarly, any sequence encoding all or a part of the protein encoded by any CACNA1D sequence disclosed herein may be used. The consensus sequence of the I.M.A.G.E. Consortium cluster is as follows, with the assigned coding region (ending with a termination codon) underlined and preceded by the 5' untranslated and/or non-coding region and followed by the 3' untranslated and/or non-coding region:

```
SEQ ID NO:4 (consensus sequence for CACNA1D, identified as
NM_000720 or NM_000720.1)
agaataaggg cagggaccgc ggctcctatc tcttggtgat ccccttcccc attccgcccc

cgcctcaacg cccagcacag tgccctgcac acagtagtcg ctcaataaat gttcgtggat

gatgatgatg atgatgatga aaaaaatgca gcatcaacgg cagcagcaag cggaccacgc

gaacgaggca aactatgcaa gaggcaccag acttcctctt tctggtgaag gaccaacttc

tcagccgaat agctccaagc aaactgtcct gtcttggcaa gctgcaatcg atgctgctag

acaggccaag gctgcccaaa ctatgagcac ctctgcaccc ccacctgtag gatctctctc

ccaaagaaaa cgtcagcaat acgccaagag caaaaaacag ggtaactcgt ccaacagccg

acctgcccgc gcccttttct gtttatcact caataacccc atccgaagag cctgcattag

tatagtggaa tggaaaccat ttgacatatt tatattattg gctatttttg ccaattgtgt

ggccttagct atttacatcc cattccctga agatgattct aattcaacaa atcataactt

ggaaaaagta gaatatgcct tcctgattat ttttacagtc gagacatttt tgaagattat

agcgtatgga ttattgctac atcctaatgc ttatgttagg aatggatgga atttactgga

ttttgttata gtaatagtag gattgtttag tgtaattttg gaacaattaa ccaaagaaac

agaaggcggg aaccactcaa gcggcaaatc tggaggcttt gatgtcaaag ccctccgtgc

ctttcgagtg ttgcgaccac ttcgactagt gtcagggtg cccagtttac aagttgtcct

gaactccatt ataaaagcca tggttcccct ccttcacata gcccttttgg tattatttgt

aatcataatc tatgctatta taggattgga actttttatt ggaaaaatgc acaaaacatg

tttttttgct gactcagata tcgtagctga agaggaccca gctccatgtg cgttctcagg

gaatggacgc cagtgtactg ccaatggcac ggaatgtagg agtggctggg ttggcccgaa

cggaggcatc accaactttg ataactttgc ctttgccatg cttactgtgt ttcagtgcat

caccatggag ggctggacag acgtgctcta ctgggtaaat gatgcgatag gatgggaatg

gccatgggtg tattttgtta gtctgatcat ccttggctca tttttcgtcc ttaacctggt

tcttggtgtc cttagtggag aattctcaaa ggaaagagag aaggcaaaag cacggggaga

tttccagaag ctccgggaga agcagcagct ggaggaggat ctaaagggct acttggattg

gatcacccaa gctgaggaca tcgatccgga gaatgaggaa gaaggaggag aggaaggcaa

acgaaatact agcatgccca ccagcgagac tgagtctgtg aacacagaga acgtcagcgg

tgaaggcgag aaccgaggct gctgtggaag tctctggtgc tggtggagac ggagaggcgc

ggccaaggcg gggccctctg ggtgtcggcg gtggggtcaa gccatctcaa aatccaaact

cagccgacgc tggcgtcgct ggaaccgatt caatcgcaga agatgtaggg ccgccgtgaa
```

-continued gtctgtcacg ttttactggc tggttatcgt cctggtgttt ctgaacacct taaccatttc ctctgagcac tacaatcagc cagattggtt gacacagatt caagatattg ccaacaaagt cctcttggct ctgttcacct gcgagatgct ggtaaaaatg tacagcttgg gcctccaagc atatttcgtc tctcttttca accggtttga ttgcttcgtg gtgtgtggtg gaatcactga gacgatcctg gtggaactgg aaatcatgtc tcccctgggg atctctgtgt ttcggtgtgt gcgcctctta agaatcttca aagtgaccag gcactggact tccctgagca acttagtggc atccttatta aactccatga agtccatcgc ttcgctgttg cttctgcttt ttctcttcat tatcatcttt tccttgcttg ggatgcagct gtttggcggc aagtttaatt ttgatgaaac gcaaaccaag cggagcacct ttgacaattt ccctcaagca cttctcacag tgttccagat cctgacaggc gaagactgga atgctgtgat gtacgatggc atcatggctt acgggggccc atcctcttca ggaatgatcg tctgcatcta cttcatcatc ctcttcattt gtggtaacta tattctactg aatgtcttct tggccatcgc tgtagacaat ttggctgatg ctgaaagtct gaacactgct cagaaagaag aagcggaaga aaaggagagg aaaaagattg ccagaaaaga gagcctagaa aataaaaaga acaacaaacc agaagtcaac cagatagcca acagtgacaa caaggttaca attgatgact atagagaaga ggatgaagac aaggacccct atccgccttg cgatgtgcca gtaggggaag aggaagagga agaggaggag gatgaacctg aggttcctgc cggaccccgt cctcgaagga tctcggagtt gaacatgaag gaaaaaattg cccccatccc tgaagggagc gctttcttca ttcttagcaa gaccaacccg atccgcgtag gctgccacaa gctcatcaac caccacatct tcaccaacct catccttgtc ttcatcatgc tgagcagcgc tgccctggcc gcagaggacc ccatccgcag ccactccttc cggaacacga tactgggtta ctttgactat gccttcacag ccatctttac tgttgagatc ctgttgaaga tgacaacttt tggagctttc ctccacaaag ggcccttctg caggaactac ttcaatttgc tggatatgct ggtggttggg gtgtctctgg tgtcatttgg gattcaatcc agtgccatct ccgttgtgaa gattctgagg gtcttaaggg tcctgcgtcc cctcagggcc atcaacagag caaaaggact taagcacgtg gtccagtgcg tcttcgtggc catccggacc atcggcaaca tcatgatcgt cactaccctc ctgcagttca tgtttgcctg tatcggggtc cagttgttca aggggaagtt ctatcgctgt acggatgaag ccaaaagtaa ccctgaagaa tgcaggggac ttttcatcct ctacaaggat ggggatgttg acagtcctgt ggtccgtgaa cggatctggc aaaacagtga tttcaacttc gacaacgtcc tctctgctat gatggcgctc ttcacagtct ccacgtttga gggctggcct gcgttgctgt ataaagccat cgactcgaat ggagagaaca tcggcccaat ctacaaccac cgcgtggaga tctccatctt cttcatcatc tacatcatca ttgtagcttt cttcatgatg aacatctttg tgggctttgt catcgttaca tttcaggaac aaggagaaaa agagtataag aactgtgagc tggacaaaaa tcagcgtcag tgtgttgaat acgccttgaa agcacgtccc ttgcggagat acatccccaa aaacccctac cagtacaagt tctggtacgt ggtgaactct tcgcctttcg aatacatgat gtttgtcctc atcatgctca acacactctg cttggccatg cagcactacg agcagtccaa gatgttcaat gatgccatgg acattctgaa catggtcttc accggggtgt tcaccgtcga gatggttttg aaagtcatcg catttaagcc taaggggtat tttagtgacg cctggaacac gtttgactcc ctcatcgtaa tcggcagcat tatagacgtg gccctcagcg aagcggaccc aactgaaagt gaaaatgtcc ctgtcccaac tgctacacct gggaactctg aagagagcaa tagaatctcc atcacctttt tccgtctttt -continued ccgagtgatg cgattggtga agcttctcag caggggggaa ggcatccgga cattgctgtg gacttttatt aagtcctttc aggcgctccc gtatgtggcc ctcctcatag ccatgctgtt cttcatctat gcggtcattg gcatgcagat gtttgggaaa gttgccatga gagataacaa ccagatcaat aggaacaata acttccagac gtttccccag gcggtgctgc tgctcttcag gtgtgcaaca ggtgaggcct ggcaggagat catgctggcc tgtctcccag ggaagctctg tgaccctgag tcagattaca accccgggga ggagtataca tgtgggagca actttgccat tgtctatttc atcagttttt acatgctctg tgcatttctg atcatcaatc tgtttgtggc tgtcatcatg gataatttcg actatctgac ccgggactgg tctattttgg ggcctcacca tttagatgaa ttcaaaagaa tatggtcaga atatgaccct gaggcaaagg gaaggataaa acaccttgat gtggtcactc tgcttcgacg catccagcct cccctggggt ttgggaagtt atgtccacac agggtagcgt gcaagagatt agttgccatg aacatgcctc tcaacagtga cgggacagtc atgtttaatg caaccctgtt tgctttggtt cgaacggctc ttaagatcaa gaccgaaggg aacctggagc aagctaatga agaacttcgg gctgtgataa agaaaatttg gaagaaaacc agcatgaaat tacttgacca agttgtccct ccagctggtg atgatgaggt aaccgtgggg aagttctatg ccactttcct gatacaggac tactttagga aattcaagaa acggaaagaa caaggactgg tgggaaagta ccctgcgaag aacaccacaa ttgccctaca ggcgggatta aggacactgc atgacattgg gccagaaatc cggcgtgcta tatcgtgtga tttgcaagat gacgagcctg aggaaacaaa acgagaagaa gaagatgatg tgttcaaaag aaatggtgcc ctgcttggaa accatgtcaa tcatgttaat agtgatagga gagattccct tcagcagacc aataccaccc accgtcccct gcatgtccaa aggccttcaa ttccacctgc aagtgatact gagaaaccgc tgtttcctcc agcaggaaat tcggtgtgtc ataaccatca taaccataat tccataggaa agcaagttcc cacctcaaca aatgccaatc tcaataatgc caatatgtcc aaagctgccc atggaaagcg gcccagcatt gggaaccttg agcatgtgtc tgaaaatggg catcattctt cccacaagca tgaccgggag cctcagagaa ggtccagtgt gaaaagaacc cgctattatg aaacttacat taggtccgac tcaggagatg aacagctccc aactatttgc cgggaagacc cagagataca tggctatttc agggaccccc actgcttggg ggagcaggag tatttcagta gtgaggaatg ctacgaggat gacagctcgc ccacctggag caggcaaaac tatggctact acagcagata cccaggcaga aacatcgact ctgagaggcc ccgaggctac catcatcccc aaggattctt ggaggacgat gactcgcccg tttgctatga ttcacggaga tctccaagga gacgcctact acctcccacc ccagcatccc accggagatc ctccttcaac tttgagtgcc tgcgccggca gagcagccag gaagaggtcc cgtcgtctcc catcttcccc catcgcacgg ccctgcctct gcatctaatg cagcaacaga tcatggcagt tgccggccta gattcaagta aagcccagaa gtactcaccg agtcactcga cccggtcgtg ggccacccct ccagcaaccc ctccctaccg ggactggaca ccgtgctaca ccccctgat ccaagtggag cagtcagagg ccctggacca ggtgaacggc agcctgccgt ccctgcaccg cagctcctgg tacacagacg agcccgacat ctcctaccgg actttcacac cagccagcct gactgtcccc agcagcttcc ggaacaaaaa cagcgacaag cagaggagtg cggacagctt ggtggaggca gtcctgatat ccgaaggctt gggacgctat gcaagggacc caaaatttgt gtcagcaaca aaacacgaaa tcgctgatgc ctgtgacctc accatcgacg agatggagag tgcagccagc accctgctta atgggaacgt gcgtccccga gccaacgggg atgtgggccc -continued cctctcacac cggcaggact atgagctaca ggactttggt cctggctaca gcgacgaaga gccagaccct gggagggatg aggaggacct ggcggatgaa atgatatgca tcaccacctt gtagccccca gcgaggggca gactggctct ggcctcaggt ggggcgcagg agagccaggg gaaaagtgcc tcatagttag gaaagtttag gcactagttg ggagtaatat tcaattaatt agacttttgt ataagagatg tcatgcctca agaaagccat aaacctggta ggaacaggtc ccaagcggtt gagcctggca gagtaccatg cgctcggccc cagctgcagg aaacagcagg ccccgccctc tcacagagga tgggtgagga ggccagacct gccctgcccc attgtccaga tgggcactgc tgtggagtct gcttctccca tgtaccaggg caccaggccc acccaactga aggcatggcg gcggggtgca ggggaaagtt aaaggtgatg acgatcatca cacctcgtgt cgttacctca gccatcggtc tagcatatca gtcactgggc ccaacatatc catttttaaa ccctttcccc caaatacact gcgtcctggt tcctgtttag ctgttctgaa ata I.M.A.G.E. Consortium Clone ID numbers and the corresponding GenBank accession numbers of sequences identified as belonging to the I.M.A.G.E. Consortium and UniGene clusters, are listed below. Also included are sequences that are not identified as having a Clone ID number but still identified as being those of CACNA1D. The sequences include those of the "sense" and complementary strands sequences corresponding to CACNA1D. The sequence of each GenBank accession number is presented in the Sequence Listing.

Table (ii)

| Clone ID numbers | GenBank accession numbers |
|---|---|
| 5676430 | BM128550 |
| 5197948 | BI755471 |
| 6027638 | BQ549084, BQ549571 |
| 2338956 | AI693324 |
| 36581 | R25307, R46658 |
| 49630 | H29256, H29339 |
| 4798765 | BG716371 |
| 2187310 | AI537488 |
| 838231 | AA458692 |
| 2111614 | AI393327 |
| 2183482 | AI520947 |
| 1851007 | AI248998 |
| 1675503 | AI075844 |
| 2434923 | AI869807 |
| 2434924 | AI869800 |
| 1845827 | AI243110 |
| 2511756 | AI955764 |
| 628568 | AA192669, AA192157 |
| 2019331 | AI361691 |
| 2337381 | AI914244 |
| 2503579 | AW008769 |
| 2503626 | AW008794 |
| 1160989 | AA877582 |
| 1653475 | AI051972 |
| 1627755 | AI017959 |
| 287750 | N79331, N62240 |
| 1867677 | AI240933 |
| 1618303 | AI015031 |
| 1881344 | AI290994 |
| 1408031 | AA861160 |
| 1557035 | AA915941 |
| 956303 | AA493341 |
| 2148234 | AI467998 |
| 1499899 | AA885585 |
| 1647592 | AI033648 |
| 2341185 | AI697633 |
| 981603 | AA523647 |
| 6281678 | BQ710377 |
| 6278348 | BQ706920 |

-continued

| Clone ID numbers | GenBank accession numbers |
|---|---|
| 5876024 | BQ016847 |
| 6608849 | CA943595 |
| 5440464 | BM008196 |
| 5209489 | BI769856 |
| 5183025 | BI758971 |
| 880540 | AA468565 |
| 757337 | AA437099 |
| 6608849 | CA867864 |
| 461797 | AA682690 |
| 434787 | AA701888 |
| 6151588 | BU182632 |
| 6295618 | BQ898429 |
| 6300779 | BQ711800 |
| 434811 | AA703120 |
| 1568025 | AA978315 |
| 3220210 | BE550599 |
| 3214121 | BE502741 |
| 3009312 | AW872382 |
| 2733394 | AW444663 |
| 2872156 | AW341279 |
| 30514550 | CF456750 |
| 2718456 | AW139850 |
| 2543682 | AW029633 |
| 2492730 | AI963788 |
| 2545866 | AI951788 |
| 2272081 | AI680744 |
| 2152336 | AI601252 |
| 2146429 | AI459166 |
| 1274498 | AA885750 |
| 2272081 | BX092736 |
| 287750 | BX114568 |
| 3233645 | BE672659 |
| 289209 | N78509, N73668 |
| 277086 | N46744, N39597 |
| 3272340 | BF439267 |
| 3273859 | BF436153 |
| 3568401 | BF110611 |
| None (mRNA sequences) | M76558, AF088004, M83566 |
| None | CB410657, BQ372430, BQ366601, BQ324528, BQ318830, AL708030, BM509161, N85902, BQ774355, CA774243, CA436347, CA389011, BU679327, BU608029, BU073743, BE175413, AW969248, AI908115, BF754485, BI015409, BG202552, BF883669, BF817590, BF807128, BF806160, BF805244, BF805235, BF805080, T27949, BE836638, BE770685, BE769065, |

In one preferred embodiment, any sequence, or unique portion thereof, of the following CACNA1D sequence, identified by AI240933 or AI240933.1, may be used in the practice of the invention.

SEQ ID NO:5 (sequence for CACNA1D):

TTTTTTTTTTTTTTTTTTTTTCTTACAAAGAAAAATTTAATATTCGATGAGAGGTTGAAC

CAGGCTTAAAGCAGACATACTAGGAAATGGTGCAGCCTGTAAGAATGCCAGTTTGTAAGT

ACTGACTTTGGAAAAGATCATCGCCTCTATCAGACACTTAGGGTCCTGGTCTGGCAATTT

TGGCCTGATGTGATGCCACAAGACCCAACAGAGAGAGACACAGAGTCCAGGATAATGTTG

ACAGTGGTGTAGCCCTTTAGGAGAAATGGCGCTCCCTGCGGCTGGTATTAGGTTACCATT

GGCACCGAAGGAACCAGGAGGATAAGAATATCCATAATTTCAGAGCTGCCCTGGCACAGT

ACCTGCCCCGTCGGAGGCTCTCACTGGCAAATGACAGCTCTGTGCAAGGAGCACTCCCAA

GTATAAAAATTATTACACAGTTTTATTCTGAAGAACATTTTGCATTTTAATAAAAAAGGA

TTTATGTCAGGAAAGAGTCATTTACAAACCTTGAAGTGTTTTTGCCTGGATCAGAGTAAG

AATGTCTTAAGAAGAGGTTTGTAAGGTCTTCATAACAAAGTGGTGTTTGTTATTTACAAA

AAAAAAAAAAAAAAAAAATTAACAGGTTGTCTGTATACTATTAAAAATTTTGGACCAAAAA

AAAAAAAAAAAAAAA

In another set of preferred embodiments of the invention, any sequence, or unique portion thereof, of the HOXB13 sequences of the I.M.A.G.E. Consortium cluster NM_006361, as well as the UniGene *Homo sapiens* cluster Hs.66731, may be used. Similarly, any sequence encoding all or a part of the protein encoded by any HOXB13 sequence disclosed herein may be used. The consensus sequence of the I.M.A.G.E. Consortium cluster is as follows, with the assigned coding region (ending with a termination codon) underlined and preceded by the 5' untranslated and/or non-coding region and followed by the 3' untranslated and/or non-coding region:

SEQ ID NO:6 (consensus sequence for HOXB13, identified as NM_006361 or NM_006361.2)

cgaatgcagg cgacttgcga gctgggagcg atttaaaacg ctttggattc ccccggcctg ggtggggaga gcgagctggg tgccccctag attccccgcc cccgcacctc atgagccgac cctcggctcc atggagcccg gcaattatgc caccttggat ggagccaagg atatcgaagg cttgctggga gcgggagggg ggcggaatct ggtcgcccac tcccctctga ccagccaccc agcggcgcct acgctgatgc ctgctgtcaa ctatgccccc ttggatctgc caggctcggc ggagccgcca aagcaatgcc acccatgccc tggggtgccc caggggacgt ccccagctcc cgtgccttat ggttactttg gaggcgggta ctactcctgc cgagtgtccc ggagctcgct gaaaccctgt gcccaggcag ccaccctggc cgcgtacccc gcggagactc ccacggccgg ggaagagtac cccagtcgcc ccactgagtt tgccttctat ccgggatatc cgggaaccta ccacgctatg gccagttacc tggacgtgtc tgtggtgcag actctgggtg ctcctggaga accgcgacat gactccctgt tgcctgtgga cagttaccag tcttgggctc tcgctggtgg ctggaacagc cagatgtgtt gccagggaga acagaaccca ccaggtccct tttggaaggc agcatttgca gactccagcg ggcagcaccc tcctgacgcc tgcgcctttc gtcgcggccg caagaaacgc attccgtaca gcaaggggca gttgcgggag ctggagcggg agtatgcggc taacaagttc atcaccaagg acaagaggcg caagatctcg gcagccacca gcctctcgga gcgccagatt accatctggt ttcagaaccg ccgggtcaaa gagaagaagg ttctcgccaa ggtgaagaac agcgctaccc cttaagagat ctccttgcct gggtgggagg agcgaaagtg ggggtgtcct ggggagacca gaaacctgcc aagcccaggc tggggccaag gactctgctg agaggcccct agagacaaca cccttcccag gccactggct gctggactgt tcctcaggag cggcctgggt acccagtatg tgcagggaga cggaacccca tgtgacaggc ccactccacc agggttccca aagaacctgg cccagtcata atcattcatc ctcacagtgg caataatcac gataaccagt I.M.A.G.E. Consortium Clone ID numbers and the corresponding GenBank accession numbers of sequences identified as belonging to the I.M.A.G.E. Consortium and UniGene clusters, are listed below. Also included are sequences that are not identified as having a Clone ID number but still identified as being those of HOXB 13. The sequences include those of the "sense" and complementary strands sequences corresponding to HOXB 13. The sequence of each GenBank accession number is presented in the Sequence Listing.

Table (iii)

| Clone ID numbers | GenBank accession numbers |
|---|---|
| 4250486 | BF676461, BC007092 |
| 5518335 | BM462617 |
| 4874541 | BG752489 |
| 4806039 | BG778198 |
| 3272315 | CB050884, CB050885 |
| 4356740 | BF965191 |
| 6668163 | BU930208 |
| 1218366 | AA807966 |
| 2437746 | AI884491 |
| 1187697 | AA652388 |
| 3647557 | BF446158 |
| 1207949 | AA657924 |
| 1047774 | AA644637 |
| 3649397 | BF222357 |
| 971664 | AA527613 |
| 996191 | AA533227 |
| 813481 | AA456069, AA455572, BX117624 |
| 6256333 | BQ673782 |
| 2408470 | AI814453 |
| 2114743 | AI417272 |
| 998548 | AA535663 |
| 2116027 | AI400493 |
| 3040843 | AW779219 |
| 1101311 | AA594847 |
| 1752062 | AI150430 |
| 898712 | AA494387 |
| 1218874 | AA662643 |
| 2460189 | AI935940 |
| 986283 | AA532530 |
| 1435135 | AA857572 |
| 1871750 | AI261980 |
| 3915135 | BE888751 |
| 2069668 | AI378797 |
| 667188 | AA234220, AA236353 |
| 1101561 | AA588193 |
| 1170268 | AI821103, AI821851, AA635855 |
| 2095067 | AI420753 |
| 4432770 | BG180547 |
| 783296 | AA468306, AA468232 |
| 3271646 | CB050115, CB050116 |
| 1219276 | AA661819 |
| 30570598 | CF146837 |
| 30570517 | CF146763 |
| 30568921 | CF144902 |
| 3099071 | CF141511 |
| 3096992 | CF139563 |
| 3096870 | CF139372 |
| 3096623 | CF139319 |
| 3096798 | CF139275 |
| 30572408 | CF122893 |
| 2490082 | AI972423 |
| 2251055 | AI918975 |
| 2419308 | AI826991 |
| 2249105 | AI686312 |
| 2243362 | AI655923 |
| 30570697 | CF146922 |
| 3255712 | BF476369 |
| 3478356 | BF057410 |
| 3287977 | BE645544 |
| 3287746 | BE645408 |
| 3621499 | BE388501 |
| 30571128 | CF147366 |
| 30570954 | CF147143 |
| None (mRNA sequences) | BT007410, BC007092, U57052, U81599 |
| None | CB120119, CB125764, AU098628, CB126130, BI023924, BM767063, BM794275, BQ363211, BM932052, AA357646, AW609525, CB126919, AW609336, AW609244, BF855145, AU126914, CB126449, AW582404, BX641644 |

In one preferred embodiment, any sequence, or unique portion thereof, of the following HOXB13 sequence, identified by BC007092 or BC007092.1, may be used in the practice of the invention.

```
SEQ ID NO:7 (sequence for HOXB13):
GGATTCCCCCGGCCTGGGTGGGGAGAGCGAGCTGGGTGCCCCCTAGATTCCCCGCCCCCG
CACCTCATGAGCCGACCCTCGGCTCCATGGAGCCCGGCAATTATGCCACCTTGGATGGAG
CCAAGGATATCGAAGGCTTGCTGGGAGCGGGAGGGGGGCGGAATCTGGTCGCCCACTCCC
CTCTGACCAGCCACCCAGCGGCGCCTACGCTGATGCCTGCTGTCAACTATGCCCCCTTGG
ATCTGCCAGGCTCGGCGGAGCCGCCAAAGCAATGCCACCCATGCCCTGGGGTGCCCCAGG
GGACGTCCCCAGCTCCCGTGCCTTATGGTTACTTTGGAGGCGGGTACTACTCCTGCCGAG
TGTCCCGGAGCTCGCTGAAACCCTGTGCCCAGGCAGCCACCCTGGCCGCGTACCCCGCGG
AGACTCCCACGGCCGGGGAAGAGTACCCCAGCCGCCCCACTGAGTTTGCCTTCTATCCGG
GATATCCGGGAACCTACCAGCCTATGGCCAGTTACCTGGACGTGTCTGTGGTGCAGACTC
TGGGTGCTCCTGGAGAACCGCGACATGACTCCCTGTTGCCTGTGGACAGTTACCAGTCTT
GGGCTCTCGCTGGTGGCTGGAACAGCCAGATGTGTTGCCAGGGAGAACAGAACCCACCAG
GTCCCTTTTGGAAGGCAGCATTTGCAGACTCCAGCGGGCAGCACCCTCCTGACGCCTGCG
CCTTTCGTCGCGGCCGCAAGAAACGCATTCCGTACAGCAAGGGGCAGTTGCGGGAGCTGG
AGCGGGAGTATGCGGCTAACAAGTTCATCACCAAGGACAAGAGGCGCAAGATCTCGGCAG
CCACCAGCCTCTCGGAGCGCCAGATTACCATCTGGTTTCAGAACCGCCGGGTCAAAGAGA
AGAAGGTTCTCGCCAAGGTGAAGAACAGCGCTACCCCTTAAGAGATCTCCTTGCCTGGGT
GGGAGGAGCGAAAGTGGGGGTGTCCTGGGGAGACCAGGAACCTGCCAAGCCCAGGCTGGG
GCCAAGGACTCTGCTGAGAGGCCCCTAGAGACAACACCCTTCCCAGGCCACTGGCTGCTG
GACTGTTCCTCAGGAGCGGCCTGGGTACCCAGTATGTGCAGGGAGACGGAACCCCATGTG
ACAGCCCACTCCACCAGGGTTCCCAAAGAACCTGGCCCAGTCATAATCATTCATCCTGAC
AGTGGCAATAATCACGATAACCAGTACTAGCTGCCATGATCGTTAGCCTCATATTTTCTA
TCTAGAGCTCTGTAGAGCACTTTAGAAACCGCTTTCATGAATTGAGCTAATTATGAATAA
ATTTGGAAAAAAAAAAAAAAAAAAAAAAAAAAAAAA
```

Sequences identified by SEQ ID NO. are provided using conventional representations of a DNA strand starting from the 5' phosphate linked end to the 3' hydroxyl linked end. The assignment of coding regions is generally by comparison to available consensus sequence(s) and therefore may contain inconsistencies relative to other sequences assigned to the same cluster. These have no effect on the practice of the invention because the invention can be practiced by use of shorter segments (or combinations thereof) of sequences unique to each of the three sets described above and not affected by inconsistencies. As non-limiting examples, a segment of IL17BR, CACNA1D, or HOXB13 nucleic acid sequence composed of a 3' untranslated region sequence and/or a sequence from the 3' end of the coding region may be used as a probe for the detection of IL17BR, CACNA1D, or HOXB13 expression, respectively, without being affected by the presence of any inconsistency in the coding regions due to differences between sequences. Similarly, the use of an antibody which specifically recognizes IL17BR, CACNA1D, or HOXB13 protein to detect its expression would not be affected by the presence of any inconsistency in the representation of the coding regions provided above.

As will be appreciated by those skilled in the art, some of the above sequences include 3' poly A (or poly T on the complementary strand) stretches that do not contribute to the uniqueness of the disclosed sequences. The invention may thus be practiced with sequences lacking the 3' poly A (or poly T) stretches. The uniqueness of the disclosed sequences refers to the portions or entireties of the sequences which are found only in IL17BR, CACNA1D, or HOXB13 nucleic acids, including unique sequences found at the 3' untranslated portion of the genes. Preferred unique sequences for the practice of the invention are those which contribute to the consensus sequences for each of the three sets such that the unique sequences will be useful in detecting expression in a variety of individuals rather than being specific for a polymorphism present in some individuals. Alternatively, sequences unique to an individual or a subpopulation may be used. The preferred unique sequences are preferably of the lengths of polynucleotides of the invention as discussed herein.

To determine the (increased or decreased) expression levels of the above described sequences in the practice of the present invention, any method known in the art may be utilized. In one preferred embodiment of the invention, expression based on detection of RNA which hybridizes to polynucleotides containing the above described sequences is used. This is readily performed by any RNA detection or amplification+detection method known or recognized as equivalent in the art such as, but not limited to, reverse transcription-PCR (optionally real-time PCR), the methods disclosed in U.S. patent application Ser. No. 10/062,857 entitled "Nucleic Acid Amplification" filed on Oct. 25, 2001 as well as U.S. Provisional Patent Application No. 60/298,847 (filed Jun. 15, 2001) and 60/257,801 (filed Dec. 22, 2000), the methods disclosed in U.S. Pat. No. 6,291,170, and quantitative PCR. Methods to identify increased RNA stability (resulting in an observation of increased expression) or decreased RNA stability (resulting in an observation of decreased expression) may also be used. These methods include the detection of sequences that increase or decrease the stability of mRNAs containing the IL17BR, CACNA1D, or HOXB13 sequences disclosed herein. These methods also include the detection of increased mRNA degradation.

In particularly preferred embodiments of the invention, polynucleotides having sequences present in the 3' untranslated and/or non-coding regions of the above disclosed sequences are used to detect expression or non-expression of IL17BR, CACNA1 D, or HOXB13 sequences in breast cells in the practice of the invention. Such polynucleotides may optionally contain sequences found in the 3' portions of the coding regions of the above disclosed sequences. Polynucleotides containing a combination of sequences from the coding and 3' non-coding regions preferably have the sequences arranged contiguously, with no intervening heterologous sequence(s).

Alternatively, the invention may be practiced with polynucleotides having sequences present in the 5' untranslated and/or non-coding regions of IL17BR, CACNA1D, or HOXB13 sequences in breast cells to detect their levels of expression. Such polynucleotides may optionally contain sequences found in the 5' portions of the coding regions. Polynucleotides containing a combination of sequences from the coding and 5' non-coding regions preferably have the sequences arranged contiguously, with no intervening heterologous sequence(s). The invention may also be practiced with sequences present in the coding regions of IL17BR, CACNA1D, or HOXB13.

Preferred polynucleotides contain sequences from 3' or 5' untranslated and/or non-coding regions of at least about 20, at least about 22, at least about 24, at least about 26, at least about 28, at least about 30, at least about 32, at least about 34, at least about 36, at least about 38, at least about 40, at least about 42, at least about 44, or at least about 46 consecutive nucleotides. The term "about" as used in the previous sentence refers to an increase or decrease of 1 from the stated numerical value. Even more preferred are polynucleotides containing sequences of at least or about 50, at least or about 100, at least about or 150, at least or about 200, at least or about 250, at least or about 300, at least or about 350, or at least or about 400 consecutive nucleotides. The term "about" as used in the preceding sentence refers to an increase or decrease of 10% from the stated numerical value.

Sequences from the 3' or 5' end of the above described coding regions as found in polynucleotides of the invention are of the same lengths as those described above, except that they would naturally be limited by the length of the coding region. The 3' end of a coding region may include sequences up to the 3' half of the coding region. Conversely, the 5' end of a coding region may include sequences up the 5' half of the coding region. Of course the above described sequences, or the coding regions and polynucleotides containing portions thereof, may be used in their entireties.

Polynucleotides combining the sequences from a 3' untranslated and/or non-coding region and the associated 3' end of the coding region are preferably at least or about 100, at least about or 150, at least or about 200, at least or about 250, at least or about 300, at least or about 350, or at least or about 400 consecutive nucleotides. Preferably, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

In another embodiment of the invention, polynucleotides containing deletions of nucleotides from the 5' and/or 3' end of the above disclosed sequences may be used. The deletions are preferably of 1-5, 5-10, 10-15, 15-20, 20-25, 25-30, 30-35, 35-40, 40-45, 45-50, 50-60, 60-70, 70-80, 80-90, 90-100, 100-125, 125-150, 150-175, or 175-200 nucleotides from the 5' and/or 3' end, although the extent of the deletions would naturally be limited by the length of the disclosed sequences and the need to be able to use the polynucleotides for the detection of expression levels.

Other polynucleotides of the invention from the 3' end of the above disclosed sequences include those of primers and optional probes for quantitative PCR. Preferably, the primers and probes are those which amplify a region less than about 350, less than about 300, less than about 250, less than about 200, less than about 150, less than about 100, or less than about 50 nucleotides from the from the polyadenylation signal or polyadenylation site of a gene or expressed sequence.

In yet another embodiment of the invention, polynucleotides containing portions of the above disclosed sequences including the 3' end may be used in the practice of the invention. Such polynucleotides would contain at least or about 50, at least or about 100, at least about or 150, at least or about 200, at least or about 250, at least or about 300, at least or about 350, or at least or about 400 consecutive nucleotides from the 3' end of the disclosed sequences.

The invention thus also includes polynucleotides used to detect IL17BR, CACNA1D, or HOXB13 expression in breast cells. The polynucleotides may comprise a shorter polynucleotide consisting of sequences found in the above provided SEQ ID NOS in combination with heterologous sequences not naturally found in combination with IL17BR, CACNA1D, or HOXB13 sequences.

As non-limiting examples, a polynucleotide comprising one of the following sequences may be used in the practice of the invention.

SEQ ID NO:8:
CAATTACAGGGAAAAAACGTGTGATGATCCTGAAGCTTACTATGCAGCCTACAAACAGCC

SEQ ID NO:9:
GCTCTCACTGGCAAATGACAGCTCTGTGCAAGGAGCACTCCCAAGTATAAAAATTATTAC

SEQ ID NO:10:
GATCGTTAGCCTCATATTTTCTATCTAGAGCTCTGTAGAGCACTTTAGAAACCGCTTTCA

Stated differently, the invention may be practiced with a polynucleotide consisting of the sequence of SEQ ID NOS:8, 9 or 10 in combination with one or more heterologous sequences that are not normally found with SEQ ID NOS:8, 9 or 10. Alternatively, the invention may also be practiced with a polynucleotide consisting of the sequence of SEQ ID NOS: 8, 9 or 10 in combination with one or more naturally occurring sequences that are normally found with SEQ ID NOS:8, 9 or 10.

Polynucleotides with sequences comprising SEQ ID NOS:8 or 9, either naturally occurring or synthetic, may be used to detect nucleic acids which are over expressed in breast cancer cells that are responsive to TAM treatment. Polynucleotides with sequences comprising SEQ ID NO:10, either naturally occurring or synthetic, may be used to detect nucleic acids which are under expressed in breast cancer cells that are responsive to TAM treatment.

Additional sequences that may be used in polynucleotides as described above for SEQ ID NOS:8 and 9 are the following:

SEQ ID NO:11:
TGCCTAATTTCACTCTCAGAGTGAGGCAGGTAACTGGGGCTCCACTGGGTCACTCTGAGA

SEQ ID NO:12:
TTGGAAGCAGAGTCCCTCTAAAGGTAACTCTTGTGGTCACTCAATATTGTATTGGCATTT

SEQ ID NO:13:
ACGTTAGACTTTTGCTGGCATTCAAGTCATGGCTAGTCTGTGTATTTAATAAATGTGTGT

SEQ ID NO:14:
CTGGTCAGCCACTCTGACTTTTCTACCACATTAAATTCTCCATTACATCTCACTATTGGT

SEQ ID NO:15:
TACAACTTCTGAATGCTGCACATTCTTCCAAAATGATCCTTAGCACAATCTATTGTATGA

SEQ ID NO:16:
GGGATGGCCTTTAGGCCACAGTAGTGTCTGTGTTAAGTTCACTAAATGTGTATTTAATGA

SEQ ID NO:17:
CTCAAAGTGCTAAAGCTATGGTTGACTGCTCTGGTGTTTTTATATTCATTCGTGCTTTAG

Additional sequences that may be used in polynucleotides as described above for SEQ ID NO:10 are the following:

```
SEQ ID NO:18:
CTATGGGGATGGTCCACTGTCACTGTTTCTCTGCTGTTGCAAATACATGGATAACACATT

SEQ ID NO:19:
ACTGGAAAAGCAGATGGTCTGACTGTGCTATGGCCTCATCATCAAGACTTTCAATCCTAT

SEQ ID NO:20:
ACGCCAAGCTCTTCAGTGAAGACACGATGTTATTAAAAGCCTGTTTTAGGGACTGCAAAA

SEQ ID NO:21:
TTTTTGTAAAATCTTTAACCTTCCCTTTGTTCTTCATGTACACGCTGAACTGCAATTCTT

SEQ ID NO:22:
AACCTGGGGCATTTAGGGCAGAGGACAAAAGGATGTCAGCAATTGCTTGGGCTGCTTGGC

SEQ ID NO:23:
CTGGAACCTCTGGACTCCCCATGCTCTAACTCCCACACTCTGCTATCAGAAACTTAAACT

SEQ ID NO:24:
AACCCCAGAACCATCTAAGACATGGGATTCAGTGATCATGTGGTTCTCCTTTTAACTTAC

SEQ ID NO:25:
GGCCATGTGCCATGGTATTTGGGTCCTGGGAGGGTGGGTGAAATAAAGGCATACTGTCTT

SEQ ID NO:26:
GTGTAGGCAGTCATGGCACCAAAGCCACCAGACTGACAAATGTGTATCAGATGCTTTTGT

SEQ ID NO:27:
GAAAACCTCTTCAAAAGACAAAAAGCTGGCACTGCATTCTCTCTCTGTAGCAGGACAGAA

SEQ ID NO:28:
CACATCTTTAGGGTCAGTGAACAATGGGGCACATTTGGCACTAGCTTGAGCCCAACTCTG

SEQ ID NO:29:
GCCTTAATTTCCTCATCTGAAAACTGGAAGGCCTGACTTGACTTGTTGAGCTTAAGATCC

SEQ ID NO:30:
CTTCAGGGGAGGATCAAGCTTTGAACCAAAGCCAATCACTGGCTTGATTTGTGTTTTTTA

SEQ ID NO:31:
ACAAGTTTTCACTGAATGAGCATGGCAGTGCCACTCAAGAAAATGAATCTCCAAAGTATC
```

Additionally, polynucleotides containing other sequences, particularly unique sequences, present in naturally occurring nucleic acid molecules comprising SEQ ID NOS:8-31 may be used in the practice of the invention.

Other polynucleotides for use in the practice of the invention include those that have sufficient homology to those described above to detect expression by use of hybridization techniques. Such polynucleotides preferably have about or 95%, about or 96%, about or 97%, about or 98%, or about or 99% identity with IL17BR, CACNA1D, or HOXB13 sequences as described herein. Identity is determined using the BLAST algorithm, as described above. The other polynucleotides for use in the practice of the invention may also be described on the basis of the ability to hybridize to polynucleotides of the invention under stringent conditions of about 30% v/v to about 50% formamide and from about 0.01M to about 0.15M salt for hybridization and from about 0.01M to about 0.15M salt for wash conditions at about 55 to about 65° C. or higher, or conditions equivalent thereto.

In a further embodiment of the invention, a population of single stranded nucleic acid molecules comprising one or both strands of a human IL17BR or CACNA1D sequence is provided as a probe such that at least a portion of said population may be hybridized to one or both strands of a nucleic acid molecule quantitatively amplified from RNA of a breast cancer cell. The population may be only the antisense strand of a human IL17BR or CACNA1D sequence such that a sense strand of a molecule from, or amplified from, a breast cancer cell may be hybridized to a portion of said population. The population preferably comprises a sufficiently excess amount of said one or both strands of a human IL17BR or CACNA1D sequence in comparison to the amount of expressed (or amplified) nucleic acid molecules containing a complementary IL17BR or CACNA1D sequence from a normal breast cell. This condition of excess permits the increased amount of nucleic acid expression in a breast cancer cell to be readily detectable as an increase.

Alternatively, the population of single stranded molecules is equal to or in excess of all of one or both strands of the nucleic acid molecules amplified from a breast cancer cell such that the population is sufficient to hybridize to all of one or both strands. Preferred cells are those of a breast cancer patient that is ER+ or for whom tamoxifen treatment is contemplated. The single stranded molecules may of course be the denatured form of any IL17BR and/or CACNA1D sequence containing double stranded nucleic acid molecule or polynucleotide as described herein.

The population may also be described as being hybridized to IL17BR or CACNA1D sequence containing nucleic acid molecules at a level of at least twice as much as that by nucleic acid molecules of a normal breast cell. As in the embodiments described above, the nucleic acid molecules may be those quantitatively amplified from a breast cancer cell such that they reflect the amount of expression in said cell.

The population is preferably immobilized on a solid support, optionally in the form of a location on a microarray. A portion of the population is preferably hybridized to nucleic acid molecules quantitatively amplified from a non-normal or abnormal breast cell by real time PCR. The real time PCR may be practiced by use of amplified RNA from a breast cancer cell, as long as the amplification used was quantitative with respect to IL17BR or CACNA1D containing sequences.

In another embodiment of the invention, expression based on detection of DNA status may be used. Detection of the HOXB13 DNA as methylated, deleted or otherwise inactivated, may be used as an indication of decreased expression as found in non-normal breast cells. This may be readily performed by PCR based methods known in the art. The status of the promoter regions of HOXB13 may also be assayed as an indication of decreased expression of HOXB13 sequences. A non-limiting example is the methylation status of sequences found in the promoter region.

Conversely, detection of the DNA of a sequence as amplified may be used for as an indication of increased expression as found in non-normal breast cells. This may be readily performed by PCR based, fluorescent in situ hybridization (FISH) and chromosome in situ hybridization (CISH) methods known in the art.

A preferred embodiment using a nucleic acid based assay to determine expression is by immobilization of one or more of the sequences identified herein on a solid support, including, but not limited to, a solid substrate as an array or to beads or bead based technology as known in the art. Alternatively, solution based expression assays known in the art may also be used. The immobilized sequence(s) may be in the form of polynucleotides as described herein such that the polynucleotide would be capable of hybridizing to a DNA or RNA corresponding to the sequence(s).

The immobilized polynucleotide(s) may be used to determine the state of nucleic acid samples prepared from sample breast cancer cell(s), optionally as part of a method to detect ER status in said cell(s). Without limiting the invention, such a cell may be from a patient suspected of being afflicted with, or at risk of developing, breast cancer. The immobilized polynucleotide(s) need only be sufficient to specifically hybridize to the corresponding nucleic acid molecules derived from the sample (and to the exclusion of detectable or significant hybridization to other nucleic acid molecules).

In yet another embodiment of the invention, a ratio of the expression levels of two of the disclosed genes may be used to predict response to TAM treatment. Preferably, the ratio is that of two genes with opposing patterns of expression, such as an underexpressed gene to an overexpressed gene. Non-limiting examples include the ratio of HOXB13 over IL17BR or the ratio of HOXB13 over CACNA1D. This aspect of the invention is based in part on the observation that such a ratio has a stronger correlation with TAM treatment outcome than the expression level of either gene alone. For example, the ratio of HOXB13 over IL17BR has an observed classification accuracy of 77%.

Additional Embodiments of the Invention

In embodiments where only one or a few genes are to be analyzed, the nucleic acid derived from the sample breast cancer cell(s) may be preferentially amplified by use of appropriate primers such that only the genes to be analyzed are amplified to reduce contaminating background signals from other genes expressed in the breast cell. Alternatively, and where multiple genes are to be analyzed or where very few cells (or one cell) is used, the nucleic acid from the sample may be globally amplified before hybridization to the immobilized polynucleotides. Of course RNA, or the cDNA counterpart thereof may be directly labeled and used, without amplification, by methods known in the art.

Sequence expression based on detection of a presence, increase, or decrease in protein levels or activity may also be used. Detection may be performed by any immunohistochemistry (IHC) based, bodily fluid based (where a IL17BR, CACNA1D, and/or HOXB13 polypeptide is found in a bodily fluid, such as but not limited to blood), antibody (including autoantibodies against the protein where present) based, ex foliate cell (from the cancer) based, mass spectroscopy based, and image (including used of labeled ligand where available) based method known in the art and recognized as appropriate for the detection of the protein. Antibody and image based methods are additionally useful for the localization of tumors after determination of cancer by use of cells obtained by a non-invasive procedure (such as ductal lavage or fine needle aspiration), where the source of the cancerous cells is not known. A labeled antibody or ligand may be used to localize the carcinoma(s) within a patient.

Antibodies for use in such methods of detection include polyclonal antibodies, optionally isolated from naturally occurring sources where available, and monoclonal antibodies, including those prepared by use of IL17BR, CACNA1D, and/or HOXB13 polypeptides as antigens. Such antibodies, as well as fragments thereof (including but not limited to Fab fragments) function to detect or diagnose non-normal or cancerous breast cells by virtue of their ability to specifically bind IL17BR, CACNA1D, or HOXB13 polypeptides to the exclusion of other polypeptides to produce a detectable signal. Recombinant, synthetic, and hybrid antibodies with the same ability may also be used in the practice of the invention. Antibodies may be readily generated by immunization with a IL17BR, CACNA1D, or HOXB13 polypeptide, and polyclonal sera may also be used in the practice of the invention.

Antibody based detection methods are well known in the art and include sandwich and ELISA assays as well as Western blot and flow cytometry based assays as non-limiting examples. Samples for analysis in such methods include any that contain IL17BR, CACNA1D, or HOXB13 polypeptides. Non-limiting examples include those containing breast cells and cell contents as well as bodily fluids (including blood, serum, saliva, lymphatic fluid, as well as mucosal and other cellular secretions as non-limiting examples) that contain the polypeptides.

The above assay embodiments may be used in a number of different ways to identify or detect the response to TAM treatment based on gene expression in a breast cancer cell sample from a patient. In some cases, this would reflect a secondary screen for the patient, who may have already undergone mammography or physical exam as a primary screen. If positive from the primary screen, the subsequent needle biopsy, ductal lavage, fine needle aspiration, or other analogous methods may provide the sample for use in the assay embodiments before, simultaneous with, or after assaying for ER status. The present invention is particularly useful in combination with non-invasive protocols, such as ductal lavage or fine needle aspiration, to prepare a breast cell sample.

The present invention provides a more objective set of criteria, in the form of gene expression profiles of a discrete set of genes, to discriminate (or delineate) between breast cancer outcomes. In particularly preferred embodiments of the invention, the assays are used to discriminate between good and poor outcomes after tamoxifen treatment. Comparisons that discriminate between outcomes after about 10, about 20, about 30, about 40, about 50, about 60, about 70, about 80, about 90, about 100, or about 150 months may be performed.

While good and poor survival outcomes may be defined relatively in comparison to each other, a "good" outcome may be viewed as a better than 50% survival rate after about 60 months post surgical intervention to remove breast cancer tumor(s). A "good" outcome may also be a better than about 60%, about 70%, about 80% or about 90% survival rate after about 60 months post surgical intervention. A "poor" outcome may be viewed as a 50% or less survival rate after about 60 months post surgical intervention to remove breast cancer tumor(s). A "poor" outcome may also be about a 70% or less survival rate after about 40 months, or about a 80% or less survival rate after about 20 months, post surgical intervention.

In another embodiment of the invention based on the expression of multiple genes in an expression pattern or profile, the isolation and analysis of a breast cancer cell sample may be performed as follows:

(1) Ductal lavage or other non-invasive procedure is performed on a patient to obtain a sample.

(2) Sample is prepared and coated onto a microscope slide. Note that ductal lavage results in clusters of cells that are cytologically examined as stated above.

(3) Pathologist or image analysis software scans the sample for the presence of non-normal and/or atypical breast cancer cells.

(4) If such cells are observed, those cells are harvested (e.g. by microdissection such as LCM).

(5) RNA is extracted from the harvested cells.

(6) RNA is purified, amplified, and labeled.

(7) Labeled nucleic acid is contacted with a microarray containing polynucleotides of the genes identified herein as correlated to discriminations between breast cancer outcomes under suitable hybridization conditions, then processed and scanned to obtain a pattern of intensities of each spot (relative to a control for general gene expression in cells) which determine the level of expression of the gene(s) in the cells.

(8) The pattern of intensities is analyzed by comparison to the expression patterns of the genes in known samples of breast cancer cells correlated with outcomes (relative to the same control).

A specific example of the above method would be performing ductal lavage following a primary screen, observing and collecting non-normal and/or atypical cells for analysis. The comparison to known expression patterns, such as that made possible by a model generated by an algorithm (such as, but not limited to nearest neighbor type analysis, SVM, or neural networks) with reference gene expression data for the different breast cancer survival outcomes, identifies the cells as being correlated with subjects with good or poor outcomes. Another example would be taking a breast tumor removed from a subject after surgical intervention, optionally converting all or part of it to an FFPE sample prior to subsequent isolation and preparation of breast cancer cells from the tumor for determination/identification of atypical, non-normal, or cancer cells, and isolation of said cells followed by steps 5 through 8 above.

Alternatively, the sample may permit the collection of both normal as well as cancer cells for analysis. The gene expression patterns for each of these two samples will be compared to each other as well as the model and the normal versus individual comparisons therein based upon the reference data set. This approach can be significantly more powerful that the cancer cells only approach because it utilizes significantly more information from the normal cells and the differences between normal and cancer cells (in both the sample and reference data sets) to determine the breast cancer outcome of the patient based on gene expression in the cancer cells from the sample.

In yet another embodiment of the invention based on the expression of a few genes, the isolation and analysis of a breast cancer cell sample may be performed as follows:

(1) Ductal lavage or other non-invasive procedure is performed on a patient to obtain a sample.

(2) Sample is prepared and coated onto a microscope slide. Note that ductal lavage results in clusters of cells that are cytologically examined as stated above.

(3) Pathologist or image analysis software scans the sample for the presence of atypical cells.

(4) If atypical cells are observed, those cells are harvested (e.g. by microdissection such as LCM).

(5) RNA is extracted from the harvested cells.

(6) RNA is assayed, directly or after conversion to cDNA or amplification therefrom, for the expression of IL17BR, CACNA1D, and/or HOXB13 sequences.

One example of the above method would be performing ductal lavage following a primary screen, observing and collecting non-normal cells (or cells suspected of being non-normal) for analysis. Alternatively, the sample may permit the collection of both normal and non-normal cells (or cells suspected of being non-normal) for analysis. The expression levels of IL17BR, CACNA1D, and/or HOXB13 sequences in each of these two populations may be compared to each other. This approach can be significantly more powerful than one using the non-normal cells only approach because it utilizes information from the normal cells and the differences between normal and non-normal cells to determine the status of the non-normal cells from the sample.

With use of the present invention, skilled physicians may prescribe or withhold TAM treatment based on prognosis determined via practice of the instant invention.

The above discussion is also applicable where a palpable lesion is detected followed by fine needle aspiration or needle biopsy of cells from the breast. The cells are plated and reviewed by a pathologist or automated imaging system which selects cells for analysis as described above.

The present invention may also be used, however, with solid tissue biopsies, including those stored as an FFPE specimen. For example, a solid biopsy may be collected and prepared for visualization followed by determination of expression of one or more genes identified herein to determine the breast cancer outcome. As another non-limiting example, a solid biopsy may be collected and prepared for visualization followed by determination of increased IL17BR and/or CACNA1D expression. One preferred means is by use of in situ hybridization with polynucleotide or protein identifying probe(s) for assaying expression of said gene(s). An analogous method may be used to detect decreased expression of HOXB13 sequences.

In an alternative method, the solid tissue biopsy may be used to extract molecules followed by analysis for expression of one or more gene(s). This provides the possibility of leaving out the need for visualization and collection of only cancer cells or cells suspected of being cancerous. This method may of course be modified such that only cells that have been positively selected are collected and used to extract molecules for analysis. This would require visualization and selection as a prerequisite to gene expression analysis. In the case of an FFPE sample, cells may be obtained followed by RNA extraction, amplification and detection as described herein.

In a further modification of the above, both normal cells and cancer cells are collected and used to extract molecules for analysis of gene expression. The approach, benefits and results are as described above using non-invasive sampling.

In a further alternative to all of the above, the sequence(s) identified herein may be used as part of a simple PCR or array based assay simply to determine the response to TAM treatment by use of a sample from a non-invasive sampling procedure. The detection of sequence expression from samples may be by use of a single microarray able to assay expression of the disclosed sequences as well as other sequences, including sequences known not to vary in expression levels between normal and non-normal breast cells, for convenience and improved accuracy.

Other uses of the present invention include providing the ability to identify breast cancer cell samples as having different responses to TAM treatment for further research or study. This provides an advance based on objective genetic/molecular criteria.

The genes identified herein also may be used to generate a model capable of predicting the breast cancer survival and recurrence outcomes of an ER+ breast cell sample based on the expression of the identified genes in the sample. Such a model may be generated by any of the algorithms described herein or otherwise known in the art as well as those recognized as equivalent in the art using gene(s) (and subsets thereof) disclosed herein for the identification of breast cancer outcomes. The model provides a means for comparing expression profiles of gene(s) of the subset from the sample against the profiles of reference data used to build the model. The model can compare the sample profile against each of the reference profiles or against a model defining delineations made based upon the reference profiles. Additionally, relative values from the sample profile may be used in comparison with the model or reference profiles.

In a preferred embodiment of the invention, breast cell samples identified as normal and cancerous from the same subject may be analyzed, optionally by use of a single microarray, for their expression profiles of the genes used to generate the model. This provides an advantageous means of identifying survival and recurrence outcomes based on relative differences from the expression profile of the normal sample. These differences can then be used in comparison to differences between normal and individual cancerous reference data which was also used to generate the model.

Articles of Manufacture

The materials and methods of the present invention are ideally suited for preparation of kits produced in accordance with well known procedures. The invention thus provides kits comprising agents (like the polynucleotides and/or antibodies described herein as non-limiting examples) for the detection of expression of the disclosed sequences. Such kits, optionally comprising the agent with an identifying description or label or instructions relating to their use in the methods of the present invention, are provided. Such a kit may comprise containers, each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes of the present invention (e.g., appropriate length poly(T) or random primers linked to a promoter reactive with the RNA polymerase). A set of instructions will also typically be included.

The methods provided by the present invention may also be automated in whole or in part. All aspects of the present invention may also be practiced such that they consist essentially of a subset of the disclosed genes to the exclusion of material irrelevant to the identification of breast cancer survival outcomes via a cell containing sample.

Having now generally described the invention, the same will be more readily understood through reference to the following examples which are provided by way of illustration, and are not intended to be limiting of the present invention, unless specified.

EXAMPLES

Example 1

Gene Expression Signature Predicting TAM Treatment Outcome in Breast Cancer

A cohort of 62 estrogen receptor-positive breast cancer patients were uniformly treated with the anti-estrogen drug tamoxifen (TAM), and followed for up to 14 years. 33 patients recurred whereas 29 patients remained disease-free during the entire follow up periods. Correlating gene expression patterns with tumor recurrence/non-recurrence, a set of genes was discovered whose expression levels differ significantly between these two groups. This gene expression signature can thus be used to predict whether a patient will respond to TAM as first-line treatment based on the gene expression profile of a routine biopsy of the primary cancer.

Laser capture microdissection was performed on each tumor biopsy to procure pure populations of cancerous epithelial cells, which were then analyzed on a 22000-gene high-density oligonucleotide microarray. The top 25% genes with the greatest variances across all samples (n=5475) were selected for signature extraction. Genes showing statistically significant correlations with tumor recurrence/non-recurrence were identified using two different statistical techniques.

In the first approach, patients were divided into two groups (recurrence vs. non-recurrence), and a standard t-test was performed for each gene, which identified 149 genes with p values <0.001. The results for this analysis are shown in Table 1. Genes identified by their accession numbers correlate with non-responders when the t-statistic is less than zero while genes with a t-statistic greater than zero correlate to positive responders.

TABLE 1

149-gene signature identified by t-test

| Accession | p value | t-statistic | Description |
|---|---|---|---|
| BC002595 | 5.49E−10 | −8.186189 | NDUFB7 \| NADH dehydrogenase (ubiquinone) 1 beta subcomplex, 7 (18 kD, B18) |
| BC002705 | 1.65E−09 | −7.550191 | C22orf3 \| chromosome 22 open reading frame 3 |
| AL080126 | 1.82E−09 | −7.410723 | KIAA0683 \| KIAA0683 gene product |
| AI767799 | 2.02E−09 | −7.768777 | BBC3 \| Bcl-2 binding component 3 |

TABLE 1-continued 149-gene signature identified by t-test

| Accession | p value | t-statistic | Description |
|---|---|---|---|
| AL021683 | 2.78E−09 | −7.083131 | SCO2 \| SCO cytochrome oxidase deficient homolog 2 (yeast) |
| BC000507 | 4.38E−09 | −7.026423 | MAAT1 \| melanoma-associated antigen recognised by cytotoxic T lymphocytes |
| AK027124 | 1.70E−08 | −6.740214 | FLJ23471 \| hypothetical protein FLJ23471 |
| BC016737 | 1.99E−08 | −6.742271 | MPST \| mercaptopyruvate sulfurtransferase |
| BC011874 | 3.53E−08 | −6.327036 | MGC20486 \| hypothetical protein MGC20486 |
| BC008832 | 3.86E−08 | −6.388736 | HMGIY \| high-mobility group (nonhistone chromosomal) protein isoforms I and Y |
| AF044959 | 5.20E−08 | −6.222993 | NDUFS6 \| NADH dehydrogenase (ubiquinone) Fe-S protein 6 (13 kD) (NADH-coenzyme Q reductase) |
| BC016832 | 6.61E−08 | −6.627917 | MGC4607 \| hypothetical protein MGC4607 |
| BC011680 | 6.61E−08 | −6.427017 | DKFZp434G0522 \| hypothetical protein DKFZp434G0522 |
| AA811922 | 6.75E−08 | −6.634444 | FLJ10140 \| hypothetical protein FLJ10140 |
| AW075691 | 1.03E−07 | −6.272638 | KIAA1847 \| hypothetical protein FLJ14972 |
| AK024627 | 1.14E−07 | −6.019024 | FLJ20974 \| hypothetical protein FLJ20974 |
| BC002389 | 1.15E−07 | −6.05372 | ATP5D \| ATP synthase, H+ transporting, mitochondrial F1 complex, delta subunit |
| AK055295 | 1.24E−07 | −6.391213 | *Homo sapiens* cDNA FLJ30733 fis, clone FEBRA2000129, moderately similar to PROBABLE TRNA (5-METHYLAMINOMETHYL-2-THIOURIDYLATE)-METHYLTRANSFERASE (EC 2.1.1.61) |
| BC011621 | 1.54E−07 | 5.943998 | HOOK1 \| hook1 protein |
| AK023601 | 1.69E−07 | 5.919878 | *Homo sapiens* cDNA FLJ13539 fis, clone PLACE1006640 |
| BC013959 | 1.83E−07 | −6.09348 | GNL1 \| guanine nucleotide binding protein-like 1 |
| BC018346 | 1.84E−07 | −5.929725 | LAK-4P \| expressed in activated T/LAK lymphocytes |
| AF052052 | 3.46E−07 | −5.920813 | TFPT \| TCF3 (E2A) fusion partner (in childhood Leukemia) |
| AL136921 | 3.66E−07 | −5.742098 | DKFZp586I021 \| hypothetical protein DKFZp586I021 |
| AI968598 | 6.33E−07 | −5.685799 | *Homo sapiens* cDNA FLJ12182 fis, clone MAMMA1000761 |
| BC011754 | 7.93E−07 | −5.671882 | ERP70 \| protein disulfide isomerase related protein (calcium-binding protein, intestinal-related) |
| BC014270 | 3.58E−06 | −5.155079 | PRKCZ \| protein kinase C, zeta |
| NM_001130 | 3.82E−06 | −5.120513 | AES \| amino-terminal enhancer of split |
| BF116098 | 4.09E−06 | 5.101295 | ESTs |
| BC015594 | 5.01E−06 | −5.027872 | *Homo sapiens* mRNA for FLJ00083 protein, partial cds |
| AK000081 | 5.74E−06 | −4.996636 | CDC2L1 \| cell division cycle 2-like 1 (PITSLRE proteins) |
| NM_006278 | 6.23E−06 | −4.968186 | SIAT4C \| sialyltransferase 4C (beta-galactosidase alpha-2,3-sialytransferase) |
| BC008841 | 6.32E−06 | −5.039493 | KIAA0415 \| KIAA0415 gene product |
| AI972367 | 7.05E−06 | −4.93464 | *Homo sapiens* cDNA FLJ32384 fis, clone SKMUS1000104, weakly similar to *Homo sapiens* mRNA for HEXIM1 protein, complete cds |
| AI467849 | 7.34E−06 | −4.933176 | TBC1D1 \| TBC1 (tre-2/USP6, BUB2, cdc16) domain family, member 1 |
| NM_014298 | 9.19E−06 | −4.869139 | QPRT \| quinolinate phosphoribosyltransferase (nicotinate-nucleotide pyrophosphorylase (carboxylating)) |
| H19223 | 1.15E−05 | 4.786877 | ESTs, Weakly similar to JC5238 galactosylceramide-like protein, GCP [*H. sapiens*] |
| AI638324 | 1.22E−05 | 4.783615 | *Homo sapiens* cDNA FLJ30332 fis, clone BRACE2007254 |
| AF208111 | 1.30E−05 | 4.761353 | IL17BR \| interleukin 17B receptor |
| NM_020978 | 1.34E−05 | 4.803041 | AMY2B \| amylase, alpha 2B; pancreatic |
| BC015497 | 1.59E−05 | −4.722392 | TEAD4 \| TEA domain family member 4 |
| AI561249 | 1.69E−05 | 4.681189 | KTN1 \| kinectin 1 (kinesin receptor) |
| BC004235 | 1.73E−05 | −4.684545 | DDX38 \| DEAD/H (Asp-Glu-Ala-Asp/His) box polypeptide 38 |
| NM_013347 | 1.89E−05 | 4.67568 | HSU24186 \| replication protein A complex 34 kd subunit homolog Rpa4 |
| AL117616 | 1.90E−05 | 4.645713 | SRI \| sorcin |
| AL117478 | 2.00E−05 | −4.634086 | AGS3 \| likely ortholog of rat activator of G-protein signaling 3 |
| NM_006304 | 2.28E−05 | 4.59794 | DSS1 \| Deleted in split-hand/split-foot 1 region |
| BC009507 | 2.29E−05 | −4.59323 | ISG15 \| interferon-stimulated protein, 15 kDa |
| AK025141 | 2.89E−05 | 4.529022 | *Homo sapiens* cDNA: FLJ21488 fis, clone COL05445 |
| AA581602 | 4.04E−05 | 4.43179 | ESTs |
| BC006499 | 4.22E−05 | −4.422009 | HRAS \| v-Ha-ras Harvey rat sarcoma viral oncogene homolog |
| BC007066 | 5.23E−05 | 4.379391 | CDA11 \| CDA11 protein |
| BC009869 | 5.35E−05 | 4.352129 | SERF2 \| small EDRK-rich factor 2 |
| AA206609 | 5.68E−05 | −4.339494 | *Homo sapiens* cDNA FLJ30002 fis, clone 3NB691000085 |
| AI682928 | 5.76E−05 | 4.350598 | EST |
| BC006284 | 7.29E−05 | −4.359234 | *Homo sapiens*, clone IMAGE: 3957135, mRNA, partial cds |
| AI871458 | 7.41E−05 | −4.303954 | ESTs |
| AF068918 | 7.50E−05 | −4.284961 | BIN1 \| bridging integrator 1 |
| NM_018936 | 7.50E−05 | −4.254075 | PCDHB2 \| protocadherin beta 2 |
| AI469557 | 7.83E−05 | −4.248879 | EPHB3 \| EphB3 |
| AL137521 | 8.02E−05 | −4.27827 | *Homo sapiens* mRNA; cDNA DKFZp434D0218 (from clone DKFZp434D0218); partial cds |
| AI268007 | 8.04E−05 | 4.245279 | *Homo sapiens* cDNA FLJ30137 fis, clone BRACE2000078 |
| AW070918 | 8.56E−05 | −4.21829 | ESTs, Weakly similar to T2D3_HUMAN TRANSCRIPTION INITIATION FACTOR TFIID 135 KDA SUBUNIT [*H. sapiens*] |
| AK025862 | 8.75E−05 | 4.237223 | *Homo sapiens* cDNA: FLJ22209 fis, clone HRC01496 |
| AI264644 | 9.54E−05 | −4.240955 | KIAA0775 \| KIAA0775 gene product |
| BF438928 | 9.75E−05 | 4.180144 | ESTs |
| BC001403 | 9.83E−05 | −4.17366 | CPSF5 \| cleavage and polyadenylation specific factor 5, 25 kD subunit |

TABLE 1-continued 149-gene signature identified by t-test

| Accession | p value | t-statistic | Description |
|---|---|---|---|
| AI270018 | 1.01E-04 | −4.167464 | ECE1 \| endothelin converting enzyme 1 |
| AL133427 | 1.04E-04 | 4.19331 | *Homo sapiens* mRNA full length insert cDNA clone EUROIMAGE 261172 |
| AI400775 | 1.12E-04 | −4.148062 | RABL2B \| RAB, member of RAS oncogene family-like 2B |
| AW016075 | 1.21E-04 | 4.132864 | ESTs, Weakly similar to ALUA_HUMAN !!!! ALU CLASS A WARNING ENTRY !!! [*H. sapiens*] |
| AI033912 | 1.26E-04 | 4.100849 | RLN2 \| relaxin 2 (H2) |
| AA668884 | 1.28E-04 | 4.104243 | ESTs |
| AL133661 | 1.38E-04 | 4.085685 | DKFZp434C0328 \| hypothetical protein DKFZp434C0328 |
| BC009874 | 1.40E-04 | −4.074407 | JUN \| v-jun sarcoma virus 17 oncogene homolog (avian) |
| AI357434 | 1.52E-04 | 4.055067 | HSP105B \| heat shock 105 kD |
| AF119871 | 1.54E-04 | 4.081889 | PRO2268 \| hypothetical protein PRO2268 |
| AK024715 | 1.54E-04 | 4.043172 | FLJ21062 \| hypothetical protein FLJ21062 |
| X62534 | 1.58E-04 | 4.048006 | HMG2 \| high-mobility group (nonhistone chromosomal) protein 2 |
| BI793002 | 1.60E-04 | 4.039819 | OSBPL8 \| oxysterol binding protein-like 8 |
| L13738 | 1.61E-04 | −4.041465 | ACK1 \| activated p21cdc42Hs kinase |
| AW297123 | 1.74E-04 | 4.019412 | ESTs |
| NM_020235 | 1.80E-04 | 4.011596 | BBX \| bobby sox homolog (*Drosophila*) |
| AI686003 | 1.83E-04 | 4.035297 | ESTs |
| AK022916 | 1.84E-04 | 3.989755 | ZNF281 \| zinc finger protein 281 |
| AK025701 | 1.86E-04 | −3.99009 | PLXNB2 \| plexin B2 |
| AA806831 | 1.91E-04 | −4.126686 | ESTs |
| AL117396 | 1.93E-04 | 3.982093 | DKFZP586M0622 \| DKFZP586M0622 protein |
| AW192535 | 1.93E-04 | 3.982278 | ESTs |
| AW076080 | 1.94E-04 | 3.972626 | *Homo sapiens*, clone IMAGE: 3463399, mRNA, partial cds |
| AB014541 | 1.95E-04 | −3.97255 | AATK \| apoptosis-associated tyrosine kinase |
| AK024967 | 1.96E-04 | 4.008564 | *Homo sapiens* cDNA: FLJ21314 fis, clone COL02248 |
| BC018644 | 2.10E-04 | −3.981862 | NUDT8 \| nudix (nucleoside diphosphate linked moiety X)-type motif 8 |
| AK026817 | 2.11E-04 | 3.9468 | FLJ23577 \| hypothetical protein FLJ23577 |
| BC000692 | 2.20E-04 | −3.943535 | HYAL2 \| hyaluronoglucosaminidase 2 |
| BE967259 | 2.26E-04 | 3.927279 | BCL2 \| B-cell CLL/lymphoma 2 |
| NM_004038 | 2.29E-04 | 3.946754 | AMY1A \| amylase, alpha 1A; salivary |
| AF052110 | 2.34E-04 | −3.915428 | DAF \| decay accelerating factor for complement (CD55, Cromer blood group system) |
| AW069725 | 2.38E-04 | 3.914238 | CRYZ \| crystallin, zeta (quinone reductase) |
| BM127867 | 2.44E-04 | 3.908237 | MDM1 \| nuclear protein double minute 1 |
| AL050227 | 2.50E-04 | 3.894782 | *Homo sapiens* mRNA; cDNA DKFZp586M0723 (from clone DKFZp586M0723) |
| BC005377 | 2.61E-04 | 3.949255 | ACADM \| acyl-Coenzyme A dehydrogenase, C-4 to C-12 straight chain |
| BC006437 | 2.66E-04 | −3.880036 | C321D2.4 \| hypothetical protein C321D2.4 |
| AF153330 | 2.73E-04 | 3.871579 | SLC19A2 \| solute carrier family 19 (thiamine transporter), member 2 |
| AA635853 | 2.86E-04 | 3.856068 | EST |
| AK021798 | 2.92E-04 | 3.858723 | FLJ11736 \| hypothetical protein FLJ11736 |
| BE675157 | 3.06E-04 | 3.882041 | ESTs |
| T52873 | 3.08E-04 | 3.831368 | ESTs, Moderately similar to G02075 transcription repressor zinc finger protein 85 [*H. sapiens*] |
| BE645958 | 3.30E-04 | 3.812843 | ESTs |
| BF589163 | 3.37E-04 | 3.857405 | ESTs |
| AA040945 | 3.44E-04 | −3.797113 | ESTs |
| AK001783 | 3.74E-04 | 3.771144 | FLJ10921 \| hypothetical protein FLJ10921 |
| R43003 | 4.06E-04 | 3.80021 | ESTs, Highly similar to COBW-like protein [*H. sapiens*] |
| AW135596 | 4.10E-04 | 3.742774 | FLJ10058 \| hypothetical protein FLJ10058 |
| NM_003489 | 4.20E-04 | 3.736095 | NRIP1 \| nuclear receptor interacting protein 1 |
| AL136663 | 4.25E-04 | −3.748587 | DKFZp564A176 \| hypothetical protein DKFZp564A176 |
| AI376433 | 4.47E-04 | 3.774197 | KIAA1912 \| KIAA1912 protein |
| BC015792 | 4.49E-04 | −3.725478 | *Homo sapiens*, clone MGC: 23665 IMAGE: 4866941, mRNA, complete cds |
| AI478784 | 4.63E-04 | 3.705085 | FLJ11267 \| hypothetical protein FLJ11267 |
| U50532 | 4.91E-04 | 3.723884 | CG005 \| hypothetical protein from BCRA2 region |
| AI700363 | 4.92E-04 | −3.719752 | ESTs |
| BC005956 | 5.22E-04 | 3.679274 | RLN1 \| relaxin 1 (H1) |
| AI240933 | 5.44E-04 | 3.657963 | ESTs |
| AF330046 | 5.51E-04 | 3.652748 | PIBF1 \| progesterone-induced blocking factor 1 |
| AI128331 | 5.55E-04 | 3.648721 | ENDOFIN \| endosome-associated FYVE-domain protein |
| BC008381 | 5.63E-04 | 3.654514 | IMPA1 \| inositol(myo)-1(or 4)-monophosphatase 1 |
| AF023676 | 5.64E-04 | −3.647402 | TM7SF2 \| transmembrane 7 superfamily member 2 |
| AL050179 | 5.73E-04 | 3.665736 | TPM1 \| tropomyosin 1 (alpha) |
| BC002355 | 5.73E-04 | 3.654105 | HNRPA1 \| heterogeneous nuclear ribonucleoprotein A1 |
| AK056075 | 5.84E-04 | 3.632268 | *Homo sapiens* cDNA FLJ31513 fis, clone NT2RI1000127 |
| AK024999 | 6.01E-04 | 3.641434 | *Homo sapiens* cDNA: FLJ21346 fis, clone COL02705 |
| AK000305 | 6.30E-04 | 3.666154 | FLJ20298 \| hypothetical protein FLJ20298 |
| AF085243 | 6.47E-04 | 3.601667 | ZNF236 \| zinc finger protein 236 |
| AW510501 | 6.56E-04 | 3.620023 | ARHGAP5 \| Rho GTPase activating protein 5 |
| AI953054 | 6.57E-04 | −3.59919 | TKT \| transketolase (Wernicke-Korsakoff syndrome) |
| BC012628 | 7.09E-04 | −3.610827 | TCAP \| titin-cap (telethonin) |
| BC007092 | 7.12E-04 | −3.598786 | HOXB13 \| homeo box B13 |
| AB000520 | 7.40E-04 | −3.558109 | APS \| adaptor protein with pleckstrin homology and src homology 2 domains |

TABLE 1-continued

| 149-gene signature identified by t-test | | | |
|---|---|---|---|
| Accession | p value | t-statistic | Description |
| AW150267 | 7.47E−04 | 3.566503 | C21orf9 \| chromosome 21 open reading frame 9 |
| AI800042 | 7.64E−04 | 3.575129 | ESTs |
| AF033199 | 8.01E−04 | −3.541312 | ZNF204 \| zinc finger protein 204 |
| BC002607 | 8.15E−04 | −3.529271 | KIAA1446 \| KIAA1446 protein |
| BC002480 | 8.43E−04 | −3.525938 | FLJ13352 \| hypothetical protein FLJ13352 |
| AI568728 | 9.04E−04 | −3.501174 | SKI \| v-ski sarcoma viral oncogene homolog (avian) |
| AA648536 | 9.20E−04 | −3.48714 | MYO1E \| myosin IE |
| AI335002 | 9.28E−04 | 3.502278 | PBEF \| pre-B-cell colony-enhancing factor |
| AW452172 | 9.45E−04 | 3.483191 | ESTs |
| AF334676 | 9.50E−04 | 3.476947 | TEKT3 \| tektin 3 |
| AF085233 | 9.77E−04 | 3.479809 | SGKL \| serum/glucocorticoid regulated kinase-like |

In the second approach, the actual times of recurrence or follow-up (for those who remained disease-free) were used in a Cox proportional hazard regression model using each gene as the single predictor variable, identifying 149 genes with p values (Wald statistic)<0.001. The results for this analysis are shown in Table 2. Genes identified by their accession numbers correlate with subjects likely to suffer a reoccurrence after TAM therapy when the hazard ratio is greater than one while genes with a hazard ration of less than one correlate to individuals who are likely not to suffer a reoccurrence of breast cancer.

TABLE 2

| 149-gene signature identified by Cox regression | | | |
|---|---|---|---|
| Accession | p value | hazard ratio | Description |
| BC002595 | 3.00E−08 | 1.9899702 | NDUFB7 \| NADH dehydrogenase (ubiquinone) 1 beta subcomplex, 7 (18 kD, B18) |
| BC000507 | 3.66E−08 | 2.3494974 | MAAT1 \| melanoma-associated antigen recognised by cytotoxic T lymphocytes |
| BC016832 | 5.45E−08 | 2.2890356 | MGC4607 \| hypothetical protein MGC4607 |
| BC002705 | 1.52E−07 | 2.5669791 | C22orf3 \| chromosome 22 open reading frame 3 |
| AI767799 | 1.93E−07 | 2.1989649 | BBC3 \| Bcl-2 binding component 3 |
| BC011874 | 2.51E−07 | 2.8556338 | MGC20486 \| hypothetical protein MGC20486 |
| AL021683 | 3.74E−07 | 2.1946935 | SCO2 \| SCO cytochrome oxidase deficient homolog 2 (yeast) |
| BC008832 | 4.28E−07 | 2.3960849 | HMGIY \| high-mobility group (nonhistone chromosomal) protein isoforms I and Y |
| AL080126 | 4.46E−07 | 2.1613379 | KIAA0683 \| KIAA0683 gene product |
| BC013959 | 4.68E−07 | 2.4974081 | GNL1 \| guanine nucleotide binding protein-like 1 |
| AF052052 | 5.29E−07 | 2.1949663 | TFPT \| TCF3 (E2A) fusion partner (in childhood Leukemia) |
| AA811922 | 6.00E−07 | 1.9841656 | FLJ10140 \| hypothetical protein FLJ10140 |
| BC011680 | 6.96E−07 | 2.373463 | DKFZp434G0522 \| hypothetical protein DKFZp434G0522 |
| BC016737 | 1.06E−06 | 1.8482073 | MPST \| mercaptopyruvate sulfurtransferase |
| AI968598 | 1.24E−06 | 2.6284635 | *Homo sapiens* cDNA FLJ12182 fis, clone MAMMA1000761 |
| AW075691 | 1.35E−06 | 2.0681292 | KIAA1847 \| hypothetical protein FLJ14972 |
| AK024627 | 1.53E−06 | 2.6015319 | FLJ20974 \| hypothetical protein FLJ20974 |
| AF044959 | 1.56E−06 | 2.8966077 | NDUFS6 \| NADH dehydrogenase (ubiquinone) Fe-S protein 6 (13 kD) (NADH-coenzyme Q reductase) |
| BC002389 | 1.64E−06 | 1.8888501 | ATP5D \| ATP synthase, H+ transporting, mitochondrial F1 complex, delta subunit |
| AK055295 | 3.03E−06 | 1.8815611 | *Homo sapiens* cDNA FLJ30733 fis, clone FEBRA2000129, moderately similar to PROBABLE TRNA (5-METHYLAMINOMETHYL-2-THIOURIDYLATE)-METHYLTRANSFERASE (EC 2.1.1.61) |
| BC005377 | 3.41E−06 | 0.5676057 | ACADM \| acyl-Coenzyme A dehydrogenase, C-4 to C-12 straight chain |
| H19223 | 4.47E−06 | 0.4802045 | ESTs, Weakly similar to JC5238 galactosylceramide-like protein, GCP [*H. sapiens*] |
| AK023601 | 4.81E−06 | 0.4390305 | *Homo sapiens* cDNA FLJ13539 fis, clone PLACE1006640 |
| NM_001130 | 5.72E−06 | 2.1351138 | AES \| amino-terminal enhancer of split |
| NM_014298 | 6.39E−06 | 1.8007172 | QPRT \| quinolinate phosphoribosyltransferase (nicotinate-nucleotide pyrophosphorylase (carboxylating)) |
| AK027124 | 7.12E−06 | 1.968632 | FLJ23471 \| hypothetical protein FLJ23471 |
| AL117396 | 7.58E−06 | 0.4156321 | DKFZP586M0622 \| DKFZP586M0622 protein |
| AL136921 | 8.27E−06 | 2.3643799 | DKFZp586I021 \| hypothetical protein DKFZp586I021 |
| U50532 | 8.81E−06 | 0.4216183 | CG005 \| hypothetical protein from BCRA2 region |
| BC018346 | 1.14E−05 | 1.8491373 | LAK-4P \| expressed in activated T/LAK lymphocytes |
| NM_013347 | 1.35E−05 | 0.3648298 | HSU24186 \| replication protein A complex 34 kd subunit homolog Rpa4 |

TABLE 2-continued 149-gene signature identified by Cox regression

| Accession | p value | hazard ratio | Description |
|---|---|---|---|
| BC011621 | 1.37E−05 | 0.5264059 | HOOK1 \| hook1 protein |
| BC006284 | 1.48E−05 | 2.1550372 | *Homo sapiens*, clone IMAGE: 3957135, mRNA, partial cds |
| BC004235 | 2.01E−05 | 2.4910338 | DDX38 \| DEAD/H (Asp-Glu-Ala-Asp/His) box polypeptide 38 |
| NM_006278 | 2.06E−05 | 1.9872895 | SIAT4C \| sialyltransferase 4C (beta-galactosidase alpha-2,3-sialytransferase) |
| AI972367 | 2.13E−05 | 2.1500078 | *Homo sapiens* cDNA FLJ32384 fis, clone SKMUS1000104, weakly similar to *Homo sapiens* mRNA for HEXIM1 protein, complete cds |
| BC012628 | 2.31E−05 | 2.0388066 | TCAP \| titin-cap (telethonin) |
| AA581602 | 2.44E−05 | 0.4839842 | ESTs |
| NM_018936 | 2.46E−05 | 1.4853858 | PCDHB2 \| protocadherin beta 2 |
| AA746504 | 2.68E−05 | 0.667095 | *Homo sapiens* cDNA FLJ30188 fis, clone BRACE2001267 |
| AF220030 | 2.73E−05 | 0.4441676 | TRIM6 \| tripartite motif-containing 6 |
| AI682928 | 2.90E−05 | 0.4144403 | EST |
| AA206609 | 3.05E−05 | 2.0738914 | *Homo sapiens* cDNA FLJ30002 fis, clone 3NB691000085 |
| AL117616 | 3.06E−05 | 0.5506486 | SRI \| sorcin |
| U08997 | 3.06E−05 | 0.548039 | GLUD2 \| Glutamate dehydrogenase-2 |
| BC009869 | 3.17E−05 | 0.4884412 | SERF2 \| small EDRK-rich factor 2 |
| AL137521 | 3.24E−05 | 2.4199381 | *Homo sapiens* mRNA; cDNA DKFZp434D0218 (from clone DKFZp434D0218); partial cds |
| AI871458 | 3.26E−05 | 2.0738428 | ESTs |
| BC008841 | 3.27E−05 | 1.8195551 | KIAA0415 \| KIAA0415 gene product |
| AI467849 | 4.07E−05 | 1.689976 | TBC1D1 \| TBC1 (tre-2/USP6, BUB2, cdc16) domain family, member 1 |
| BC011754 | 4.42E−05 | 1.6224459 | ERP70 \| protein disulfide isomerase related protein (calcium-binding protein, intestinal-related) |
| AL050227 | 4.44E−05 | 0.7135796 | *Homo sapiens* mRNA; cDNA DKFZp586M0723 (from clone DKFZp586M0723) |
| AK021798 | 4.56E−05 | 0.6377454 | FLJ11736 \| hypothetical protein FLJ11736 |
| AI268007 | 4.58E−05 | 0.7185686 | *Homo sapiens* cDNA FLJ30137 fis, clone BRACE2000078 |
| BC001403 | 4.70E−05 | 2.4561451 | CPSF5 \| cleavage and polyadenylation specific factor 5, 25 kD subunit |
| AK000081 | 5.38E−05 | 2.3154373 | CDC2L1 \| cell division cycle 2-like 1 (PITSLRE proteins) |
| BC014270 | 5.53E−05 | 2.0457284 | PRKCZ \| protein kinase C, zeta |
| AL117478 | 5.97E−05 | 1.7598438 | AGS3 \| likely ortholog of rat activator of G-protein signaling 3 |
| BF116098 | 7.56E−05 | 0.4180467 | ESTs |
| BC006499 | 7.83E−05 | 1.8287714 | HRAS \| v-Ha-ras Harvey rat sarcoma viral oncogene homolog |
| NM_003489 | 7.94E−05 | 0.4637752 | NRIP1 \| nuclear receptor interacting protein 1 |
| AI469557 | 8.50E−05 | 1.8599762 | EPHB3 \| EphB3 |
| AI561249 | 9.19E−05 | 0.4329273 | KTN1 \| kinectin 1 (kinesin receptor) |
| BC015497 | 9.45E−05 | 1.9287915 | TEAD4 \| TEA domain family member 4 |
| AL133661 | 1.08E−04 | 0.4897642 | DKFZp434C0328 \| hypothetical protein DKFZp434C0328 |
| BC015594 | 1.10E−04 | 2.0502453 | *Homo sapiens* mRNA for FLJ00083 protein, partial cds |
| AW135596 | 1.14E−04 | 0.6460164 | FLJ10058 \| hypothetical protein FLJ10058 |
| AI033912 | 1.18E−04 | 0.6482864 | RLN2 \| relaxin 2 (H2) |
| NM_020978 | 1.28E−04 | 0.598655 | AMY2B \| amylase, alpha 2B; pancreatic |
| BC006437 | 1.49E−04 | 2.0560166 | C321D2.4 \| hypothetical protein C321D2.4 |
| AW016075 | 1.51E−04 | 0.5312489 | ESTs, Weakly similar to ALUA_HUMAN !!!! ALU CLASS A WARNING ENTRY !!! [*H. sapiens*] |
| NM_001354 | 1.52E−04 | 1.4085552 | AKR1C2 \| aldo-keto reductase family 1, member C2 (dihydrodiol dehydrogenase 2; bile acid binding protein; 3-alpha hydroxysteroid dehydrogenase, type III) |
| BC007932 | 1.56E−04 | 0.5115812 | FLJ11588 \| hypothetical protein FLJ11588 |
| AF319520 | 1.57E−04 | 1.4189657 | ARG99 \| ARG99 protein |
| AA806831 | 1.62E−04 | 1.470609 | ESTs |
| AI638324 | 1.64E−04 | 0.4669648 | *Homo sapiens* cDNA FLJ30332 fis, clone BRACE2007254 |
| AK025141 | 1.70E−04 | 0.6098107 | *Homo sapiens* cDNA: FLJ21488 fis, clone COL05445 |
| AF068918 | 2.11E−04 | 1.7571167 | BIN1 \| bridging integrator 1 |
| AF208111 | 2.18E−04 | 0.6637063 | IL17BR \| interleukin 17B receptor |
| AK024715 | 2.34E−04 | 0.5237823 | FLJ21062 \| hypothetical protein FLJ21062 |
| BC007836 | 2.45E−04 | 1.8806038 | MDFI \| MyoD family inhibitor |
| AW192535 | 2.64E−04 | 0.46396 | ESTs |
| AA480069 | 2.68E−04 | 1.970316 | KIAA1925 \| KIAA1925 protein |
| AK025862 | 2.84E−04 | 0.4739154 | *Homo sapiens* cDNA: FLJ22209 fis, clone HRC01496 |
| AI800042 | 2.92E−04 | 0.4939835 | ESTs |
| AA977269 | 3.02E−04 | 1.3578379 | FOXD1 \| forkhead box D1 |
| BC018644 | 3.03E−04 | 1.6098715 | NUDT8 \| nudix (nucleoside diphosphate linked moiety X)-type motif 8 |
| NM_004419 | 3.08E−04 | 0.6155024 | DUSP5 \| dual specificity phosphatase 5 |
| AW070918 | 3.10E−04 | 2.0916912 | ESTs, Weakly similar to T2D3_HUMAN TRANSCRIPTION INITIATION FACTOR TFIID 135 KDA SUBUNIT [*H. sapiens*] |

TABLE 2-continued 149-gene signature identified by Cox regression

| Accession | p value | hazard ratio | Description |
|---|---|---|---|
| AA040945 | 3.22E−04 | 2.2990713 | ESTs |
| AF035282 | 3.30E−04 | 0.6524492 | C1orf21 \| chromosome 1 open reading frame 21 |
| NM_006304 | 3.34E−04 | 0.4895086 | DSS1 \| Deleted in split-hand/split-foot 1 region |
| R62589 | 3.47E−04 | 0.6003814 | ESTs |
| AI400775 | 3.52E−04 | 2.2438708 | RABL2B \| RAB, member of RAS oncogene family-like 2B |
| AI128331 | 3.60E−04 | 0.5099963 | ENDOFIN \| endosome-associated FYVE-domain protein |
| AW069725 | 3.62E−04 | 0.5812922 | CRYZ \| crystallin, zeta (quinone reductase) |
| AK024967 | 3.82E−04 | 0.4618762 | *Homo sapiens* cDNA: FLJ21314 fis, clone COL02248 |
| AK022916 | 3.88E−04 | 0.5564747 | ZNF281 \| zinc finger protein 281 |
| BC015484 | 3.92E−04 | 1.5502435 | CALB2 \| calbindin 2, (29 kD, calretinin) |
| AI953054 | 4.06E−04 | 1.9805492 | TKT \| transketolase (Wernicke-Korsakoff syndrome) |
| BE675157 | 4.28E−04 | 0.6073104 | ESTs |
| AF153330 | 4.33E−04 | 0.5983906 | SLC19A2 \| solute carrier family 19 (thiamine transporter), member 2 |
| AL133427 | 4.35E−04 | 0.4914871 | *Homo sapiens* mRNA full length insert cDNA clone EUROIMAGE 261172 |
| BF438928 | 4.77E−04 | 0.5752913 | ESTs |
| NM_002428 | 4.77E−04 | 1.81811 | MMP15 \| matrix metalloproteinase 15 (membrane-inserted) |
| AI264644 | 4.82E−04 | 1.8613174 | KIAA0775 \| KIAA0775 gene product |
| BE967259 | 4.88E−04 | 0.7445998 | BCL2 \| B-cell CLL/lymphoma 2 |
| AW076080 | 4.93E−04 | 0.5435194 | *Homo sapiens*, clone IMAGE: 3463399, mRNA, partial cds |
| T52873 | 5.05E−04 | 0.5449457 | ESTs, Moderately similar to G02075 transcription repressor zinc finger protein 85 [*H. sapiens*] |
| AF085233 | 5.10E−04 | 0.635643 | SGKL \| serum/glucocorticoid regulated kinase-like |
| BE671445 | 5.12E−04 | 0.5796479 | ESTs |
| AI356375 | 5.23E−04 | 1.7149531 | CDKN2A \| cyclin-dependent kinase inhibitor 2A (melanoma, p16, inhibits CDK4) |
| BF589163 | 5.28E−04 | 0.5585288 | ESTs |
| AA909006 | 5.35E−04 | 1.5526313 | LBP-32 \| LBP protein 32 |
| BC015792 | 5.47E−04 | 1.841097 | *Homo sapiens*, clone MGC: 23665 IMAGE: 4866941, mRNA, complete cds |
| BC000692 | 5.61E−04 | 2.0170046 | HYAL2 \| hyaluronoglucosaminidase 2 |
| AL050090 | 5.73E−04 | 0.7500215 | DKFZP586F1018 \| DKFZP586F1018 protein |
| NM_020235 | 5.94E−04 | 0.5893936 | BBX \| bobby sox homolog (*Drosophila*) |
| BF433657 | 5.99E−04 | 1.9378811 | ESTs |
| AI692302 | 6.01E−04 | 1.899281 | ESTs |
| AK024782 | 6.05E−04 | 1.9756718 | KIAA1608 \| KIAA1608 protein |
| AF124735 | 6.12E−04 | 1.4649329 | LHX2 \| LIM homeobox protein 2 |
| BC007066 | 6.12E−04 | 0.5216856 | CDA11 \| CDA11 protein |
| AW135238 | 6.20E−04 | 0.4896724 | ESTs |
| AK026747 | 6.44E−04 | 0.5015784 | LOC54103 \| hypothetical protein |
| AA542898 | 6.46E−04 | 0.7842204 | P28 \| dynein, axonemal, light intermediate polypeptide |
| BC014913 | 6.52E−04 | 0.6913458 | *Homo sapiens*, Similar to synaptotagmin-like 4, clone MGC: 17313 IMAGE: 3908307, mRNA, complete cds |
| AI270018 | 6.72E−04 | 2.0809844 | ECE1 \| endothelin converting enzyme 1 |
| L13738 | 6.90E−04 | 1.6894154 | ACK1 \| activated p21cdc42Hs kinase |
| BC002607 | 7.01E−04 | 1.5250234 | KIAA1446 \| KIAA1446 protein |
| BI793002 | 7.18E−04 | 0.4917655 | OSBPL8 \| oxysterol binding protein-like 8 |
| BC007092 | 7.20E−04 | 1.2827239 | HOXB13 \| homeo box B13 |
| BC009874 | 7.40E−04 | 1.730815 | JUN \| v-jun sarcoma virus 17 oncogene homolog (avian) |
| AF321193 | 7.41E−04 | 1.5356899 | DSCR8 \| Down syndrome critical region gene 8 |
| AK000397 | 7.70E−04 | 1.5631718 | FLJ10351 \| likely ortholog of mouse piwi like homolog 1 (*Drosophila*)-like |
| AF052110 | 7.76E−04 | 1.6400255 | DAF \| decay accelerating factor for complement (CD55, Cromer blood group system) |
| AA648536 | 8.03E−04 | 1.6290887 | MYO1E \| myosin IE |
| BF436400 | 8.31E−04 | 0.7911405 | EST |
| AL050179 | 8.59E−04 | 0.5180149 | TPM1 \| tropomyosin 1 (alpha) |
| AI700363 | 8.60E−04 | 1.3675668 | ESTs |
| NM_004038 | 8.72E−04 | 0.6247207 | AMY1A \| amylase, alpha 1A; salivary |
| AF060555 | 8.75E−04 | 1.5560891 | ESR2 \| estrogen receptor 2 (ER beta) |
| AK026756 | 8.85E−04 | 0.6360787 | KIAA1603 \| KIAA1603 protein |
| AI686003 | 8.97E−04 | 0.6087104 | ESTs |
| NM_019120 | 9.14E−04 | 1.4302118 | PCDHB8 \| protocadherin beta 8 |
| NM_020957 | 9.50E−04 | 1.4881037 | PCDHB16 \| protocadherin beta 16 |
| AI921700 | 9.73E−04 | 0.522736 | ITGAV \| integrin, alpha V (vitronectin receptor, alpha polypeptide, antigen CD51) |
| X62534 | 9.87E−04 | 0.5796731 | HMG2 \| high-mobility group (nonhistone chromosomal) protein 2 |
| BC002738 | 9.90E−04 | 1.8608522 | CRIP1 \| cysteine-rich protein 1 (intestinal) |

Between the two approaches, 114 genes were in common. At the significance level of 0.001, about 6 genes are expected by chance if there are no real differences between the patient groups, indicating that the 149 genes identified by either method are highly statistically significant.

Example 2

Kaplan-Meier Survival Curves of Patients Stratified by Cross-Validation

Kaplan-Meier analysis was performed to assess the differential survival of patients stratified by the gene expression signature. Leave-one-out-cross-validation was performed. Briefly, one of the 62 patients was left out as a test sample, and the other 61 samples were used in Cox regression to both select significant genes ($p<0.001$) and obtain gene-specific weights (Cox regression coefficients $\beta$). A linear sum of the gene-specific weights ($\beta$) times expression levels (x) across all selected genes was calculated as the overall risk score for each patient: $S=\text{sum}(\beta_i x_i)$ for all selected genes. The mid-point m between the median scores for the two patient groups (recurrence/non-recurrence) in the training set was calculated: m=(median score of recurrence group+median score of non-recurrence group)/2, and the score for the test sample S was compared with m to classify the test sample to either the recurrence (S>m, TAM signature−) or non-recurrence group (S<=m, TAM signature+). This entire procedure was repeated 62 times to generate a classification for each patient. Disease-free survival curves of the two groups as assigned by the cross-validation procedure are compared. The results are shown in FIG. 1.

Example 3

Identification of Biomarker Predictors of TAM Treatment Outcome

Samples from 60 patients with ER+ primary breast cancer, and treated with adjuvant TAM, were selected tamoxifen based on treatment outcome. 28 had developed tumor recurrence with a median time of 4 years, and 32 remained disease-free with a median follow-up of 10 years (Table 3). Patients who remained disease-free during the entire follow up period were likely to represent responders to TAM, although a small subset of them might have been cured by surgery alone. Those patients who developed tumor recurrence despite TAM therapy either did not respond or developed resistance to TAM and are hereafter referred to as non-responders for brevity. To control for known prognostic factors, tumors between these two groups were matched by tumor size, lymph node status and tumor grade.

TABLE 3

Patients and tumor characteristics

| Sample ID | Tumor type | Size | Grade | Nodes | ER | PR | Age | DFS | Status |
|---|---|---|---|---|---|---|---|---|---|
| 1389 | D | 1.7 | 2 | 0/1 | Pos | Pos | 80 | 94 | 0 |
| 648 | D | 1.1 | 2 | 0/15 | Pos | ND | 62 | 160 | 0 |
| 289 | D | 3 | 2 | 0/15 | Pos | ND | 75 | 63 | 1 |
| 749 | D | 1.8 | 2 | 2/9 | Pos | Pos | 61 | 137 | 0 |
| 420 | D/L | 2 | 3 | ND | Pos | Pos | 72 | 58 | 1 |
| 633 | D | 2.7 | 3 | 0/11 | Pos | ND | 61 | 20 | 1 |
| 662 | D | 1 | 3 | 6/11 | Pos | Pos | 79 | 27 | 1 |
| 849 | D | 2 | 1 | 0/26 | Pos | Neg | 75 | 23 | 1 |
| 356 | D | 1 | 2 | 2/20 | Pos | ND | 58 | 24 | 1 |
| 1304 | D | 2 | 3 | 0/14 | Pos | Pos | 57 | 20 | 1 |
| 1419 | D | 2.5 | 2 | 1/8 | Pos | Pos | 59 | 86.04 | 0 |
| 1093 | D | 1 | 3 | 1/14 | Pos | Pos | 66 | 84.96 | 0 |
| 1047 | D/L | 2.6 | 2 | 0/18 | Pos | Neg | 70 | 127.92 | 0 |
| 1037 | D/L | 1.5 | 2 | 0/4 | Pos | Pos | 85 | 83.04 | 0 |
| 319 | D | 4 | 2 | 1/13 | Pos | ND | 67 | 44 | 1 |
| 25 | D | 3.5 | 2 | 0/9 | Neg | Pos | 62 | 75 | 1 |
| 180 | D | 1.6 | 2 | 2/19 | Pos | Pos | 69 | 168.96 | 0 |
| 687 | D | 3.5 | 3 | 3/16 | Pos | ND | 73 | 141.96 | 0 |
| 856 | D | 1.6 | 2 | 0/16 | Pos | Pos | 73 | 87.96 | 0 |
| 1045 | D | 2.5 | 3 | 1/12 | Pos | Neg | 73 | 120.96 | 0 |
| 1205 | D | 2.7 | 2 | 1/19 | Pos | Pos | 71 | 87.96 | 0 |
| 1437 | D | 1.7 | 2 | 2/22 | Pos | Pos | 67 | 89.04 | 0 |
| 1507 | D | 3.7 | 3 | 0/40 | Pos | Pos | 70 | 69.96 | 0 |
| 469 | D | 1 | 1 | 0/19 | Pos | ND | 66 | 161.04 | 0 |
| 829 | D | 1.2 | 2 | 0/9 | Pos | ND | 69 | 135.96 | 0 |
| 868 | D | 3 | 3 | 0/13 | Pos | Pos | 65 | 129.96 | 0 |
| 1206 | D | 4.1 | 3 | 0/15 | Pos | Neg | 84 | 56 | 1 |
| 843 | D | 3.4 | 2 | 11/20 | Pos | Neg | 76 | 122 | 1 |
| 342 | D | 3 | 2 | 9/21 | Pos | ND | 62 | 102 | 1 |
| 1218 | D | 4.5 | 1 | 3/16 | Pos | Pos | 62 | 10 | 1 |
| 547 | D/L | 1.5 | 2 | ND | Pos | ND | 74 | 129 | 1 |
| 1125 | D | 2.6 | 2 | 0/18 | Pos | Pos | 54 | 123 | 0 |
| 1368 | D | 2.6 | 2 | ND | Pos | Pos | 82 | 63 | 0 |
| 605 | D | 2.2 | 2 | 6/18 | Pos | ND | 70 | 110.04 | 0 |
| 59 | L | 3 | 2 | 33/38 | Pos | ND | 70 | 21 | 1 |
| 68 | D | 3 | 2 | 0/17 | Pos | ND | 53 | 38 | 1 |
| 317 | D | 1.2 | 3 | 1/10 | Pos | Pos | 71 | 5 | 1 |
| 374 | D | 1 | 3 | 0/15 | Pos | Neg | 57 | 47 | 1 |
| 823 | D | 2 | 2 | 0/6 | Pos | Pos | 51 | 69 | 1 |
| 280 | D | 2.2 | 3 | 0/12 | Pos | ND | 66 | 44 | 1 |
| 651 | D | 4.7 | 3 | 10/13 | Pos | ND | 48 | 137 | 1 |

TABLE 3-continued

Patients and tumor characteristics

| Sample ID | Tumor type | Size | Grade | Nodes | ER | PR | Age | DFS | Status |
|---|---|---|---|---|---|---|---|---|---|
| 763 | D | 1.8 | 2 | 0/14 | Pos | Pos | 63 | 117.96 | 0 |
| 1085 | D | 4.7 | 2 | 0/8 | Pos | Pos | 48 | 101 | 1 |
| 1363 | D | 2.1 | 2 | 0/15 | Pos | Pos | 56 | 114 | 0 |
| 295 | D | 3.5 | 2 | 3/21 | Pos | Pos | 52 | 118 | 1 |
| 871 | D | 4 | 3 | 0/16 | Pos | Neg | 61 | 6 | 1 |
| 1343 | D | 2.5 | 3 | ND | Pos | Pos | 79 | 21 | 1 |
| 140 | L | >2.0 | 2 | 18/28 | Pos | ND | 63 | 43 | 1 |
| 260 | D/L | 0.9 | 2 | 1/13 | Pos | ND | 73 | 42 | 1 |
| 297 | D | 0.8 | 2 | 1/16 | Pos | Pos | 66 | 169 | 0 |
| 1260 | D | 3.5 | 2 | 0/14 | Pos | Pos | 58 | 79 | 0 |
| 1405 | D | 1 | 3 | ND | Pos | Pos | 81 | 95.04 | 0 |
| 518 | L | 5.5 | 2 | 3/20 | Pos | ND | 68 | 156 | 0 |
| 607 | D | 1.2 | 2 | 5/14 | Pos | Pos | 76 | 114 | 0 |
| 638 | D | 2 | 2 | 1/24 | Pos | Pos | 67 | 147.96 | 0 |
| 655 | D | 2 | 3 | ND | Pos | Pos | 73 | 143.04 | 0 |
| 772 | D | 2.5 | 2 | 0/18 | Pos | Pos | 68 | 69 | 1 |
| 878 | D/L | 1.6 | 2 | 0/9 | Pos | Neg | 76 | 138 | 0 |
| 1279 | D | 2 | 2 | 0/12 | Pos | Pos | 68 | 102 | 0 |
| 1370 | D | 2 | 2 | ND | Pos | Pos | 73 | 60.96 | 0 |

Abbreviations:
D, ductal;
L, lobular;
pos, positive;
neg, negative;
ND, not determined;
ER, estrogen receptor;
PR, progesterone receptor;
DFS, disease-free survival;
status = 1, recurred;
status = 0, disease-free.

The samples were used to identify gene expression signatures correlated with outcome of TAM treatment. Each breast cancer biopsy contains a mixture of cell types including epithelial breast cancer cells, infiltrating lymphocytes, endothelial cells and stromal fibroblasts. It has been suggested that complex interactions among these cell types in the tumor microenvironment determine the biological behavior of the tumor. Therefore, to identify gene expression differences in primary tumors between TAM responders and non-responders, expression profiling of both whole tissue sections, which represent this microenvironment, and microdissected, largely pure populations of epithelial cancer cells from each tumor biopsy were conducted on a custom 22k oligonucleotide microarray.

This generated two parallel datasets corresponding to each patient: one set from whole tissue sections ("sections dataset") and another from laser capture microdissected cancer cells ("LCM dataset"). Each expression dataset was first filtered based on overall variance of each gene and the top 5475 high-variance genes (75th percentile) were selected. Using the reduced datasets, t-test on each gene between the TAM responders and non-responders were carried out. From the sections dataset, 19 genes were identified at the p value cutoff of 0.001 (Table 4). The probability of selecting this many or more differentially expressed genes by chance was 0.035 as estimated by randomly permuting the patient class with respect to treatment outcome and repeating the t-test procedure 1000 times. Among the 19 genes identified in the sections dataset, genes involved in immune response are particularly prominent.

TABLE 4

19-gene signature identified by t-test in the Sections dataset

| | Parametric p-value | Mean in responders | Mean in non-responders | Fold difference of means | GB acc | Description |
|---|---|---|---|---|---|---|
| 1 | 1.96E−05 | 0.759 | 1.317 | 0.576 | AW006861 | SCYA4 \| small inducible cytokine A4 |
| 2 | 2.43E−05 | 1.31 | 0.704 | 1.861 | AI240933 | ESTs |
| 3 | 8.08E−05 | 0.768 | 1.424 | 0.539 | X59770 | IL1R2 \| interleukin 1 receptor, type II |
| 4 | 9.57E−05 | 0.883 | 1.425 | 0.62 | AB000520 | APS \| adaptor protein with pleckstrin homology and src homology 2 domains |
| 5 | 9.91E−05 | 1.704 | 0.659 | 2.586 | AF208111 | IL17BR \| interleukin 17B receptor |
| 6 | 0.0001833 | 0.831 | 1.33 | 0.625 | AI820604 | ESTs |
| 7 | 0.0001935 | 0.853 | 1.459 | 0.585 | AI087057 | DOK2 \| docking protein 2, 56 kD |
| 8 | 0.0001959 | 1.29 | 0.641 | 2.012 | AJ272267 | CHDH \| choline dehydrogenase |
| 9 | 0.0002218 | 1.801 | 0.943 | 1.91 | N30081 | ESTs, Weakly similar to I38022 hypothetical protein [*H. sapiens*] |

TABLE 4-continued 19-gene signature identified by t-test in the Sections dataset

| | Parametric p-value | Mean in responders | Mean in non-responders | Fold difference of means | GB acc | Description |
|---|---|---|---|---|---|---|
| 10 | 0.0004234 | 1.055 | 2.443 | 0.432 | AI700363 | ESTs |
| 11 | 0.0004357 | 0.451 | 1.57 | 0.287 | AL117406 | ABCC11 \| ATP-binding cassette, sub-family C (CFTR/MRP), member 11 |
| 12 | 0.0004372 | 1.12 | 3.702 | 0.303 | BC007092 | HOXB13 \| homeo box B13 |
| 13 | 0.0005436 | 0.754 | 1.613 | 0.467 | M92432 | GUCY2D \| guanylate cyclase 2D, membrane (retina-specific) |
| 14 | 0.0005859 | 1.315 | 0.578 | 2.275 | AL050227 | *Homo sapiens* mRNA; cDNA DKFZp586M0723 (from clone DKFZp586M0723) |
| 15 | 0.000635 | 1.382 | 0.576 | 2.399 | AW613732 | *Homo sapiens* cDNA FLJ31137 fis, clone IMR322001049 |
| 16 | 0.0008714 | 0.794 | 1.252 | 0.634 | BC007783 | SCYA3 \| small inducible cytokine A3 |
| 17 | 0.0008912 | 2.572 | 1.033 | 2.49 | X81896 | C11orf25 \| chromosome 11 open reading frame 25 |
| 18 | 0.0009108 | 0.939 | 1.913 | 0.491 | BC004960 | MGC10955 \| hypothetical protein MGC10955 |
| 19 | 0.0009924 | 1.145 | 0.719 | 1.592 | AK027250 | *Homo sapiens* cDNA: FLJ23597 fis, clone LNG15281 |

Repeating the same analysis on the LCM dataset yielded 9 significant genes at the cutoff of p<0.001 (Table 5); however, the probability of finding 9 or more genes by chance is 0.154 in permutation analysis (n=1000). These results established that significant differences in gene expression between the two patient groups exist, but differences were subtle.

TABLE 5

9-gene signature identified by t-test in the LCM dataset

| | Parametric p-value | Mean in responders | Mean in non-responders | Fold difference of means | GB acc | Description |
|---|---|---|---|---|---|---|
| 1 | 2.67E−05 | 1.101 | 4.891 | 0.225 | BC007092 | HOXB13 \| homeo box B13 |
| 2 | 0.0003393 | 1.045 | 2.607 | 0.401 | AI700363 | ESTs |
| 3 | 0.0003736 | 0.64 | 1.414 | 0.453 | NM_014298 | QPRT \| quinolinate phosphoribosyltransferase (nicotinate-nucleotide pyrophosphorylase (carboxylating)) |
| 4 | 0.0003777 | 1.642 | 0.694 | 2.366 | AF208111 | IL17BR \| interleukin 17B receptor |
| 5 | 0.0003895 | 0.631 | 1.651 | 0.382 | AF033199 | ZNF204 \| zinc finger protein 204 |
| 6 | 0.0004524 | 1.97 | 0.576 | 3.42 | AI688494 | FLJ13189 \| hypothetical protein FLJ13189 |
| 7 | 0.0005329 | 1.178 | 0.694 | 1.697 | AI240933 | ESTs |
| 8 | 0.0007403 | 0.99 | 1.671 | 0.592 | AL57459 | Homo sapiens mRNA; cDNA DKFZp434B0425 (from clone DKFZp434B0425) |
| 9 | 0.0007739 | 0.723 | 1.228 | 0.589 | BC002480 | FLJ13352 \| hypothetical protein FLJ13352 |

The sequence of each GenBank accession number in Tables 4 and 5 is presented in the Sequence Listing.

Due to the limited sample size (n=60), leave-one-out cross validation was used to assess the predictive significance of the gene expression signature. In each round of cross validation, significant genes were identified using the training set by t-test at p<0.001, and a compound covariate predictor was built as the linear combination oft he gene expression values over all significant genes weighted by their t-statistics. The predictor was then used to predict the left-out sample. Repeating this procedure 60 times generated an "honest" prediction on each sample.

Figure 2:
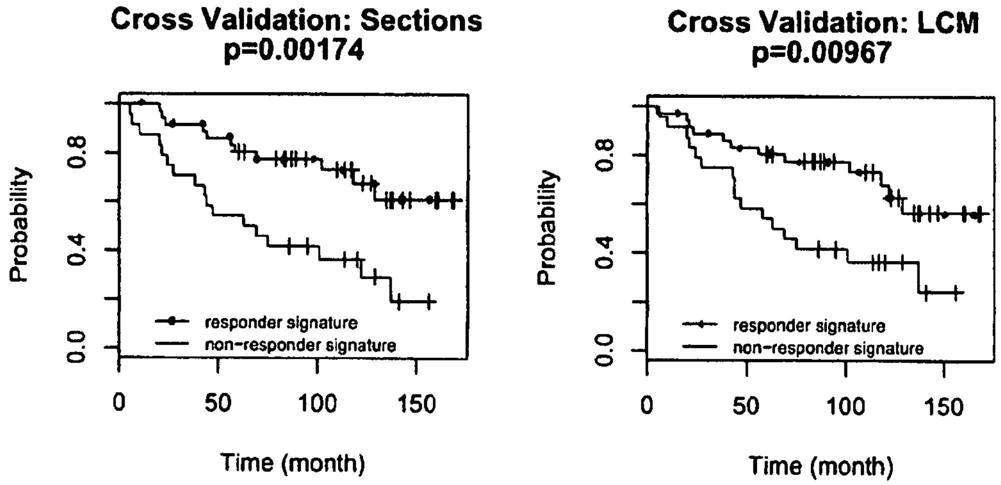
FIG. 2 shows survival curves for two groups of breast cancer patients defined by expression signatures based on genes sets identified for whole tissue sections (left graph) and laser microdissected cells (right graph) as described herein.

Using the sections dataset, the overall accuracy of cross validation results are 70%, and the sensitivity, specificity, positive and negative predictive values are 60%, 78%, 71%, and 69%, respectively. The results of analyzing the LCM dataset were slightly lower, with an overall accuracy of 67%, and sensitivity, specificity, positive and negative predictive values of 57%, 75%, 67%, and 67%, respectively. Patients having the "responder signature" and those having the "non-responder signature" as predicted from cross validation demonstrate significantly different disease-free survival curves (FIG. 2).

Previously a 70-gene prognostic classifier was derived from correlating gene expression profiles with distant metastasis from node-negative breast cancer patients, most of which received no adjuvant chemotherapy or endocrine therapy. 61 of the 70 genes from the study were on the microarrays used in this example. Expression data corresponding to these 61 genes were extracted from the sections dataset because the 70-gene signature study used whole tissue sections. None of these 61 genes were significantly differentially expressed between TAM responders and non-responders at the significance level of 0.001, and only 3 genes were significant at $p<0.05$. Leave-one-out cross-validation analysis using either all 61 genes or only genes with $p<0.05$ gave overall accuracies of 52% and 53% respectively. Thus the 70-gene classifier derived from mostly untreated patients cannot predict tumor recurrence after adjuvant TAM treatment. Without being bound by theory, and offered to improve the understanding of the invention, this suggests that the treatment outcome by TAM is not simply a reflection of the aggressiveness of the primary tumor, but may directly reflect the responsiveness to TAM.

Example 4

Identification of 3 Biomarker Predictors of TAM Treatment Outcome

Figure 3:
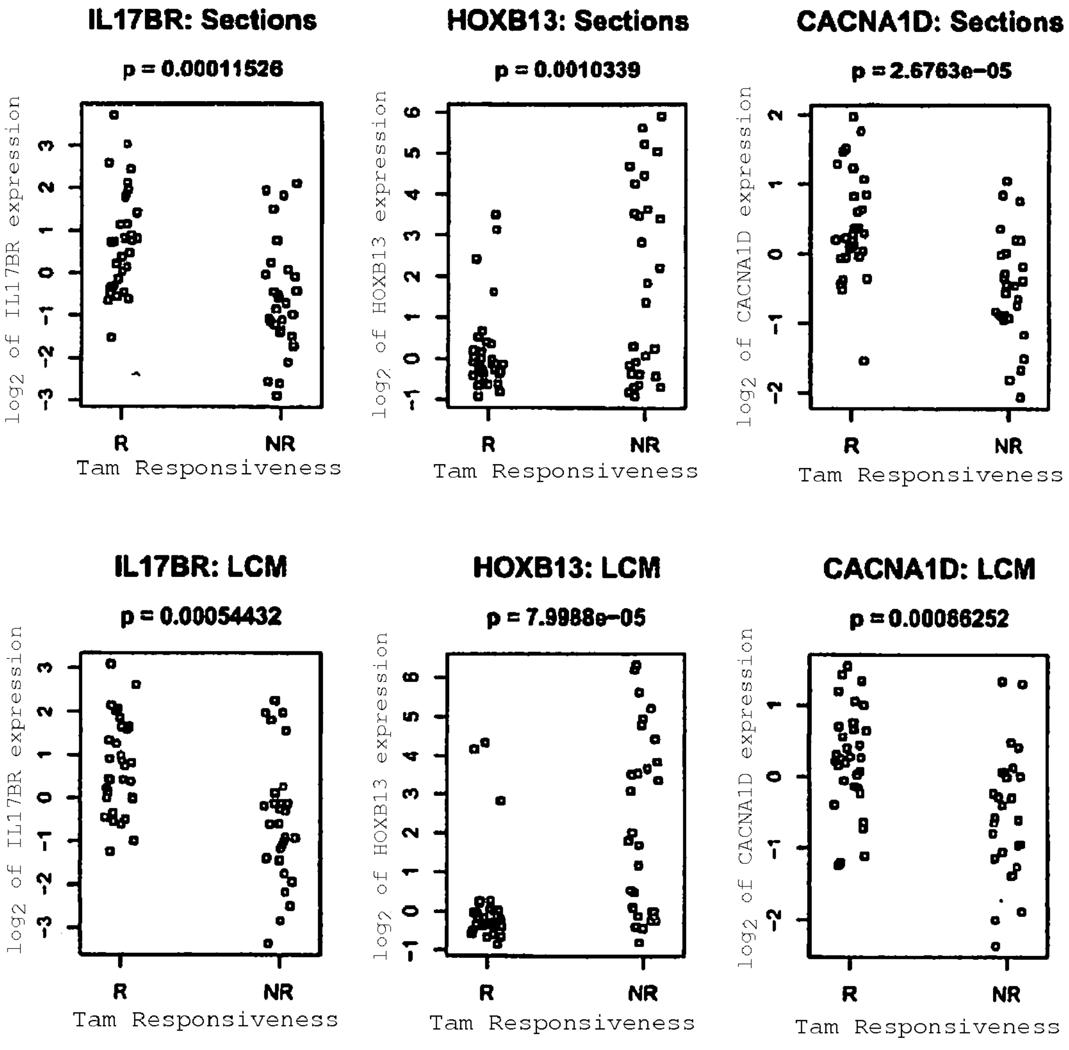
FIG. 3 shows the expression levels of IL17BR, HOXB13, and CACNA1D in whole tissue sections (top three graphs) and laser microdissected cells (bottom three graphs).

Between the two sets of significant genes identified with the sections and LCM datasets of Example 3, 4 genes (AI700363, EST; BC007092, HOXB13; AF208111, IL17BR; AI240933, EST) were in common. Further sequence analysis indicated that the EST sequence AI700363 represents a splicing variant of HOXB13 and the other EST (AI240933) represents the 3' end of the putative calcium channel gene CACNA1D. Therefore, these analyses identified three distinct genes having statistically significant differential expression between responders and non-responders (FIG. 3). It is noteworthy that HOXB13 had a more significant difference between responders and non-responders in the LCM dataset. The fact that these three genes were identified both in the sections and LCM datasets serves to validate the microarray measurements, and also suggest that they are likely to be differentially expressed by the tumor cells themselves.

The significant correlations of CACNA1D, HOXB13 and IL17BR with TAM treatment outcome suggest that these three genes may be novel predictors of TAM response. Estrogen receptor status is a powerful predictor of response to tamoxifen, as 60% ER+ vs. <10% ER− tumors respond to TAM. However, among ER+ tumors, no established predictors exist to identify the 40% non-responders. Therefore, the predictive usefulness of CACNA1D, HOXB13 and IL17BR as potential biomarkers to identify the ER+, TAM responders and non-responders was tested.

Figure 4:
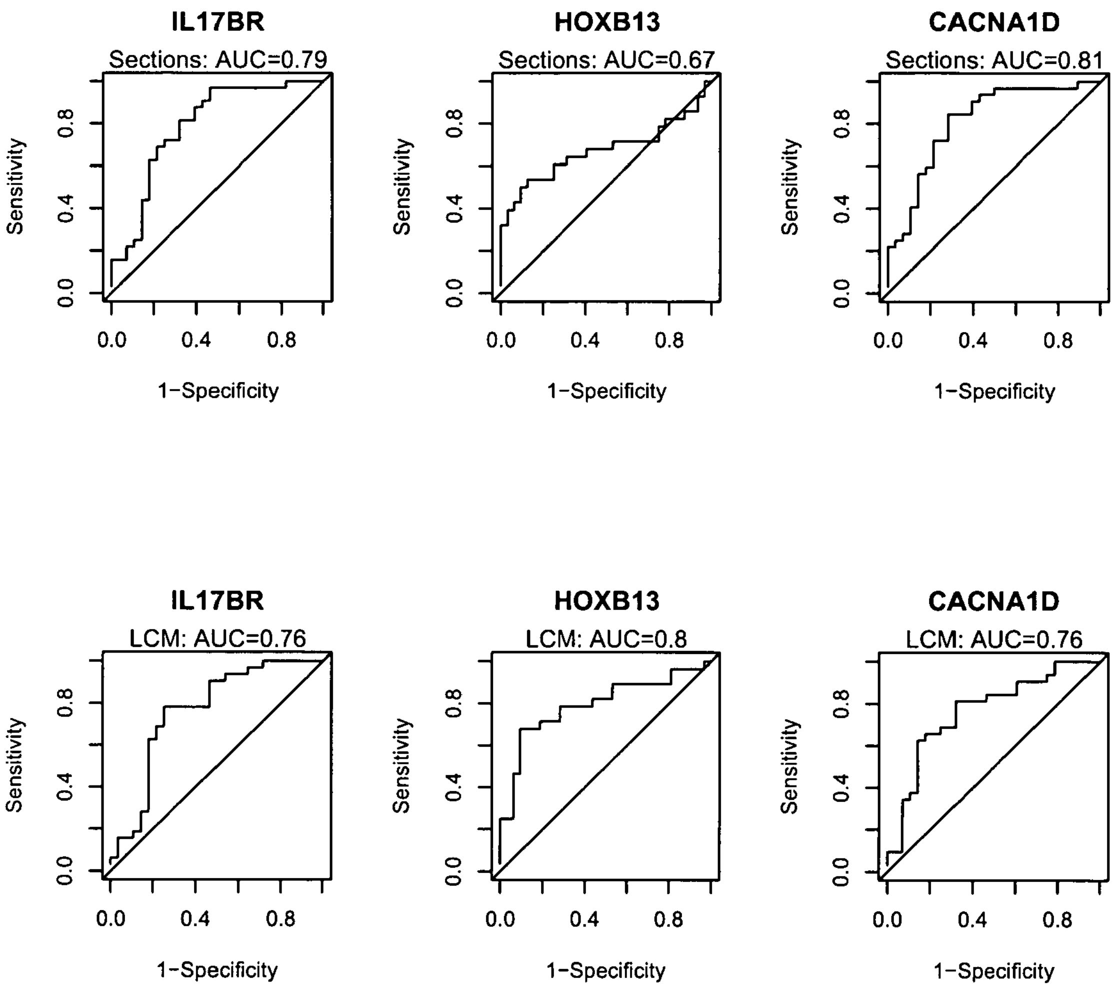
FIG. 4 shows receiver operating characteristic (ROC) analyses of IL17BR, HOXB13, and CACNA1D expression levels as predictors of breast cancer outcomes in whole tissue sections (top three graphs) and laser microdissected cells (bottom three graphs). AUC refers to area under the curve.

Receiver operating characteristic (ROC) analysis evaluates the sensitivity and specificity of a clinical test. The area under the curve (AUC) of plotting the false positive rate against the true positive rate measures the overall accuracy. In both the sections and LCM datasets, all three genes demonstrated consistent predictive ROC curves (FIG. 3). The AUC values (Table 4) for IL17BR and CACNA1D ranges from 0.76 to 0.81 with higher values in the sections data; HOXB13 has considerably higher AUC in the LCM dataset than in the sections dataset (0.79 vs. 0.69), consistent with the t-test results (FIG. 4). Statistical test for AUC>0.5 indicates that all AUC values are significant (Table 6).

TABLE 6

ROC analysis summary

| | Sections | | LCM | | FFPE | |
|---|---|---|---|---|---|---|
| | AUC | P | AUC | P | AUC | P |
| IL17BR | 0.79 | 1.58E−06 | 0.76 | 2.73E−05 | 0.83 | 4.94E−06 |
| CACNA1D | 0.81 | 3.02E−08 | 0.76 | 1.59E−05 | 0.79 | 1.54E−04 |
| HOXB13 | 0.67 | 0.012 | 0.79 | 9.94E−07 | 0.58 | 0.216 |
| ESR1 | 0.55 | 0.277 | 0.63 | 0.038 | 0.58 | 0.218 |
| PGR | 0.65 | 0.020 | 0.63 | 0.039 | 0.58 | 0.247 |
| ERBB2 | 0.69 | 0.004 | 0.64 | 0.027 | 0.59 | 0.226 |
| EGFR | 0.56 | 0.200 | 0.61 | 0.068 | 0.62 | 0.133 |

AUC, area under the curve;
P values compare AUC > 0.5.

Figure 5:
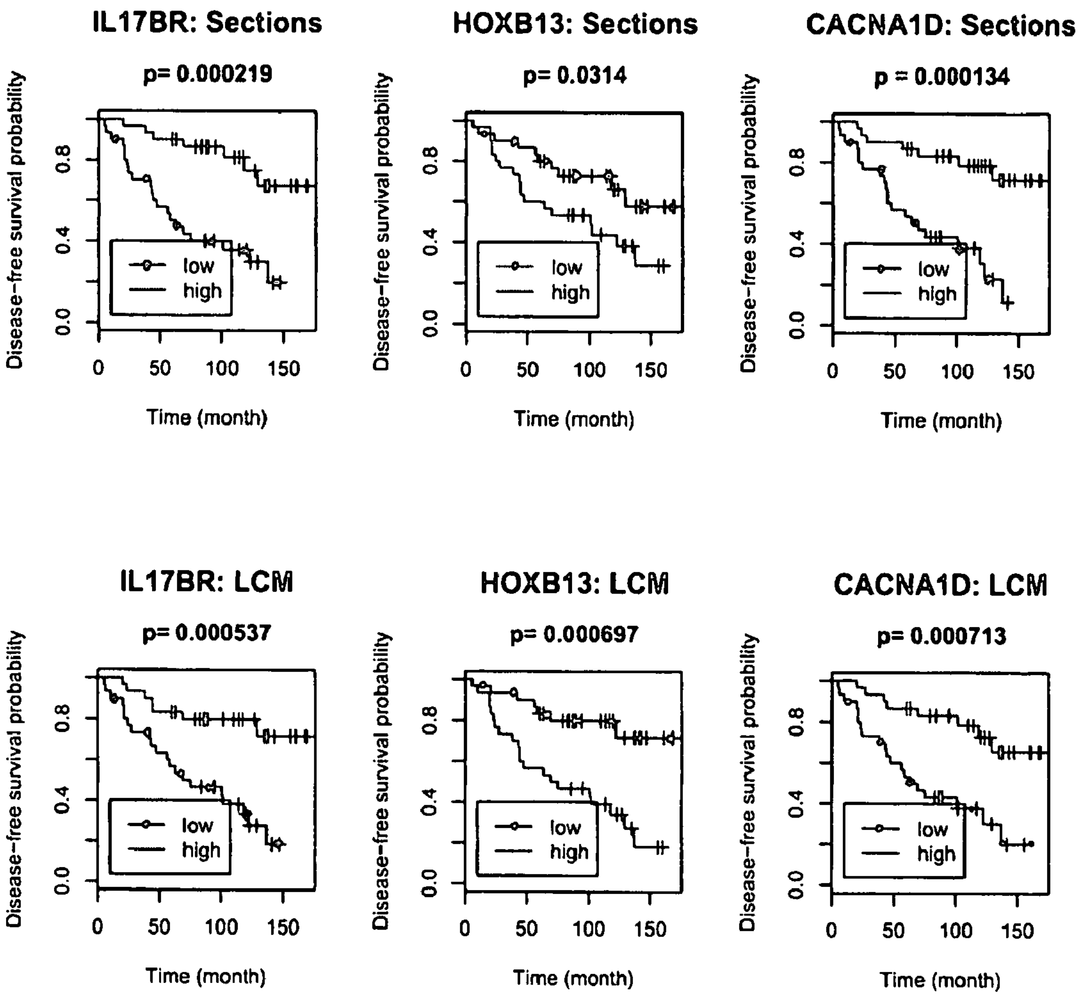
FIG. 5 shows Kaplan-Meier (KM) analyses of IL17BR, HOXB13, and CACNA1D expression levels as predictors of breast cancer outcomes in whole tissue sections (top three graphs) and laser microdissected cells (bottom three graphs).

As a further demonstration for the predictive utility of CACNA1D, HOXB13 and IL17BR, Kaplan-Meier analysis was performed to assess the correlation of the expression levels with disease-free survival. For each gene, patients were stratified into two groups using the median as cut point: low (<=median) and high (>median), and the Kaplan-Meier curves were compared in log-rank test (FIG. 5). Stratification by each of these three genes results in two groups with highly significant different disease-free survival times.

Considerable evidence suggests that the activity of growth factor signaling pathways may negatively regulate estrogen signaling, which may contribute to loss of responsiveness or developing resistance to TAM. Therefore, we evaluated the predictive utility of ESR1, PGR (positive predictors), ERBB2 and EGFR (negative predictors) in our datasets by ROC analysis. The AUCs ranged from 0.55 to 0.69 for these genes, but the values of PGR and ERBB2 were significantly higher than 0.5 in both sections and LCM datasets (Table 6), which is consistent with prior studies. Taken together, these results demonstrate that the three genes identified in this study are significantly stronger than estrogen and progesterone receptors as positive predictors and ERBB2 and EGFR as negative predictors.

Figure 6:
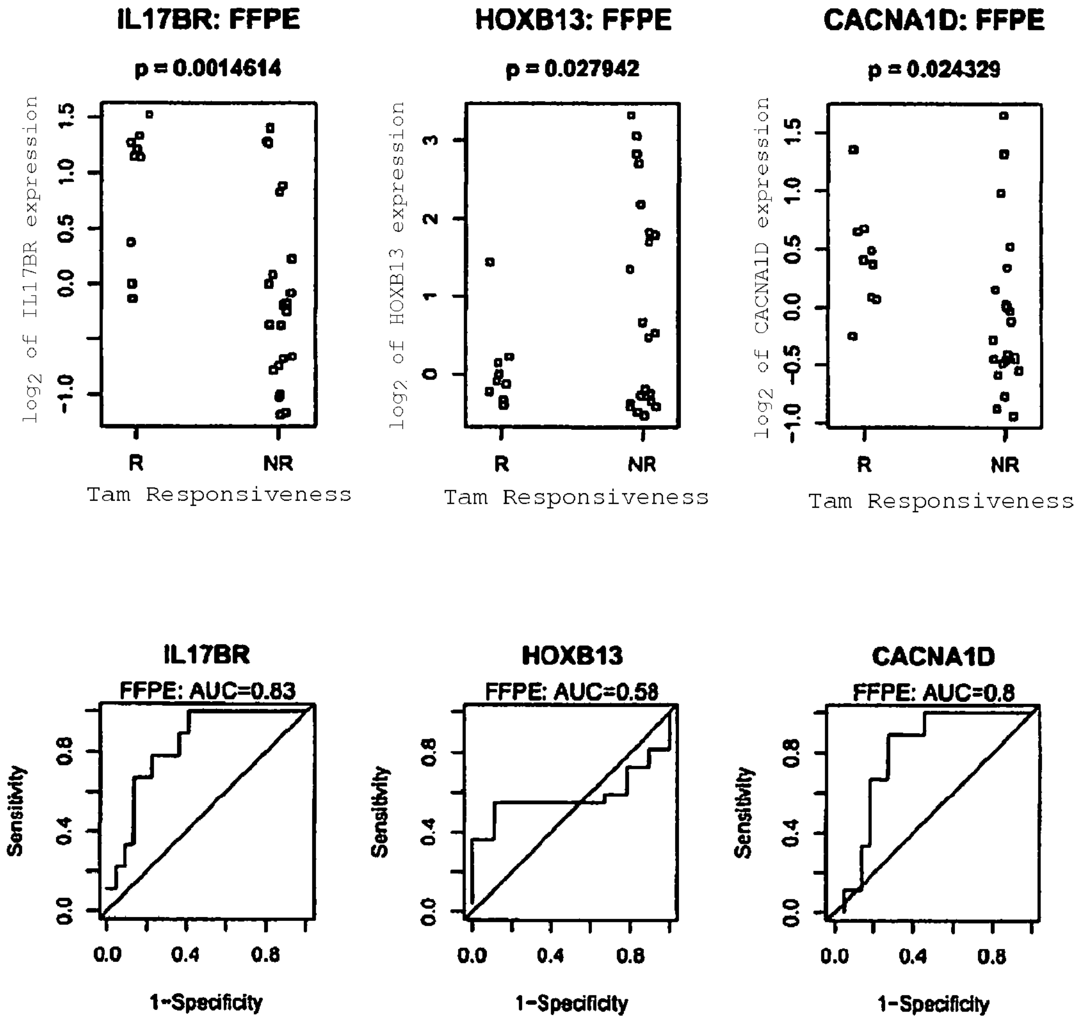
FIG. 6 shows expression levels (top three graphs) and ROC (bottom three graphs) analysis of IL17BR, HOXB13, and CACNA1D as predictors of breast cancer outcomes in macrodissected formalin fixed, paraffin embedded (FFPE) samples from a cohort of 31 patients treated with tamoxifen.

We next validated these results using an independent cohort of 31 patients uniformly treated with TAM. Primary breast cancer biopsies in the form of formalin-fixed paraffin-embedded (FFPE) blocks were used for microarray analysis; macro-dissection was performed to enrich for tumor content. The expression levels of CACNA1D, HOXB13, and IL17BR were compared between responders (n=9) and non-responders (n=22) (FIG. 6) and ROC analysis performed as before (FIG. 6; Table 6). The three genes showed statistically significant differences in gene expression between TAM responders and non-responders similar to those seen in the sections and LCM datasets (FIG. 6, cf. FIGS. 3-4). The AUC values for IL17BR and CACNA1D are 0.83 and 0.79, respectively; AUC for HOXB13 was insignificant but with a consistent trend in the earlier portions of the ROC curve. Compared to the known genes (ESR1, PGR, ERBB2 and EGFR), IL17BR and CACNA1D were significantly stronger predictors of TAM response (Table 6).

Figure 7:
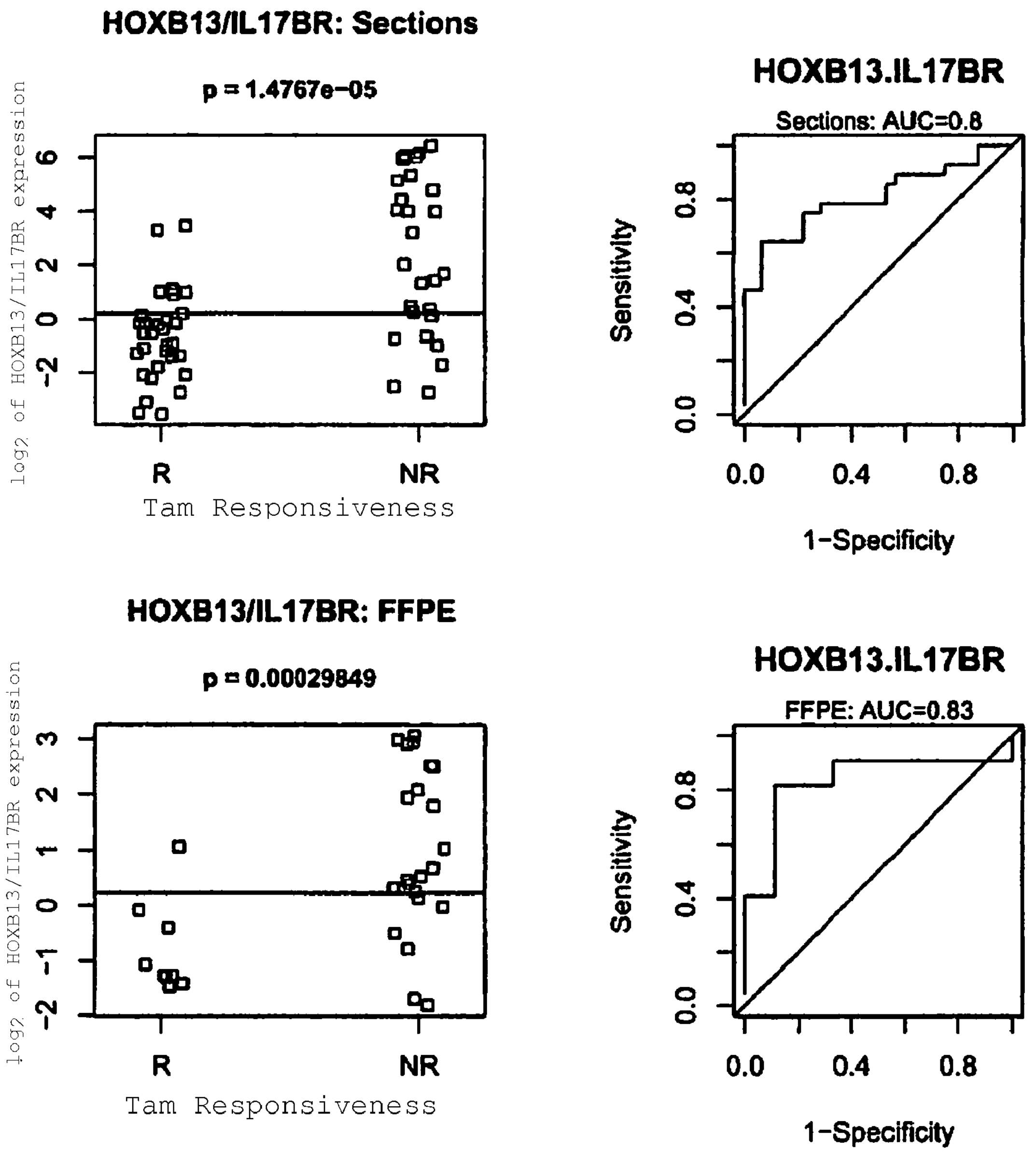
FIG. 7 shows analysis and use of a ratio of HOXB13 to IL17BR expression levels as a predictor of breast cancer outcome. Plots of the ratios in whole tissue sections and macrodissected FFPE samples as well as ROC analysis are shown in the first four graphs. Survival curves based on "high" and "low" ratios (relative to 0.22, the horizontal line in the plots of the ratios) are shown in the last graph.

Because HOXB13 and IL17BR display opposing patterns of expression, the idea of using the ratio of HOXB13 over IL17BR as a composite predictor was tested (FIG. 7). Two sample t-tests indicated that the two-gene ratio had a stronger correlation with treatment outcome than either gene alone in both the sections and FFPE datasets (FIG. 7; cf. FIG. 3). ROC curves have AUCs of 0.8 and 0.83 for the sections and FFPE data, respectively. From the ROC curve for the sections data, minimizing the absolute difference between sensitivity and specificity yielded an optimal cut point of −0.22 (log2 scale) (horizontal line in FIG. 7). Classifying the patients in the sections data into responders (log ratio<=−0.22) and non-responders (log ratio>−0.22) resulted in correct classification of 46 of the 60 patients (77%, p=4.224e−05, 95% CI 64%-87%). Applying the same classification rule to the FFPE dataset, 8 of the 9 responders and 16 of the 22 non-responders were correctly classified (overall accuracy=77%, p-value=0.003327, 95% CI 59%-90%).

Example 5

Multivariate Analysis

Expression data from the three genes were used in logistic regression models by calculating cross-validated compound covariate scores as linear combinations of the expression values of the three genes weighted by their t-test statistics in each round of leave-one-out cross validation. The compound covariate score has a univariate p value of 0.0003 with both sections and LCM datasets, and the model had a bootstrap-adjusted accuracy of 81% (Table 7). Next, multivariate logistic regression analysis was performed using clinicopathological factors plus the compound covariate score. Because only two samples were grade 1, grades 1 and 2 were combined into one level (low-grade) and compared to grade 3 (high-grade). Due to missing values in clinical parameters, 53 cases were used for modeling. The multivariate model shows that the compound covariate score was the only independent significant predictor (Table 7). Clinical factors (such as tumor size, grade and nodal status) were not significantly associated with TAM treatment outcome.

TABLE 7

Multivariate analysis
PREDICTIVE POWER OF BREAST CANCER RECURRENCE OF EACH INDIVIDUAL PREDICTOR[1]

| | LCM DATA | | | | SECTION DATA | | | |
|---|---|---|---|---|---|---|---|---|
| **Model 1:** | | | | | | | | |
| Accuracy[2] | 0.807 | | | | 0.817 | | | |
| Predictors | Odds Ratio | Lower 95% Cl of Odds Ratio | Upper 95% Cl of Odds Ratio | P Value | Odds Ratio | Lower 95% Cl of Odds Ratio | Upper 95% Cl of Odds Ratio | P Value |
| Score of Genes[3] | 7.4 | 2.5 | 21.8 | 0.0003 | 8.7 | 2.7 | 28.2 | 0.0003 |
| **Model 2:** | | | | | | | | |
| Accuracy[2] | 0.796 | | | | 0.798 | | | |
| Predictor | Odds Ratio | Lower 95% Cl of Odds Ratio | Upper 95% Cl of Odds Ratio | P Value | Odds Ratio | Lower 95% Cl of Odds Ratio | Upper 95% Cl of Odds Ratio | P Value |
| Tumor Size | 1.2 | 0.5 | 3.0 | 0.662 | 1.3 | 0.6 | 3.1 | 0.544 |
| Nodal status (pos:neg) | 0.8 | 0.2 | 3.2 | 0.777 | 0.9 | 0.2 | 3.4 | 0.840 |
| Tumor grade (high:low) | 1.5 | 0.3 | 6.5 | 0.619 | 1.2 | 0.3 | 5.9 | 0.793 |
| Score of Genes[3] | 8.5 | 2.2 | 33.3 | 0.0021 | 10.8 | 2.4 | 48.0 | 0.0018 |

[1]Model P value is estimated based upon a multivariate logistic regression model against tumor recurrence status.
[2]Model predictive accuracy is estimated based on bias-adjusted AUC index by 200 bootstraps.
[3]Score of genes is a pre-validated compound covariance score based on gene expressions levels and the regression coefficient for each predictor based on univariate logistic regression model.

The results reflected in Table 7 are expected because the responder and non-responder groups were matched by these parameters in patient selection. Bootstrap validation analysis indicated that the full model has a concordance index of 80%. Taken together, these results demonstrate that the three genes identified in this study were strong independent predictors of treatment outcome by adjuvant therapy independent of known clinicopathological parameters.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

We claim:

1. A method to determine the risk of cancer recurrence in a human subject afflicted with ER+ (estrogen receptor positive) breast cancer, said method comprising determining an expected cancer recurrence for said subject by assaying a sample of breast cancer cells from said subject for a ratio of HoxB13 and IL17BR RNA expression levels that is higher than the mean (average) ratio of HoxB13 and IL17BR RNA expression levels in ER+ breast cancer cells; or determining an expected lack of cancer recurrence for said subject by assaying a sample of breast cancer cells from said subject for a ratio of HoxB13 and IL17BR RNA expression levels that is below the mean (average) ratio of HoxB13 and IL17BR RNA expression levels in ER+ breast cancer cells;

wherein said mean (average) ratio of HoxB13 and IL17BR RNA expression levels is determined from the mean (average) of HoxB13 RNA expression levels, and the mean (average) of IL17BR RNA expression levels, in ER+ breast cancer cell samples from human breast cancer subjects that respond to treatment with tamoxifen and human breast cancer subjects that do not respond to treatment with tamoxifen.

2. A method of determining the outcome of a human subject having ER+ (estrogen receptor positive) breast cancer, or of a subject afflicted with ER+ breast cancer, if said subject is treated with tamoxifen, said method comprising:

assaying a breast cancer cell sample from said subject wherein a ratio of HoxB13 and IL17BR RNA expression levels that is below the mean (average) ratio of HoxB13 and IL17BR expression levels in ER+ breast cancer cells indicates a cancer-free outcome, and a ratio above the mean (average) ratio of HoxB13 and IL17BR RNA expression levels in ER+ breast cancer cells indicates an outcome comprising cancer recurrence;

wherein said mean (average) ratio of HoxB13 and IL17BR RNA expression levels is determined from the mean (average) of HoxB13 RNA expression levels, and the mean (average) of IL17BR RNA expression levels, in ER+ breast cancer cell samples from human breast cancer subjects that respond to treatment with tamoxifen and human breast cancer subjects that do not respond to treatment with tamoxifen.

3. A method to predict an expected lack of response to tamoxifen treatment in a human ER+ (estrogen receptor positive) breast cancer patient, said method comprising determining an expected lack of response to tamoxifen treatment for said patient by assaying a sample of breast cancer cells from said patient for a ratio of HoxB13 and IL17BR expression levels that is higher than the mean (average) ratio of HoxB13 and IL17BR expression levels in ER+ breast cancer cells;

wherein said mean (average) ratio of HoxB13 and IL17BR RNA expression levels is determined from the mean (average) of HoxB13 RNA expression levels, and the mean (average) of IL17BR RNA expression levels, in ER+ breast cancer cell samples from human breast cancer subjects that respond to treatment with tamoxifen and human breast cancer subjects that do not respond to treatment with tamoxifen.

4. A method to determine risk of cancer recurrence in a human subject having ER+ (estrogen receptor positive) breast cancer if treated with tamoxifen, said method comprising assaying a sample of breast cells from said subject for increased expression of human HOXB 13 sequences, or decreased expression of IL17BR sequences, relative to the mean (average) expression thereof in ER+ breast cancer cell samples from human breast cancer subjects that respond to treatment with tamoxifen and human breast cancer subjects that do not respond to treatment with tamoxifen, as an indicator of tamoxifen non-responsiveness; or decreased expression of human HOXB 13 sequences, or increased expression of IL17BR sequences, relative to the mean (average) expression thereof in ER+ breast cancer cell samples from human breast cancer subjects that respond to treatment with tamoxifen and human breast cancer subjects that do not respond to treatment with tamoxifen, as an indicator of tamoxifen responsiveness.

5. The method of claim 1 wherein said assaying comprises determining the expression levels of HoxB13 and IL17BR mRNAs.

6. The method of claim 1 wherein said assaying for the expression levels of HoxB13 and IL17BR RNA comprises mRNA amplification from said sample of breast cancer cells.

7. The method of claim 1 wherein said RNA expression levels are determined by quantitative PCR.

8. The method of claim 1 wherein said assaying comprises RT-PCR (reverse transcription polymerase chain reaction).

9. The method of claim 1 wherein said sample is a formalin fixed paraffin embedded (FFPE), ductal lavage or fine needle aspiration sample.

10. The method of claim 1 wherein said sample is a section of tissue from a subject or comprises cells microdissected from said section.

11. The method of claim 1, wherein said assaying for expression of a HoxB13 sequence comprises assaying for expression of a sequence selected from SEQ ID NOS: 6, 7, 10 or 11-31.

12. The method of claim 1, wherein said assaying for expression of an IL17BR sequence comprises assaying for expression of a sequence selected from SEQ ID NOS: 1, 2, 3, or 8.

13. The method of claim 2 wherein said assaying comprises determining the expression levels of HoxB13 and IL17BR mRNAs.

14. The method of claim 2 wherein said assaying for the expression levels of HoxB13 and IL17BR comprises detection of nucleic acids mRNA amplification from said sample of ER+ breast cancer cells.

15. The method of claim 2 wherein said RNA expression levels are determined by quantitative PCR.

16. The method of claim 2 wherein said assaying comprises RT-PCR (reverse transcription polymerase chain reaction).

17. The method of claim 2 wherein said sample is a formalin fixed paraffin embedded (FFPE), ductal lavage or fine needle aspiration sample.

18. The method of claim 2 wherein said sample is a section of tissue from a subject or comprises cells microdissected from said section.

19. The method of claim 2, wherein said assaying for expression of a HoxB13 sequence comprises assaying for expression of a sequence selected from SEQ ID NOS: 6, 7, 10 or 11-31.

20. The method of claim 2, wherein said assaying for expression of an IL17BR sequence comprises assaying for expression of a sequence selected from SEQ ID NOS: 1, 2, 3, or 8.

21. The method of claim 3 wherein said assaying comprises determining the expression levels of HoxB 13 and IL17BR mRNAs.

22. The method of claim 3 wherein said assaying comprises mRNA amplification from said sample of ER+ breast cancer cells.

23. The method of claim 3 wherein said RNA expression levels are determined by quantitative PCR.

24. The method of claim 3 wherein said assaying comprises RT-PCR (reverse transcription polymerase chain reaction).

25. The method of claim 3 wherein said sample is a formalin fixed paraffin embedded (FFPE), ductal lavage or fine needle aspiration sample.

26. The method of claim 3 wherein said sample is a section of tissue from a subject or comprises cells microdissected from said section.

27. The method of claim 3, wherein said assaying for expression of a HoxB13 sequence comprises assaying for expression of a sequence selected from SEQ ID NOS: 6, 7, 10 or 11-31.

28. The method of claim 3, wherein said assaying for expression of an IL17BR sequence comprises assaying for expression of a sequence selected from SEQ ID NOS: 1, 2, 3, or 8.

29. The method of claim 4 wherein said assaying comprises determining the expression levels of HoxB13 and IL17BR mRNAs.

30. The method of claim 4 wherein said assaying for the expression levels of HoxB13 and IL17BR comprises mRNA amplification from said sample of ER+ breast cancer cells.

31. The method of claim 4 wherein said RNA expression levels are determined by quantitative PCR.

32. The method of claim 4 wherein said assaying comprises RT-PCR (reverse transcription polymerase chain reaction).

33. The method of claim 4 wherein said sample is a formalin fixed paraffin embedded (FFPE), ductal lavage or fine needle aspiration sample.

34. The method of claim 4 wherein said sample is a section of tissue from a subject or comprises cells microdissected from said section.

35. The method of claim 4 wherein said sample is obtained by solid tissue biopsy or a non-invasive procedure.

36. The method of claim 4, wherein said assaying for expression of a HoxB13 sequence comprises assaying for expression of a sequence selected from SEQ ID NOS: 6, 7, 10 or 11-31.

37. The method of claim 4, wherein said assaying for expression of an IL17BR sequence comprises assaying for expression of a sequence selected from SEQ ID NOS: 1, 2, 3, or 8.

38. The method of claim 1 wherein said assaying comprises hybridization to a polynucleotide comprising sequences of at least 24 nucleotides from the 3' untranslated region, the coding region, or the 5' untranslated region, of a human HOXB 13 or IL17BR RNA transcript.

39. The method of claim 2 wherein said assaying comprises hybridization to a polynucleotide comprising sequences of at least 24 nucleotides from the 3' untranslated region, the coding region, or the 5' untranslated region, of a human HOXB 13 or IL17BR RNA transcript.

40. The method of claim 3 wherein said assaying comprises hybridization to a polynucleotide comprising sequences of at least 24 nucleotides from the 3' untranslated region, the coding region, or the 5' untranslated region, of a human HOXB 13 or IL17BR RNA transcript.

41. The method of claim 4 wherein said assaying comprises hybridization to a polynucleotide comprising sequences of at least 24 nucleotides from the 3' untranslated region, the coding region, or the 5' untranslated region, of a human HOXB 13 or IL17BR RNA transcript.

42. The method of claim 2 wherein said breast-cancer-free subject has a low risk of cancer tumor recurrence.

43. The method of claim 2 wherein said outcome comprises survival outcome.

* * * * *